United States Patent [19]

Angehrn et al.

[11] Patent Number: 5,438,052
[45] Date of Patent: Aug. 1, 1995

[54] CEPHALOSPORIN DERIVATIVES

[75] Inventors: Peter Angehrn, Böckten; André Furlenmeier, Basel; Paul Hebeisen, Reinach; Werner Hofheinz, Bottmingen; Helmut Link, Basel, all of Switzerland

[73] Assignee: Hoffmann-La Roche Inc., Nutley, N.J.

[21] Appl. No.: 979,519

[22] Filed: Nov. 20, 1992

[30] Foreign Application Priority Data

Nov. 26, 1991 [CH] Switzerland ............. 3463/91
Nov. 26, 1991 [CH] Switzerland ............. 3464/91
Sep. 4, 1992 [CH] Switzerland ............. 2787/92

[51] Int. Cl.$^6$ ............. C07D 501/36; A61K 31/545
[52] U.S. Cl. ............. 514/202; 514/206; 540/222; 540/225; 540/227
[58] Field of Search ............. 540/227, 222, 225; 514/206, 202

[56] References Cited

U.S. PATENT DOCUMENTS

| | | | |
|---|---|---|---|
| 5,001,121 | 3/1991 | Ohnishi et al. | 540/227 |
| 5,055,572 | 10/1991 | Furlenmeier et al. | 540/227 |
| 5,061,794 | 10/1991 | Nakagawa et al. | 540/227 |
| 5,262,410 | 11/1993 | Jung | 540/227 |

FOREIGN PATENT DOCUMENTS

| | | |
|---|---|---|
| 182210 | 11/1985 | European Pat. Off. . |
| 186187 | 12/1985 | European Pat. Off. . |
| 241901 | 4/1987 | European Pat. Off. . |
| 267733 | 11/1987 | European Pat. Off. . |
| 269087 | 11/1987 | European Pat. Off. . |
| 272827 | 12/1987 | European Pat. Off. . |
| 373216 | 2/1988 | European Pat. Off. . |
| 286145 | 4/1988 | European Pat. Off. . |
| 304155 | 7/1988 | European Pat. Off. . |
| 341948 | 5/1989 | European Pat. Off. . |
| 435333 | 12/1990 | European Pat. Off. . |
| 472060 | 8/1991 | European Pat. Off. . |
| 62-077391 | 4/1987 | Japan . |
| 62-158289 | 7/1987 | Japan . |
| 62-158290 | 7/1987 | Japan . |
| 62-226986 | 10/1987 | Japan . |
| 62-238292 | 10/1987 | Japan . |
| 62-270589 | 11/1987 | Japan . |
| 62-289585 | 12/1987 | Japan . |
| 86/05786 | 10/1986 | WIPO . |
| 88/03924 | 6/1988 | WIPO . |

OTHER PUBLICATIONS

Derwent Abstract No. 87-187390/27 (1987).
Derwent Abstract No. 87-232825/33 (1987).
Derwent Abstract No. 87-232826/33 (1987).
Derwent Abstract No. 87-318207/45 (1987).
Derwent Abstract No. 87-331897/47 (1987).
Derwent Abstract No. 88-004888/01 (1988).
Derwent Abstract No. 88-031457/05 (1988).

*Primary Examiner*—Nicholas Rizzo
*Attorney, Agent, or Firm*—George M. Gould; George W. Johnston; John P. Parise

[57] ABSTRACT

Cephalosporin derivatives have the formula

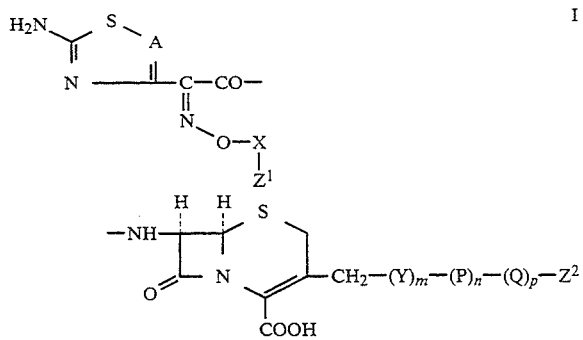

wherein $Z^1$, $Z^2$, X, Y, P, Q, m, n and p are as defined in the following text. Also described are the readily hydrolyzable esters and pharmaceutically compatible salts of these compounds, and hydrates of compounds of formula I, their esters and salts. Processes are provided for manufacture and pharmaceutical preparations which contain these compounds. Intermediates from the manufacture of these compounds are described, as is the use of the compounds in the control of illnesses and for the manufacture of the aforementioned preparations.

30 Claims, No Drawings

CEPHALOSPORIN DERIVATIVES

FIELD OF THE INVENTION

The invention is directed to cephalosporin derivatives, a process for their manufacture, and to medicaments containing the cephalosporin derivatives.

SUMMARY OF THE INVENTION

The invention is concerned with novel cephalosporin derivatives of the formula

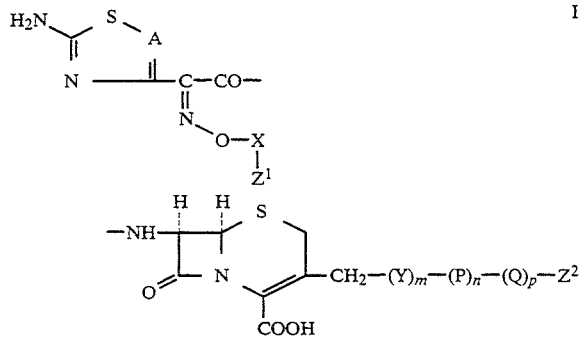

wherein $Z^1$ and $Z^2$ each independently signify a 6-membered aromatic ring which is substituted by two vicinal —$OR^1$ groups, wherein $R^1$ represents hydrogen or lower alkanoyl, wherein $Z^1$ and $Z^2$ each independently can contain 1 or 2 O or N atoms and/or which can be substituted by halogen, carboxy or carboxy-lower alkyl, or —X—$Z^1$ and —$(Q)_p$—$Z^2$ each independently signify a group —$X^1$—$CONR^2OH$ or —$(Q^1)_p$—$CONR^2OH$, wherein $R^2$ represents hydrogen, lower alkyl or phenyl; and wherein further A represents a nitrogen atom or a methine group (—CH=), X represents lower alkylene, phenylene or lower alkylene-phenylene, which is optionally substituted by carboxy and optionally linked via one of the groups —S—, —SO—, —$SO_2$—, —CO—, —OCO—, —NHCO—, —$NHSO_2$— and —CONHNHCO—, $X^1$ represents lower alkylene, phenylene or lower alkylene-phenylene, Y represents one of the groups —O—, —OCO—, —$OCH_2$—, —S—, —SCO—, —SO— and —$SO_2$—, P represents a 5- or 6-membered N-monoheterocycle, which is optionally substituted by lower alkyl, phenyl, hydroxy or oxo, or an 8- to 10-membered N-biheterocycle, which is optionally substituted by lower alkyl, carboxy, lower alkoxycarbonyl, carbamoyl, hydroxymethyl or lower alkanoyloxymethyl, Q represents lower alkylene, phenylene or lower alkylene-phenylene, which is optionally linked via one of the groups —CO—, —OCO—, —$SO_2$—, —NHCO— and —$NHSO_2$—, or Q represents one of the groups —S—, —SO—, —$SO_2$—, —CO—, —OCO—, —NHCO—, —$NHSO_2$— and —CONHNHCO—, $Q^1$ represents lower alkylene, phenylene or lower alkylene-phenylene and m, n and p each represent the number 0 or 1;
as well as readily hydrolyzable esters and pharmaceutically compatible salts of these compounds and hydrates of compounds of formula I and of their esters and salts.

The compounds of the invention have valuable antibiotic properties. They can be used in the control or prevention of infectious diseases.

It is an object of the present invention, to have the above compounds of formula I, their readily hydrolyzable esters and pharmaceutically compatible salts as well as the hydrates of these substances per se as therapeutically active substances. The invention is further directed to a process for the manufacture of the compounds of formula I.

DETAILED DESCRIPTION OF THE INVENTION

The invention is directed to a cephalosporin derivative of the formula

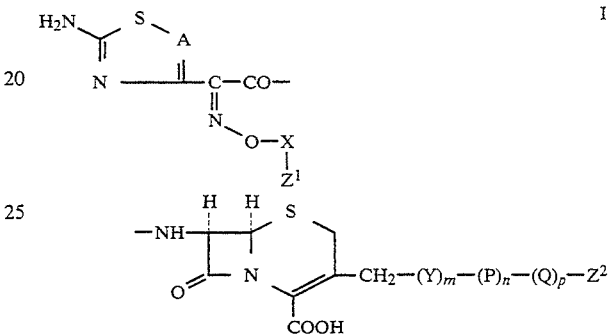

wherein $Z^1$ and $Z^2$ each independently is a 6-membered aromatic ring which is substituted by two vicinal —$OR^1$ groups, wherein $R^1$ represents hydrogen or lower alkanoyl, which each of $Z^1$ and $Z^2$ independently can contain 1 or 2 O or N atoms, and/or which can be substituted by halogen, carboxy or carboxy-lower alkyl; or the groups —X—$Z^1$ and —$(Q)_p$—$Z^2$ each independently is a group —$X^1$—$CONR^2OH$ or —$(Q^1)_p$—$CONR^2OH$, wherein $R^2$ is hydrogen, lower alkyl or phenyl; and wherein A is a nitrogen atom or —CH=, X is lower alkylene, phenylene or lower alkylene-phenylene, which is optionally substituted by carboxy and optionally linked via one of the groups —S—, —SO—, —$SO_2$—, —CO—, —OCO—, —NHCO—, —$NHSO_2$— and —CONHNHCO—; $X^1$ is lower alkylene, phenylene or lower alkylene-phenylene; Y is one of the groups —O—, —OCO—, —$OCH_2$—, —S—, —SCO—, —SO— and —$SO_2$—, P is a 5- or 6-membered N-monoheterocycle, which is optionally substituted by lower alkyl, phenyl, hydroxy or oxo, or P is an 8- to 10-membered N-biheterocycle, which is optionally substituted by lower alkyl, carboxy, lower alkoxycarbonyl, carbamoyl, hydroxymethyl or lower alkanoyloxymethyl; Q is lower alkylene, phenylene or lower alkylene-phenylene, which Q is optionally linked via one of the groups —CO—, —OCO—, —$SO_2$—, —NHCO— and —$NHSO_2$—, or Q is one of the groups —S—, —SO—, —$SO_2$—, —CO—, —OCO—, —NHCO—, —$NHSO_2$— and —CONHNHCO—, $Q^1$ is lower alkylene, phenylene or lower alkylene-phenylene and m, n and p each is the number 0 or 1;
and the readily hydrolyzable esters and pharmaceutically compatible salts of these compounds and hydrates of compounds of formula I and of their esters and salts.

The compounds of formula I preferably exists in the syn-isomeric form presented in the above formula. They can, however, also exists as mixtures with the corresponding anti-isomeric form in which the syn-isomeric form predominates.

The term "lower" denotes residues and compounds with a maximum of 7, preferably a maximum of 4, carbon atoms. The term "alkyl" denotes straight-chain or branched, saturated hydrogen residues such as methyl, ethyl, propyl, isopropyl and t-butyl, etc. The term "alkylene" denotes corresponding hydrocarbon residues which, however, have two free valences, such as methylene, ethylene, ethylidene, 1,3-propylene, 1,4-butylene, butylidene, isopropylidene and 1,2-isobutylene, etc. In "phenylene" the two free valences are preferably situated in the 1,4-position (1,4-phenylene). Also, "lower alkylene-phenylene" denotes groups with two free valencies, e.g. 1,4-phenylene-methylene, 1,4-phenylene-1,3-propylene and 1,4-phenylene-dimethylene. The term "alkoxy" alone or in combination, such as "alkoxycarbonyl", denotes alkyl groups linked via an oxygen atom, such as, for example, methoxy and ethoxy. The term "alkanoyl" alone or in combination, such as "alkanoyloxy" denotes residues derived from straight-chain or branched, saturated fatty acids, such as, for example, formyl and acetyl.

The term "halogen" denotes the four forms chlorine, fluorine, bromine and iodine, with chlorine being preferred.

The term "6-membered aromatic ring which is substituted by two vicinal —OR$^1$ groups" preferably signifies a dihydroxyphenyl group such as 2,3-dihydroxyphenyl or, especially, 3,4-dihydroxyphenyl. The hydroxy groups can be substituted by lower alkanoyl, e.g. 3,4-diacetoxyphenyl. The phenyl nucleus can be substituted as indicated above, e.g. by halogen, as, for example, in 2-fluoro-3,4-dihydroxyphenyl, 3-chloro-4,5-dihydroxyphenyl, 2,5-dichloro-3,4-dihydroxyphenyl and 5-bromo-2-chloro-3,4-dihydroxyphenyl. The aromatic ring can additionally contain a further 1 or 2 O or N atoms, whereby resulting in tautomeric keto forms which are likewise embraced by the present invention, e.g. 1,4-dihydro-5-hydroxy-4-oxo-2-pyrimidyl and 5-hydroxy-4-oxo-4H-pyran-2-yl.

In a preferred embodiment of the invention both of the substituents $Z^1$ and $Z^2$ signify a 6-membered aromatic ring which is substituted by two vicinal —OR$^1$ groups. In accordance with a further preferred embodiment only $Z^2$ represents such a ring, while —X—$Z^1$ represents the hydroxamic acid residue —X$^1$—CONR$^2$OH. In accordance with a further embodiment the substitution is reversed, i.e. $Z^1$ is the aforementioned ring, while —(Q)$_p$—$Z^2$ signifies the hydroxyamic acid residue —(Q$^1$)$_p$—CONR$^2$OH.

The "5- or 6-membered monoheterocycle" used under the symbol P preferably signifies partially saturated or aromatic groups which preferably contain an oxygen or sulphur atom and/or 1-4 nitrogen atoms as the hetero atom(s). In the scope of the invention these groups have two free valences; examples thereof being oxadiazolylene, pyrimidylene and tetrazolylene. The monoheterocycle can also be substituted such as e.g. in 5-(2-phenyl-pyrimidin-4-yl)-ene and 5-(2-methyl-pyrimidin-4-yl)-ene.

A preferred meaning for P is an 8- to 10-membered N-biheterocycle, which is optionally substituted by lower alkyl, carboxy, lower alkoxycarbonyl, carbamoyl, hydroxymethyl or lower alkanoyloxymethyl. This "8- to 10-membered N-biheterocycle" likewise has two free valences and preferably signifies a group of the formula

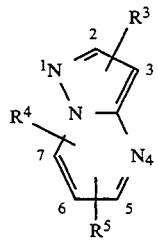 (a)

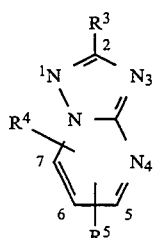 (b)

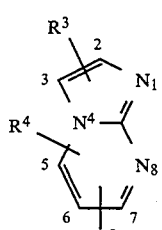 (c)

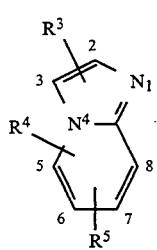 (d)

wherein one of the symbols $R^3$-$R^5$ signifies hydrogen, lower alkyl, carboxy, lower alkoxycarbonyl, carbamoyl, hydroxymethyl or lower alkanoyloxymethyl and the two remaining symbols $R^3$-$R^5$ each represent covalent bonds.

The group (b) with $R^5$=5-methyl and $R^3$ and $R^4$=covalent bonds in the 2- and 7-positions, i.e. 2-(5-methyl-s-triazolo[1,5-a]pyrimidin-7-yl)-ene, is preferred.

The following are preferred substituents in the compounds of formula I and in the corresponding esters, salts and hydrates:

A: methine (—CH=);

$Z^1$: 3,4-dihydroxyphenyl, 2-fluoro-3,4-dihydroxyphenyl, 2,5-dichloro-3,4-dihydroxyphenyl, 5-bromo-2-chloro-3,4-dihydroxyphenyl; 1,4-dihydro-5-hydroxy-4-oxo-2-pyrimidyl, 5-hydroxy-4-oxo-4H-pyran-2-yl;

X: —CH$_2$—, —CH$_2$—SO$_2$—, —CH(COOH)—, —C(CH$_3$)$_2$—;

$Z^2$: 3,4-dihydroxyphenyl, 3-chloro-4,5-dihydroxyphenyl;

(Q)$_p$: —CH$_2$NHSO$_2$—, —CH$_2$—OCO—, —CH$_2$—SO$_2$—, absent (i.e. p=0);

(P)$_n$: 5-(1,3,4-oxadiazol-2-yl)-ene, 5-(pyrimidin-4-yl)-ene, 5-(2-methyl-pyrimidin-4-yl)-ene, 5-(2-phenyl-pyrimidin-4-yl)-ene, 5-(1H)-tetrazol-1-yl)-ene, 5-(2H-tetrazol-2-yl)-ene, 2-(5-methyl-s-triazolo[1,5-a]pyrimidin-7-yl)-ene, 5-(pyrazolo[1,5-a]pyrimidin-7-yl)ene, 5-(2-methyl-s-triazolo[1,5-a]pyrimidin-7-yl)-ene, 2-(5,6-dimethyl-s-triazolo[1,5-a]pyrimidin-7-yl)-ene.

(Y)$_m$: —S—, —SO$_2$—, absent (i.e. m=0);

X—Z$^1$: 1-(hydroxycarbamoyl)-1-methylethyl, 3,4-dihydroxybenzyl, 3,4-dihydroxyphenylsulphonylmethyl, (1,4-dihydro-5-hydroxy-4-oxo-2-pyrimidyl)-methyl, 2-fluoro-3,4-dihydroxy-benzyl, 2,5-dichloro-3,4-dihydroxybenzyl, 5-bromo-2-chloro-3,4-dihydroxybenzyl, (5-hydroxy-4-oxo-4H-pyran-2-yl)-methyl, α-carboxy-3,4-dihydroxybenzyl and, especially, 1-[3-(3,4-dihydroxybenzoyl)carbazoyl]-1-methylethyl;

(Q)$_p$—Z$^2$: (3,4-dihydroxybenzenesulphonamido)-methyl, [(3,4-dihydroxybenzoyl)oxy]methyl, [(3,4-dihydroxyphenyl)sulphonyl]methyl, [(3,4-dihydroxybenzoyl)amino]methyl, 3,4-dihydroxyphenyl (i.e. p=0), 3-chloro-4,5-dihydroxyphenyl (i.e. p=0), hydroxycarbamoyl (i.e. p=0), N-hydroxy-N-methyl-carbamoyl (i.e. p=0), N-methyl-N-hydroxy-carbamoyl (i.e. p=0);

(P)$_n$—(Q)$_p$Z$^2$: 2-[(3,4-dihydroxybenzenesulphonamido)methyl]-5-methyl-s-triazolo[1,5-a]pyrimidin-7-yl, 2-[[(3,4-dihydroxybenzoyl)oxy]methyl]-5-methyl-s-triazolo[1,5-a]pyrimidin-7-yl, 2[[(3,4-dihydroxyphenyl)sulphonyl]methyl]-5-methyl-s-triazolo[1,5-a]pyrimidin-7-yl, 2-[[(3,4-dihydroxybenzoyl)amino]methyl]-5-methyl-s-triazolo[1,5-a]pyrimidin-7-yl, 5-(3,4-dihydroxyphenyl)pyrazolo[1,5-a]pyrimidin-7-yl (i.e. p=0), 5-(3,4-dihydroxyphenyl)-1,3,4-oxadiazol-2-yl (i.e. p=0), 5-(3,4-dihydroxyphenyl)-2-phenyl-pyrimidin-4-yl (i.e. p=0); 5-(3,4-dihydroxypyrimidin-4-yl (i.e. p=0), 5-(3,4-dihydroxyphenyl)-2-methyl-pyrimidin-4-yl (i.e. p=0), 3,4-dihydroxyphenyl (i.e. p=n=0), 2-(hydroxycarbamoyl)-5-methyl-s-triazolo[1,5-a]pyrimidin-7-yl (i.e. p=0), 5-(2-hydroxycarbamoyl)-2-methyl-s-triazolo[1,5-a]pyrimidin-7-yl (i.e. p=0), 5-(3,4-dihydroxyphenyl)-1H-tetrazol-1-yl (i.e. p=0), 5-(3,4-dihydroxyphenyl)-2H-tetrazol-2-yl (i.e. p=0), 5-(3,4-dihydroxybenzoylamino)-1H-tetrazol-1-yl, 5-(3,4-dihydroxybenzoylamino)-2H-tetrazol-2-yl, 2-[3,4-dihydroxyphenyl]-5-methyl-s-triazolo[1,5-a]pyrimidin-7-yl (i.e. p=0), 2-[3-chloro-3,4-dihydroxyphenyl]-5,6-dimethyl-s-triazolo[1,5-a]pyrimidin-7-yl (i.e. p=0), 5-(3,4-dihydroxyphenyl)-pyrazolo[1,5-a]pyrimidin-7-yl (i.e. p=0), 2-(N-hydroxy-N-methylcarbamoyl)-5-methyl-s-triazolo[1,5-a]pyrimidin-7-yl (i.e. p=0), 2-(hydroxycarbamoyl)-5-hydroxymethyl-s-triazolo[1,5-a]pyrimidin-7-yl (i.e. p=0), 5-(hydroxycarbamoyl)-2-methyl-s-triazolo[1,5-a]pyrimidin-7-yl (i.e. p=0), 5-(hydroxycarbamoyl)-2-hydroxymethyl-s-triazolo[1,5-a]pyrimidin-7-yl (i.e. p=0), 5-[(2-hydroxycarbamoyl)ethyl]-2-methyl-s-triazolo[1,5-a]pyrimidin-7-yl;

(Y)$_m$—(P)$_n$—Q$_p$—Z$^2$: [2-[(3,4-dihydroxybenzenesulphonamido)methyl]-5-methyl-s-triazolo[1,5-a]pyrimidin-7-yl]thio, [2-[[(3,4-dihydroxybenzoyl)oxy]methyl]-5-methyl-s-triazolo[1,5-a]pyrimidin-7-yl]thio, [2-[[(3,4-dihydroxyphenyl)sulphonyl]methyl]-5-methyl-s-triazolo[1,5-a]pyrimidin-7-yl]thio, [5-(3,4-dihydroxyphenyl)pyrazolo[1,5-a]pyrimidin-7-yl]thio (i.e. p=0), [5-(3,4-dihydroxyphenyl)-1,3,4-oxadiazol-2-yl]thio (i.e. p=0), [5-(3,4-dihydroxyphenyl)-2-phenyl-pyrimidin-4-yl]thio (i.e. p=0), [5-(3,4-dihydroxyphenyl)-pyrimidin-4-yl]thio (i.e. p=0), [5-(3,4-dihydroxyphenyl)-2-methyl-pyrimidin-4-yl]thio (i.e. p=0), (3,4-dihydroxyphenyl)sulphonyl (i.e. p=n=0), [2-(hydroxycarbamoyl)-5-methyl-s-triazolo[1,5-a]pyrimidin-7-yl]thio (i.e. p=0), [5-(hydroxycarbamoyl)-2-methyl-s-triazolo[1,5a]pyrimidin-7-yl]thio (i.e. p=0), 5-(3,4-dihydroxyphenyl)-1H-tetrazol-1-yl (i.e. p=m=0), 5-(3,4-dihydroxyphenyl)-2H-tetrazol-2-yl (i.e. p=m=0), [5-(3,4-dihydroxybenzoylamino)-1H-tetrazol-1-yl]thio (i.e. m=0), [5-(3,4-dihydroxybenzoylamino)-2H-tetrazol-2-yl]thio (i.e. m=0), [2-[3,4-dihydroxyphenyl]-5-methyl-s-triazolo[1,5-a]pyrimidin-7-yl]thio (i.e. p=0), [2-[3-chloro-3,4-dihydroxyphenyl]-5,6-dimethyl-s-triazolo[1,5-a]pyrimidin-7-yl]thio (i.e. p=0), [5-(3,4-dihydroxyphenyl)pyrazolo[1,5-a]pyrimidin-7-yl]thio (i.e. p=0), [2-(N-hydroxy-N-methylcarbamoyl)-5-methyl-s-triazolo[1,5-a]pyrimidin-7-yl]thio (i.e. p=0), [2-(hydroxycarbamoyl)-5-hydroxymethyl-s-triazolo[1,5-a]pyrimidin-7-yl]thio (i.e. p=0), [5-(hydroxycarbamoyl)-2-methyl-s-triazolo[1,5-a]pyrimidin-7-yl]thio (i.e. p=0), [5-(hydroxycarbamoyl)-2-hydroxymethyl-s-triazolo[1,5-a]pyrimidin-7-yl]thio (i.e. p=0), [5-[(2-hydroxycarbamoyl)ethyl]-2-methyl-s-triazolo[1,5-a]pyrimidin-7-yl]thio.

A group of cephalosporin derivatives in accordance with the invention comprises those of formula I in which X represents lower alkylene, phenylene or lower alkylene-phenylene, which is optionally substituted by carboxy and optionally linked via one of the groups —S—, —SO—, —SO$_2$—, —CO—, —OCO—, —NHCO— and —NHSO$_2$—, as well as the corresponding esters, salts and hydrates. Preferred compounds which fall under this group are:

(6R,7R)-7-[(Z)-2-(2-Amino-4-thiazolyl)-2-[[(3,4-dihydroxybenzyl)oxy]imino]acetamido]-3-[[[2-[(3,4-dihydroxybenzenesulphonamido)methyl]-5-methyl-s-triazolo[1,5-a]pyrimidin-7-yl]thio]methyl]-8-oxo-5-thia-1-azabicyclo[4.2.0]oct-2-ene-2-carboxylic acid, 7-[(Z)-2-(2-amino-4-thiazolyl)-2-[[(2-fluoro-3,4-dihydroxybenzyl)oxy]imino]acetamido]-3-[[[2-[(3,4-dihydroxybenzenesulphonamido)methyl]-5-methyl-s-triazolo[1,5-a]pyrimidin-7-yl]thio]methyl]-8-oxo-5-thia-1-azabicyclo[4.2.0]oct-2-ene-2-carboxylic acid, (6R,7R)-7-[(Z)-2-(2-amino-4-thiazolyl)-2-[[(3,4-dihydroxybenzyl)oxy]imino]acetamido]-3-[[[2-[[(3,4-dihydroxybenzoyl)oxy]methyl]-5-methyl-s-triazolo[1,5-a]pyrimidin-7-yl]thio]methyl]-8-oxo-5-thia-1-azabicyclo[4.2.0]oct-2-ene-2-carboxylic acid, (6R,7R)-7-[(Z)-2-(2-amino-4-thiazolyl)-2-[[[(3,4-dihydroxy-2-fluorobenzyl)oxy]imino]acetamido]-3-[[[-2-[[(3,4-dihydroxybenzoyl)oxy]methyl]-5-methyl-s-triazolo[1,5-a]pyrimidin-7-yl]thio]methyl]-8-oxo-5-thia-1-azabicyclo[4.2.0]oct-2-ene-2-carboxylic acid, (6R,7R)-7-[(Z)-2-(2-amino-4-thiazolyl)-2-[[(3,4-dihydroxybenzyl)oxy]imino]acetamido-3-[[[2-[[(3,4-dihydroxyphenyl)sulphonyl]methyl]-5-methyl-s-triazolo[1,5-a]pyrimidin-7-yl]thio]methyl]-8-oxo-5- thia-1-azabicyclo[4.2.0]oct-2-ene-2-carboxylic acid, (6R,7R)-7-[(Z)-2-(2-amino-4-thiazolyl)-2-[[(2-fluoro-3,4-dihydroxybenzyl)oxy]imino]acetamido]-3-[[[2-[[(3,4-dihydroxyphenyl)sulphonyl]methyl]-5-methyl-s-triazolo[1,5-a]pyrimidin-7-yl]thio]methyl]-8-oxo-5-thia-1-azabicyclo[4.2.0]oct-2-ene-2-carboxylic acid and their pharmaceutically compatible salts.

A further preferred group of cephalosporin derivatives in accordance with the invention comprises those of formula I in which X represents the group -(lower alkylene)-CONHNHCO— as well as the corresponding esters, salts and hydrates. Especially preferred compounds which fall under this group are:

(6R,7R)-7-[(Z)-2-(2-Amino-4-thiazolyl)-2-[[1-[3-(3,4--dihydroxybenzoyl)carbazoyl]-1-methylethoxy-]imino]acetamido]-3-[[[2-[(3,4-dihydroxybenzenesulphonamido)methyl]-5-methyl-s-triazolo[1,5-a]pyrimidin-7-yl]thio]methyl]-8-oxo-5-thia-1-azabicyclo[4.2.0]oct-2-ene-2-carboxylic acid (6R,7R)-7-[(Z)-2-(2-amino-4-thiazolyl)-2-[[1-[3-(3,4-dihydroxybenzoyl)carbazoyl]-1-methylethoxy]iminoacetamido]-3-[[[2-[[(3,4-dihydroxybenzoyl)oxy]methyl]-5-methyl-s-triazolo[1,5-a]pyrimidin-7-yl]thio]methyl]-8-oxo-5-thia-1-azabicyclo[4.2.-0]oct-2-ene-2-carboxylic acid (6R,7R)-7-[(Z)-2-(2-amino-4-thiazolyl)-2-[[1-[3-(3,4-dihydroxybenzoyl)carbazoyl]-1-methylethoxy]imino]acetamido]-3-[[-[2-[[(3,4-dihydroxyphenyl)sulphonyl]methyl]-5-methyl-s-triazolo-[1,5-a]pyrimidin-7-yl]thio]methyl]-8-oxo-5-thiaazabicyclo[4.2.0]oct-2-ene-2-carboxylic acid (6R,7R)-7-[(Z)-2-(2-amino-4-thiazolyl)-2-[[1-[3-(3,-4-dihydroxybenzoyl)carbazoyl]-1-methylethoxy]imino]acetamido]-3-[[[2-[[(3,4-dihydroxybenzoyl)amino]methyl]-5-methyl-s-triazolo[1,5-a]pyrimidin-7-yl]thio]methyl]-8-oxo-5-thia-azabicyclo[4.2.0]oct-2-ene-2-carboxylic acid and their pharmaceutically compatible salts.

Further products in accordance with the invention will be evident from the Examples hereinafter.

The compounds of formula I form pharmaceutically acceptable salts with bases. Examples of salts of compounds of formula I are alkali metal salts, for example the sodium and potassium salts, ammonium salts, salts with organic bases, for example with amines such as diisopropylamine, benzylamine, dibenzylamine, triethanolamine, triethylamine, N,N-dibenzylethylenediamine, N-methylmorpholine, pyridine, piperazine, N-ethylpiperidine, N-methyl-D-glucamine and procaine, or with amino acids such as arginine and lysine. Mono-, di-, trisalts etc. can result depending on the number of acidic groups in the compound of formula I.

The compounds of formula I also form acid addition salts with organic and inorganic acids. Examples of acid addition salts of compounds of formula I are salts with mineral acids, for example hydrohalic acids such as hydrochloric acid, hydrogen bromide and hydrogen iodide, sulphuric acid, nitric acid, phosphoric acid and the like, salts with organic sulphonic acids, for example with alkylsulphonic acid and arylsulphonic acids such as ethanesulphonic acid, p-toluenesulphonic acid, benzenesulphonic acid and the like, as well as salts with organic carboxylic acids, for example with acetic acid, tartaric acid, maleic acid, citric acid, benzoic acid, salicylic acid, ascorbic acid and the like.

The readily hydrolyzable esters of compounds of formula I are preferably esters which can be hydrolyzed under mild conditions, especially those which can be hydrolyzed under physiological conditions, for example enzymatically. Examples of such esters, which can be of the conventional type, are the 1-(lower alkanoyloxy)-lower alkyl esters, e.g. the acetoxymethyl, pivaloyloxymethyl, 1-acetoxyethyl and the 1-pivaloyloxyethyl ester, the 1-(lower alkoxycarbonyloxy)-lower alkyl esters, e.g. the (methoxycarbonyloxy)methyl, 1-(ethoxycarbonyloxy)ethyl and the 1-(isopropoxycarbonyloxy)ethyl ester, the lactonyl esters, e.g. the phthalidyl and the thiophthalidyl ester, the 1-(lower alkoxy)-lower alkyl esters, e.g. the methoxymethyl ester, the 1-(lower alkanoylamino)-lower alkyl esters, e.g. the acetamidomethyl ester, the benzyl ester, the cyanomethyl ester and the (2-oxo-1,3-dioxol-4-yl)methyl ester.

Any carboxy groups additionally present in a compound of formula I can likewise be present in the form of readily hydrolyzable ester groups.

The products in accordance with the invention, i.e. the compounds of formula I above, their readily hydrolyzable esters and pharmaceutically compatible salts as well as the hydrates of these compounds, esters and salts, can be manufactured in accordance with the invention by a) acylating a compound of the formula $$H_2N-\overset{H}{\underset{O}{\subset}}\overset{H}{\underset{N}{\subset}}\overset{S}{\underset{COOH}{\subset}}CH_2-(Y)_m-(P)_n-(Q)_p-Z^2 \quad \text{II}$$

wherein Y, P, Q, $Z^2$, m, n and p have the significances given above, or a readily hydrolyzable ester thereof or an acid addition salt of one of these compounds with a carboxylic acid of the formula $$H_2N\underset{N}{\overset{S}{\diagdown}}\overset{A}{\underset{N}{\diagup}}C-COOH \quad \text{III}$$
$$\underset{\underset{Z^1}{|}}{\overset{N}{\diagdown}}O-X$$

wherein A, X and $Z^1$ have the significances given above, or with a reactive derivative of this compound, or wherein A, X and $Z^1$ have the significances given above,

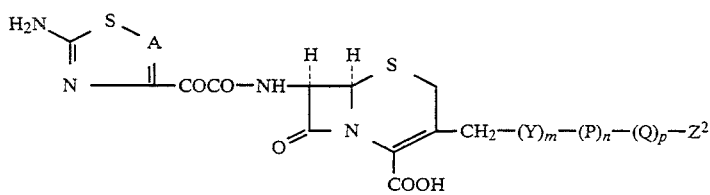

wherein A, Y, P, Q, $Z^2$, m, n and p have the significances given above, or a readily hydrolyzable ester thereof with a compound of the general formula $$H_2N-O-X-Z^1 \qquad V$$

wherein X and $Z^1$ have the significances given above, or with an acid addition salt thereof, or c) for the manufacture of a compound of formula I in which m represents 1 and Y represents —S— or of a readily hydrolyzable ester thereof, reacting a compound of the general formula

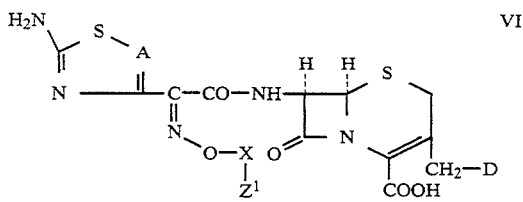

wherein A, X, $Z^1$ have the significances given above and D represents a leaving group, or a readily hydrolyzable ester thereof with a compound of the general formula $$HS-(P)_n-(Q)_p-Z^2 \qquad VII$$

wherein P, Q, $Z^2$, n and p have the significances given above, or d) for the manufacture of a readily hydrolyzable ester of a compound of formula I, subjecting a carboxylic acid of formula I to a corresponding esterification, whereby in process variants a)–d) hydroxy groups present in $Z^1$ and, respectively, $Z^2$ can be protected and the corresponding protecting groups can subsequently cleaved off where required, or e) for the manufacture of salts and hydrates of a compound of formula I and of hydrates of these salts, converting a compound of formula I into a salt or hydrate or into a hydrate of this salt.

In certain of the above processes in accordance with the invention any reactive amino, hydroxyl and/or carboxy groups which may be present must be blocked by protecting groups, whereby these protecting groups are subsequently cleaved off in a manner known per se. These instances will be readily recognizable by a person skilled in the art and also the choice of the respective suitable protecting groups as well as the subsequent cleavage methods will present no problems to the artisan.

Further, it is possible that the products in accordance with the invention occur as mixtures with the isomeric products corresponding to the products in accordance with the invention. Thus, for example, it can be a question of oximes having the [E]-configuration or $\Delta^2$-isomers of the cephalosporin derivatives in accordance with the invention. The separation of these byproducts as well as their possible recycling to products in accordance with the invention can be effected according to methods which are known and which will be familiar to any person skilled in the art. Chromatographic methods and crystallization methods especially come into consideration.

The acylation in accordance with process variant a) of the process in accordance with the invention can be carried out according to methods which are known per se and which will be familiar to any person skilled in the art. For example, the compound of formula II can be acylated with the free carboxylic acid of formula III or a salt thereof with a base, whereby in this case the acylation is carried out in the presence of a suitable condensation agent and the compound of formula II is converted previously into a readily hydrolyzable ester. Suitable condensation agents are, for example, N,N'-disubstituted carbodiimides such as N,N'-dicyclohexylcarbodiimide, which are preferably used together with N-hydroxybenzotriazole or N-hydroxysuccinimide, 2-halopyridinium salts such as 2-chloro-1-methylpyridinium chloride, phosphorus oxychloride, thionyl chloride and oxalyl chloride.

It is, however, also possible to use the carboxylic acid of formula III in the form of a reactive derivative. As reactive derivatives there come into consideration especially acid chlorides, acid anhydrides, mixed anhydrides (for example anhydrides with trifluoroacetic acid, benzenesulphonic acid, mesitylenesulphonic acid, p-toluenesulphonic acid and p-chlorosulphonic acid) and active thiol esters, for example S-(2-benzothiazolyl) thioesters. When this S-(2-benzothiazolyl) thioester is used, the amine of formula II is preferably employed in the form of an acid addition salt, e.g. a toluenesulphonate, methanesulphonate or hydrochloride.

If desired, the acylation can be carried out in the presence of an acid-binding agent, with sodium hydrogen carbonate, potassium carbonate, triethylamine, pyridine or N-methylmorpholine especially coming into consideration as the acid-binding agent. Suitable solvents are, for example, cyclic ethers such as tetrahydrofuran and dioxan, halogenated lower hydrocarbons such as chloroform and methylene chloride, dimethylformamide, dimethylacetamide, acetonitrile, acetone and water as well as mixtures thereof. The reaction temperature can vary in a wide range and as a rule lies between −50° C. and 50° C., preferably between about −10° C. and 30° C.

The oxime formation is accordance with process variant b) of the process in accordance with the invention can also be carried out according to methods which are known per se and which will be familiar to any person skilled in the art. The compound of formula V is preferably used in the form of an acid addition salt, for example as the hydrochloride or as the p-toluenesulphonate. Suitable solvents are, for example, water, lower alcohols such as methanol, cyclic ethers such as tetrahydrofuran and dioxan, acetonitrile, N-methylpyrrolidone, dimethylformamide and dimethylacetamide as well as mixtures thereof. In a preferred embodiment dimethylacetamide is used as the solvent. In a further preferred embodiment the reaction is carried out in the presence of a copper salt, with not only copper(I) salts, but also copper(II) salts coming into consideration. Suitable salts are, for example, the corresponding halides, e.g. chlorides and bromides, sulphates, acetates, nitrates, oxides, carbonates, perchlorates and the tetrafluoroborates. The reaction temperature lies in a range of $-20°$ C. to $40°$ C., preferably of $0°$ C. to $30°$ C.

Compounds of formula I in which n represents 1 and Y represents —S— and the remaining symbols have the above significance can be manufactured in accordance with variant c) of the process in accordance with the invention. This process can also be carried out according to methods which are known per se and which will be familiar to any person skilled in the art. The leaving group denoted by D is preferably a halogen atom, e.g. chlorine, bromine or iodine, a lower alkylsulphonyloxy or arylsulphonyloxy group, such as methanesulphonyloxy or p-toluenesulphonyloxy or a lower alkanoyloxy group, such as acetoxy. The symbol D preferably signifies acetoxy. The reaction can be carried out, for example, in an inert solvent, for example in a halogenated lower hydrocarbon such as methylene chloride and chloroform, in a cyclic ether such as tetrahydrofuran or dioxan, in an open-chain ether such as diethyl ether, in dimethylformamide, dimethylacetamide, dimethyl sulphoxide or in acetone, in the presence of a base such as potassium carbonate or a tertiary amine such as triethylamine. It is, however, also possible to use the mercaptan of formula VII in the form of a salt, whereby especially the lithium, sodium and potassium salts come into consideration for this purpose. The reaction can be carried out in a wide temperature range, but is preferably carried out at room temperature.

For the manufacture of the readily hydrolyzable esters of the carboxylic acids of formula I in accordance with variant d), the carboxylic acid is preferably reacted with the corresponding halide, preferably with the iodide, which contains the ester group. The reaction can be expedited with the aid of a base, e.g. an alkali metal hydroxide, alkali metal hydrogen carbonate or alkali metal carbonate or an organic amine such as triethylamine, 1,8-diazabicyclo[5.4.0]undec-7-ene (DBU) or tetramethylguanidine. This reaction is preferably carried out in an inert organic solvent such as dimethylacetamide, hexamethylphosphoric acid triamide, dimethyl sulphoxide or, preferably, dimethylformamide. The temperature preferably lies in the range of about $0°$ to $40°$ C.

Where an end product of formula I in which $Z^1$ and $Z^2$ contain two vicinal hydroxy groups is to be manufactured in accordance with process variants a)–d), these hydroxy groups can be protected in the corresponding starting compounds of formula I–VII; the hydroxy groups are liberated after the reaction has been effected. In process variants a), b) and c) preferably only the hydroxy groups present in $Z^1$ are protected (the protection is not necessary in $Z^2$), whereas in process variant d) preferably the hydroxy groups not only in $Z^1$, but also in $Z^2$ are protected.

The hydroxy protecting groups are preferably introduced at a pre-product stage (see the working Examples hereinafter). Preferably, protection is by diphenylmethyl (for example a 3,4-dihydroxyphenyl group is then converted into the 2,2-diphenyl-1,3-benzodioxol-5-yl group) by heating with diphenyldichloromethane. The cleavage of the diphenylmethyl group is preferably effected by the action of an acidic agent in a trace of water, e.g. by concentrated hydrochloric acid or, especially, by trifluoroacetic acid with a trace of water. The suitable reaction temperature is $0°$ C. to about room temperature.

The hydroxy groups can also be protected by lower alkanoyl groups, e.g. acetyl. Introduction is e.g. by treatment with a lower alkanoyl halide or anhydride, e.g. the chloride, in the presence of a base such as sodium hydroxide, DBU or diisopropylethylamine. The cleavage is effected under mild alkaline conditions (pH about 7–8), e.g. with sodium hydroxide or sodium carbonate, at about $0°$ to $50°$ C.

A further possibility of protecting the hydroxy groups lies in the use of silyl groups, e.g. trimethylsilyl, t-butyldimethylsilyl. These are advantageously introduced by treatment with the corresponding silyl chloride. The cleavage can be effected by the action of a fluoride, preferably tetrabutylammonium fluoride, in an organic solvent, e.g. acetonitrile, at about $0°$ C. to $50°$ C.

The manufacture of the salts and hydrates of the compounds of formula I and, respectively, of the hydrates of these salts in accordance with variant e) can be effected in a manner known per se, e.g. by reacting the carboxylic acid of formula I or salt thereof with an equivalent amount of the desired base, conveniently in a solvent such as water or in an organic solvent such as ethanol, methanol, acetone or the like. Correspondingly, salt formation is achieved by the addition of an organic or inorganic acid. The temperature of the salt formation is not critical. In general, it lies at room temperature, but can also be slightly thereover or thereunder, for example in the range of $0°$ C. to $+50°$ C.

The manufacture of the hydrates is effected for the most part automatically in the course of the manufacturing process or as a consequence of hygroscopic properties of an initially anhydrous product. For the planned manufacture of a hydrate, a wholly or partially anhydrous product (carboxylic acid of formula I or ester or salt thereof) can be exposed to a moist atmosphere, e.g. at about $+10°$ C. to $+40°$ C.

The various compounds which are used as starting materials are known or can be prepared according to methods known per se and starting from known starting materials. The following Examples contain detailed information concerning the preparation of these starting materials.

As already mentioned, the products in accordance with the invention posses valuable pharmacological, especially antibiotic, properties. They have a broad spectrum of activity against gram-positive and gram-negative microorganisms. In order to show this, the following demonstration of activity was carried out:

1. Minimum Inhibitory Concentration in vitro

In order to demonstrate the antimicrobial activity of the products in accordance with the invention, various compounds manufactured in accordance with the working Examples hereinafter where tested for their activity in vitro using the agar dilution method. The activities ascertained, minimum inhibitory concentration (MIC) in µg/ml, are compiled in Table 1 hereinafter:

TABLE 1

| | Activities in vitro (MIC μg/ml) | | | | | | |
|---|---|---|---|---|---|---|---|
| End product From Ex. No. | S. aureus 6538 | S. pyogenes 15 | S. pneumoniae BA | E. coli 25922 | K. pneumoniae 418 | K. oxytoca 1082 | S. marcescens 69438 |
| 1 | 16 | 4 | . | 0.25 | 0.12 | 0.5 | 0.25 |
| 2 | 32 | 2 | . | <0.1 | <0.25 | 4 | <0.25 |
| 3 | 32 | 4 | 2 | <0.1 | <0.1 | 0.25 | 0.12 |
| 4 | 4 | 0.25 | . | <0.1 | <0.1 | 16 | 0.12 |
| 5 | 4 | 0.5 | . | <0.1 | <0.1 | 0.25 | <0.1 |
| 6 | 16 | 2 | . | <0.1 | <0.1 | 0.12 | 0.12 |
| 7 | 32 | 4 | 2 | <0.1 | <0.1 | <0.1 | 0.12 |
| 8 | 4 | 1 | . | <0.1 | <0.1 | <0.1 | 0.12 |
| 9 | 8 | 1 | . | <0.1 | <0.1 | <0.1 | <0.1 |
| 10 | 32 | 4 | . | <0.1 | <0.1 | 4 | 0.12 |
| 11 | 8 | 2 | . | <0.1 | <0.1 | <0.1 | 0.25 |
| 12 | 16 | 2 | . | <0.1 | <0.1 | 0.5 | <0.1 |
| 13 | 16 | 1 | . | 0.06 | 0.06 | 0.06 | 0.12 |
| 14 | 16 | 0.5 | 0.5 | 0.12 | 0.06 | 0.12 | 0.25 |
| 15 | 32 | 0.12 | . | <0.1 | <0.1 | 0.5 | 1 |
| 16 | 32 | 0.25 | . | <0.1 | <0.1 | 0.25 | 1 |
| 17 | >32 | 0.12 | . | <0.1 | 0.25 | 2 | 0.5 |
| 18 | >32 | 1 | . | 0.12 | 0.12 | 0.25 | 1 |
| 19a | 16 | 0.5 | . | <0.1 | <0.1 | 1 | 0.12 |
| 19b | 16 | 0.25 | . | <0.1 | <0.1 | 0.5 | <0.1 |
| 21 | >32 | 16 | 8 | 1 | 0.5 | 1 | 1 |
| 22 | >32 | 16 | 16 | 8 | 0.5 | 0.5 | 16 |
| 23 | 16 | 4 | 4 | 0.25 | 0.12 | 16 | 2 |

| End product From Ex. No. | E. cloacae 908SSi | E. cloacae 908R | E. cloacae P99 | E. aerogenes CF153 | C. freundii 902 | P. mirabilis 2117 |
|---|---|---|---|---|---|---|
| 1 | 4 | 16 | 32 | . | 1 | 0.12 |
| 2 | 4 | 1 | 16 | 0.5 | <0.1 | 0.25 |
| 3 | 8 | 1 | 0.5 | . | 0.12 | <0.1 |
| 4 | 4 | 1 | 32 | . | <0.1 | 0.25 |
| 5 | 1 | 0.25 | 4 | . | <0.1 | 0.25 |
| 6 | 4 | 0.12 | 4 | <0.1 | <0.1 | 0.25 |
| 7 | 4 | 2 | 1 | . | 0.12 | 0.12 |
| 8 | 2 | 0.25 | 8 | . | <0.1 | <0.1 |
| 9 | 4 | 0.12 | 8 | <0.1 | <0.1 | <0.1 |
| 10 | 8 | 2 | 16 | . | 0.12 | <0.1 |
| 11 | 4 | 2 | 16 | 1 | 0.12 | 0.12 |
| 12 | 4 | 2 | 8 | 4 | <0.1 | 0.12 |
| 13 | 4 | 1 | 8 | . | 0.25 | 0.06 |
| 14 | 1 | 2 | 16 | . | 1 | 0.5 |
| 15 | 16 | 2 | 16 | 0.12 | 0.25 | 0.12 |
| 16 | 8 | 0.25 | 8 | 0.12 | 0.12 | 0.25 |
| 17 | 8 | 1 | 16 | 0.25 | 0.5 | 0.5 |
| 18 | 8 | 2 | 16 | 0.12 | 0.12 | <0.1 |
| 19a | 2 | 16 | 16 | 0.12 | 0.25 | 0.25 |
| 19b | 2 | 2 | 8 | <0.1 | <0.1 | 0.25 |
| 21 | 8 | 8 | 16 | . | 4 | 1 |
| 22 | 16 | 32 | 32 | . | 16 | 16 |
| 23 | 16 | >32 | >32 | . | 4 | 1 |

| End product From Ex. No. | P. vulgaris 1028 | P. aeruginosa BA | P. aeruginosa 799/WT | P. aeruginasa 799/61 | P. aeruginosa MK1184 | P. aeruginosa 27853 |
|---|---|---|---|---|---|---|
| 1 | 0.5 | 0.5 | 0.5 | 0.25 | 4 | 4 |
| 2 | 0.5 | <0.1 | 0.12 | <0.1 | 0.25 | <0.1 |
| 3 | <0.1 | <0.1 | 0.12 | <0.1 | <0.1 | 0.25 |
| 4 | 1 | <0.1 | 0.25 | 0.12 | 0.25 | 0.5 |
| 5 | 0.5 | 0.12 | <0.1 | <0.1 | <0.1 | 0.12 |
| 6 | <0.1 | <0.1 | <0.1 | <0.1 | <0.1 | <0.1 |
| 7 | 0.12 | 0.12 | 0.5 | 0.25 | <0.1 | 1 |
| 8 | <0.1 | <0.1 | <0.1 | <0.1 | <0.1 | 0.12 |
| 9 | <0.1 | <0.1 | . | <0.1 | <0.1 | <0.1 |
| 10 | <0.1 | <0.1 | <0.1 | <0.1 | <0.1 | <0.1 |
| 11 | 0.25 | 0.12 | 0.12 | <0.1 | <0.1 | <0.1 |
| 12 | 0.25 | <0.1 | <0.1 | <0.1 | <0.1 | <0.1 |
| 13 | 0.06 | 2 | 1 | 0.06 | 8 | 4 |
| 14 | 0.25 | 4 | 1 | 0.06 | 16 | 4 |
| 15 | 0.5 | 0.5 | 0.5 | <0.1 | 32 | 1 |
| 16 | 0.25 | 4 | 0.5 | <0.1 | >32 | 1 |
| 17 | 0.25 | 2 | 2 | <0.1 | 8 | 1 |
| 18 | 0.12 | 1 | 0.12 | <0.1 | 2 | 2 |
| 19a | 0.12 | 1 | 0.25 | <0.1 | 16 | 2 |
| 19b | <0.1 | 0.5 | 0.25 | <0.1 | 8 | 0.25 |
| 21 | 2 | 8 | 8 | 0.25 | >32 | 8 |
| 22 | 16 | >32 | 16 | 0.25 | >32 | 32 |
| 23 | 2 | 32 | 1 | 0.12 | >32 | 32 |

| End product From Ex. No. | S. aureus 6538 | S. pyogenes 15 | S. pneumoniae BA | E. coli 25922 | K. pneumoniae 418 | K. oxytoca 1082 | S. marcescens 69438 |
|---|---|---|---|---|---|---|---|

TABLE 1-continued

Activities in vitro (MIC μg/ml)

| | | | | | | | |
|---|---|---|---|---|---|---|---|
| 42 | 32 | 8 | 4 | <0.1 | <0.1 | <0.1 | 0.12 |
| 43 | 16 | 8 | 4 | <0.1 | <0.1 | <0.1 | 0.12 |
| 44 | 32 | 8 | 1 | <0.1 | <0.1 | <0.1 | 0.25 |
| 45 | 16 | 1 | 0.25 | 0.06 | 0.06 | 0.06 | 0.06 |
| 46 | >32 | 4 | . | 0.12 | 0.25 | 2 | 4 |
| 47 | 32 | 1 | 1 | 0.12 | <0.1 | 0.25 | 0.25 |
| 61 | 16 | 1 | 4 | <0.1 | <0.1 | <0.1 | <0.1 |

| End product From Ex. No. | E. cloacae 908SSi | E. cloacae 908R | E. cloacae P99 | E. aerogenes CF153 | C. freundii 902 | P. mirabilis 2117 |
|---|---|---|---|---|---|---|
| 42 | 4 | 0.5 | . | . | <0.1 | 0.12 |
| 43 | 2 | 0.12 | 0.12 | . | <0.1 | 0.12 |
| 44 | 8 | 1 | . | . | 0.25 | 0.25 |
| 45 | 2 | >32 | >32 | . | 0.06 | . |
| 46 | 16 | 1 | 16 | 0.25 | 0.5 | 0.25 |
| 47 | 8 | 1 | 16 | . | 0.5 | 0.12 |
| 61 | 1 | 0.5 | 1 | . | <0.1 | <0.1 |

| End product From Ex. No. | P. vulgaris 1028 | P. aeruginosa BA | P. aeruginosa 799/WT | P. aeruginasa 799/61 | P. aeruginosa MK1184 | P. aeruginosa 27853 |
|---|---|---|---|---|---|---|
| 42 | 0.25 | <0.1 | <0.1 | <0.1 | <0.1 | 0.25 |
| 43 | 0.12 | <0.1 | <0.1 | <0.1 | <0.1 | 0.25 |
| 44 | 0.25 | <0.1 | 0.12 | <0.1 | 0.12 | 0.5 |
| 45 | . | . | 0.06 | 0.06 | 0.64 | 1 | 0.12 |
| 46 | 0.5 | 0.5 | 0.25 | <0.1 | 2 | 0.25 |
| 47 | 0.25 | 4 | 4 | 0.25 | >32 | 4 |
| 61 | <0.1 | <0.1 | <0.1 | <0.1 | <0.1 | <0.1 |

2. Experimental systemic septicaemia in the mouse

An experimental systemic septicaemia was produced in albino mice weighing 16–20 g by intraperitoneally injecting into the experimental animals a sample of a dilute culture of the test organism which had been grown overnight. The sample administered is calculated such that the dosage administered is about 5–100 times greater than the dosage which is required to kill 50% of untreated experimental animals within 48 hours. The bacteria were injected as a suspension in the culture broth. Groups of 5 experimental animals each were used not only for the control, but also for the treatment for each dosage tested. The products in accordance with the invention were administered subcutaneously as a suspension in Tween 80 (2%), whereby the concentrations were chosen such that each experimental animal received 500 μl per administration. The respective concentrations were administered twice, namely 1 and 3 hours after the infection (in the case of P. aeruginosa three times, namely 1, 3 and 5 hours after the infection). The $ED_{50}$ is that dosage which protects 50% of the experimental animals and was calculated by means of the Probit method on the basis of the survial rate after 4 days following the infection. The $ED_{50}$ values in mg/kg s.c. (subcutaneous) for representatives of the class of substance in accordance with the invention are given in Table 2 hereinafter.

TABLE 2

Activities in mg/kg s.c. in the case of experimental systemic septicaemia in the mouse

| End product from Ex. No. | S. aureus Schoch | E. coli 25922 | Pseudomonas aeruginosa BA |
|---|---|---|---|
| 2 | . | 0.3 | . |
| 3 | . | 0.1 | 0.04 |
| 4 | 3.1 | <0.1 | 0.12 |
| 5 | 3.1 | <0.1 | 0.034 |
| 6 | . | <0.2 | 0.3 |
| 7 | . | <0.3 | 0.08 |
| 8 | 2 | <0.1 | 0.45 |
| 9 | . | <0.05 | 0.24 |
| 10 | . | <0.1 | 0.15 |
| 11 | 3.5 | <0.05 | 0.035 |
| 12 | 6.2 | <0.05 | 0.028 |
| 13 | . | . | 4 |
| 14 | >12 | 4.4 | 7.1 |
| 15 | . | 0.9 | >2 |
| 16 | . | <0.5 | >2 |
| 19b | . | 0.78 | >3 |
| 21 | . | <0.3 | 0.39 |
| 22 | . | <0.05 | 1.8 |
| 42 | 10 | 0.005 | 0.017 |
| 43 | 12 | 0.05 | 0.019 |
| 44 | >12 | <0.05 | <0.01 |
| 45 | . | 0.13 | 2.1 |
| 46 | . | <0..5 | |
| 47 | . | <0.1 | 0.1 |
| 61 | 8.4 | <0.1 | 0.06 |

The products in accordance with the invention can be used as medicaments, e.g. in the form of pharmaceutical preparations for enteral or parenteral administration. The products in accordance with the invention can be administered, for example, perorally, e.g. in the form of tablets, coated tablets, dragées, hard and soft gelatine capsules, solutions, emulsions or suspensions, rectally, e.g. in the form of suppositories, or parenterally, e.g. in the form of injection solutions.

The manufacture of the pharmaceutical preparations can be effected in a manner familiar to any person skilled in the art by bringing the substances in accordance with the invention, optionally in combination with other therapeutically valuable substances, into a galenical administration form together with suitable, non-toxic, inert, therapeutically compatible solid or liquid carrier materials and, if desired, the usual pharmaceutical adjuvants.

Suitable carrier materials are inorganic carrier materials as well as organic carrier materials. Thus, lactose, corn starch or derivatives thereof, talc, stearic acid or its salts can be used, for example, as carrier materials for tablets, coated tablets, dragées and hard gelatine capsules. Suitable carriers for soft gelatine capsules are, for example vegetable oils, waxes, fats and semi-solid and liquid polyols (depending on the nature of the active ingredient no carriers are, however, required in the case of soft gelatine capsules). Suitable carrier materials for the manufacture of solutions and syrups are, for example, water, polyols, saccharose, invert sugar and glucose. Suitable carrier materials for injection solutions are, for example, water, alcohols, polyols, glycerine and vegetable oils. Suitable carrier materials for suppositories are, for example, natural or hardened oils, waxes, fats and semi-liquid or liquid polyols.

As pharmaceutical adjuvants there come into consideration the usual preservatives, solibilizers, stabilizers, wetting agents, emulsifiers, sweeteners, colorants, flavorants, salts for varying the osmotic pressure, buffers, coating agents and antioxidants.

The compounds of formula I and their salts and hydrates come into consideration especially for parenteral administration and for this purpose are preferably provided as lyophilizates or dry powders for dilution with usual carriers such as water or isotonic saline. The readily hydrolyzable esters of compounds of formula I and their salts and hydrates come into consideration especially for enteral administration.

The pharmaceutical preparations can contain the substances in accordance with the invention in amounts of about 25–2000 mg, preferably 100–1000 mg, per unit dosage form. For the prophylaxis and therapy of infectious diseases a daily dosage of about 0.05 g to about 4 g, especially about 0.1 g to about 2 g, comes into consideration for adults.

The following Examples are intended to illustrate the present invention in more detail, but are not intended to limit its scope in any manner. Unless indicated otherwise, the Examples were carried out as written.

EXAMPLE 1

Manufacture of (6R,7R)-7-[(Z)-2-(2-amino-4-thiazolyl)-2-[[(1-hydroxycarbamoyl)-1-methylethoxy]imino]acetamido]-3-[[[2-[(3,4-dihydroxybenzenesulphonamido)-methyl]-5-methyl-s-triazolo[1.5-a]pyrimidin-7-yl]thio]-methyl]-8-oxo-5-thia-1-azabicyclo[4.2.0]oct-2-ene-2-carboxylic acid (6R,7R)-7-(2-Amino-4-thiazoleglyoxylamido)-3-[[[2-[(3,4-dihydroxybenzenesulphonamido)methyl]-5-methyl-s-triazolo[1,5-a]pyrimidin-7-yl]thio]methyl]-8-oxo-5-thia-1-azabicyclo[4.2.0]oct-2-ene-2-carboxylic acid (0.05 g) and 0.02 g of 2-(aminooxy)-N-hydroxy-2-methylpropionamide hydrochloride are stirred in 0.5 ml of dimethylacetamide for 16 hours at room temperature. The dimethylacetamide is evaporated in a high vacuum, the residue is digested with water and the precipitate formed is filtered off and dried. There is obtained 0.015 g of (6R,7R)-7-[(Z)-2-(2-amino-4-thiazolyl)-2-[(1-hydroxycarbamoyl)-1-methylethoxy)imino]acetamido]-3-[-[[2-[(3,4-dihydroxybenzenesulphonamido)methyl]-5-methyl-s-triazolo[1.5-a]pyrimidin-7-yl]thio]methyl]-8-oxo-5-thia-1-azabicyclo[4.2.0]oct-2-ene-2-carboxylic acid as a pale beige powder.

$^1$H-NMR (DMSO-d$_6$, 250 MHz): signals at, inter alia, δ (ppm) 1.40 (s, 3H), 1.42 (s, 3H), 2.57 (s, 3H), 3.62 (d, J=18 Hz, 1H), 3.85 (d, J=18 Hz, 1H), 4.13 (d, J=6 Hz, 2H), 4.33 (d, J=12,5 Hz, 1H), 4.50 (d, J=12.5 Hz, 1H), 5.26 (d, J=5 Hz, 1H), 5.90 (d,d J=5 Hz, J=8 Hz, 1H), 6.76 (d, J=8,5 Hz, 1H), 6.80 (s, 1H), 7.06 (d,d J=2,5 Hz, J=8,5 Hz, 1H), 7.15 (d, J=2,5 Hz, 1H), 7.25 (s, 1H), 7.37 (s, 2H), 8.05 (t, J=6 Hz, 1H). IR (KBr) 1775 cm$^{-1}$ MS 849.9 (M+H$^\oplus$)

The 2-(aminooxy)-N-hydroxy-2-methylpropionamide hydrochloride used as the starting material can be prepared as follows:

Hydroxylamine hydrochloride (0.35 g), 0.7 ml of triethylamine and 2.03 g of bis(trimethylsilyl)-acetamide are stirred in 20 ml of dichloromethane for 2 hours and then 2 g of 2-methyl-2-(phthalimidooxy)propionic acid 2-benzothiazole thioester (known from EPOS 286,145) are added thereto. The mixture is stirred for a further 3 hours and thereafter the solvent is evaporated, 25 ml of ethanol are added and the mixture is again evaporated. Thereafter, the residue is dissolved in 50 ml of ethyl acetate and 50 ml of water, the organic phase is separated, washed with water and evaporated. After recrystallization from 25 ml of ethyl acetate there is obtained 1 g of N-hydroxy-2-methyl-2-(phthalimidooxy)-2-methylpropionamide of m.p. 184°–187° C. (dec.).

N-Hydroxy-2-methyl-2-(phthalimidooxy)-2-methylpropionamide (15.8 g) are brought into solution in 150 ml of ethanol and 110 ml of dimethylacetamide. After the addition of 3 g of hydrazine hydrate the mixture is stirred at 0° C. for 1 hour, the precipitate is filtered off and the filtrate is evaporated in a vacuum. The residue is triturated in 150 ml of water and 50 ml of 1N aqueous hydrochloric acid. After repeated filtration the filtrate is evaporated and the residue is crystallized from 100 ml of ethanol by the addition of 450 ml of diethyl ether. There are obtained 7.8 g of crystalline 2-(aminooxy)-N-hydroxy-2-methylpropionamide hydrochloride of m.p. 158°–160° C. (dec.).

The (6R,7R)-7-(2-amino-4-thiazoleglyoxylamido)-3-[[[2-[(3,4-dihydroxybenzenesulphonamido)methyl]-5-methyl-s-triazolo[1,5-a]pyrimidin-7-yl]thio]methyl]-8-oxo-5-thia-1-azabicyclo[4.2.0]oct-2-ene-2-carboxylic acid used as the starting material can be prepared as follows:

2-(Chloromethyl)-5-methyl-s-triazolo[1.5-a]pyrimidin-7-ol (1.0 g) (known from C.A. 104/09-068678) is dissolved in 20 ml of conc. aqueous ammonia and stirred at room temperature overnight. The precipitate formed is filtered off under suction. The mother liquor is concentrated and the residue is taken up in ethanol. The product thereby crystallizes. There is obtained 0.66 g of 2-(aminomethyl)-5-methyl-s-triazolo[1,5-a]pyrimidin-7-ol as a white powder of m.p. 204°–207° C.

2,2-Diphenyl-1,3-benzodioxol-5-sulphinic acid lithium salt (0.35 g) (preparation see Example 21) is converted by the addition of one equivalent of 1N aqueous hydrochloric acid into the free acid. The latter is treated in 5 ml of methylene chloride with 0.140 g of N-chlorosuccinimide and stirred at room temperature for 1 hour. The resulting precipitate is filtered off and the mother liquor is concentrated to dryness. The residue is crystallized from acetonitrile. There is obtained 0.27 g of [3,4-[(diphenylmethylene)dioxy]phenyl]sulphonyl chloride as white crystals of m.p. 109°–110° C.

2-(Aminomethyl)-5-methyl-s-triazolo[1,5-a]pyrimidin-7-ol (0.37 g) is dissolved in 3.0 ml of dimethylformamide, treated with 0.17 ml of N-ethyl-diisopropylamine and 0.18 g of [3,4-[(diphenylmethylene)dioxy]-phenyl]sulphonyl chloride and stirred at room temperature for 4 hours. The dimethylformamide is evaporated in a high vacuum and the residue is partitioned between water and ethyl acetate. The organic phase is washed twice with water and once with saturated aqueous sodium chloride solution, dried with magnesium sulphate and concentrated. The residue is taken up in water. A precipitate results, which is filtered off and dried. There is obtained 0.370 g of N-[[7-hydroxy-5-methyl-s-triazolo[1,5-a]pyridin-2-yl]methyl]-2,2-diphenyl-1,3-benzodioxol-5-sulphonamide as a white powder.

N-[[7-Hydroxy-5-methyl-s-triazolo[1,5-a]pyridin-2-yl]methyl]-2,2-diphenyl-1,3-benzodioxol-5-sulphonamide (0.26 g) is heated under reflux conditions in 5.0 ml of phosphorus oxychloride for 15 minutes. The phosphorus oxychloride is evaporated in a water-jet vacuum and the residue is partitioned between methylene chloride and water. The organic phase is dried with magnesium sulphate and concentrated. The residue is treated with a 5% solution of sodium hydrogen sulphide in dimethylformamide and stirred at room temperature for 2 hours. The dimethylformamide is evaporated and the residue is taken up in water. The pH value is adjusted to 2.0 with 1N aqueous hydrochloric acid. The precipitate formed is filtered off and dried. There is obtained 0.18 g of N-[[7-mercapto-5-methyl-s-triazolo[1,5-a]pyrimidine-2-yl]methyl]-2,2-diphenyl-1,3-benzodioxol-5-sulphonamide as a yellow powder.

N-[[7-Mercapto-5-methyl-s-triazolo[1,5-a]pyrimidin-2-yl]methyl]-2,2-diphenyl-1,3-benzodioxol-5-sulphonamide (0.27 g) and 0.14 g of 7-aminocephalosporanic acid are stirred at room temperature for 4 hours with 3.0 ml of a 20% solution of boron trifluoride in acetonitrile. After the addition of 5 ml of ice-water the reaction mixture is partitioned between water and ethyl acetate. The pH value is adjusted to 7.0 with 3N aqueous sodium hydroxide solution. The phases are separated. The aqueous phase is adjusted to pH 2.0 with concentrated aqueous hydrochloric acid. The precipitate formed is filtered off. The still moist precipitate is dissolved in trifluoroacetic acid and stirred at room temperature for 2 hours. The trifluoroacetic acid is evaporated in a water-jet vacuum and the residue is treated with ethyl acetate. The precipitate is filtered off and dried under a high vacuum. There is obtained 0.2 g of (6R,7R)-7-amino-3-[[[2-[(3,4-dihydroxybenzenesulphonamido)methyl]-5-methyl-s-triazolo[1,5-a]pyrimidin-7-yl]thio]methyl]-8-oxo-5-thia-1-azabicyclo[4.2.0]oct-2-ene-2-carboxylic acid as a pale beige powder.

$^1$H-NMR (D$_2$O, 250 MHz): signals at δ (ppm) 2.60 (s, 3H), 3.50 (d, J=18 Hz, 1H), 3.83 (d, J=18 Hz, 1H), 4.11 (d, J=12.5 Hz, 1H), 4.44 (s, 2H), 4.77 (d, J=5 Hz, 1H), 5.07 (d, J=5 Hz, 1H), 6.46 (d, J=8 Hz, 1H), 6.85 (m, 2H), 7.07 (s, 1H). IR: (KBr) 1781 cm$^{-1}$ MS: 580 (M+H$^⊕$)

(6R,7R)-7-Amino-3-[[[2-[(3,4-dihydroxybenzenesulphonamido)methyl]-5-methyl-s-triazolo[1,5-a]pyrimidin-7-yl]thio]methyl]-8-oxo-5-thia-1-azabicyclo[4.2.0]oct-2-ene-2-carboxylic acid (0.15 g) is suspended in 1 ml of water and 1 ml of acetonitrile and brought into solution by the addition of 0.036 ml of triethylamine. The mixture is cooled to 0° C., treated with 0.20 g of 2-amino-4-thiazolethioglyoxylic acid S-(2-benzothiazolyl) ester and stirred in an ice bath for 1 hour. The reaction mixture is centrifuged at 3000 rpm for 15 minutes and the clear supernatant solution is partitioned between water and ethyl acetate. The aqueous phase is adjusted to pH 2. A yellow precipitate forms and this is filtered off and dried. There is obtained 0.12 g of (6R,7R)-7-(2-amino-4-thiazoleglyoxylamido)-3-[[[2-[(3,4-dihydroxybenzenesulphonamido)methyl]-5-methyl-s-triazolo[1,5-a]pyrimidin-7-yl]thio]methyl]-8-oxo-5-thia-1-azabicyclo[4.2.0]oct-2-ene-2-carboxylic acid as a yellow powder.

$^1$H-NMR (DMSO-d$_6$, 250 MHz): signals at δ (ppm) 2.57 (s, 3H), 3.30 (d, J=18 Hz, 1H), 3.81 (d, J=18 Hz, 1H), 4.10 (d, J=6 Hz, 2H), 4.32 (d, J=12,5 Hz, 1H), 4.50 (d, J=12.5 Hz, 1H), 5.21 (d, J=5 Hz, 1H), 5.76 (d,d, J=5 Hz, J=8 Hz, 1H), 6.77 (d, J=8.5 Hz, 1H), 7.06 (d,d, J=2.5 Hz, J=8.5 Hz, 1H), 7.14 (d, J=2.5 Hz, 1H), 7.26 (s, 1H), 7.41 (s, 2H), 7.82 (s, 1H), 8.03 (t, J=6 Hz, 1H), 9.5 (s, broad 1H), 9.81 (d, J=8 Hz, 1H) to broad 1H, 14.0 (s, broad, 1H). IR: KBr 1769 cm$^{-1}$ MS: 734 (M+H$^⊕$)

EXAMPLE 2

Manufacture of (6R,7R)-7-[(Z)-2-(2-amino-4-thiazolyl)-2-[[(1,4-dihydro-5-hydroxy-4-oxo-2-pyrimidinyl)methoxy]imino]acetamido]-3-[[[2-[(3,4-dihydroxybenzenesulphonamido)methyl]-5-methyl-s-triazolo[1,5-a]pyrimidinyl-7-yl]thio]methyl]-8-oxo-5-thia-1-azabicyclo[4.2.0]oct-2-ene-2-carboxylic acid sodium salt (1:1)

(6R,7R)-7-(2-Amino-4-thiazoleglyoxylamido)-3-[[[2-[(3,4-dihydroxybenzenesulphonamido)methyl]-5-methyl-s-triazolo[1,5-a]pyrimidin-7-yl]thio]methyl]-8-oxo-5-thia-1-azabicyclo[4.2.0]oct-2-ene-2-carboxylic acid (0.37 g), 0.16 g of 2-(aminooxy)methyl-5-hydroxy-4(1H)-pyrimidinone and 0.065 ml of methanesulphonic acid are stirred in 4 ml of dimethylacetamide for 16 hours at room temperature. The dimethylacetamide is evaporated under a high vacuum and the residue is digested with water. The product is filtered off and resuspended in water, brought into solution at pH 7.0 by the addition of 1N aqueous sodium hydroxide solution and chromatographed on RP12-Kieselgel with water-/acetonitrile (RP12-Kieselgel="reversed phase" silica gel, e.g. Optiup C12 ® from the company ANTEC, Bennwil, Switzerland; a silica gel with a particle size 0.040–0.063 mm, treated with dodecyltrichlorosilane). The product fractions are concentrated and lyophilized. There is obtained 0.15 g of (6R,7R)-7-[(Z)-2-(2-amino-4-thiazolyl)-2-[[(1,4-dihydro-5-hydroxy-4-oxo-2-pyrimidinyl)methoxy]imino]acetamido]-3-[[[2-[(3,4-dihydroxybenzenesulphonamido)methyl]-5-methyl-s-triazolo[1,5-a]pyrimidinyl-7-yl]thio]methyl]-8-oxo-5-thia-1-azabicyclo[4.2.0]oct-2-en-2-carboxylic acid sodium salt (1:1) as a pale beige powder.

$^1$H-NMR (DMSO-d$_6$, 250 MHz): signals at, inter alia, δ (ppm) 2.53 (s, 3H), 3.28 (d, J=18 Hz, 1H), 3.57 (d, J=18 Hz, 1H), 4.17 (m, 3H), 4.66 (d J=12,5 Hz, 1H), 4.86 (s, 2H), 5.04 (d, J=5 Hz, 1H), 5.64 (d, J=5 Hz, 1H), 6.66 (d, J=8 Hz, 1H), 6.86 (s, 1H), 6.96 (m, 2H), 7.21 (s, 1H), 7.42 (s, 1H) IR: (KBr) 1764 cm$^{-1}$ MS: 894,8 (M+H$^⊕$)

The 2-(aminooxy)methyl-5-hydroxy-4(1H)-pyrimidinone used as the starting compound can be prepared as follows:

5-(Benzyloxy)-2-(hydroxymethyl)-4(1H)-pyrimidinone (0.696 g) (3 mmol), 0.787 g (3 mmol) of triphenylphosphine and 0.489 g (3 mmol) of N-hydroxyphthalimide are dissolved in 50 ml of dimethylacetamide. A solution of 0.640 g (3.3 mmol) of diethyl azodicarboxylate in 2 ml of dimethylacetamide is added dropwise at 20° C. The mixture is stirred at room temperature for 20 hours, the solvent is evaporated in a high vacuum and the residual yellow oil is crystallized from ethanol/ether. After recrystallization from ethanol there is obtained N-[(5-benzyloxy)-1,4-dihydro-4-oxo-2-pyrimidinyl]methoxy]phthalimide as white crystals of m.p. 157° C.

N-[(5-Benzyloxy)-1,4-dihydro-4-oxo-2-pyrimidinyl]methoxy]phthalimide (0.754 g) (2 mmol) is suspended in 60 ml of methylene chloride. 560 mg (2.2 mmol) of boron tribromide are added at −70° C. The mixture is stirred at −70° C. for 4 hours, left to warm to room temperature and stirred for a further 16 hours. The solvent is evaporated in a vacuum, the residue is treated with 30 ml of water and stirred. The product is filtered off, washed with water and ether and dried in a high vacuum at 35° C. There is obtained 5-hydroxy-2-[(phthalimidooxy)methyl]-4(1H)-pyrimidinone as white crystals of m.p. 174°–175° C.

5-Hydroxy-2-[(phthalimidooxy)methyl]-4(1H)-pyrimidinone (0.875 g) (3 mmol) is suspended in 7 ml of dimethylformamide. 136 mg (3 mmol) of methylhydrazine are added thereto at 10° C. and the mixture is stirred at room temperature for 1 hour. The solution is washed four times with 50 ml of n-pentane, the solid residue is taken up in ether, the product is filtered off and crystallized from ethanol. There is obtained 2-(aminooxy)methyl-5-hydroxy-4(1H)-pyrimidinone of m.p. 163° C. (dec.) as white crystals.

EXAMPLE 3

Manufacture of (6R,7R)-7-[(Z)-2-(2-amino-4-thiazolyl)-2-[[[(3,4-dihydroxyphenyl)sulphonyl]methoxy]imino]acetamido]-3-[[[2-[(3,4-dihydroxybenzenesulphonamido)methyl]-5-methyl-s-triazolo[1,5-a]pyrimidin-7-yl]thio]methyl]-8-oxo-5-thia-1-azabicyclo[4.2.0]oct-2-ene-2-carboxylic acid sodium salt (1:1)

(6R,7R)-7-(2-Amino-4-thiazoleglyoxylamido)-3-[[[2-[(3,4-dihydroxybenzenesulphonamido)methyl]-5-methyl-s-triazolo[1,5-a]pyrimidin-7-yl]thio]methyl]-8-oxo-5-thia-1-azabicyclo[4.2.0]-oct-2-ene-2-carboxylic acid (0.70 g) and 0.32 g of 4-[[(aminooxy)methyl]sulphonyl]pyrocatechol hydrochloride (known from EPOS 303,172) are stirred in 7.0 ml of dimethylacetamide for 2 days at room temperature. The dimethylacetamide is evaporated in a high vacuum and the residue is taken up in water. The resulting precipitate is filtered off, dried, resuspended in water, brought into solution at pH 7.0 by the addition of 1N aqueous sodium hydroxide solution and chromatographed on RP12-Kieselgel with water/acetonitrile. The uniform fractions are concentrated, the product is precipitated by acidification to pH 2.0, filtered off, dried, resuspended in water, brought into solution at pH 7.0 by the addition of 1N aqueous sodium hydroxide solution and lyophilized. There is obtained 0.44 g of (6R,7R)-7-[(Z)-2-(2-amino-4-thiazolyl)-2-[[[(3,4-dihydroxyphenyl)sulphonyl]methoxy]imino]acetamido]-3-[[[2-[(3,4-dihydrooxybenzenesulphonamido)methyl]-5-methyl-s-triazolo[1,5-a]pyrimidin-7-yl]thio]methyl]-8-oxo-5-thia-1-azabicyclo[4.2.0]oct-2-ene-2-carboxylic acid sodium salt (1:1) as a pale beige powder.

$^1$H-NMR (DMSO-d$_6$, 250 MHz): signals at δ (ppm) 2.54 (s, 3H), 3.16 (d, J=18 Hz, 1H), 3.54 (d, J=18 Hz, 1H), 4.14 (d, J=12.5 Hz, 1H), 4.16 (s, 2H), 4.60 (d, J=12.5 Hz, 1H), 4.95 (d, J=5 Hz, 1H), 5.16 (m, 2H), 5.48 (m, 1H), 7 (m, 7H), 7.42 (s, 1H), 9.5 (m, broad, 1H) IR: (KBr) 1765 cm$^{-1}$ MS: 935 (M+H$^\oplus$)

EXAMPLE 4

Manufacture of (6R,7R)-7-[(Z)-2-(2-amino-4-thiazolyl)-2-[[(3,4-dihydroxybenzyl)oxy]imino]acetamido]-3-[[[2-[(3,4-dihydroxybenzenesulphonamido)methyl]-5-methyl-s-triazolo[1,5-a]pyrimidin-7-yl]thio]methyl]-8-oxo-5-thia-1-azabicyclo[4.2.0]oct-2-ene-2carboxylic acid (6R,7R)-7-(2-Amino-4-thiazoleglyoxylamido)-3-[[[2-[(3,4-dihydroxybenzenesulphonamido)methyl]-5-methyl-s-triazolo[1,5-a]pyrimidin-7-yl]thio]methyl]-8-oxo-5-thia-1-azabicyclo[4.2.0]-oct-2-ene-2-carboxylic acid (0.370 g) and 0.18 g of O-[3,4-[(diphenylmethylene)dioxy]benzyl]hydroxylamine hydrochloride are stirred in 4 ml of dimethylacetamide for 16 hours at room temperature. The dimethylacetamide is evaporated in a high vacuum, the residue is digested with water, the precipitate formed is dissolved in water at pH 7.0 by the addition of 1N aqueous sodium hydroxide solution and chromatographed on silica gel with water-/acetonitrile. The product fractions are concentrated and the product is precipitated by acidification to. pH 2.0. The precipitate is filtered off, dissolved while still moist in trifluoroacetic acid and stirred at room temperature for 2 hours. The trifluoroacetic acid is evaporated in a water-jet vacuum and the residue is partitioned between water and ethyl acetate at pH 7.0 (by the addition of 1N aqueous sodium hydroxide solution). The aqueous phase is chromatographed on silica gel with water/acetonitrile. The product fractions are concentrated and precipitated at pH 2.0. The product is filtered off and dried. There is obtained 0.080 g of (6R,7R)-7-[(Z)-2-(2-amino-4-thiazolyl)-2-[[(3,4-dihydroxybenzyl)oxy]imino]acetamido]-3-[[[2-[(3,4-dihydroxybenzenesulphonamido)methyl]-5-ethyl-s-triazolo[1,5-a]pyrimidin-7yl]thio]methyl]-8-oxo-5-thia-1-azabicyclo[4.2.0]oct-2-ene-2-carboxylic acid as a pale beige powder.

$^1$H-NMR (DMSO-d$_6$, 250 MHz): signals at δ (ppm) 2.57 (s, 3H), 3.55 (d, J=18 Hz, 1H), 3.77 (d, J=18 Hz, 1H), 4.10 (d, J=6 Hz, 2H), 4.32 (d, J=12,5 Hz, 1H), 4.47 (d, J=12.5 Hz, 1H), 4.92 (s, 2H), 5.15 (d, J=5 Hz, 1H), 5.79 (d,d, J=5 Hz, J=8 Hz, 1H), 6.7 (m, 6H), 7.1 (m, 2H), 7.25 (s, 1H) overlapping of broad s 7.27, 2H, 8.03 (t, J=6 Hz, 1H), 8.88 (s, broad, 2H), 9.54 (s, broad, 1H), 9.67 (d, J=8 Hz, 1H), 9.80 (s, broad, 1H), 14.0 (s, very broad, 1H) IR: (KBr) 1770 cm$^{-1}$ MS: 870.9 (M+H$^\oplus$)

The O-[3,4-[(diphenylmethylene)dioxy]benzyl]hydroxylamine hydrochloride used as starting material can be prepared as follows:

2,2-Diphenyl-1,3-benzodioxol-5-methanol, 0.40 g of triphenylphosphine (0.30 g) and 0.33 g of N-hydroxyphthalimide are dissolved i 5 ml of methylene chloride and cooled to 0° C. Thereupon, 0.30 ml of diethyl azodicarboxylate dissolved in 2 ml of methylene chloride are added and the mixture is stirred while warming to room temperature for 30 minutes. The reaction mixture is applied to 30 g of silica gel and the product is eluted with methylene chloride. The uniform fractions are concentrated. Thereby, crystallization sets in spontaneously. After drying there is obtained 0.370 g of N-[[3,4-[(diphenylmethylene)dioxy]benzyl]oxy]phthalimide as white crystals of m.p. 155° C.

N-[[3,4-[(Diphenylmethylene)dioxy]benzyl]oxy]phthalimide (0.90 g) is suspended in 10 ml of ethanol, treated with 0.25 ml of N,N-dimethylaminopropylamine and stirred at room temperature for 1 hour. The ethanol is evaporated, the residue is taken up in ethyl acetate and chromatographed on silica gel with ethyl acetate as the eluent. Uniform fractions are concentrated and the residual foam-like resin is crystallized from n-hexane. There is obtained 0.48 g of O-[3,4-[(diphenylmethylene)dioxy]benzyl]hydroxylamine as white crystals of m.p. 159°–163° C. The corresponding hydrochloride of m.p. 154°–157° C. is obtained therefrom with ethanolic hydrochloric acid.

EXAMPLE 5

Manufacture of 7-[(Z)-2-(2-amino-4-thiazolyl)-2-[[(2-fluoro-3,4-dihydroxybenzyl)oxy]imino]acetamido]-3-[[[-2-[(3,4-dihydroxybenzenesulphonamido)methyl]-5-methyl-s-triazolo[1,5-a]pyrimidin-7-yl]thio]methyl]-8-oxo-5-thia-1-azabicyclo[4.2.0]oct-2-ene-2-carboxylic acid sodium salt (1:1)

(6R,7R)-7-(2-Amino-4-thiazoleglyoxylamido)-3-[[[2-[(3,4-dihydroxybenzenesulphonamido)methyl]-5-methyl-s-triazolo[1,5-a]pyrimidin-7-yl]thio]methyl]-8-oxo-5-thia-1-azabicyclo[4.2.0]oct-2-ene-2-carboxylic acid (0.37 g) and 0.24 g of O-[(4-fluoro-2,2-diphenyl-1,3-benzodioxol-5-yl)methyl]hydroxylamine hydrochloride are stirred in 4 ml of dimethylacetamide for 16 hours at room temperature. The dimethylacetamide is evaporated in a high vacuum and the residue is digested with water. The resulting precipitate is filtered off, dissolved while still moist in 5 ml of trifluoroacetic acid and stirred at room temperature for 3 hours. The trifluoroacetic acid is removed in a water-jet vacuum and the residue is digested with ethyl acetate. The precipitate is filtered off, dried, dissolved in water at pH 7.0 by the addition of 1N aqueous sodium hydroxide solution and chromatographed on RP12-Kieselgel with water-/acetonitrile. The product fractions are concentrated and lyophilized. There is obtained 0.14 g of 7-[(Z)-2-(2--amino-4-thiazolyl)-2-[[(2-fluoro-3,4-dihydroxyben zyl)oxy]imino]acetamido]-3-[[[2-[(3,4-dihydroxybenzenesulphonamido)methyl]-5-methyl-s-triazolo[1,5-a]pyrimidin-7-yl]thio]methyl]-8-oxo-5-thia-1-azabicyclo[4.2.0]oct-2-ene-2-carboxylic acid sodium salt (1:1) as a pale beige powder.

$^1$H-NMR (DMSO-$d_6$, 250 MHz): signals at $\delta$ (ppm) 2.54 (s, 3H), 3.30 (d, J=18 Hz, 1H), 3.60 (d, J=18 Hz, 1H), 4.12 (d, J=12.5 Hz, 1H), 4.20 (m, 2H), 4.72 (d, J=12.5 Hz, 1H), 5.01 (d, J=5 Hz, 1H), 5.02 (s, 2H), 5.60 (d,d, J=5 Hz, J=8 Hz, 1H), 6.8 (m, 8H), 7.23 (s, broad, 2H), 7.40 (s, 1H), 8.04 (m, broad, 1H), 9.51 (d, J=8 Hz, 1H) IR (KBr) 1765 cm$^{-1}$ MS: 889.3 (M+H$^\oplus$)

The O-[(4-fluoro-2,2-diphenyl-1,3-benzodioxol-5-yl)methyl]hydroxylamine hydrochloride used as the starting material can be prepared as follows:

3-Fluorocatechol (7.2 g) in 50 ml of carbon tetrachloride and 40 ml of chloroform are treated at −10° C. within 10 minutes with a solution of 2.88 ml of bromine in 30 ml of carbon tetrachloride. After stirring at −10° C. for 1 hour the reaction mixture is filtered. The residual solid is washed with a small amount of cold carbon tetrachloride and dried. There are obtained 6.30 g of 4-bromo-3-fluorocatechol as a white powder. This is treated with 6.0 ml of diphenylchloromethane and heated to 130° C. within 1 hour. Subsequently, the product is distilled at 135° C./0.05 Torr and recrystallized from ethanol. There are obtained 6.40 g of 5-bromo-4-fluoro-2,2-diphenyl-1,3-benzodioxol as a white crystalline powder of m.p. 61.5°–63° C.

Elementary analysis: Calculated: C 61.48 H 3.26 F 5.12 Br 21.53% Found: 61.42 3.48 5.26 21.69%

5-Bromo-4-fluoro-2,2-diphenyl-1,3-benzodioxol (17.3 g) is dissolved in 150 ml of tetrahydrofuran, treated at −78° C. with 29.1 ml of a 0.6M solution of n-butyllithium in n-hexane and stirred at −78° C. for 15 minutes. Thereupon, 10 ml of dimethylformamide are added, after stirring for a further 15 minutes the mixture is treated with semi-saturated, aqueous ammonium chloride solution and extracted with ethyl acetate. The organic phase is dried with magnesium sulphate and evaporated. The residue is crystallized from ethanol. After drying there are obtained 12.7 g of 4-fluoro-2,2-diphenyl-1,3-benzodioxol-5-carboxaldehyde as white crystals of m.p. 92°–94° C.

Elementary analysis: Calculated: C 74.99 H 4.09 F 5.93% Found: 74.48 4.30 5.90%

4-Fluoro-2,2-diphenyl-1,3-benzodioxol-5-carboxaldehyde (0.32 g) is dissolved in 5 ml of tetrahydrofuran and treated with 20 mg of lithium borohydride. After stirring at room temperature for 20 minutes semi-saturated, aqueous ammonium chloride solution is added and the mixture is extracted with ethyl acetate. The organic phase is dried with magnesium sulphate, concentrated and dried overnight in a high vacuum. There is obtained 0.320 g of colourless oil which is dissolved in 5 ml of methylene chloride and treated in succession with 0.40 g of triphenylphosphine and 0.33 g of N-hydroxyphthalimide. The mixture is cooled to 0° C. and treated with 0.30 ml of diethyl azodicarboxylate dissolved in 2 ml of methylene chloride. After stirring at 0° C. for 1 hour the entire reaction mixture is applied to 30 g of silica gel and the product is eluted with methylene chloride. The uniform fractions are concentrated and the residue is crystallized from ethyl acetate. There is obtained 0.35 g of N-[(4-fluoro-2,2-diphenyl-1,3-benzodioxol-5-yl)methoxy]phthalimide as white crystals of m.p. 177°–179° C.

N-[(4-Fluoro-2,2-diphenyl-1,3-benzodioxol-5-yl)methoxy]phthalimide (5.13 g) are suspended in 20 ml of ethanol, treated with 1.62 ml of 3-dimethylaminopropylamine and stirred at room temperature for 1 hour. The ethanol is evaporated in a water-jet vacuum and the residue is chromatographed on silica gel (250 g) with ethyl acetate. The uniform fractions are concentrated; the oily residue is treated with 20 ml of 1M ethanolic hydrochloric acid. A white precipitate forms and, after stirring in an ice-bath for 1 hour, it is filtered off and washed with a small amount of cold ethanol. After drying there are obtained 3.80 g of O-[(4-fluoro-2,2-diphenyl-1,3-benzodioxol-5-yl)methyl]hydroxylamine hydrochloride was a white, crystalline powder of m.p. 167°–173° C.

$^1$H-NMR (DMSO-$d_6$, 250 MHz): signals at $\delta$ (ppm) 5.00 (s, 2H), 7.0 (m, 2H), 7.5 (m, 10H), 10.8 (s, broad, 3H)

EXAMPLE 6

Manufacture of (6R,7R)-7-[(Z)-2-(2-amino-4-thiazolyl)-2-[[(1,4-dihydro-5-hydroxy-4-oxo-2-pyrimidinyl)methoxy]imino]acetamido]-3-[[[2-[[(3,4-dihydroxybenzoyl)oxy]methyl]-5-methyl-s-triazolo[1,5-a]pyrimidin-7-yl]thio]methyl]-8-oxo-5-thia-1-azabicyclo[4.2.0]oct-2-ene-2-carboxylic acid sodium salt (1:1)

2-(Aminooxy)methyl-5-hydroxy-4(1H)-pyrimidinone (0.16 g), 0.065 ml of methanesulphonic acid and 0.37 g of (6R,7R)-7-(2-amino-4-thiazoleglyoxylamido )-3-[[[2-[[(3,4-dihydroxybenzoyl)oxy]methyl]-5-methyl-s-triazolo[1,5-a]pyrimidin-7yl]thio]methyl]-8-oxo-5-thia-1-azabicyclo[4.2.0]oct-2-ene-2-carboxylic acid are stirred in 3.0 ml of dimethylformamide for 16 hours at room temperature. The dimethylacetamide is evaporated in a high vacuum, the residue is digested with water and the resulting precipitate is filtered off. This solid is resuspended in water, brought into solution at pH 7.0 by the addition of 1N aqueous sodium hydroxide solution and chromatographed on RP12-Kieselgel with water/acetonitrile. Uniform fractions are concentrated and lyophilized. There is obtained (6R,7R)-7-[(Z)-2-(2-amino-4-thiazolyl)-2-[[(1,4-dihydro-5-hydroxy-4-oxo-2-pyrimidinyl)methoxylimino]acetamido]-3-[[[2-[[(3,4-dihydroxybenzoyl)oxy]methyl]-5-methyl-s-triazolo[1,5-a]pyrimidin-7-yl]thio]methyl]-8-oxo-5-thia-1-azabicyclo[4.2.0]oct-2-ene-2-carboxylic acid sodium salt (1:1) as a white powder.

¹H-NMR (DMSO-d₆, 250 MHz): signals at δ (ppm) 2.55 (s, 3H), 3.32 (d, J=18 Hz, 1H), 3.62 (d, J=18 Hz, 1H), 4.35 (d, J=12.5 Hz, 1H), 4.68 (d, J=12,5 Hz, 1H), 4.92 (s, 2H), 5.02 (d, J=5 Hz, 1H), 5.47 (s, 2H), 5.62 (d,d, J=5 Hz, J=8 Hz, 1H), 6.84 (m, 2H), 7.28 (s, broad, 2H), 7.40 (m, 3H), 7.71 (s, 1H), 9.92 (d, J=8 Hz, 1H) IR (KBr) 1766 cm⁻¹ MS: 860 (M+H⊕)

The (6R,7R)-7-(2-amino-4-thiazoleglyoxylamido)-3-[[[2-[[(3,4-dihydroxybenzoyl)oxy]methyl]-5-methyl-s-triazolo[1,5-a]pyrimidin-7-yl]thio]methyl]-8-oxo-5-thia-1-azabicyclo[4.2.0]oct-2-ene-2-carboxylic acid used as the starting material can be prepared as follows:

(6R,7R)-7-Amino-3-[[[2-(hydroxymethyl)-5-methyl-s-triazolo[1,5-a]pyrimidin-7-yl]thio]methyl]-8-oxo-5-thia-1azabicyclo[4.2.0]oct-2-ene-2-carboxylic acid (4.08 g) (known from EPOS 302,633) and 1.54 g of 3,4-dihydroxybenzoic acid are treated with 30 ml of a 20% solution of boron trifluoride in acetonitrile and stirred at room temperature for 2 hours. A further 25 ml of a 20% solution of boron trifluoride in acetonitrile are added; the reaction mixture is stirred at room temperature under argon for 2 days. After the addition of 100 ml of ice-water the reaction mixture is concentrated to about half. The product is precipitated by adjusting the pH value to 2.0 with concentrated aqueous ammonia. The precipitated material is suspended in water, brought into solution with 1N aqueous sodium hydroxide solution and purified by chromatography on RP12-Kieselgel with water/acetonitrile. The product fractions are concentrated to about 50 ml and the product is precipitated by acidification to pH 2.0. After drying in a high vacuum there are obtained 1.60 g of (6R,7R)-7-amino-3-[[[2-[[(3,4-dihydroxybenzoyl)oxy]methyl]-5-methyl-s-triazolo[1,5-a]pyrimidin-7-yl]thio]methyl]-8-oxo-5-thia-1-azabicyclo[4.2.0]oct-2-ene-2-carboxylic acid as a white powder.

¹H-NMR (DMSO-d,) 250 MHz): signals at δ (ppm) 2.58 (s, 3H), 3.55 (d, J=18 Hz, 1H), 3.76 (d, J=18 Hz, 1H), 4.33 (d, J=12.5 Hz, 1H), 4.45 (d, J=12.5 Hz, 1H), 4.89 (d, J=5 Hz, 1H), 5.06 (d, J=5 Hz, 1H), 5.46 (s, 2H), 6.83 (d, J=8 Hz, 1H), 7.36 (m, 3H), 9.44 (s, broad, 1H), 9.88 (s, broad, 1H) IR: (KBr) 1778 cm⁻¹ MS: 545 (M+H⊕)

(6R,7R)-7-Amino-3-[[[2-[[(3,4-dihydroxybenzoyl)oxy]methyl]-5-methyl-s-triazolo[1,5-a]pyrimidin-7-yl]thio]methyl]-8-oxo-5-thia-1-azabicyclo[4.2.0]oct-2-ene-2-carboxylic acid (1.55 g) are suspended in 12 ml of water and 12 ml of acetonitrile. The pH value is adjusted to 7.0 by the addition of 0.5 ml of triethylamine. 1.80g of 2-amino-4-thiazolethioglyoxylic acid S-(2-benzothiazolyl) ester are subsequently added at 0° C. and the reaction mixture is stirred at 0° C. for 2 hours. The reaction mixture is centrifuged and the clear supernatant solution is partitioned between water and ethyl acetate. The aqueous phase is separated, concentrated and acidified to pH 2.0. The resulting yellow precipitate is filtered off and dried in a high vacuum. There are obtained 1.72 g of (6R,7R)-7-(2-amino-4-thiazoleglyoxylamido)-3-[[[2-[[(3,4-dihydroxybenzoyl)oxy]methyl]-5-methyl-s-triazolo[1,5-a]pyrimidin-7-yl]thio]methyl]-8-oxo-5-thia-1-azabicyclo[4.2.0]oct-2-ene-2-carboxylic acid as a yellow powder.

¹H-NMR (DMSO-d₆, 250 MHz): signals at δ (ppm) 2.58 (s, 3H), 3.60 (d, J=18 Hz, 1H), 3.79 (d, J=18 Hz, 1H), 4.37 (d, J=12.5 Hz, 1H), 4.48 (d, J=12.5 Hz, 1H), 5.71 (d, J=5 Hz, 1H), 5.75 (dd, J=5 Hz, J=8 Hz, 1H), 6.83 (d, J=8 Hz, 1H), 7.35 (m, 5H), 7.82 (s, 1H), 9.43 (s, 1H), 9.81 (d, J=8 Hz, 1H), 9.87 (s, 1H) IR: (KBr) 1776 cm⁻¹ MS: 699 (M+H⊕)

EXAMPLE 7

Manufacture of (6R,7R)-7-[(Z)-2-(2-amino-4-thiazolyl)-2-[[[(3,4-dihydroxyphenyl)sulphonyl]methoxy]imino]acetamido]-3-[[[2-[[(3,4-dihydroxybenzoyl)oxy]methyl]-5-methyl-s-triazolo[1,5-a]pyrimidin-7-yl]thio]methyl]-8-oxo-5-thia-1-azabicyclo[4.2.0]oct-2-ene-2-carboxylic acid sodium salt (1:1)

(6R,7R)-7-(2-Amino-4-thiazoleglyoxylamido)-3-[[[2-[[(3,4-dihydroxybenzoyl)oxy]methyl]-5-methyl-s-triazolo[1,5-a]pyrimidin-7-yl]thio]methyl]-8-oxo-5-thia-1-azabicyclo[4.2.0]oct-2-ene-2-carboxylic acid (0.35 g) and 0.13 g of 4-[[(aminooxy)methyl]sulphonyl]-pyrocatechol hydrochloride are stirred in 4 ml of dimethylacetamide for 72 hours at room temperature. The dimethylacetamide is evaporated in a high vacuum and the residue is digested in water. The solid is filtered off, resuspended in water, brought into solution at pH 7.0 by the addition of 1N aqueous sodium hydroxide solution and chromatographed on RP12-Kieselgel with water/acetonitrile. The uniform fractions are concentrated and lyophilized. There is obtained 0.16 g of (6R,7R)-7-[(Z)-2-(2-amino-4-thiazolyl)-2-[[[(3,4-dihydrooxyphenyl)sulphonyl]methoxy]imino]acetamido]-3-[[[2-[[(3,4-dihydroxybenzoyl)oxy]methyl]-5-methyl-s-triazolo[1,5-a]pyrimidin-7-yl]thio]methyl]-8-oxo-5-thia-1-azabicyclo[4.2.0]oct-2-ene-2-carboxylic acid sodium salt (1:1) as a pale beige powder.

¹H-NMR (DMSO-d₆, 250 MHz): signals at δ (ppm) 2.60 (s, 3H), 3.05 (d, J=18 Hz, 1H), 3.48 (d, J=18 Hz, 1H), 4.28 (d, J=12.5 Hz, 1H), 4.53 (d, J=12.5 Hz, 1H), 4.91 (d, J=5 Hz, 1H), 5.16 (m, 2H), 5.41 (dd, J=5 Hz, J=8 Hz, 1H), 5.44 (s, 2H), 6.80 (m, 3H), 7.30 (m, 6H), 7.65 (s, 1H), 9.38 (d, J=8 Hz, 1H) IR: (KBr) 1766 cm⁻¹ MS: 900 (M+H⊕)

EXAMPLE 8

Manufacture of (6R,7R)-7-[(Z)-2-(2-amino-4-thiazolyl)-2-[[(3,4-dihydroxybenzyl)oxy]imino]acetamido]-3 -[[[2-[[(3,4-dihydroxybenzoyl)oxy]methyl]-5-methyl-s-triazolo[1,5-a]pyrimidin-7-yl]thio]methyl]-8-oxo-5-thia-1-azabicyclo[4.2.0]oct-2-ene-2-carboxylic acid sodium salt (1:1)

(6R,7R)-7-(2-Amino-4-thiazoleglyoxylamido)-3-[[[2-[[(3,4-dihydroxybenzoyl)oxy]methyl]-5-methyl-s-triazolo[1,5-a]pyrimidin-7-yl]thio]methyl]-8-oxo-5-thia-1-azabicyclo[4.2.0]oct-2-ene-2-carboxylic acid (0.42 g) and 0.37 g O-[3,4-[(diphenylmethylene)dioxy]-benzyl]hydroxylamine are stirred in 5.0 ml of dimethylacetamide for 2 days at room temperature. The dimethylacetamide is evaporated in a high vacuum and the residue is digested in water. The resulting solid is filtered off, resuspended in water, brought into solution at pH 7.0 by the addition of 1N aqueous sodium hydroxide solution and chromatographed on RP12-Kieselgel with water/acetonitrile. The uniform fractions are concentrated and the product is precipitated by acidification to pH 2.0. The solid is stirred in 10 ml of trifluoroacetic acid and 5 drops of water at room temperature for 2 hours. The trifluoroacetic acid is evaporated in a water-jet vacuum and the residue is digested with ethyl acetate. The solid is filtered off, brought into solution in water at pH 7.0 by the addition of 1N aqueous sodium hydroxide solution and chromatographed on RP12-Kieselgel with water/acetonitrile. The uniform fractions are concentrated and lyophilized. There is obtained 0.07 g of (6R,7R)-7-[(Z)-2-(2-amino-4-thiazolyl)-2-[[(3,4-dihydroxybenzyl)oxy]imino]acetamido]-3-[[[2-[[(3,4-dihydroxybenzoyl)oxy]methyl]-5-methyl-s-triazolo[1,5-a]pyrimidin-7-yl]thio]methyl]-8-oxo-5-thia-1-azabicyclo[4.2.0]oct-2-ene-2-carboxylic acid sodium salt (1:1) as a beige powder.

$^1$H-NMR (DMSO-d$_6$, 250 MHz): signals at δ (ppm) 2.55 (s, 3H), 3.30 (d, J=18 Hz, 1H), 3.56 (d, J=18 Hz, 1H), 4.36 (d, J=12.5 Hz, 1H), 4.65 (d, J=12.5 Hz, 1H), 4.90 (s, 2H), 4.98 (d, J=5 Hz, 1H), 5.44 (s, 2H), 5.54 (dd, J=5 Hz, J=8 Hz, 1H), 6.70 (m, 5H), 7.21 (s, 2H), 7.40 (m, 2H), 7.76 (s, 1H), 8.90 (s, broad, 2H), 9.54 (d, J=8 Hz, 1H), 9.84 (s, broad, 2H) IR: (KBr) 1764 cm$^{-1}$

EXAMPLE 9

Manufacture of (6R,7R)-7-[(Z)-2-(2-amino-4-thiazolyl)-2-[[[(3,4-dihydroxy-2-fluorobenzyl)oxy]imino]acetamido]-3-[[[2-[[(3,4-dihydroxybenzoyl)oxy]methyl]-5-methyl-s-triazolo[1,5-a]pyrimidin-7-yl]thio]methyl]-8-oxo-5-thia-1-azabicyclo[4.2.0]oct-2-ene-2-carboxylic acid sodium salt (1:1)

(6R,7R)-7-(2-Amino-4-thiazoleglyoxylamido)-3-[[[2-[[(3,4-dihydroxybenzoyl)oxy]methyl]-5-methyl-s-triazolo[1,5-a]pyrimidin-7-yl]thio]methyl]-8-oxo-5-thia-1-azabicyclo[4.2.0]oct-2-ene-2-carboxylic acid (0.42 g) and 0.32 g O-[(4-fluoro-2,2-diphenyl-1,3-benzodioxol-5-yl)methyl]hydroxylamine hydrochloride are stirred in 5.0 ml of dimethylacetamide for 24 hours at room temperature. The dimethylacetamide is evaporated in a high vacuum, the residue is digested with water, the resulting precipitate is filtered off, resuspended in water, brought into solution at pH 7.0 by the addition of 1N aqueous NaOH and chromatographed on RP12-Kieselgel with water/acetonitrile. The uniform fractions are concentrated and the product is precipitated by acidification to pH 2.0. The solid is dissolved while moist in trifluoroacetic acid and stirred at room temperature for 1 hour. The trifluoroacetic acid is evaporated in a water-jet vacuum, the residue is adjusted to pH 7 with 1N aqueous sodium hydroxide solution and partitioned between water and ethyl acetate. The aqueous phase is chromatographed on silica gel with water/acetonitrile. Uniform fractions are concentrated and lyophilized. There is obtained 0.17 g of (6R,7R)-7-[(Z)-2-(2-amino-4-thiazolyl)-2-[[[(3,4-dihydroxy-2-fluorobenzyl)oxy]imino]acetamido]-3-[[[2-[[(3,4-dihydroxybenzoyl)oxy]methyl-s-triazolo[1,5-a]pyrimidin-7-yl]thio]methyl]-8-oxo-5-thia-1azabicyclo[4.2.0]oct-2-ene-2-carboxylic acid sodium salt (1:1) as a white powder.

$^1$H-NMR (DMSO-d$_6$, 250 MHz): signals at δ (ppm) 2.55 (s, 3H), 3.31 (d, J=18 Hz, 1H), 3.53 (d, J=18 Hz, 1H), 4.36 (d, J=12.5 Hz, 1H), 4.64 (d, J=12.5 Hz, 1H), 4.97 (d, J=5 Hz, 1H), 5.01 (s, 2H), 5.46 (s, 2H), 5.54 (d,d, J=5 Hz, J=8 Hz, 1H), 6.70 (m, 4H), 7.22 (s, broad, 2H), 7.40 (m, 2H), 7.74 (s, 1H), 9.54 (d, J=8 Hz, 1H) IR: (KBr) 1766 cm$^{-1}$ MS: 854.3 (M+H$^\oplus$)

EXAMPLE 10

Manufacture of (6R,7R)-7-[(Z)-2-(2-amino-4-thiazolyl)-2-[[[(3,4-dihydroxyphenyl)sulphonyl]methoxy]imino]acetamido]-3-[[[2-[[(3,4-dihydroxyphenyl)sulphonyl]methyl]-5-methyl-s-triazolo[1,5-a]pyrimidin-7-yl]thio]methyl]-8-oxo-5-thia-1-azabicyclo[4.2.0]oct-2-ene-2-carboxylic acid sodium salt (1:1)

(6R,7R)-7-(2-Amino-4-thiazoleglyoxylamido)-3-[[[2-[[(3,4-dihydroxyphenyl)sulphonyl]methyl]-5-methyl-s-triazolo[1,5-a]pyrimidin-7-yl]thio]methyl]-8-oxo-5-thia-1-azabicyclo[4.2.0]-oct-2-ene-2-carboxylic acid (0.30 g) and 0.190 g of 4-[[(aminooxy)methyl]sulphonyl]pyrocatechol hydrochloride are stirred for 2 days in 5 ml of dimethylacetamide at room temperature. The dimethylacetamide is evaporated; in a high vacuum and the residue is digested in water. The resulting precipitate is filtered off, suspended in water, brought into solution at pH 7.0 by the addition of 1N aqueous sodium hydroxide solution and chromatographed on RP12-Kieselgel with water/acetonitrile. After lyophilization of the product fractions there is obtained 0.10 g of (6R,7R)-7-[(Z)-2-(2-amino-4-thiazolyl)-2-[[[(3,4-dihydroxyphenyl)sulphonyl]methoxy]imino]acetamido]-3-[[[2-[[(3,4-dihydroxyphenyl)sulphonyl]-methyl]-5-methyl-s-triazolo[1,5-a]pyrimidin-7-yl]thio]methyl]-8-oxo-5-thia-1-azabicyclo[4.2.0]oct-2-ene-2-carboxylic acid sodium salt (1:1) as a white powder.

$^1$H-NMR (DMSO-d$_6$, 250 MHz): signals at δ (ppm) 2.54 (s, 3H), 3.12 (d, J=18 Hz, 1H), 3.40 (d, J=18 Hz, 1H), 4.26 (d, J=12.5 Hz, 1H), 4.70 (s, 2H), 4.83 (d, J=5 Hz, 1H), 5.04 (d, J=12 Hz, 1H), 5.15 (d, J=12 Hz, 1H), 5.47 (d, broad, J=5 Hz, 1H), 6.64 (m, 1H), 6.79 (m, 2H), 6.95 (m, 1H), 7.10 (m, 2H), 7.30 (s, broad, 2H), 7.67 (s, 1H) IR: (KBr) 1765 cm$^{-1}$ MS: 942 (M+Na$^\oplus$)

The (6R,7R)-7-(2-amino-4-thiazoleglyoxylamido)-3-[[[2-[[(3,4-dihydroxyphenyl)sulphonyl]methyl]-5-methyl-s-triazolo[1,5-a]pyrimidin-7-yl]thio]methyl]-8-oxo-5-thia-1-azabicyclo[4.2.0]oct-2-ene-2-carboxylic acid used as the starting material can be prepared as follows:

2-(Chloromethyl)-5-methyl-s-triazolo[1,5-a]pyrimidin-7-ol and 4.20 g of sodium iodide (5.00 g) are stirred in 75 ml of dimethylformamide for 2 hours at room temperature. 9.60 g of 2-2-diphenyl-1,3-benzodioxol-5-sulphinic acid lithium salt (1:1) are added. After stirring at room temperature for 2 hours a clear solution results. It is stirred at room temperature for a further 16 hours. The solvent is evaporated under a high vacuum. The residue is partitioned between water and ethyl acetate. The organic phase is washed with water (three times) and with saturated aqueous sodium chloride solution, dried with magnesium sulphate and concentrated. The residue is crystallized from tetrahydrofuran. There are obtained 5.70 g of 2-[[[3,4-[(diphenylmethylene)dioxy]phenyl]sulphonyl]methyl]-5-methyl-s-triazolo[1,5-a]pyrimidin-7-ol as a white powder. M.p. 259°–263° C.

Elementary analysis: Calculated: C 62.39 H 4.03 N 11.19 S 6.41% Found: C 62.64 H 4.08 N 10.92 S 6.22%

2-[[[3,4-[(Diphenylmethylene)dioxy]phenyl]sulphonyl]methyl]-5-methyl-s-triazolo[1,5-a]pyrimidin-7-ol (0.25 g) in 2.0 ml of phosphorus oxychloride is treated with 0.040 ml of pyridine and subsequently heated to 80° C. for 30 minutes. The reaction mixture is concentrated under a water-jet vacuum and the residue is partitioned between semi-saturated, ice-cold aqueous sodium chloride solution and ethyl acetate. The organic phase is washed with ice-cold, aqueous sodium chloride solution, dried with magnesium sulphate and concentrated. The residue in 30 ml of ethanol is heated at reflux with 0.04 g of thiourea for 15 minutes. The substance crystallizes as yellow crystals upon cooling. There is obtained 0.200 g of 2-[[[3,4-[(diphenylmethylene)dioxy]phenyl]sulphonyl]methyl]-5-methyl-s-triazolo[1,5-a]pyrimidine-7-thiol as a yellow powder. M.p. 272°-275° C. (dec.).

Elementary analysis: Calculated: C 60.45 H 3.90 N 10.85 S 12.41% Found: C 60.29 H 3.81 N 10.95 S 12.35%

2-[[[3,4-[(Diphenylmethylene)dioxy]phenyl]sulphonyl]-methyl]-7-methyl-s-triazolo[1,5-a]pyrimidine-7-thiol (1.00 g) and 0.54 g of 7-aminocephalosporanic acid are suspended in 10 ml of acetonitrile and treated with 5.0 ml of a 20% solution of boron trifluoride in acetonitrile. After stirring at room temperature for 2 hours 20 ml of ice-water are added. The reaction mixture is concentrated to 15 ml and the resulting suspension is stirred in an ice-bath for 1 hour. The resulting white precipitate is filtered off and dried under a high vacuum overnight. This solid is dissolved in 10 ml of trifluoroacetic acid and 0.5 ml of water and stirred at room temperature for 1 hour. The reaction mixture is concentrated to dryness. The residue is digested with ethyl acetate. There is obtained 0.60 g of (6R,7R)-7-amino-3-[[[2-[[(3,4-dihydroxyphenyl)sulphonyl]methyl]-5-methyl-s-triazolo[1,5-a]pyrimidin-7-yl]thio]methyl]-8-oxo-5-thia-1-azabicyclo[4.2.0]oct-2-ene-2-carboxylic acid trifluoroacetate (1:1) as a pale beige powder.

$^1$H-NMR (DMSO-d$_6$, 250 MHz): signals at δ (ppm) 2.60 (s, 3H), 3.64 (d, J=17.5 Hz, 1H), 3.83 (d, J=17.5 Hz, 1H), 4.38 (d, J=12.5 Hz, 1H), 4.48 (d, J=12.5 Hz, 1H), 4.82 (s, 2H), 5.06 (d, J=5 Hz, 1H), 5.18 (d, J=5 Hz, 1H), 6.86 (d, J=8 Hz, 1H), 7.11 (m, 3H), 7.35 (s, 1H), 9.74 (s, broad, 1H), 10.14 (s, broad, 1H) IR (KBr): 1785 cm$^{-1}$ MS: 565 (M+H)$^⊕$ (6R,7R)-7-Amino-3-[[[2-[[(3,4-dihydroxyphenyl)sulphonyl]methyl]-5-methyl-s-triazolo[1,5-a]pyrimidin-7-yl]thio]methyl]-8-oxo-5-thia-1-azabicyclo[4.2.0]oct-2-ene-2-carboxylic acid trifluoroacetate (1:1) (2.00 g) are suspended in 10 ml of water and 10 ml of acetonitrile and dissolved at pH 7.0 by the addition of triethylamine. The reaction mixture is cooled to 0° C. and stirred at 0° C. for 4 hours with 1.90 g of 2-amino-4-thiazoleglyoxylic acid S-(2-benzothiazolyl) ester. The reaction mixture is centrifuged and the clear supernatant is partitioned between water and ethyl acetate. The aqueous phase is concentrated slightly and the product is precipitated by acidification to pH 2.0. After filtration and drying in a high vacuum there are obtained 2.46 g of yellow powder which is purified by chromatography on silica gel with water/acetonitrile. There is obtained 1.00 g of (6R,7R)-7-(2-amino-4-thiazoleglyoxylamido)-3-[[[2-[[(3,4-dihydroxyphenyl)sulphonyl]methyl]-5-methyl-s-triazolo[1,5-a]pyrimidin-7-yl]thio]methyl]-8-oxo-5-thia-1-azabicyclo[4.2.0]oct-2-ene-2-carboxylic acid as a yellow powder.

$^1$H-NMR (DMSO-d$_6$, 250 MHz): signals at δ (ppm) 2.58 (s, 3H), 3.60 (d, J=18 Hz, 1H), 3.79 (d, J=18 Hz, 1H), 4.36 (d, J=12.5 Hz, 1H), 4.47 (d, J=12.5 Hz, 1H), 4.81 (s, 2H), 5.21 (d, J=5 Hz, 1H), 5.77 (d,d J=5 Hz, J=8 Hz, 1H), 6.67 (d, J=9 Hz, 1H), 7.09 (m, 2H), 7.61 (s, 1H), 7.41 (s, broad, 2H), 7.63 (s, 1H), 9.70 (s, broad, 1H), 9.81 (d, J=8 Hz, 1H), 10.10 (s, broad, 1H), 14.00 (s, very broad, 1H) IR (KBr): 1774 cm$^{-1}$ MS: 719 (M+H$^⊕$)

EXAMPLE 11

Manufacture of (6R,7R)-7-[(Z)-2-(2-amino-4-thiazolyl)-2-[[(3,4-dihydroxybenzyl)oxy]imino]acetamido]-3-[[[2-[[(3,4-dihydroxyphenyl)sulphonyl]methyl]-5-methyl-s-triazolo[1,5-a]pyrimidin-7-yl]thio]methyl]-8-oxo-5-thia-1-azabicyclo[4.2.0]oct-2-ene-2-carboxylic acid sodium salt (1:1)

(6R,7R)-7-(2-Amino-4-thiazoleglyoxylamido)-3-[[[2-[[(3,4-dihydroxyphenyl)sulphonyl]methyl]-5-methyl-s-triazolo[1,5-a]pyrimidin-7-yl]thio]methyl]-8-oxo-5-thia-1-azabicyclo[4.2.0]-oct-2-ene-2-carboxylic acid (0.400 g) and 0.38 g of O-[3,4-[(diphenylmethylene)dioxy]benzyl]hydroxylamine are stirred in 4 ml of dimethylacetamide for 16 hours at room temperature. The dimethylacetamide is evaporated in a high vacuum, the residue is digested in water, the resulting precipitate is filtered off, suspended in water, brought into solution at pH 7.0 by the addition of 1N aqueous sodium hydroxide solution and chromatographed on RP12-Kieselgel with water/acetonitrile. A white precipitate separates after concentration of the product fractions to about 10 ml and acidification to pH 2 and this is dried in a high vacuum overnight. There is obtained 0.330 g of white powder which is dissolved 3 ml of trifluoroacetic acid and 3 drops of water and stirred at room temperature for 1 hour. The trifluoroacetic acid is evaporated in a water-jet vacuum. The residue is digested in ethyl acetate, filtered off, suspended in water, brought into solution at pH 7.0 by the addition of 1N aqueous sodium hydroxide solution and chromatographed on RP12-Kieselgel with water/acetonitrile. The product fractions are lyophilized. There is obtained 0.10 g of (6R,7R)-7-[(Z)-2-(2-amino-4-thiazolyl)-2-[[(3,4-dihydroxybenzyl)oxy]imino]acetamido]-3-[[[2-[[(3,4-dihydroxyphenyl)sulphonyl]methyl]-5-methyl-s-triazolo[1,5-a]pyrimidin-7-yl]thio]methyl]-8-oxo-5-thia-1-azabicyclo[4.2.0]oct-2-ene-2-carboxylic acid sodium salt (1:1) as a white powder.

$^1$H-NMR (DMSO-d$_6$, 250 MHz): signals at δ (ppm) 2.56 (s, 3H), 3.35 (d, J=18 Hz, 1H), 3.57 (d, J=18 Hz, 1H), 4.34 (d, J=12.5 Hz, 1H), 4.60 (d, J=12.5 Hz, 1H), 4.72 (s, 2H), 4.92 (s, 2H), 5.02 (d, J=5 Hz, 1H), 5.58 (d, broad, J=5 Hz, 1H), 6.7 (m, ~6H), 6.98 (m, 2H), 7.23 (s, broad, 2H), 7.63 (s, 1H)

EXAMPLE 12

Manufacture of (6R,7R)-7-[(Z)-2-(2-amino-4-thiazolyl)-2-[[(2-fluoro-3,4-dihydroxybenzyl)oxy]imino]acetamido]-3-[[[2-[[(3,4-dihydroxyphenyl)sulphonyl]methyl]-5-methyl-s-triazolo[1,5-a]pyrimidin-7-yl]thio]methyl]-8-oxo-5-thia-1-azabicyclo[4.2.0]oct-2-ene-2-carboxylic acid sodium salt (1:1)

(6R,7R)-7-(2-Amino-4-thiazoleglyoxylamido)-3-[[[2-[[(3,4-dihydroxyphenyl)sulphonyl]methyl]-5-methyl-s-triazolo[1,5-a]pyrimidin-7-yl]thio]methyl]-8-oxo-5-thia-1-azabicyclo[4.2.0]oct-2-ene-2-carboxylic acid (0.50 g) is dissolved in 5.0 ml of dimethylacetamide, treated with 0.40 g of O-[(4-fluoro-2,2-diphenyl-1,3-benzodioxol-5-yl)methyl]hydroxylamine hydrochloride and stirred at room temperature for 16 hours. The dimethylacetamide is evaporated in a high vacuum and the residue is digested with water and filtered. The resulting solid is dissolved in water at pH 7.0 and chromatographed on RP12-Kieselgel with water/acetonitrile. The uniform fractions are combined and concentrated, and the product is precipitated by acidification to pH 2.0. After drying in a high vacuum there is obtained 0.350 g of a white powder. This is dissolved in 5 ml of trifluoroacetic acid and 5 drops of water and stirred at room temperature for 1 hour. The trifluoroacetic acid is removed in a water-jet vacuum and the residue is partitioned at pH 7.0 between water and ethyl acetate. The aqueous phase is separated and concentrated slightly, and the residue is precipitated by acidification to pH 2.0. The white powder obtained is suspended in water and brought into solution at pH 7.0 by the addition of 1N aqueous sodium hydroxide solution. After lyophilization of this solution there are obtained 180 mg of (6R,7R)-7-[(Z)-2-(2-amino-4-thiazolyl)-2-[[(2-fluoro-3,4-dihydroxybenzyl)oxy]imino]acetamido]-3-[[[2-[[(3,4-dihydroxyphenyl)sulphonyl]methyl]-5-methyl-s-triazolo[1,5-a]pyrimidin-7-yl]thio]methyl]-8-oxo-5-thia-1-azabicyclo[4.2.0]oct-2-ene-2-carboxylic acid sodium salt (1:1) as a pale beige powder.

$^1$H-NMR (DMSO-d$_6$, 250 MHz): signals at δ (ppm) 2.58 (s, 3H), 3.48 (d, J=18 Hz, 1H), 4.33 (d, J=12.5 Hz, 1H), 4.46 (d, J=12.5 Hz, 1H), 4.60 (s, 2H), 5.03 (s, 2H), 5.17 (d, J=5 Hz, 1H), 5.79 (dd, J=5 Hz, J=8 Hz, 1H), 7 (m, 7H), 9.50 (d, J=8 Hz, 1H) IR (KBr): 1765 cm$^{-1}$ MS: 873.7 (M+H⊕)

EXAMPLE 13

Manufacture of (6R,7R)-7-[(Z)-2-(2-amino-4-thiazolyl)-2-[[(1,4-dihydro-5-hydroxy-4-oxo-2-pyrimidinyl)methoxy]imino]acetamido]-3-[[[5-(3,4-dihydroxyphenyl)-pyrazolo[1,5-a]pyrimidin-7-yl]thio]methyl]-8-oxo-5-thia-1-azabicyclo[4.2.0]oct-2-ene-2-carboxylic acid (6R, 7R)-7-(2-Amino-4-thiazoleglyoxylamido)-3-[[[5-(3,4-dihydroxyphenyl)pyrazolo[1,5-a]pyrimidin-7-yl]thio]methyl]-8-oxo-5-thia-1-azabicyclo[4.2.0]oct-2-ene-2-carboxylic acid (125 mg) (0.2 mmol), 41 mg (0.26 mmol) of 2-(aminooxy)methyl-5-hydroxy-4(1H)-pyrimidinone and 50 mg (0.26 mmol) of p-toluenesulphonic acid hydrate are dissolved in 3 ml of absolute dimethylacetamide. After stirring at room temperature for 14 hours the mixture is concentrated in a high vacuum at room temperature and the residue is treated with water. The product is filtered off and washed in succession with water, ethanol and diethyl ether. There are obtained 160 mg of (6R,7R)-7-[(Z)-2-(2-amino-4-thiazolyl)-2-[[(1,4-dihydro-5-hydroxy-4-oxo-2-pyrimidinyl)methoxy]imino]acetamido]-3-[[[5-(3,4-dihydroxyphenyl)pyrazolo[1,5-a]pyrimidin-7-yl]thio]methyl]-8-oxo-5-thia-1-azabicyclo[4.2.0]oct-2-ene-2-carboxylic acid as a yellow powder.

$^1$H-NMR (DMSO-d$_6$, 250 MHz): signals at δ (ppm) 3.60 (d, J=18 Hz, 1H), 3.83 (d, J=18 Hz, 1H), 4.48 (d, J=12.5 Hz, 1H), 4.55 (d, J=12.5 Hz, 1H), 4.91 (s, 2H), 5.22 (d, J=5 Hz, 1H), 5.84 (dd, J=5 Hz and J=8 Hz, 1H), 6.65 (d, J=2 Hz, 1H), 6.84 (s, 1H), 6.88 (d, J=8 Hz, 1H), 7.28 (s, 2H), 7.40 (s, 1H), 7.42 (s, 1H), 7.54 (dd, J=8 Hz and J=2 Hz, 1H), 7.74 (d, J=2 Hz, 1H), 8.19 (d, J=2 Hz, 1H), 9.23 (s, 1H), 9.56 (s, 1H), 9.91 (d, J=8 Hz, 1H).

The (6R,7R)-7-(2-amino-4-thiazoleglyoxylamido)-3-[[[5-(3,4-dihydroxyphenyl)pyrazolo[1,5-a]pyrimidin-7-yl]thio]methyl]-8-oxo-5-thia-1-azabicyclo[4.2.0]oct-2-ene-2-carboxylic acid used as the starting material can be prepared as follows:

3-Aminopyrazole (33.2 g) and 110 g of ethyl 3,4-dimethoxybenzoylacetate are stirred in 500 ml of glacial acetic acid for 6 hours at 80° C. After cooling the crystallized-out product is filtered off under suction, washed with diethyl ether and dried. There are obtained 45 g of 5-(3,4-dimethoxyphenyl)pyrazolo[1,5-a]pyrimidin-7-ol of m.p. 268°-270° C.

5-(3,4-Dimethoxyphenyl)pyrazolo[1,5-a]pyrimidin-7-ol (15.3 g) are boiled under reflux for 5 hours in 300 ml of 47% hydrobromic acid. Thereafter, the solution is cooled, concentrated in a vacuum and treated with 500 ml of water. The precipitated 4-(7-hydroxypyrazolo[1,5-a]pyrimidin-5-yl)pyrocatechol is filtered off under suction, washed with water and dried. There are obtained 13.5 g of beige crystals, m.p.>270° C.

4-(7-Hydroxypyrazolo[1,5-a]pyrimidin-5-yl)pyrocatechol (12.16 g) are suspended in 100 ml of phosphorus oxychloride. After the dropwise addition of 19 ml of N,N-dimethylaniline the mixture is stirred at 80° C. for 1 hour, cooled and evaporated under a water-jet vacuum. 250 g of ice-water are added to the residue, the mixture is left to warm to 25° C. and then extracted with 1000 ml of ethyl acetate and 500 ml of acetone. The organic phase is washed with water and evaporated. The residue is chromatographed over silica gel using acetone/ethyl acetate 1:1. The fractions containing the product are concentrated to 50 ml in a vacuum, whereby the product crystallizes out. There are obtained 5.35 g of beige crystals of 4-(7-chloropyrazolo[1,5-a]pyrimidin-5-yl)pyrocatechol, m.p.>270° C. This product is added to a solution of 7.5 g of NaHS.H$_2$O in 100 ml of water and 100 ml ethanol. The mixture is heated to 55° C. and evaporated after ½ hour. 100 ml of water are added to the residue, the mixture is adjusted to pH 1 using about 30 ml of 3N aqueous hydrochloric acid and the reaction product is filtered off under suction, washed with water and dried. There are obtained 4.85 g of yellow, crystalline 4-(7-mercaptopyrazolo[1,5-a]pyrimidin-5-yl)pyrocatechol, m.p.>280° C.

7-Aminocephalosporanic acid (272 mg) and 272 mg of the above 4-(7-mercaptopyrazolo[1,5-a]pyrimidin-5-yl)pyrocatechol are suspended in a mixture of 2 ml of sulpholane and 2 ml of dichloromethane. 0.75 ml of boron trifluoride etherate is added thereto and the mixture is stirred at 25° C. for 5 hours. Thereafter, it is treated with 20 ml of water, the aqueous phase is separated, its pH is adjusted to 3.5 using concentrated aqueous amonia solution and the precipitated product is filtered off under suction, washed with water, methanol and finally with diethyl ether and dried at 0.1 mmHg and 40° C. There are obtained 350 mg of (6R,7R)-7-amino-3-[[[5-(3,4-dihydroxyphenyl)pyrazolo[1,5-a]pyrimidin-7yl]thio]methyl]-8-oxo-5-thia-1-azabicyclo[4.2.0]oct-2-ene-2-carboxylic acid.

Elementary analysis: Found: 51.10% C, 3.74% H, 14.74% N, 13.64% S; Calculated: 50.95% C, 3.63% H, 14.85% N, 13.60% S.

$^1$H-NMR (DMSO-d$_6$, 250 MHz): signals at δ3.60 (d, J=18 Hz, 1H), 3.77 (d, J=18 Hz, 1H), 4.48 (s, broad, 2H), 4.82 (d, J=6 Hz, 1H), 5.02 (d, J=6 Hz, 1H), 6.65 (d, J ca. 1 Hz, 1H), 6.87 (d, J=9 Hz, 1H), 7.41 (s, 1H), 7.55 (d,d, J=ca. 1 and 9 Hz, 1H), 7.74 (d, J=ca. 1 Hz, 1H), 8.18 (d, J ca. 1 Hz, 1H), 9.25 (s, broad, 1H), 9.57 (s, broad, 1H).

(6R,7R)-7-Amino-3-[[[5-(3,4-dihydroxyphenyl)-pyrazolo[1,5-a]pyrimidin-7-yl]thio]methyl]-8-oxo-5-thia-1-azabicyclo[4.2.0]-oct-2-ene-2-carboxylic acid (1.41 g) are dissolved in 30 ml of dimethylacetamide and treated with 1.45 g of 2-amino-4-thiazolethioglyoxylic acid 5-(2-benzothiazolyl) ester. The mixture is stirred at room temperature for ½ hour and then concentrated in a vacuum at 20° C. The residue is dissolved in 25 ml of dimethylformamide and 25 ml of acetone, filtered and subsequently treated with 2 ml of a 2M solution of sodium 2-ethylcaproate in acetone and thereafter with 50 l of ether. The precipitated material is filtered off under suction and chromatographed over RP12-Kieselgel with water/acetonitrile. The product fractions are concentrated and adjusted to pH 1 with 1N aqueous hydrochloric acid. The precipitated product is filtered off under suction, washed with water and dried at 0.1 mmHg/40° C. There are obtained 1.15 g of (6R,7R)-7-(2-amino-4-thiazoleglyoxylamido)-3-[[[5-(3,4-dihydroxyphenyl)pyrazolo[1,5-a]pyrimidin-7-yl]thio]methyl]-8-oxo-5-thia-1-azabicyclo[4.2.0]oct-2-ene-2-carboxylic acid.

Elementary analysis: Found: 48.32% C, 2.87% H, 15.93% N, 15.51% S; Calculated: 47.99% C, 3.06% H, 15.67% N, 15.37% S $^1$H-NMR (DMSO-d$_6$, 250 MHz): signals at δ3.68 (d, J=18 Hz, 1H), 3.82 (d, J=18 Hz, 1H), 4.56 (s, broad, 2H), 5.25 (d, J=5.5 Hz, 1H), 5.77 (dd, J=5.5 and 8.5 Hz, 1H), 6.65 (d, J=ca. 1 Hz, 1H), 6.88 (d, J=9 Hz, 1H), 7.42 (m, 3H), 7.55 (dd, J=ca. 1 and 9 Hz, 1H), 7.73 (d, J=ca. 1 Hz, 1H), 7.82 (s, 1H), 8.19 (d, J=ca. 1 Hz, 1H), 9.22 (broad, 1H), 9.57 (s, 1H), 9.83 (d, J=8.5 Hz, 1H).

EXAMPLE 14

Manufacture of (6R,7R)-7-[(Z)-2-(2-amino-4-thiazolyl)-2-[[(5-hydroxy-4-oxo-4H-pyran-2-yl)methoxy]imino]acetamido]-3-[[[5-(3,4-dihydroxyphenyl)-pyrazolo[1,5-a]pyrimidin-7-yl]thio]methyl]-8-oxo-5-thia-1-azabicyclo[4.2.0]oct-2-ene-2-carboxylic acid (6R,7R)-7-(2-Amino-4-thiazoleglyoxylamido)-3-[[[5-(3,4-dihydroxyphenyl)pyrazolo[1,5-a]pyrimidin-7-yl]thio]methyl]-8-oxo-5-thia-1-azabicyclo[4.2.0]oct-2-ene-2-carboxylic acid (59 mg) (0.095 mmol) and 41 mg (0.121 mmol) of 2-[(aminooxy)methyl]-5-hydroxy-4H-pyran-4-one p-toluenesulphonate (1:1) are dissolved in 2 ml of absolute dimethylaeetamide. After stirring at room temperature for 24 hours the solvent is removed and the residue is treated with 4 ml of water. The precipitated product is filtered off and washed with water. After drying in a high vacuum at room temperature there are obtained 67 mg of (6R,7R)-7-[(Z)-2-(2-amino-4-thiazolyl)-2-[[(5-hydroxy-4-oxo-4 H-pyran-2-yl)methoxy]imino]acetamido]-3-[[[5-(3,4-dihydroxyphenyl)-pyrazolo[1,5-a]pyrimidin-7-yl]thio]methyl]-8-oxo-5-thia-1-azabicyclo[4.2.0]oct-2-ene-2-carboxylic acid as a yellow powder.

1H NMR (DMSO-d$_6$): signals at, inter alia, δ (ppm) 3.63 (d, J=18 Hz, 1H), 3.83 (d, J=18 Hz, 1H), 4.53 (s, 2H), 4.97 (s, 2H), 5.22 (d, J=5 Hz, 1H), 5.84 (dd, J=5 Hz and J=8 Hz, 1H), 6.48 (s, 1H), 6.62 (d, J=2 Hz, 1H), 6.82 (s, 1H), 6.85 (d, J=8 Hz, 1H), 7.40 (s, 1H), 7.54 (dd, J=8 Hz and J=2 Hz, 1H), 7.74 (d, J=2 Hz, 1H), 8.06 (s, 1H), 8.20 (d, J=2 Hz, 1H), 9.85 (d, J=8 Hz, 1H).

The 2-[(aminooxy)methyl]-5-hydroxy-4H-pyran-4-one p-toluenesulphonate (1:1) used as the starting material can be prepared as follows:

Diethyl azodicarboxylate (16.68 g) (86 mmol) are dissolved in 1200 ml of absolute tetrahydrofuran. Thereto there is added a mixture consisting of 22.6 g (86 mmol) of triphenylphosphine, 14.1 g (86 mmol) of N-hydroxyphthalimide and 20.0 g (86 mmol) of 5-(benzyloxy)-2-(hydroxymethyl)-4H-pyran-4-one (known from J. Med. Chem. 17, 1, 1974). After stirring at room temperature for 20 hours the mixture is filtered and the filter material is rinsed with ethanol. The filtrate and rinse solution are combined and concentrated, and the residue is crystallized using ethanol. After repeated recrystallization from ethanol there are obtained 23.5 g of N-[[5-(benzyloxy)-4-oxo-4H-pyran-2-yl]methoxy]phthalimide as white crystals of m.p. 172° C.

N-[[5-(Benzyloxy)-4-oxo-4H-pyran-2-yl]methoxy]-phthalimide (1.77 g) (4.7 mmol) are suspended in 250 ml of dichloromethane and treated at −70° C. with 1.32 g (5.2 mmol) of boron tribromide (dissolved in 5 ml of dichloromethane). The mixture is stirred at −70° C. for 3 hours and at room temperature for 20 hours. The solvent is removed in a vacuum and the residue is treated at 0° C. with about 70 ml of water and 10 ml of ethanol. After stirring for 2 hours the product is filtered off and washed in succession with water, ethanol and diethyl ether. There are obtained 1.3 g of N-[(5-hydroxy-4-oxo-4H-pyran-2-yl)methoxy]phthalimide as a white powder of m.p. 200°–203° C. (dec.).

N-[(5-Hydroxy-4-oxo-4H-pyran-2-yl)methoxy]phthalimide (570 mg) (2 mmol) are suspended in 5 ml of absolute dimethylformamide and treated at −10° C. with 100 mg (2 mmol) of methylhydrazine. After stirring at room temperature for 1.5 hours the mixture is concentrated in a high vacuum and the residue is treated with about 15 ml of ethanol. 2 g of p-toluenesulphonic acid hydrate are added thereto and the product is precipitated by the addition of about 90 ml of diethyl ether. After two-fold recrystallization from ethanol/diethyl ether there are obtained 460 mg of 2-[(aminooxy)methyl]-5-hydroxy-4H-pyran-4-one p-toluenesulphonate (1:1) as white crystals of m.p. 167° C. (dec.).

EXAMPLE 15

Manufacture of (6R,7R)-7-[(Z)-2-(2-amino-4-thiazolyl)-2-[[(2-fluoro-(3,4-dihydroxybenzyl)oxy]imino]acetamido]-3-[[[5-(3,4-dihydroxyphenyl)-2-phenyl-4-pyrimidinyl]thio]methyl]-8-oxo-5-thia-1-azabicyclo[4.2.0]oct-2-ene-2-carboxylic acid (6R,7R)-7-(2-Amino-4-thiazoleglyoxylamido)-3-[[(5-(3,4-dihydroxyphenyl)-2-phenyl-4-pyrimidinyl)thio]-methyl]-8-oxo-5-thia-1-azabicyclo[4.2.0]oct-2-ene-2-carboxylic acid (66 mg) (0.1 mmol) and 47 mg (0.13 mmol) of O-[(4-fluoro-2,2-diphenyl-1,3-benzodioxol-5-yl)methyl]hydroxylamine hydrochloride are dissolved in 1 ml of absolute of dimethylacetamide. After stirring at room temperature for 20 hours the mixture is concentrated in a high vacuum at room temperature and the residue is treated with 0.45 ml of ethanol and 3 ml of water. The precipitated product is filtered off and washed with water. After drying in a high vacuum at room temperature there are obtained 98 mg of (6R,7R)-7-[(Z)-2(2-amino-4-thiazolyl)-2-[[(4-fluoro-2,2-di phenyl-1,3-benzodioxol-5-yl)methoxy]imino]acetamido]-3-[[5-(3,4-dihydroxyphenyl)-2-phenyl-4-pyrimidinyl]thio]methyl]-8-oxo-5-thia-1-azabicyclo[4.2.0]oct-2-ene-2-carboxylic acid as a beige powder.

$^1$H NMR (DMSO-d$_6$): signals at, inter alia, 3.64 (d, J=18 Hz, 1H), 4.18 (d, J=12.5 Hz, 1H), 4.69 (d, J=12.5 Hz, 1H), 5.06 (s, 2H), 5.09 (d, J=5 Hz, 1H), 5.73 (dd, J=5 Hz and J=8 Hz, 1H), 6.71 (s, 1H), 6.75–7.0 (5H), 7.22 (s, 2H), 7.3–7.6 (13H), 8.46 (s, 1H), 8.47 (2H), 9.25 (s, 1H), 9.33 (s, 1H), 9.60 (d, J=8 Hz, 1H).

(6R,7R)-7-[(Z)-2-(2-Amino-4-thiazolyl)-2-[[(4-fluoro-2,2-diphenyl-1,3-benzodioxol-5-yl)methoxy]imino]acetamido]-3-[[5-(3,4-dihydroxyphenyl)-2-phenyl-4-pyrimidinyl]thio]methyl]-8-oxo-5-thia-1-azabicyclo[4.2.0]oct-2-ene-2-carboxylic acid (95 mg) (0.097 mmol) are stirred in 3 ml of trifluoroacetic acid for 5.5 hours. The solution is evaporated and the residue is crystallized using 5 ml of ether. The product is filtered off under suction, washed with diethyl ether and dried in a high vacuum at room temperature. There are obtained 75 mg of (6R,7R)-7-[(Z)-2-(2-amino-4-thiazolyl)-2-[[(2-fluoro-(3,4-dihydroxybenzyl)-oxy]imino]acetamido]-3-[[[5-(3,4-dihydroxyphenyl)-2-phenyl-4-pyrimidinyl]thio]methyl]-8-oxo-5-thia-1-azabicyclo[4.2.0]oct-2-ene-2-carboxylic acid as a yellow powder.

$^1$H NMR (DMSO-d$_6$): signals at, inter alia, δ3.52 (d, J=18 Hz, 1H), 3.78 (d, J=18 Hz, 1H), 4.17 (d, J=12.5 Hz), 4.74 (d, J=12.5 Hz, 1H), 5.01 (s, 2H), 5.14 (d, J=5 Hz, 1H), 5.76 (dd, J=5 Hz and J=8 Hz, 1H), 6.52 (dd, J=8 Hz and J=2 Hz, 1H), 6.66 (d, J=8 Hz, 1H), 6.69 (s, 1H), 6.78 (dd, J=8 Hz, J=2 Hz, 1H), 6.87 (d, J=8 Hz, 1H), 6.91 (d, J=2 Hz, 1H), 7.32 (2H), 7.57 (3H), 8.44 (s, 1H), 8.48 (2H), 9.64 (d, J=5Hz, 1H).

The (6R,7R)-7-(2-amino-4-thiazoleglyoxylamido)-3-[[(5-(3,4-dihydroxyphenyl)-2-phenyl-4-pyrimidinyl]thio]methyl]-8-oxo-5-thia-1-azabicyclo[4.2.0]oct-2-ene-2-carboxylic acid used as the starting material can be prepared as follows:

(3,4-Dimethoxyphenyl)malonaldehyde acid methyl ester (7.2 g) (30 mmol) and 10 g (42 mmol) of benzamidine are melted at 100° C. The reaction mixture is chromatographed on 250 g of silica gel (0.063–0.2 mm) and the product is eluted with dichloromethane/methanol (9:1 v/v). The eluate is concentrated in a vacuum at 45° C. and the crystalline product is filtered off under suction. The whole is washed with diethyl ether and dried in a high vacuum at room temperature. There are obtained 6.2 g of 5-(3,4-dimethoxyphenyl)-2-phenyl-6(1H)-pyrimidinone as yellow crystals of m.p. 230° C.

5-(3,4-Dimethoxyphenyl)-2-phenyl-6(1H)-pyrimidinone (7.4 g) are stirred in 250 ml of 48% aqueous hydrobromic acid at 100° C. for 24 hours and at 140° C. for 24 hours. After cooling the yellow crystals obtained are filtered off, washed with water and suspended in 200 ml of water. Sodium hydrogen carbonate is added thereto until pH 7.5 has been reached. After stirring for 2 hours the product is filtered off, washed with water and dried in a vacuum at room temperature over potassium hydroxide. There are obtained 6 g of 5-(3,4-dihydroxyphenyl)-2-phenyl-4(3H)-pyrimidinone hydrobromide as a yellow powder of m.p.>250° C.

$^1$H NMR (DMSO-d$_6$): signals at δ6.77 (d, J=8 Hz, 1H), 7.07 (dd, J=8 Hz and J=2H, 1H), 7.28 (d, J=2 Hz, 1H), 7.5–7.6 (3H), 8.1–8.2 (3H), 9.07 (broad, 2H), 12.86 (broad, 1H).

5-(3,4-Dihydroxyphenyl)-2-phenyl-4(3H)-pyrimidinone hydrobromide (6.0 g) (21.4 mmol) are dissolved in 100 ml of pyridine and treated at room temperature while stirring with 5.2 g (51 mmol) of acetic anhydride. After 1.5 hours 200 ml of diethyl ether are added thereto and the precipitated product is filtered off. The solid is washed with diethyl ether and dried in a high vacuum at 35° C. There are obtained 7.1 g of 4-(3,4-dihydro-4-oxo-2-phenyl-5-pyrimidinyl)-o-phenylene diacetate as white crystals of m.p. 240° C.

4-(3,4-Dihydro-4-oxo-2-phenyl-5-pyrimidinyl)-o-phenylene diacetate (6.8 g) (18.7 mmol) are dissolved in 150 ml of phosphorus oxychloride. After stirring at 100° C. for 6 hours the mixture is concentrated in a vacuum at 50° C. and the residue is dried in a vacuum. Now, dichloromethane and ice/water are added thereto and, after good intermixing, the dichloromethane phase is separated. After drying over sodium sulphate and distilling off the solvent the product is crystallized from ethanol. The product is filtered off and washed with ethanol/diethyl ether. There are obtained 6 g of 4-(4-chloro-2-phenyl-5-pyrimidinyl)-o-phenylene diacetate as white crystals of m.p. 152°–153° C.

4-(4-Chloro-2-phenyl-5-pyrimidinyl)-o-phenylene diacetate (6.0 g) (15.7 mmol) are suspended in 200 ml of methanol. 10 g of sodium hydrogen sulphide hydrate are added at 50° C. while stirring. After a further 4 hours at 60° C. the mixture is filtered and the filtrate is concentrated. The residue is dissolved in about 150 ml of water and the solution is brought to pH 5 with 1N aqueous hydrochloric acid. The precipitated product is filtered off under suction, washed with water, dried at room temperature and crystallized from ethanol. There are obtained 3.6 g of 5-(3,4-dihydroxyphenyl)-2-phenyl-4(3H)-pyrimidinethione as yellow crystals of m.p. 220° C.

7-Aminocephalosporanic acid (162 mg) (0.6 mmol) and 216 mg (0.66 mmol) of 5-(3,4-dihydroxyphenyl)-2-phenyl-4(3H)-pyrimidinethione are suspended in 7 ml of dichloromethane/sulpholane (1:1 v/v). 4 ml of boron trifluoride diethyl etherate are added thereto while stirring. After 16 hours the mixture is concentrated in a high vacuum at room temperature, the residue is washed with diethyl ether and dissolved in about 3 ml of water. Sodium hydrogen carbonate is added thereto until the pH is adjusted to 5. Then, 1 ml of diethyl ether and 0.5 ml of ethanol are added thereto. The precipitated product is filtered off under suction, washed in succession with water, ethanol and ether and dried in a high vacuum at room temperature. There are obtained 250 mg of (6R,7R)-7-amino-3-[[[5-(3,4-dihydroxyphenyl)-2-phenyl-4-pyrimidinyl]thio]methyl]-8-oxo-5-thia-1-azabicyclo[4.2.0]oct-2-ene-2-carboxylic acid as a beige powder.

$^1$H NMR (DMSO-d$_6$): signals at, inter alia, δ3.50 (d, J=18 Hz, 1H), 3.77 (d, J=18 Hz, 1H), 4.18 (d, J=12.5 Hz, 1H), 4.72 (d, J=12.5 Hz, 1H), 4.76 (d, J=5 Hz, 1H), 4.98 (d, J=5 Hz, 1H), 6.79 (dd, J=8 Hz and J=2 Hz, 1H), 6.88 (d, J=8 Hz, 1H), 6.92 (d, J=2 Hz, 1H), 7.5–7.6 (3H), 8.42 (s, 1H), 8.45 (2H), 9.25 (s, 1H), 9.32 (s, 1H).

(6R,7R)-7-Amino-3-[[[5-(3,4-dihydroxyphenyl)-2-phenyl-4-pyrimidinyl]thio]methyl]-8-oxo-5-thia-1-azabicyclo[4.2.0]oct-2-ene-2-carboxylic acid (1.02 g) (2 mmol) are suspended in 25 ml of water and 25 ml of acetonitrile. While stirring there are added dropwise thereto at 0° C. 27 ml of 0.1N aqueous potassium hydroxide and the solution is treated portionwise with 1.0 g (3 mmol) of 2-amino-4-thiazolethioglyoxylic acid S-(2-benzothiazolyl) ester. The mixture is stirred at 0° C. for 1 hour and at 15°–20° C. for 2 hours. The suspension is now filtered and filter material is washed with water. The mother liquor and wash solution are combined, washed with ethyl acetate and finally acidified (pH~4) with dilute, aqueous hydrochloric acid. The precipitated product is filtered off under suction and washed in succession with water and diethyl ether. After drying in a high vacuum at room temperature there is obtained 0.5 g of (6R,7R)-7-(2-amino-4-thiazoleglyoxylamido)-3-[[(5-(3,4-dihydroxy-phenyl)-2-phenyl-4-pyrimidinyl]thio]methyl]-8-oxo-5-thia-1-azabicyclo[4.2.0]oct-2-ene-2-carboxylic acid as a yellow powder.

$^1$H NMR (DMSO-d$_6$): signals at, inter alia, δ3.58 (d, J=18 Hz, 1H), 3.81 (d, J=18 Hz, 1H), 4.20 (d, J=12.5 Hz, 1H), 4.75 (d, J=12.5 Hz, 1H), 5.17 (d, J=5 Hz, 1H), 5.74 (dd, J=5 Hz and J=8 Hz, 1H), 6.78 (dd, J=8 Hz and J=2 Hz, 1H), 6.86 (d, J=8 Hz, 1H), 6.92 (d, J=2 Hz, 1H), 7.40 (s, 2H), 7.5–7.6 (3H), 7.80 (s, 1H), 8.44 (s, 1H), 8.48 (2H), 9.26 (s, 1H), 9.34 (s, 1H), 9.77 (d, J=8 Hz, 1H).

EXAMPLE 16

Manufacture of (6R,7R)-7-[(Z)-2-(2-amino-4-thiazolyl)-2-[[(1,4-dihydro-5-hydroxy-4-oxo-2-pyrimidinyl)methoxy]imino]acetamido]-3-[[[5-(3,4-dihydroxyphenyl)-2-phenyl-4-pyrimidinyl]thio]methyl]-8-oxo-5-thia-1-azabicyclo[4.2.0]oct-2-ene-2-carboxylic acid (6R,7R)-7-(2-Amino-4-thiazoleglyoxylamido)-3-[[(5-(3,4-dihydroxyphenyl)-2-phenyl-4-pyrimidinyl]thio]-methyl]-8-oxo-5-thia-1-azabicyclo[4.2.0]oct-2-ene-2-carboxylic acid (60 mg) (0.09 mmol), 20.5 mg (0.13 mmol) of 2-(aminooxy)methyl-5-hydroxy-4(1H)-pyrimidinone and 13 mg (0.13 mmol) of methanesulphonic acid are dissolved in 0.6 ml of absolute dimethylacetamide. After stirring at room temperature for 18 hours the mixture is concentrated in a high vacuum at room temperature and the residue is crystallized using ethanol. The product is washed with diethyl ether and dried in a high vacuum at room temperature. There are obtained 26 mg of (6R,7R)-7-[(Z)-2-(2-amino-4-thiazolyl)-2-[[(1,4-dihydro-5-hydroxy-4-oxo-2-pyrimidinyl)methoxy]imino]acetamido]-3-[[[5-(3,4-dihydroxyphenyl)-2-phenyl-4-pyrimidinyl]thio]methyl]-8-oxo-5-thia-1-azabicyclo[4.2.0]oct-2-ene-2-carboxylic acid as a yellow powder. A further 28 mg of yellow crystals of the same compound can be obtained from the mother liquor after concentration.

$^1$H NMR (DMSO-d$_6$): signals at, inter alia, δ3.53 (d, J=18 Hz, 1H), 3.83 (d, J=18 Hz, 1H), 4.19 (d, J=12.5 Hz, 1H), 4.75 (d, J=12.5 Hz, 1H), 4.88 (2H), 5.18 (d, J=5 Hz, 1H), 5.82 (dd, J=5 Hz and J=8 Hz, 1H), 6.79 (dd, J=2 Hz and J=8 Hz, 1H), 6.83 (s, 1H), 6.87 (d, J=8 Hz, 1H), 6.92 (d, J=2 Hz, 1H), 7.27 (s, 2H), 7.36 (s, 1H), 7.56 (3H), 8.43 (s, 1H), 8.46 (2H), 9.25 (s, 1H), 9.33 (s, 1H), 9.54 (s, 1H), 9.85 (d, J=8 Hz, 1H).

EXAMPLE 17

Manufacture of (6R,7R)-7-[(Z)-2-(2-amino-4-thiazolyl)-2-[[1-(hydroxycarbamoyl)-1-methylethoxy]imino]acetamido]-3-[[[5-(3,4-dihydroxyphenyl)-2-phenyl-4-pyrimidinyl]thio]methyl]-8-oxo-5-thia-1-azabicyclo[4.2.0]oct-2-ene-2-carboxylic acid (6R,7R)-7-(2-Amino-4-thiazoleglyoxylamido)-3-[[(5-(3,4-dihydroxyphenyl)-2-phenyl-4-pyrimidinyl]thio]-methyl]-8-oxo-5-thia-1-azabicyclo[4.2.0]oct-2-ene-2-carboxylic acid (33 mg) (0.05 mmol) and 11 mg (0.065 mMol) 2-(aminooxy)-N-hydroxy-2-methylpropionamide hydrochloride are dissolved in 0.8 ml of absolute dimethylacetamide. After stirring at room temperature for 22 hours the mixture is concentrated in a high vacuum and the residue is crystallized with water. The product is filtered off, washed with water, ethanol and diethyl ether and dried in a high vacuum at room temperature. There are obtained 32 mg of (6R,7R)-7-[(Z)-2-(2-amino-4-thiazolyl)-2-[[1-(hydroxycarbamoyl)-1-methylethoxy]imino]acetamido]-3-[[[5-(3,4-dihydroxyphenyl)-2-phenyl-4-pyrimidinyl]thio]methyl]-8-oxo-5-thia-1-azabicyclo[4.2.0]oct-2-ene-2-carboxylic acid as a beige powder.

$^1$H NMR (DMSO-d$_6$): signals at, inter alia, δ1.36 (s, 6H), 3.58 (d, J=18 Hz, 1H), 3.83 (d, J=18 Hz, 1H), 4.20 (d, J=12.5 Hz, 1H), 4.76 (d, J=12.5 Hz, 1H), 5.20 (d, J=5 Hz, 1H), 5.88 (dd, J=5 Hz and J=8 Hz, 1H), 6.79 (s, 1H), 6.79 (dd, J=8 Hz and J=2 Hz, 1H), 6.87 (d, J=8 Hz, 1H), 6.91 (d, J=2 Hz, 1H), 7.34 (s, 2H), 7.55 (3H), 8.44 (s, 1H), 8.46 (2H), 8.88 (1H), 9.23 (s, 1H), 9.33 (s, 1H), 9.62 (d, J=8 Hz, 1H), 10.05 (s, 1H).

EXAMPLE 18

Manufacture of (6R,7R)-7-[(Z)-2-(2-amino-4-thiazolyl)-2-[[(2,5-dichloro-3,4-dihydroxybenzyl)oxy]imino]acetamido]-3-[[[5-(3,4-dihydroxyphenyl)-2-phenyl-4-pyrimidinyl]thio]methyl]-8-oxo-5-thia-1-azabicyclo[4.2.0]oct-2-ene-2-carboxylic acid (6R,7R)-7-(2-Amino-4-thiazoleglyoxylamido)-3-[[(5-(3,4-dihydroxyphenyl)-2-phenyl-4-pyrimidinyl]thio]methyl]-8-oxo-5-thia-1-azabicyclo[4.2.0]oct-2-ene-2-carboxylic acid (66 mg) (0.1 mmol) and 55 mg (0.13 mmol) of 5-[(aminooxy)methyl]-4,7-dichloro-2,2-diphenyl-1,3-benzodioxol hydrochloride are dissolved in 2 ml of absolute dimethylacetamide. After stirring at room temperature for 24 hours the mixture is concentrated in a high vacuum and the residue is crystallized from ethanol/diethyl ether. There are obtained 130 mg of (6R,7R)-7-[(Z)-2-(2-amino-4-thiazoyl)-2-[[(4,7-dichloro-2,2-diphenyl-1,3-benzodioxol-5-yl)methoxy]imino]acetamido]-3-[[[5-(3,4-dihydrooxyphenyl)-2-phenyl-4-pyrimidinyl]thio]methyl]-8-oxo-5-thia-1-azabicyclo[4.2.0]oct-2-en-2-carboxylic acid as a yellowish powder.

$^1$H NMR (DMSO-d$_6$): signals at, inter alia, δ3.40 (d, J=18 Hz, 1H), 3.67 (d, J=18 Hz, 1H), 4.17 (d, J=12.5 Hz, 1H), 4.73 (d, J=12,5 Hz, 1H), 5.11 (d, J=5 Hz, 1H), 5.12 (s, 2H), 5.76 (dd, J=5 Hz and J=8 Hz, 1H), 6.78 (dd, J=8 Hz and J=2 Hz, 1H), 6.81 (s, 1H), 6.87 (d, J=8 Hz, 1H), 6.92 (d, J=2 Hz, 1H), 7.14 (s, 1H), 7.4–7.6 (15H), 8.45 (s, 1H), 8.47 (2H), 9.72 (d, J=8 Hz, 1H).

(6R,7R)-7-[(Z)-2-(2-Amino-4-thiazoyl)-2-[[(4,7-dichloro-2,2-diphenyl-1,3-benzodioxol-5-yl)methoxy]imino]acetamido]-3-[[[5-(3,4-dihydroxyphenyl)-2-phenyl-4-pyrimidinyl]thio]methyl]-8-oxo-5-thia-1-azabicyclo[4.2.0]oct-2-en-2-carboxylic acid (102 mg) (0.1 mmol) are dissolved in 3 ml of trifluoroacetic acid. After stirring at room temperature for 5 hours the mixture is concentrated in a vacuum at room temperature and the residue is crystallized from ethanol/diethyl ether. There are obtained 63 mg of (6R,7R)-7-[(Z)-2-(2-amino-4-thiazolyl)-2-[[(2,5-dichloro-3,4-dihydroxybenzyl)oxy]imino]acetamido]-3-[[[5-(3,4-dihydroxyphenyl)-2-phenyl-4-pyrimidinyl]thio]methyl]-8-oxo-5-thia-1-azabicyclo[4.2.0]oct-2-ene-2-carboxylic acid as a beige powder.

$^1$H NMR (DMSO-d$_6$): signals at, inter alia, δ3.52 (d, J=18 Hz, 1H), 3.79 (d, J=18 Hz, 1H), 4.18 (d, J=12,5 Hz, 1H), 4.75 (d, J=12,5 Hz, 1H), 5.08 (s, 2H), 5.16 (d, J=5 Hz, 1H), 5.77 (dd, J=5 Hz and J=8 Hz, 1H), 6.74 (s, 1H), 6.78 (dd, J=8 Hz and J=2 Hz), 6.87 (d, J=8 Hz, 1H), 6.92 (d, J=2 Hz, 1H), 6.93 (s, 1H), 7.28 (2H), 7.56 (3H), 8.44 (s, 1H), 8.46 (2H), 9.24 (1H), 9.31 (1H), 9.67 (2H), 9.70 (d, J=8 Hz, 1H).

The preparation of 5-[(aminooxy)methyl]-4,7-dichloro-2,2-diphenyl-1,3-benzodioxol hydrochloride is described in Example 29.

EXAMPLE 19

Manufacture of a) (6R,7R)-7-[(Z)-2-(2-amino-4-thiazolyl)-2-[[1-(hydroxycarbamoyl)-1-methylethoxy]imino]acetamido]-3-[[[5-(3,4-dihydroxyphenyl)-4-pyrimidinyl]thio]methyl]-8-oxo-5-thia-1-azabicyclo[4.2.0]oct-2-ene-2-carboxylic acid and b) (6R,7R)-7-[(Z)-2-(2-amino-4-thiazolyl)-2-[[1-(hydroxycarbamoyl)-2-methylethoxy]imino]acetamido]-3-[[[5-(3,4-dihydroxyphenyl)-2-methyl-4-pyrimidinyl]thio]methyl]-8-oxo-5-thia-1-azabicyclo[4.2.0]oct-2-ene-2-carboxylic acid a) (6R,7R)-7-(2-Amino-4-thiazoleglyoxylamido)-3-[[[5-(3,4dihydroxyphenyl)-4-pyrimidinyl]thio]methyl]-8-oxo-5-thia-1-azabicyclo[4.2.0]oct-2-ene-2-carboxylic acid (90 mg) (0.15 mmol) and 34 mg (0.2 mmol) of 2-(aminooxy)-N-hydroxy-2-methylpropionamide hydrochloride are dissolved in 2 ml of absolute dimethylacetamide. After stirring at room temperature for 24 hours the mixture is concentrated in a high vacuum at room temperature and the residue is crystallized from ethanol/diethyl ether. It is filtered off under suction and washed with ether and water. After drying in a high vacuum at room temperature there are obtained 72 mg of (6R,7R)-7-[(Z)-2-(2-amino-4-thiazolyl)-2--[[1-(hydroxycarbamoyl)-1-methylethoxy]imino]acetamido]-3-[[[5-(3,4-dihydroxyphenyl)-4-pyrimidinyl]thio]methyl]-8-oxo-5-thia-1-azabicyclo[4.2.0]oct-2-ene-2-carboxylic acid as a beige powder.

$^1$H NMR (DMSO-d$_6$): signals at, inter alia, δ1.40 (s, 3H), 1.42 (s, 3H), 3.50 (d, J=18 Hz, 1H), 3.75 (d, J=18 Hz, 1H), 3.90 (d, J=12.5 Hz, 1H), 4.70 (d, J=12.5 Hz, 1H), 5.16 (d, J=5 Hz, 1H), 5.86 (dd, J=5 Hz and J=8 Hz, 1H), 6.74 (dd, J=2 Hz and J=8 Hz, 1H), 6.80 (s, 1H), 6.82 (d, J=8 Hz, 1H), 6.86 (d, J=2 Hz, 1H), 8.32 (s, 1H), 8.86 (s, 1H), 9.63 (d, J=8 Hz, 1H), 10.07 (s, 1H).

b) (6R,7R)-7-[(Z)-2-(2-Amino-4-thiazolyl)-2-[[1-(hydroxycarbamoyl)-2-methylethoxy]imino]acetamido]-3-[[[5-(3,4-dihydroxyphenyl)-2-methyl-4-pyrimidinyl]thio]methyl]-8-oxo-5-thia-1-azabicyclo[4.2.0]oct-2-ene-2-carboxylic acid is beige and is manufactured analogously.

$^1$H NMR (DMSO-d$_6$): signals at, inter alia, δ1.40 (s, 3H), 1.42 (s, 3H), 3.77 (d, J=18 Hz, 1H), 3.92 (d, J=12.5 Hz, 1H), 4.74 (d, J=12.5 Hz, 1H), 5.18 (d, J=5 Hz, 1H), 5.86 (dd, J=5 Hz and J=8 Hz, 1H), 6.69 (dd, J=2 Hz and J=8 Hz, 1H), 6.82 (s, 1H), 6.83 (d, J=2 Hz, 1H), 6.84 (d, J=8 Hz, 1H), 8.20 (s, 1H), 9.63 (d, J=8 Hz, 1H), 10.08 (s, 1H).

The (6R,7R)-7-(2-amino-4-thiazoleglyoxylamido)-3-[[[5-(3,4-dihydroxyphenyl)-4-pyrimidinyl]thio]methyl]-8-oxo-5-thia-1-azabicyclo[4.2.0]oct-2-ene-2-carboxylic acid used as the starting material can be prepared as follows:

Methyl 2-formyl-2-(3,4-dimethoxyphenyl)acetate (7.2 g) (30 mmol), 4.8 g (60 mmol) of formamidine hydrochloride and 7.74 g (60 mmol) of N-ethyldiisopropylamine (Hünig base) are stirred in 60 ml of ethanol for 55 hours at 50° C. and subsequently concentrated in a vacuum. The residue is washed several times with diethyl ether and then crystallized using ethanol/diethyl ether. The yellowish product is filtered off under suction, washed with ethanol/diethyl ether and dried in a high vacuum at room temperature. There are obtained 1.6 g of 5-(3,4-dimethoxyphenyl)-4(3H)-pyrimidinone of m.p. 205°–206° C.

5-(3,4-Dimethoxyphenyl)-2-methyl-4(3H)-pyrimidinone is prepared analogously, m.p. 187°–188° C. (white solid).

5-(3,4-Dimethoxyphenyl)-4(3H)-pyrimidinone (9.28 g) (40 mmol) are refluxed in 300 ml of 48% aqueous hydrogen bromide solution for 48 hours. The suspension obtained is suction filtered, the filter material is taken up in water and the product is precipitated by the addition of sodium hydrogen carbonate. The precipitate is filtered off, washed with water and dried at room temperature. There are obtained 8.3 g of 5-(3,4-dihydroxyphenyl)-4(3H)-pyrimidinone hydrobromide as a beige powder. M.p.>270° C.

$^1$H NMR (DMSO-d$_6$): signals at δ6.75 (d, J=8 Hz, 1H), 6.97 (dd, J=8 Hz and J=2 Hz, 1H), 7.22 (d, J=2 Hz, 1H), 8.01 (s, 1H), 8.11 (s, 1H), 8.9–9.2 (2H).

5-(3,4-Dihydroxyphenyl)-2-methyl-4(3H)-pyrimidinone is prepared analogously. Beige-coloured solid of m.p. 237° C. (dec.).

$^1$H NMR (DMSO-d$_6$): signals at, inter alia, δ2.29 (s, 3H), 6.73 (d, J=8 Hz, 1H), 6.94 (dd, J=8 Hz and J=2 Hz, 1H), 7.20 (d, J=2 Hz, 1H), 7.91 (s, 1H), 8.8–9.2 (2H).

5-(3,4-Dihydroxyphenyl)-4(3H)-pyrimidinone hydrobromide (7.8 g) (38 mmol) are dissolved in 60 ml of absolute pyridine and treated with 15.3 ml (115 mmol) of acetic anhydride. The solution is stirred at room temperature for 5 hours and subsequently concentrated in a vacuum. The residue is crystallized from diethyl ether and recrystallized from ethanol. There are obtained 7.3 g of 4-(3,4-dihydro-4-oxo-5-pyrimidinyl)-o-phenylene diacetate as beige crystals of m.p. 183°–184° C.

4-(3,4-Dihydro-2-methyl-4-oxo-5-pyrimidinyl)-o-phenylene diacetate is prepared analogously. White crystals of m.p. 178°–179° C.

4-(3,4-Dihydro-4-oxo-5-pyrimidinyl)-o-phenylene diacetate (194 mg) (0.67 mmol) are added to 5 ml of phosphorus oxychloride. After stirring at 100° C. for 6 hours the mixture is concentrated in a vacuum at 40° C. The residue is dissolved in dichloromethane/methanol (99:1 v/v) and the solution is washed with water. The solution is dried over sodium sulphate and concentrated. The residue is crystallized using ethanol. The beige crystals are filtered off under suction, washed with petroleum ether and dried in a high vacuum at room temperature. There are obtained 90 mg of 4-(4-chloro-5-pyrimidinyl)-o-phenylene diacetate of m.p. 108° C.

4-(4-Chloro-2-methyl-5-pyrimidinyl)-o-phenylene diacetate is prepared analogously. M.p. 111° C. (white crystals).

4-(4-Chloro-5-pyrimidinyl)-o-phenylene diacetate (1.1 g) (3.6 mmol) are dissolved in 30 ml of methanol. 1.56 g of sodium hydrogen sulphide hydrate are added thereto and the mixture is stirred at 60° C. for 4.5 hours. The solvent is distilled off in a vacuum and the residue is dissolved in 20 ml of water. The solution is acidified with dilute aqueous hydrochloric acid to pH 5, the precipitated product is filtered off under suction and washed with water and diethyl ether. After drying in a high vacuum there are obtained 770 mg of 5-(3,4-dihydroxyphenyl)-4(3H)-pyrimidinethione as yellow crystals of m.p. 235° C. (dec.).

$^1$H NMR (DMSO-d$_6$): signals at δ6.74 (d, J=8 Hz, 1H), 6.81 (dd, J=8 Hz and J=2 Hz, 1H), 7.08 (d, J=2 Hz, 1H), 7.92 (s, 1H), 8.24 (1H), 8.98 (s, 1H), 9.08 (s, 1H), 14.18 (1H).

5-(3,4-Dihydroxyphenyl)-2-methyl-4(3H)-pyrimidinethione is prepared analogously. Yellow solid of m.p. 213°–215° C. (dec.).

$^1$H NMR (DMSO-d$_6$): signals at δ2.42 (s, 3H), 6.73 (d, J=8 Hz, 1H), 6.78 (dd, J=8 Hz and J=2 Hz, 1H), 7.06 (d, J=2 Hz, 1H), 7.82 (s, 1H), 9.0 (2H), 14.0 (1H).

7-Aminocephalosporanic acid (220 mg) (0.81 mmol) and 250 mg (1.04 mmol) of 5-(3,4-dihydroxyphenyl)-4(3H)-pyrimidinethione are suspended in 8 ml of sulpholane/dichloromethane (1:1 v/v) and treated with 5 ml of boron trifluoride diethyl etherate while stirring.

After 18 hours the mixture is concentrated in a vacuum and the residue is washed with diethyl ether. Then, 2 ml of ethanol and 4 ml of water are added thereto and sodium hydrogen carbonate is added until pH 5 has been reached. The product is filtered off under suction, washed with water and diethyl ether and dried in a high vacuum at room temperature. There are obtained 311 mg of (6R,7R)-7-amino-3-[[[5-(3,4-dihydroxyphenyl)-4-pyrimidinyl]thio]methyl]-8-oxo-5-thia-1-azabicyclo[4.2.0]oct-2-ene-2-carboxylic acid as a beige powder.

$^1$H NMR (DMSO-d$_6$): signals at, inter alia, δ3.41 (d, J=18 Hz, 1H), 3.70 (d, J=18 Hz, 1H), 3.89 (d, J=12.5 Hz, 1H), 4.66 (d, J=12.5 Hz, 1H), 4.73 (d, J=5 Hz, 1H), 4.94 (d, J=5 Hz, 1H), 6.72 (dd, J=2 Hz and J=8 Hz, 1H), 6.82 (d, J=8 Hz, 1H), 6.85 (d, J=2 Hz, 1H), 8.31 (s, 1H), 8.86 (s, 1H), 9.22 (s, 1H), 9.30 (s, 1H).

(6R,7R)-7-Amino-3-[[5-(3,4-dihydroxyphenyl)-2-methyl-4-pyrimidinyl]thio]methyl]-8-oxo-5-thia-1-azabicyclo[4.2.0]oct-2-ene-2-carboxylic acid is prepared analogously (beige solid).

$^1$H NMR (DMSO-d$_6$): signals at, inter alia, δ3.42 (d, J=18 Hz, 1H), 3.68 (d, J=18 Hz, 1H), 3.87 (d, J=12.5 Hz, 1H), 4.68 (d, J=12.5 Hz, 1H), 4.73 (d, J=5 Hz, 1H), 4.96 (d, J=5 Hz, 1H), 6.69 (dd, J=2 Hz and J=8 Hz, 1H), 6.81 (d, J=8 Hz, 1H), 6.81 (d, J=2 Hz, 1H), 8.18 (s, 1H), 9.20 (s, 1H), 9.25 (s, 1H).

(6R,7R)-7-Amino-3-[[[5-(3,4-dihydroxyphenyl)-4-pyrimidinyl]thio]methyl]-8-oxo-5-thia-1-azabicyclo[4.2.0]oct-2-ene-2-carboxylic acid (215 mg) (0.5 mmol) are suspended in 10 ml of water and 5 ml of acetonitrile. At 0° C. there are added dropwise thereto while stirring 7.5 ml of 0.1N aqueous potassium hydroxide solution and after 30 minutes there are added portionwise thereto within one hour 210 mg (0.65 mmol) of 2-amino-4-thiazoleglyoxylic acid S-(2-benzothiazolyl) ester. After a further 5 hours 0.1N aqueous potassium hydroxide solution is added thereto until pH 7.8 has been reached. The suspension obtained is filtered, the filtrate is washed with ethyl acetate and acidified (pH 5) with dilute aqueous hydrochloric acid. The precipitated product is filtered off under suction and washed with water and diethyl ether. After drying in a high vacuum there are obtained 200 mg of (6R,7R)-7-(2-amino-4-thiazoleglyoxylamido)-3-[[[5-(3,4-dihydroxyphenyl)-4-pyrimidinyl]thio]methyl]-8-oxo-5-thia-1-azabicyclo[4.2.0]oct-2-ene-2-carboxylic acid as a beige powder.

$^1$H NMR (DMSO-d$_6$): signals at, inter alia, δ3.52 (d, J=18 Hz, 1H), 3.74 (d, J=18 Hz, 1H), 3.93 (d, J=12.5 Hz, 1H), 4.70 (d, J=12.5 Hz, 1H), 5.13 (d, J=5 Hz, 1H), 5.72 (dd, J=5 Hz and J=8 Hz, 1H), 6.73 (dd, J=2 Hz and J=8 Hz, 1H), 6,85 (d, J=8 Hz, 1H), 6.86 (d, J=2 Hz, 1H), 7.40 (s, 2H), 7.81 (s, 1H), 8.32 (s, 1H), 8.86 (s, 1H), 9.23 (s, 1H), 9.31 (s, 1H), 9.77 (d, J=8 Hz, 1H).

(6R,7R)-7-(2-Amino-4-thiazoleglyoxylamido)-3-[[[5-(3,4-dihydroxyphenyl)-2-methyl-4-pyrimidinyl]thio]methyl]-8-oxo-5-thia-1-azabicyclo[4.2.0]oct-2-ene-2-carboxylic acid is prepared in the same manner (beige powder).

$^1$H NMR (DMSO-d$_6$): signals at, inter alia, δ2.60 (s, 3H), 3.52 (d, J=18 Hz, 1H), 3.73 (d, J=18 Hz, 1H), 3.94 (d, J=12.5 Hz, 1H), 4.70 (d, J=12.5 Hz, 1H), 5.16 (d, J=5 Hz, 1H), 5.72 (dd, J=5 Hz and J=8 Hz, 1H), 6.68 (dd, J=2 Hz and J=8 Hz, 1H), 6.82 (d, J=2 Hz, 1H), 6.83 (d, J=8 Hz, 1H), 7.40 (s, 2H), 7.80 (s, 1H), 8.19 (s, 1H), 9.18 (s, 1H), 9.24 (s, 1H), 9.75 (d, J=8 Hz, 1H).

EXAMPLE 20

Manufacture of (6R,7R)-7-[(Z)-2-(2-amino-4-thiazolyl)-2-[[(2,5-dichloro-3,4-dihydroxybenzyl)oxy]imino]acetamido]-3-[[[5-(3,4-dihydroxyphenyl)-4-pyrimidinyl]thio]methyl]-8-oxo-5-thia-1-azabicyclo[4.2.0]oct-2-ene-2-carboxylic acid (6R,7R)-7-(2-Amino-4-thiazoleglyoxylamido)-3-[[[5-(3,4-dihydroxyphenyl)-4-pyrimidinyl]thio]methyl]-8-oxo-5-thia-1-azabicyclo[4.2.0]oct-2-ene-2-carboxylic acid (100 mg) (0.17 mmol) and 93 mg (0.22 mmol) of 5-[(aminooxy)methyl]-4,7-dichloro-2,2-diphenyl-1,3-benzodioxol hydrochloride are dissolved in 2 ml of absolute dimethylacetamide. After stirring at room temperature for 20 hours the solvent is distilled off in a high vacuum at room temperature. The residue is crystallized using diethyl ether. The product is filtered off under suction and washed with diethyl ether and water. There are obtained 160 mg of (6R,7R)-7-[(Z)-2-(2-amino-4-thiazolyl)-2-[[(4,7-dichloro-2,2-diphenyl-1,3-benzodioxol-5-yl)methoxy]imino]-acetamido]-3-[[[5-(3,4-dihydroxyphenyl)-4-pyrimidinyl]thio]-methyl]-8-oxo-5-thia-1-azabicyclo[4.2.0]oct-2-ene-2-carboxylic acid as a beige powder after drying in a high vacuum at room temperature.

$^1$H NMR (DMSO-d$_6$): signals at, inter alia, δ3.89 (d, J=12.5 Hz, 1H), 4.66 (d, J=12.5 Hz, 1H), 5.08 (d, J=5 Hz, 1H), 5.11 (2H), 5.74 (dd, J=5 Hz and J=8 Hz, 1H), 6.72 (dd, J=2 Hz and J=8 Hz, 1H), 6.78 (s, 1H), 6.86 (d, J=2 Hz, 1H), 6.86 (d, J=8 Hz, 1H), 7.14 (s, 1H), 7.4–7.6 (10H), 8.32 (s, 1H), 8.84 (s, 1H), 9.67 (d, J=8 Hz, 1H).

(6R,7R)-7-[(Z)-2-(2-Amino-4-thiazolyl)-2-[[(4,7-dichloro-2,2-diphenyl-1,3-benzodioxol-5-yl)methoxy]imino]acetamido]-3-[[[5-(3,4-dihydroxyphenyl)-4-pyrimidinyl]thio]methyl]-8-oxo-5-thia-1-azabicyclo[4.2.0]oct-2-ene-2-carboxylic acid (165 mg) are dissolved in 3 ml of trifluoroacetic acid. After stirring at room temperature for 15 hours the mixture is concentrated in a vacuum and the residue is crystallized from diethyl ether. The crystals are filtered off under suction and washed with diethyl ether/ethanol (10:1 v/v). After drying in a high vacuum there are obtained 115 mg of (6R,7R)-7-(2-amino-4-thiazoleglyoxylamido)-3-[[[5-(3,4-dihydroxyphenyl)-4-pyrimidinyl]thio]methyl]-8-oxo-5-thia-1-azabicyclo[4.2.0]oct-2-ene-2-carboxylic acid as a yellowish powder.

$^1$H NMR (DMSO-d$_6$): signals at, inter alia, δ3.41 (d, J=18 Hz, 1H), 3.69 (d, J=18 Hz, 1H), 3.87 (d, J=12.5 Hz, 1H), 4.67 (d, J=12.5 Hz, 1H), 5.08 (2H), 5.10 (d, J=5 Hz, 1H), 5.74 (dd, J=5 Hz and J=8 Hz, 1H), 6.72 (dd, J=2 Hz and J=8 Hz, 1H), 6.75 (s, 1H), 6.84 (d, J=8 Hz, 1H), 6.84 (d, J=2 Hz, 1H), 6.96 (s, 1H), 8.32 (s, 1H), 8.88 (s, 1H), 9.70 (d, J=8 Hz, 1H).

The preparation of 5-[(aminooxy)methyl]-4,7-dichloro-2,2-diphenyl-1,3-benzodioxol hydrochloride is described in Example 29.

EXAMPLE 21

Manufacture of (6R,7R)-7-[(Z)-2-(2-amino-4-thiazolyl)-2-[[(1-hydroxycarbamoyl)-1-methylethoxy]imino]acetamido]-3-[[(3,4-dihydroxyphenyl)sulphonyl]methyl]-8-oxo-5-thia-1-azabicyclo[4.2.0]oct-2-ene-2-carboxylic acid (6R, 7R)-7-(2-Amino-4-thiazoleglyoxylamido)-3-[[(3,4-dihydroxyphenyl)sulphonyl]methyl]-8-oxo-5-thia-1-azabicyclo[4.2.0]oct-2-ene-2-carboxylic acid (0.50 g) (0.93 mmol) is dissolved in 5 ml of dimethylacetamide and stirred with 0.21 g (1.20 mmol) of 2-

(aminooxy)-N-hydroxy-2-methylpropionamide hydrochloride for 20 hours at room temperature. The dimethylacetamide is evaporated in a high vacuum and the residue is triturated with water. The solid is collected by filtration and purified by chromatography on silica gel with water/acetonitrile as the eluent. There are obtained 240 mg of (6R,7R)-7-[(Z)-2-(2-amino-4-thiazolyl)-2-[[(1-hydroxycarbamoyl)-1-methylethoxy]imino]acetamido]-3-[[(3,4-dihydroxyphenyl)sulphonyl]methyl]-8-oxo-5-thia-1-azabicyclo[4.2.0]oct-2-ene-2-carboxylic acid as a white lyophilizate.

$^1$H-NMR (D$_2$O, 250 MHz): signals at δ (ppm): 1.56 (s, 3H), 1.57 (s, 3H), 3.37 (d, J=18 Hz, 1H), 3.68 (d, J=18 Hz, 1H), 4.13 (d, J=12.5 Hz, 1H), 5.16 (d, J=12.5 Hz, 1H), 5.22 (d, J=5 Hz, 1H), 5.81 (d, J=5 Hz, 1H), 7.00–7.40 (m, 4H). IR: 1768 cm$^{-1}$ MS: 679 (M+H$^\oplus$)

The (6R,7R)-7-(2-amino-4-thiazoleglyoxylamido)-3-[[(3,4-dihydroxyphenyl)sulphonyl]methyl]-8-oxo-5-thia-1-azabicyclo[4.2.0]oct-2-ene-2-carboxylic acid required as the starting material can be prepared as follows:

A solution of butyllithium (0.6M) (74 ml) in n-hexane are mixed with 116 ml of diethyl ether and cooled to −55° C. Thereupon, a solution of 40.0 g of 5-bromo-2,2-diphenyl-1,3-benzodioxol in 170 ml of diethyl ether is added dropwise. The reaction mixture is stirred for 1 hour, whereby the temperature rises to −15° C. Subsequently, the mixture is cooled to −50° C. and dry sulphur dioxide gas is introduced for 45 minutes. The excess sulphur dioxide gas is removed by passing dry argon through the mixture for 1 hour. The reaction mixture is left to come to room temperature. There thereby results a white precipitate, which is filtered off and dried. There are obtained 22.2 g of 2,2-diphenyl-1,3-benzodioxol-5-sulphinic acid lithium salt as white crystals of m.p.>300° C. (dec.).

7-Amino-3-chloromethyl-cephalosporanic acid p-methoxybenzyl ester hydrochloride (6.00 g) are dissolved in 60 ml of dimethyl sulphoxide, treated with 3.00 g of sodium iodide and 7.20 g of 2,2-diphenyl-1,3-benzodioxol-5-sulphinic acid lithium salt and stirred at room temperature for 2 hours. The solvent is evaporated under a high vacuum and the residue is partitioned between ethyl acetate and saturated aqueous potassium hydrogen carbonate solution. Their thereby results a white precipitate which is filtered off and dissolved in 20 ml of trifluoroacetic acid, 10 ml of anisole and 2 ml of water and stirred at room temperature for 5 hours. The solvents are evaporated firstly in a water-jet vacuum, then in a high vacuum. The dark residue is partitioned between ethyl acetate and 1N aqueous hydrochloric acid. The aqueous phase is treated with active charcoal and the product is precipitated by adjusting the pH to 3.50. There are obtained 2.20 g of (6R,7R)-7-amino-3-[[(3,4-dihydroxyphenyl)sulphonyl]methyl]-8-oxo-5-thia-1-azabicyclo[4.2.0]oct-2-ene-2-carboxylic acid as a white powder.

$^1$H-NMR (DMSO-d$_6$, 250 MHz): signals at δ (ppm) 3.46 (s, 2H), 4.17 (d, J=14 Hz, 1H), 4.76 (d, J=5 Hz, H), 4.92 (d, J=14 Hz, 1H), 4.98 (d, J=5 Hz, 1H), 6.90 (d, J=8.5 Hz, 1H), 7.10 (m, 2H), 9.8 (s, broad, 1H), 10.2 (s, broad, 1H) IR (KBr) 1777 cm$^{-1}$ MS: 384 (M+H$^\oplus$)

(6R, 7R)-7-Amino-3-[[(3,4-dihydroxyphenyl)sulphonyl]methyl]-8-oxo-5-thia-1-azabicyclo[4.2.0]oct-2-ene-2-carboxylic acid (190 mg) (0.50 mmol) are dissolved in 2.0 ml of a 1:1 mixture of water and acetonitrile by the addition of 0.075 ml (0.50 mmol) of triethylamine. This solution is cooled to 0° C. and treated with 280 mg (~0.75 mmol) of 2-amino-4-thiazoleglyoxylic acid S-(2-benzothiazolyl) ester and stirred for 1.5 hours. The solids are separated by centrifugation. The clear supernatant is partitioned between water and ethyl acetate, the aqueous phase is concentrated to about half and the product is precipitated by acidification to pH 2.0. After drying in a high vacuum there are obtained 180 mg of (6R,7R)-7-(2-amino-4-thiazoleglyoxylamido)-3-[[(3,4-dihydroxyphenyl)sulphonyl]methyl]-8-oxo-5-thia-1-azabicyclo[4.2.0]oct-2-ene-2-carboxylic acid as a yellow powder.

$^1$H-NMR (DMSO-d$_6$, 250 MHz): signals at δ (ppm): 3.58 (m, 2H), 4.27 (d, J=12.5 Hz, 1H), 4.94 (d, J=12.5 Hz, 1H), 5.20 (d, J=5 Hz, 1H), 5.76 (dd, J=5 Hz, J=7 Hz, 1H), 6.92 (d, J=8 Hz, 1H), 7.14 (m, 2H), 7.41 (s, 2H), 7.83 (s, 1H), 9.77 (s, 1H), 9.81 (d, J=8 Hz), 10.18 (s, 1H), 13.62 (s, broad, 1H). MS: 541 (M+H$^\oplus$) IR: 1773 cm$^{-1}$

EXAMPLE 22

Manufacture of (6R,7R)-7-[(Z)-2-(2-amino-4-thiazolyl)-2-[[(3,4-dihydroxysulphonyl)methoxy]imino]acetamido]-3-[[(3,4-dihydroxyphenyl)sulphonyl]methyl]-8-oxo-5-thia-1-azabicyclo[4.2.0]oct-2-ene-2-carboxylic acid sodium salt (6R,7R)-7-(2-Amino-4-thiazoleglyoxylamido)-3-[[(3,4-dihydroxyphenyl)sulphonyl]methyl]-8-oxo-5-thia-1-azabicyclo[4.2.0]oct-2-ene-2-carboxylic acid (0.50 g) (0.93 mmol) is dissolved in 5.00 ml of dimethylacetamide, treated with 0.31 g (1.20 mmol) of 4-[[(aminooxy)methyl]sulphonyl]pyrocatechol hydrochloride and stirred at room temperature for 20 hours. The dimethylacetamide is evaporated in a high vacuum. The residue is treated with water and the resulting precipitate is isolated by filtration and resuspended in water. This precipitate is brought into solution at pH 6.6 by the addition of 1N aqueous sodium hydroxide solution. Purification is effected by chromatography on RP12-Kieselgel with water/acetonitrile as the eluent. After lyophilization there are obtained 520 mg of (6R,7R)-7-[(Z)-2-(2-amino-4-thiazolyl)-2-[[(3,4-dihydroxysulphonyl)methoxy]imino]acetamido]-3-[[(3,4-dihydroxyphenyl)sulphonyl]methyl]-8-oxo-5-thia-1-azabicyclo[4.2.0]oct-2-ene-2-carboxylic acid sodium salt as a pale yellow solid.

$^1$H-NMR (D$_2$O, 250 MHz): signals at δ (ppm): 3.09 (d, J=18 Hz, 1H), 3.50 (d, J=18 Hz, 1H), 4.10 (d, J=12.5 Hz, 1H), 4.96 (d, J=5 Hz, 1H), 5.15 (d, J=12.5 Hz, 1H), 5.45 (m, 2H), 5.61 (d, J=5 Hz, 1H), 7.0–7.4 (m, 7H) MS: 763,9 (M+H$^\oplus$) IR (KBr): 1767 cm$^{-1}$

EXAMPLE 23

Manufacture of (6R,7R)-7-[(Z)-2-(2-amino-4-thiazolyl)-2-[[(3,4-dihydroxybenzyl)oxy]imino]acetamido]-3-[[(3,4-dihydroxyphenyl)sulphonyl]methyl]-8-oxo-5-thia-1-azabicyclo[4.2.0]oct-2-ene-2-carboxylic acid (6R,7R)-7-(2-Amino-4-thiazoleglyoxylamido)-3-[[(3,4-dihydroxyphenyl)sulphonyl]methyl]-8-oxo-5-thia-1-azabicyclo[4.2.0]oct-2-ene-2-carboxylic acid (190 mg) (0.50 mmol) are dissolved in 3 ml of dimethylacetamide, treated with 220 mg (0.62 mmol) of O-[3,4-[(diphenylmethylene)dioxy]benzyl]hydroxylamine hydrochloride and stirred at room temperature for 20 hours. The dimethylacetamide is evaporated in a high vacuum. The residue is triturated with water. The solid is filtered off, dissolved in trifluoroacetic acid and left to stand at room temperature for 1 hour. The trifluoroacetic acid is evaporated and the residue is triturated with ether. The solid is filtered off and subsequently purified by chromatography on RP12-Kieselgel with water/acetonitrile as the eluent. After lyophilization there are obtained 100 mg of (6R,7R)-7-[(Z)-2-(2-amino-4-thiazolyl)-2-[[(3,-4-dihydroxybenzyl)oxy]imino]acetamido]-3-[[(3,4-dihydroxyphenyl)sulphonyl]methyl]-8-oxo-5-thia-1-azabicyclo[4.2.0]oct-2-ene-2-carboxylic acid as a white solid.

$^1$H-NMR (DMSO-d$_6$, 250 MHz): signals at δ (ppm) 3.37 (m, 2H), 3.86 (d, J=12.5 Hz, 1H), 4.91 (s, 2H), 4.95 (d, J=5 Hz, 1H), 5.54 (m, 2H), 6.6–7.2 (m, 6H, aromat.), 6.71 (s, 1H), 7.21 (s, 2H), 9.5 (d, J=8 Hz, 1H) MS: 678 (M+H⊕) IR: 1767 cm$^-$

EXAMPLE 24

Manufacture of (6R,7R)-7-[(Z)-2-(2-amino-4-thiazolyl)-2-[[(3,4-dihydroxybenzyl)oxy]imino]acetamido]-3-[[[2-(hydrooxycarbamoyl)-5-methyl-s-triazolo[1,5-a]pyrimidin-7-yl]thio]methyl]-8-oxo-5-thia-1-azabicyclo[4.2.-0]oct-2-ene-2-carboxylic acid A solution of 200 mg (0.457 mmol) of (6R,7R)-7-amino-3-[[[2-(hydroxycarbamoyl)-5-methyl-s-triazolo[1,5-a]pyrimidin-7-yl]thio]methyl]-8-oxo-5-thia-1-azabicyclo[4.2.0]oct-2-ene-2-carboxylic acid and 346 mg (0.55 mmol) of S-(2-benzothiazolyl)-2-amino-4-thiazoleglyoxylate (Z)-O-[3,4-[(diphenylmethylene]dioxybenzyl]oxime in 19 ml of dimethylacetamide is stirred at room temperature for 7 hours and subsequently concentrated in a high vacuum. The residue is suspended in water and filtered off under suction. The filter material is suspended three times in ethyl acetate, filtered off under suction and subsequently washed with ethyl acetate, ethanol, dichloromethane and diethyl ether. There are obtained 295 mg of (6R,7R)-7-[(Z)-2-(2-amino-4-thiazolyl)-2-[[[3,4-[(diphenylenemethylene)dioxy]benzyl]oxy]imino]acetamido]-3-[[[2-(hydroxycarbamoyl)-5-methyl-s-triazolo[1,5-a]pyridin-7-yl]thio]methyl]-8-oxo-5-thia-1-azabicyclo[4.2.0]oct-2-ene-2-carboxylic acid as a beige powder.

$^1$H NMR (DMSO-d$_6$): signals at, inter alia, δ2.60 (s, 3H), 3.52 (d, J=18 Hz, 1H), 3.74 (d, J=18 Hz, 1H), 4.36 (d, J=12.5 Hz, 1H), 4.42 (d, J=12.5 Hz, 1H), 5.02 (s, 2H), 5.18 (d, J=5 Hz, 1H), 5.81 (dd, J=5 Hz and 8 Hz, 1H), 6.71 (s, 1H), 6.88 (dd, 1H), 6.98 (d, J=9 Hz), 7.04 (d, 1H), 7.29 (s, 2H), 7.34–7.60 (10H), 9.72 d (d, J=8 Hz, 1H).

(6R,7R)-7-[(Z)-2-(2-Amino-4-thiazolyl)-2-[[[3,4-[(d iphenylenemethylene)dioxy]benzyl]oxy]imino]acetamido]-3-[[[2-(hydroxycarbamoyl)-5-methyl-s-triazolo[1,5-a]pyridin-7-yl]thio]methyl]-8-oxo-5-thia-1-azabicyclo[4.2.0]oct-2-ene-2-carboxylic acid (250 mg) (0.28 mmol) are dissolved in 16 ml of trifluoroacetic acid at 0° C. After stirring at 0° C. for 5 hours the solvent is removed in a high vacuum at room temperature. The residue is suspended in ethanol/diethyl ether. The product is filtered off and washed with diethyl ether. There are obtained 80 mg of (6R,7R)-7-[(Z)-2-(2-amino-4-thiazolyl)-2-[[(3,4-dihydroxybenzyl)oxy]imino]acetamido]-3-[[[2-(hydroxycarbamoyl)-5-methyl-s-triazolo[1,5-a]pyrimidin-7-yl]thio]methyl]-8-oxo-5-thia-1-azabicyclo[4.2.0]oct-2-ene-2-carboxylic acid as a pale beige coloured powder.

$^1$H NMR (DMSO-d$_6$): signals at, inter alia, δ2.60 (s, 3H), 3.56 (d, J=18 Hz), 3.78 (d, J=18 Hz, 1H), 4.40 (d, J=12.5 Hz, 1H), 4.47 (d, J=12.5 Hz, 1H), 4.92 (s, 2H), 5.17 (d, J=5 Hz, 1H), 5.80 (dd, J=5 Hz and J=8 Hz, 1H), 6.6–6.8 (4H), 7.23 (s (broad), 2H), 7.39 (s, 1H), 8.84 (s, 1H), 8.89 (s, 1H), 9.37 (s (broad), 1H), 9.66 (d, J=8 Hz, 1H).

The (6R,7R)-7-amino-3-[[[2-(hydroxycarbamoyl)-5-methyl-s-triazolo[1,5-a]pyrimidin-7-yl]thio]methyl]-8-oxo-5-thia-1-azabicyclo[4.2.0]oct-2-ene-2-carboxylic acid used as the starting material can be prepared as follows:

Triethylamine (1.35 g) (13.37 mmol) are added dropwise at 0° C. to a solution of 0.62 g (8.92 mmol) of hydroxylamine hydrochloride in 15 ml of absolute methanol. The mixture is stirred for 10 minutes and subsequently a solution of 1.0 g (4.46 mmol) of methyl 7-mercapto-5-methyl-s-triazolo[1,5-a]pyrimidine-2-carboxylate (known from EPOS 303,172) in 30 ml of absolute methanol is added dropwise. After stirring at room temperature for 3 days the beige suspension is made acid (pH 4) with 1N aqueous hydrochloric acid and suction filtered. The filter material is washed with water and diethyl ether and crystallized from methanol/dichloromethane. There are obtained 510 mg of N-hydroxy-7-mercapto-5-methyl-s-triazolo[1,5-a]pyrimidine-2-carboxamide as beige crystals of m.p. 213° C. (dec.).

N-Hydroxy-7-mercapto-5-methyl-s-triazolo[1,5-a]pyrimidine-2-carboxamide and 3.4 g (12.5 mmol) of 7-aminocephalosporanic acid (3.1 g) (13.9 mmol) are suspended in 75 ml of sulpholane/dichloromethane (1:1 v/v). 7.5 ml of boron trifluoride etherate are added dropwise thereto at 0° C. and the mixture is stirred at 0° C. for 2.5 hours and at room temperature for 15 hours. 200 ml of dichloromethane are now added. After stirring for 30 minutes the mixture is suction filtered. The filter material is dissolved in 100 ml of water. The product is precipitated with saturated sodium hydrogen carbonate solution (pH~5), filtered off and washed with water, ethanol and ether. There are obtained 3.5 g of (6R,7R)-7-amino-3-[[[2-(hydroxycarbamoyl)-5-methyl-s-triazolo[1,5-a]pyrimidin-7-yl]thio]methyl]-8-oxo-5-thia-1-azabicyclo[4.2.0]oct-2-ene-2-carboxylic acid as a beige powder.

$^1$H NMR (DMSO-d$_6$): δ2.60 (s, 3H), 3.56 (d, J=18 Hz, 1H), 3.77 (d, J=18 Hz, 1H), 4.36 (d, J=12.5 Hz, 1H), 4.45 (d, J=12.5 Hz, 1H), 4.83 (d, J=5 Hz, 1H), 5.04 (d, J=5 Hz, 1H), 7.38 (s, 1H), 9.36 (s, 1H), 11.68 (s, 1H).

The S-(2-benzothiazolyl)-2-amino-4-thiazoleglyoxylate (Z)-O-[3,4-[(diphenylmethylene]dioxybenzyl]oxime used as the starting material can be prepared as follows:

3,4-[(Diphenylmethylene)dioxy]benzylchloride (81.4 g) [known from Tetrahedron Letters, 2745 (1977)] and 53.5 g of the lithium salt of allyl 2-(2-amino-4-thiazole)-2-hydroxyiminoacetate (known from EPOS 96,297) are stirred in 1.21 of dimethylformamide for 24 hours. Thereafter, the mixture is concentrated in a vacuum to about 300 ml, 700 ml of water are added thereto and the mixture is extracted twice with 1 l of ethyl acetate each time. The combined ethyl acetate extracts are washed with water and concentrated to about 350 ml, whereby the reaction product crystallizes out. The crystallizate is filtered off under suction and recrystallized from dichloromethane/ethanol. There are obtained 73.8 g of allyl 2-(2-amino-4-thiazole)-2-[3,4-[(diphenylmethylene)dioxy]benzyloxyiminoacetate of m.p. 151°–153° C.

This product is suspended in 1.3 l of acetonitrile. After the addition of 344 mg of Pd-(II) acetate and 1.24 ml of triethyl phosphite the mixture is cooled to 0° C., 16.7 ml of N-methylpyrrolidine are added thereto and the suspension obtained is stirred at 0° C. for 24 hours. Thereafter, the resulting N-allyl-N-methylpyrrolidinium salt of 2-(2-amino-4-thiazole)-2-[3,4-[(diphenylmethylene)dioxy]benzyloxyiminoacetic acid is filtered off under suction, washed with acetonitrile and diethyl ether and dried. 80.6 g are obtained.

Forty-six grams of the above salt are suspended in 600 ml of acetonitrile. After the addition of 8.5 ml of N-methylmorpholine and 30.7 g of 2,2-dithio-bis-benzothiazole the mixture is stirred at room temperature and a solution of 23 ml of triethyl phosphite in 150 ml of acetonitrile is added dropwise thereto over 2 hours. After a further 2 hours the mixture is filtered and the filtrate is left to stand for 3 days, whereby the product crystallizes. It is filtered off under suction and washed with acetonitrile and diethyl ether and dried in a vacuum at 35° C. There are obtained 22.5 g of S-(2-benzothiazolyl)-2-amino-4-thiazoleglyoxylate (Z)-O-[3,4-[(diphenylmethylene]dioxybenzyl]oxime as a yellow crystalline powder of m.p. 155°–157° C.

Elementary analysis: Found: 61.38% C, 3.59% H, 8.92% N, 15.37% S; Calculated: 61.72% C, 3.56% H, 9.00% N, 15.44% S.

EXAMPLE 25

Manufacture of (6R,7R)-7-[(Z)-2-(2-amino-4-thiazolyl)-2-[[[(3,4-dihydroxyphenyl)sulphonyl]methoxy]imino]acetamido]-3-[[[2-(hydroxycarbamoyl)-5-methyl-s-triazolo[1,5-a]pyrimidin-7-yl]thio]methyl]-8-oxo-5-thia-1-azabicyclo[4.2.0]oct-2-ene-2-carboxylic acid (6R,7R)-7-(2-Amino-4-thiazoleglyoxylamido)-3-[[[2-(hydroxycarbamoyl)-5-methyl-s-triazolo[1,5-a]pyrimidin-7-yl]thio]methyl]-8-oxo-5-thia-1-azabicyclo[4.2.0]oct-2-ene-2-carboxylic acid (80 mg) (0.135 mmol) and 45 mg (0.176 mmol) of 4-[[(aminooxy)-methyl]sulphonyl]pyrocatechol hydrochloride are dissolved in 4 ml of absolute dimethyl-acetamide. After stirring at room temperature for 24 hours a further 14 mg (0.06 mmol) of 4-[[(aminooxy)-methyl]sulphonyl]-pyrocatechol hydrochloride are added. After a further 24 hours the solvent is removed in a high vacuum at room temperature and the residue is treated with 4 ml of water. The precipitated product is filtered off under suction and washed in succession with water and diethyl ether. There are obtained 100 mg of (6R,7R)-7-[(Z)-2-(2-amino-4-thiazolyl)-2-[[[(3,4-dihydroxyphenyl)sulphonyl]methoxy]imino]acetamido]-3-[[[2-(hydroxy-carbamoyl)-5-methyl-s-triazolo[1,5-a]pyrimidin-7-yl]thio]methyl]-8-oxo-5-thia-1-azabicyclo[4.2.0]oct-2-ene-2-carboxylic acid as a brown powder.

$^1$H NMR (DMSO-d$_6$): signals at, inter alia, δ2.61 (s, 3H), 3.60 (d, J=18 Hz, 1H), 3.75 (d, J=18 Hz, 1H), 4.38 (d, J=12.5 Hz, 1H), 4.46 (d, J=12.5 Hz, 1H), 5.14 (d, J=5 Hz, 1H), 5.22 (2H), 5.75 (dd, J=5 Hz and J=8 Hz, 1H), 6.70 (s, 1H), 6.91 (d, J=7.5 Hz, 1H), 7.2 (2H), 7.29 (s, 2H), 7.40 (s, 1H), 9.36 (s, 1H), 9.67 (s, 1H), 9.72 (d, J=8 Hz, 1H), 10.10 (s, 1H), 11.68 (s, 1H).

The (6R,7R)-7-(2-amino-4-thiazoleglyoxylamido)-3-[[[2-(hydroxycarbamoyl)-5-methyl-s-triazolo[1,5-a]pyrimidin-7-yl]thio]methyl]-8-oxo-5-thia-1-azabicyclo[4.2.0]oct-2-ene-2-carboxylic acid used as the starting material can be prepared as follows:

(6R,7R)-7-Amino-3-[[[2-(hydroxycarbamoyl)-5-methyl-s-triazolo[1,5-a]pyrimidin-7-yl]thio]methyl]-8-oxo-5-thia-1-azabicyclo[4.2.0]oct-2-ene-2-carboxylic acid (43.7 mg) (0.1 mmol) are suspended in a mixture consisting of 2 ml of water and 1 ml of acetonitrile. 2 ml of 0.1N aqueous potassium hydroxide solution are added dropwise thereto at room temperature while stirring. Subsequently, 84 mg (0.26 mmol) of 2-amino-4-thiazolethioglyoxylic acid S-(2-benzothiazolyl) ester are added to the solution. The suspension is stirred at room temperature for 3 hours and filtered. The filter material is washed with water, the filtrate and wash solution are combined and again washed with ethyl acetate. The aqueous solution is adjusted to pH 5 with dilute aqueous hydrochloric acid. The precipitated product is filtered off under suction and washed with water and diethyl ether. After drying in a high vacuum there are obtained 30 mg of (6R,7R)-7-(2-amino-4-thiazoleglyoxylamido)-3-[[[2-(hydroxycarbamoyl)-5-methyl-s-triazolo[1,5-a]pyrimidin-7-yl]thio]methyl]-8-oxo-5-thia-1-azabicyclo[4.2.0]oct-2-ene-2-carboxylic acid as a yellow powder.

$^1$H NMR (DMSO-d$_6$): signals at δ2.61 (s, 3H), 3.63 (d, J=18 Hz, 1H), 3.80 (d, J=18 Hz, 1H), 4.40 (d, J=12.5 Hz, 1H), 4.48 (d, J=12.5 Hz, 1H), 5.21 (d, J=5 Hz, 1H), 5.77 (dd, J=5 Hz and J=8 Hz, 1H), 7.40 (s, 3H), 7.82 (s, 1H), 9.35 (s, 1H), 9.81 (d, J=8 Hz, 1H), 11.68 (s, 1H).

EXAMPLE 26

Manufacture of (6R,7R)-7-[(Z)-2-(2-amino-4-thiazolyl)-2-[[(1,4-dihydro-5-hydroxy-4-oxo-2-pyrimidinyl)methoxy]imino]acetamido]-3-[[[2-(hydroxycarbamoyl)-5-methyl-s-triazolo[1,5-a]pyrimidin-7-yl]thio]methyl]-8-oxo-5-thia-1-azabicyclo[4.2.0]oct-2-ene-2-carboxylic acid (6R,7R)-7-(2-Amino-4-thiazoleglyoxylamido)-3-[[[2-(hydroxycarbamoyl)-5-methyl-s-triazolo[1,5-a]pyrimidin-7-yl]thio]methyl]-8-oxo-5-thia-1-azabicyclo[4.2.0]oct-2-ene-2-carboxylic acid (25 mg) (0.042 mmol), 8.6 mg (0.055 mmol) of 2-(aminooxy)methyl-5-hydroxy-4(1H)-pyrimidinone and 10.5 mg (0.055 mmol) of p-toluenesulphonic acid hydrate are dissolved in 3 ml of absolute dimethylacetamide. After stirring at room temperature for 24 hours the solvent is removed in a high vacuum at room temperature and the residue is treated with 3 ml of water. The precipitated product is filtered off and washed in succession with water and diethyl ether. After drying in a high vacuum there are obtained 20 mg of (6R,7R)-7-[(Z)-2-(2-amino-4-thiazolyl)-2-[[(1,4-dihydro-5-hydroxy-4-oxo-2-pyrimidinyl)methoxy]imino]acetamido]-3-[[[2-(hydroxycarbamoyl)-5-methyl-s-triazolo[1,5-a]pyrimidin-7-yl]thio]methyl]-8-oxo-5-thia-1-azabicyclo[4.2.0]oct-2-ene-2-carboxylic acid as a beige powder.

$^1$H NMR (DMSO-d$_6$): signals at, inter alia, δ2.61 (s, 3H), 3.52 (d, J=18 Hz, 1H), 3.80 (d, J=18 Hz, 1H), 4.36 (d, J=12.5 Hz, 1H), 4.46 (d, J=12.5 Hz, 1H), 4.90 (2H), 5.20 (d, J=5 Hz, 1H), 5.84 (dd, J=5 Hz and J=8 Hz, 1H), 6.84 (s, 1H), 7.37 (s, 1H), 7.39 (s, 1H), 9.36 (1H), 9.55 (2H), 9.90 (d, J=8 Hz, 1H), 11.68 (s, 1H).

EXAMPLE 27

Manufacture of (6R,7R)-7-[(Z)-2-(2-amino-4-thiazolyl)-2-[[(1,6-dihydro-5-hydroxy-1-methyl-6-oxo-2-pyrimidinyl)methoxy]imino]acetamido]-3-[[[2-(hydroxycarbamoyl)-5-methyl-s-triazolo[1,5-a]pyrimidin-7-yl]thio]methyl]-8-oxo-5-thia-1-azabicyclo[4.2.0]oct-2-ene-2-carboxylic acid (6R,7R)-7-(2-Amino-4-thiazoleglyoxylamido)-3-[[[2-(hydroxycarbamoyl)-5-methyl-s-triazolo[1,5-a]pyrimidin-7-yl]thio]methyl]-8-oxo-5-thia-1-azabicyclo[4.2.0]oct-2-ene-2-carboxylic acid (65 mg) (0.11 mmol) are dissolved in 4 ml of absolute dimethylacetamide. 24 mg (0.14 mmol) of 2-[(aminooxy)methyl]-5-hydroxy-3-methyl-4(3H)-pyrimidinone and 14 mg (0.14 mmol) of methanesulphonic acid are added. After stirring at room temperature for 20 hours the dimethylacetamide is evaporated in a high vacuum and the residue is taken up in water and stirred for 15 minutes in order to precipitate the product completely. The product is filtered off, washed with water and diethyl ether and dried in a high vacuum at room temperature. There are obtained 48 mg of (6R,7R)-7-[(Z)-2-(2-amino-4-thiazolyl)-2-[[(1,6-dihydro-5-hydroxy-1-methyl-6-oxo-2-pyrimidinyl)methoxy]imino]acetamido]-3-[[[2-(hydroxycarbamoyl)-5-methyl-s-triazolo[1,5-a]pyrimidin-7-yl]thio]methyl]-8-oxo-5-thia-1-azabicyclo[4.2.0]oct-2-ene-2-carboxylic acid as a beige powder.

$^1$H NMR (DMSO-d$_6$): δ2.61 (s, 3H), 3.52 (s, 3H), 4.38 (d, J=15 Hz, 1H), 4.47 (d, J=15 Hz, 1H), 5.09 (d, J=14 Hz, 1H), 5.19 (d, J=14 Hz, 1H), 5.19 (d, J=5 Hz, 1H), 5.82 (dd, J=8 Hz and J=5 Hz, 1H), 6.78 (s, 1H), 7.29 (s, 2H, broad), 7.4 (2H), 9.37 (s, 1H), 9.65 (s, 1H), 9.84 (d, J=8 Hz, 1H), 11.70 (s, 1H).

The 2-[(aminooxy)methyl]-5-hydroxy-3-methyl-4(3H)-pyrimidinone used as the starting material can be prepared as follows:

5-(Benzyloxy)-2-(hydroxymethyl)-4(1H)-pyrimidinone (2.3 g) are dissolved in 20 ml of absolute methanol. The solution is treated with 4.24 g (40 mmol) of sodium carbonate and 10 ml of methyl iodide and stirred at room temperature for 4 days. Now, 400 ml of dichloromethane and 100 ml of saturated sodium chloride solution are added thereto, the organic phase is separated, dried over sodium sulphate and concentrated. The residue is chromatographed of 100 g of silica gel (0.063–0.2 mm). The two products are eluted in succession with dichloromethane/methanol (9:1 v/v). There are obtained 1.2 g of 5-(benzyloxy)-2-(hydroxymethyl)-3-methyl-4(3H)-pyrimidinone as white crystals from ether, m.p. 83°–84° C. 5-(Benzyloxy)-2-(hydroxymethyl)-1-methyl-4(1H)-pyrimidinone also forms white crystals from ether, m.p. 172°–173° C. 0.6 g is obtained.

Diethyl azodicarboxylate (4.8 g) (20 mmol) are added dropwise at 0° C. while stirring to a mixture of 3.69 g (15 mmol) of 5-(benzyloxy)-2-(hydroxymethyl)-3-methyl-4(3H)-pyrimidinone, 3.26 g (20 mmol) of N-hydroxyphthalimide and 5.24 g (20 mmol) of triphenylphosphine in 100 ml of absolute dimethylacetamide. The mixture is stirred at 0° C. for 2 hours and at room temperature for 16 hours. Subsequently, the solvent is removed in a high vacuum at room temperature. The residue is crystallized from ethanol/diethyl ether. After drying in a high vacuum for 18 hours at room temperature there are obtained 5.5 g of N-[[5-(benzyloxy)-3,4-dihydro-3-methyl-4-oxo-2-pyrimidinyl]methoxy]phthalimide as white crystals of m.p. 170° C.

N-[[5-(Benzyloxy)-3,4-dihydro-3-methyl-4-oxo-2-pyrimidinyl]methoxy]phthalimide (1.56 g) (4 mmol) are dissolved in 110 ml of dichloromethane and treated dropwise at about −70° C. while stirring with 0.42 ml (4.4 mmol) of boron tribromide. After stirring at about −70° C. for 4 hours and at room temperature for 16 hours the solvent is removed in a water-jet vacuum at room temperature. The residue is treated with about 30 ml of water, the insoluble product is filtered off and washed firstly with water and subsequently with diethyl ether. After drying in a high vacuum at room temperature for 18 hours there are obtained 1.1 g of N-[(3,4-dihydro-5-hydroxy-3-methyl-4-oxo-2-pyrimidinyl)methoxy]phthalimide as a white powder, m.p. 172° C. (dec.).

Methylhydrazine (92 mg) (2 mmol) are added at 0° C. to a suspension of 301 mg (1 mmol) of N-[(3,4-dihydro-5-hydroxy-3-methyl-4-oxo-2-pyrimidinyl)methoxy]phthalimide in 9 ml of absolute dimethylformamide. A solution gradually results and this is then stirred at room temperature for 3 hours. The solution is concentrated in a high vacuum at room temperature, the residue is washed with petroleum ether and finally 10 ml of water are added thereto. After good intermixing the mixture is filtered. The filtrate is concentrated, finally with toluene/ethanol. After crystallization from ethanol there are obtained 125 mg of 2-[(aminooxy)methyl]-5-hydroxy-3-methyl-4(3H)-pyrimidinone as white crystals of m.p. 106° C.

The analogous starting material 2-[(aminooxy)methyl]-5-hydroxy-1-methyl-4(1H)-pyrimidinone is obtained in an analogous manner to 2-[(aminooxy)methyl]-5-hydroxy-3-methyl-4(3H)-pyrimidinone. The intermediates are:

N-[[5-(Benzyloxy)-1,4-dihydro-1-methyl-4-oxo-2-pyrimidinyl]methoxy]phthalimide (m.p. 154°–155° C.; from ethanol/ether)

N-[(1,4-dihydro-5-hydroxy-1-methyl-4-oxo-2-pyrimidinyl)methoxy]phthalimide (m.p. 145° C., dec.).

The 2-[(aminooxy)methyl]-5-hydroxy-1-methyl-4(1H)-pyrimidinone melts at 115° C. (dec.) after recrystallization from ethanol.

EXAMPLE 28

Manufacture of (6R,7R)-7-[(Z)-2-(2-amino-4-thiazolyl)-2-[[[p-(hydroxycarbamoyl)benzyl]oxy]imino]acetamido]-3-[[[2-(hydroxycarbamoyl)-5-methyl-s-triazolo[1,5-a]pyrimidin-7-yl]thio]methyl]-8-oxo-5-thia-1-azabicyclo[4.2.0]oct-2-ene-2-carboxylic acid (6R,7R)-7-(2-Amino-4-thiazoleglyoxylamido)-3-[[[2-(hydroxycarbamoyl)-5-methyl-s-triazolo[1,5-a]pyrimidin-7yl]thio]methyl]-8-oxo-5-thia-1-azabicyclo[4.2.0]oct-2-ene-2-carboxylic acid (17.7 mg) (0.03 mmol), 7 mg (0.039 mmol) of α-(aminooxy)-N-hydroxy-p-toluamide and 3.7 mg (0.039 mmol) of methanesulphonic acid are dissolved in 0.3 ml of absolute dimethylacetamide. After stirring at room temperature for 24 hours the mixture is concentrated in a high vacuum at room temperature and the residue is treated with water. The precipitated product is filtered off, washed with water and dried in a high vacuum at room temperature. There are obtained 23 mg of (6R,7R)-7-[(Z)-2-(2-amino-4-thiazolyl)-2-[[[p-(hydroxycarbamoyl)benzyl]oxy]imino]acetamido]-3-[[[2-(hydroxycarbamoyl)-5-methyl-s-triazolo[1,5-a]pyrimidin-7-yl]thio]methyl]-8-oxo-5-thia-1-azabicyc[4.2.0]oct-2-ene-2-carboxylic acid as a beige powder of m.p. 250° C. (dec.).

$^1$H NMR (DMSO-d$_6$): signals at, inter alia, δ2.52 (s, 3H), 3.58 (d, J=18 Hz, 1H), 3.80 (d, J=18 Hz, 1H), 4.38 (d, J=12.5 Hz, 1H), 4.46 (d, J=12.5 Hz, 1H), 5.18 (s, 2H), 5.21 (d, J=5 Hz, 1H), 5.85 (dd, J=5 Hz and J=8 Hz, 1H), 6.72 (s, 1H), 7.24 (s, 2H), 7.39 (s, 1H), 7.43 (d, J=8 Hz, 2H), 7.71 (d, J=8 Hz, 2H), 9.03 (1H), 9.36 (s, 1H), 9.76 (d, J=8 Hz, 1H), 11.20 (s, 1H), 11.68 (s, 1H).

The α-(aminooxy)-N-hydroxy-p-toluamide used as the starting material can be prepared as follows:

4-Chloromethyl-benzoyl chloride (18.9 g) (0.1 mol) and 13.8 g (0.2 mol) of hydroxylamine hydrochloride are suspended in 200 ml of water and 150 ml of diethyl ether. 25.2 g (0.3 mol) of sodium hydrogen carbonate are added while stirring. After 30 minutes the product is filtered off under suction and washed with water and diethyl ether. After drying in a high vacuum at room temperature there are obtained 17 g of white α-chloro-N-hydroxy-p-toluamide of m.p. 120°–145° C. (dec.).

$^1$H NMR (DMSO-d$_6$): signals at δ4.80 (s, 2H), 7.51 (d, J=8 Hz, 1H), 7.75 (d, J=8 Hz, 1H), 9.07 (s, 1H), 11.25 (s, 1H).

α-Chloro-N-hydroxy-p-toluamide, 6.52 g (40 mmol) of N-hydroxyphthalimide (7.4 g) (40 mmol) and 0.28 g of potassium iodide are dissolved in 50 ml of absolute dimethylformamide and treated with 5.16 g (40 mmol) of N-ethyldiisopropylamine while stirring. After stirring at room temperature for 16 hours 50 ml of diethyl ether are added. The precipitated product is filtered off under suction and washed with diethyl ether. There are obtained 7.5 g of N-hydroxy-α-(phthalimidooxy)-p-toluamide as a white powder of m.p. 202° C. (dec.).

$^1$H NMR (DMSO-d$_6$): signals at δ5.22 (s, 2H), 7.60 (d, J=8 Hz, 1H), 7.78 (d, J=8 Hz, 1H), 7.87 (s, 4H), 9.08 (s, 1H), 11.28 (s, 1H).

N-Hydroxy-α-(phthalimidooxy)-p-toluamide (10.0 g) (32 mmol) are suspended in 80 ml of absolute dimethylformamide and treated at −5° C. with 1.86 g (40 mmol) of methylhydrazine. After stirring at room temperature for 2.5 hours 40 ml of solvent are distilled off in a high vacuum at room temperature. Insoluble material is filtered off and washed with a small amount of dimethylformamide. The mother liquor and wash solution are treated with 70 ml of ethanol. After stirring at 0° C. for ½ hour the precipitated crystalline product is filtered off under suction and washed with a small amount of ethanol. After drying in a high vacuum at room temperature there are obtained 3.9 g of α-(aminooxy)-N-hydroxy-p-toluamide as white crystals of m.p. 145° C. (dec.).

$^1$H NMR (DMSO-d$_6$): signals at, inter alia δ4.60 (s, 2H), 6.12 (s, 2H), 7.38 (d, J=8 Hz, 1H), 7.73 (d, J=8 Hz, 1H).

EXAMPLE 29

Manufacture of (6R,7R)-7-[(Z)-2-(2-amino-4-thiazolyl)-2-[[(2,5-dichloro-3,4-dihydroxybenzyl)oxy]imino]acetamido]-3-[[[2-(hydroxycarbamoyl)-5-methyl-s-triazolo[1,5-a]pyrimidin-7-yl]thio]methyl]-8-oxo-5-thia-1-azabicyclo[4.2.0]oct-2-ene-2-carboxylic acid (6R,7R)-7-(2-Amino-4-thiazoleglyoxylamido)-3-[[[2-(hydroxycarbamoyl)-5-methyl-s-triazolo[1,5-a]pyrimidin-7-yl]thio]methyl]-8-oxo-5-thia-1-azabicyclo[4.2.0]oct-2-ene-2-carboxylic acid (52 mg) (0.088 mmol) and 47 mg (0.11 mmol) of 5-[(aminooxy)methyl]-4,7-dichloro-2,2-diphenyl-1,3-benzodioxol are dissolved in 1 ml of absolute dimethylacetamide. After stirring at room temperature for 20 hours the solvent is removed in a high vacuum at room temperature and the residue is crystallized by the addition of diethyl ether. The product is filtered off and washed in succession with diethyl ether and water. After drying in a high vacuum at room temperature there are obtained 88 mg of (6R,7R)-7-[(Z)-2-(2-amino-4-thiazolyl)-2-[[(4,7-dichloro-2,2-diphenyl-1,3-benzodioxol-5-yl)methoxy]imino]acetamido]-3-[[[2-(hydroxycarbamoyl)-5-methyl-s-triazolo[1,5-a]pyrimidin-7-yl]thio]methyl]-8-oxo-5-thia-1-azabicyclo[4.2.0]oct-2-ene-2-carboxylic acid as a yellow powder.

$^1$H NMR (DMSO-d$_6$): signals at, inter alia, δ2.57 (s, 3H), 3.46 (d, J=18 Hz, 1H), 3.70 (d, J=18 Hz, 1H), 4.37 (d, J=12.5 Hz, 1H), 4.43 (d, J=12.5 Hz, 1H), 5.11 (s, 2H), 5.17 (d, J=5 Hz, 1H), 5.81 (dd, J=5 Hz and J=8 Hz, 1H), 6.76 (s, 1H), 7.14 (s, 1H), 7.24 (s, 2H), 7.40 (s, 1H), 7.5 (10H), 9.34 (s, 1H), 9.73 (d, J=8 Hz, 1H), 11.69 (s, 1H).

(6R,7R)-7-[(Z)-2-(2-Amino-4-thiazolyl)-2-[[(4,7-dichloro-2,2-diphenyl-1,3-benzodioxol-5-yl)methoxy]imino]acetamido]-3-[[[2-(hydroxycarbamoyl)-5-methyl-s-triazolo[1,5-a]pyrimidin-7-yl]thio]methyl]-8-oxo-5-thia-1-azabicyclo[4.2.0]oct-2-ene-2-carboxylic acid (80 mg) (0.08 mmol) are dissolved in 2 ml of trifluoroacetic acid. After stirring at room temperature for 16 hours the solvent is removed at room temperature in a vacuum and the residue is crystallized using diethyl ether. The product is filtered off, washed with diethyl ether and dried in a high vacuum at room temperature. There are obtained 50 mg of (6R,7R)-7-[(Z)-2-(2-amino-4-thiazolyl)-2-[[(2,5-dichloro-3,4-dihydroxybenzyl)oxy]imino]acetamidol-3-[[[2-(hydroxycarbamoyl)-5-methyl-s-triazolo[1,5-a]pyrimidin-7-yl]thio]methyl]-8-oxo-5-thia-1-azabicyclo[4.2.0]oct-2-ene-2-carboxylic acid as a beige powder.

$^1$H NMR (DMSO-d$_6$): signals at, inter alia, δ2.63 (s, 3H), 3.54 (d, J=18 Hz, 1H), 3.77 (d, J=18 Hz, 1H), 4.40 (d, J=12.5 Hz, 1H), 4.47 (d, J=12.5 Hz, 1H), 5.08 (s, 2H), 5.18 (d, J=5 Hz, 1H), 5.81 (dd, J=5 Hz and J=8 Hz, 1H), 6.76 (s, 1H), 6.95 (s, 1H), 7.24 (s, 2H), 7.40 (s, 1H), 9.36 (s, 1H), 9.6–10.0 (2H), 9.74 (d, J=8 Hz, 1H), 11.69 (s, 1H).

The 5-[(aminooxy)methyl]-4,7-dichloro-2,2-diphenyl-1,3-benzodioxol used as the starting material can be prepared as follows:

Methyl 2,5-dichloro-3,4-dihydroxybenzoate (1.1 g) (about 4.6 mmol) and 2.0 g (8.4 mmol) of dichlorodiphenylmethane are heated together to 150° C. After stirring for 1.5 hours the melt is cooled and the product is crystallized from diethyl ether. There are obtained 1.3 g of methyl 4,7-dichloro-2,2-diphenyl-1,3-benzodioxol-5-carboxylate as white crystals of m.p. 112° C.

In another experiment the product is crystallized from ethanol. M.p. 69°–70° C.

Methyl 4,7-dichloro-2,2-diphenyl-1,3-benzodioxol-5-carboxylate (0.4 g) (1 mmol) are dissolved in 15 ml of absolute tetrahydrofuran. 5 ml of a 1M solution of diisobutylaluminium hydride in toluene are added at 0° C. under argon. After stirring at 0° C. for 4 hours saturated, aqueous ammonium chloride solution is added thereto while cooling until pH 5 has been reached. Insoluble material is filtered off under suction and extracted intensively with diethyl ether and methanol. After concentration of the extracts there remains 0.3 g of 4,7-dichloro-2,2-diphenyl-1,3-benzodioxol-5-methanol as a greenish coloured oil.

$^1$H NMR (CDCl$_3$): signals at δ1.8 (broad, 1H), 4.67 (d, J=3 Hz, 2H), 6.98 (s, 1H), 7.4 (6H), 7.6 (4H).

4,7-Dichloro-2,2-diphenyl-1,3-benzodioxol-5-methanol (250 mg) (0.67 mmol), 108 mg (0.67 mmol) of N-hydroxyphthalimide and 175 mg (0.67 mmol) of triphenylphosphine are suspended in 20 ml of absolute tetrahydrofuran. 128 mg (0.73 mmol) of diethyl azodicarboxylate are added dropwise at 0° C. while stirring. The mixture is stirred at 0° C. for 1 hour and at room temperature for 24 hours. Subsequently, the solvent is removed in a high vacuum. The residue is crystallized and recrystallized from ethanol/diethyl ether. There are obtained 230 mg of N-[(4,7-dichloro-2,2-diphenyl-1,3-benzodioxol-5-yl)methoxy]phthalimide as white crystals of m.p. 127°–129° C.

Methylhydrazine (47 mg) (1.02 mmol) are added at 0° C. to a solution of 530 mg (1.02 mmol) of N-[(4,7- dichloro-2,2-diphenyl-1,3-benzodioxol-5-yl)methoxy]phthalimide in 10 ml of absolute dimethylformamide. The mixture is stirred at 0° C. for 1 hour and at room temperature for 4 hours. The solvent is removed in a high vacuum at room temperature and the residue is chromatographed on 30 g of silica gel (0.063–0.2 mm). The product is eluted with dichloromethane/ethanol (19:1 v/v). There are obtained 310 mg of 5-[(aminooxy)-methyl]-4,7-dichloro-2,2-diphenyl-1,3-benzodioxol as a colourless oil.

$^1$H NMR (CDCl$_3$): signals at $\delta$4.75 (s, 2H), 6.97 (s, 1H), 7.4 (6H), 7.6 (4H).

The above amine (305 mg) is treated with ethanolic hydrogen chloride solution. The amine hydrochloride crystallizes out after the addition of diethyl ether. There are obtained 310 mg of 5-[(aminooxy)methyl]-4,7-dichloro-2,2-diphenyl-1,3-benzodioxol hydrochloride as white crystals of m.p. 133°–134° C. after recrystallization from ethanol/diethyl ether.

EXAMPLE 30

Manufacture of (6R,7R)-7-[(Z)-2-amino-4-thiazolyl)-2-[[[(3,4-dihydroxyphenyl)sulphonyl]methoxy]imino]acetamido]-3-[[[5-(hydroxycarbamoyl)-2-methyl-s-triazolo[1,5-a]pyrimidin-7-yl]thio]methyl]-8-oxo-5-thia-1-azabicyclo[4.2.0]oct-2-ene-2-carboxylic acid (6R,7R)-7-(2-Amino-4-thiazoleglyoxylamido)-3-[[[5-(hydroxycarbamoyl)-2-methyl-s-triazolo[1,5-a]pyrimidin-7-yl]thio]methyl]-8-oxo-5-thia-1-azabicyclo[4.2.0]oct-2-ene-2-carboxylic acid (65 mg) (0.11 mmol) and 37 mg (0.14 mmol) of 4-[[(aminooxy)methyl]sulphonyl]-pyrocatechol hydrochloride are dissolved in 3 ml of absolute dimethylacetamide. After stirring at room temperature for 24 hours a further 4.2 mg (0.016 mmol) of 4-[[(aminooxy)methyl]sulphonyl]pyrocatechol hydrochloride are added. After a further 24 hours the solvent is removed in a high vacuum at room temperature and the residue is treated with water. The precipitated product is filtered off and washed in succession with water and diethyl ether. After drying in a high vacuum there are obtained 55 mg of (6R,7R)-7-[(Z)-2-amino-4-thiazolyl)-2-[[[(3,4-dihydroxyphenyl)sulphonyl]methoxy]imino]acetamido]-3-[[[5-(hydroxycarbamoyl)-2-methyl-s-triazolo[1,5-a]pyrimidin-7-yl]thio]methyl]-8-oxo-5-thia-1-azabicyclo[4.2.0]oct-2-ene-2-carboxylic acid as a beige powder.

$^1$H NMR (DMSOd$_6$): signals at, inter alia, $\delta$2.54 (s, 3H), 3.55 (d, J=18 Hz, 1H), 3.76 (d, J=18 Hz, 1H), 4.46 (d, J=12.5 Hz, 1H), 4.54 (d, J=12.5 Hz, 1H), 5.11 (d, J=5 Hz, 1H), 5.15 (d, J=15 Hz, 1H), 5.25 (d, J=15 Hz, 1H), 5.75 (dd, J=5 Hz and J=8 Hz, 1H), 6.69 (s, 1H), 6.91 (d, J=8 Hz, 1H), 7.2 (2H), 7.29 (s, 2H), 7.74 (s, 1H), 9.34 (s, 1H), 9.66 (s, 1H), 9.73 (d, J=8 Hz, 1H), 10.09 (s, 1H), 11.88 (s, 1H).

The (6R,7R)-7-(2-amino-4-thiazoleglyoxylamido)-3-[[[5-(hydroxycarbamoyl)-2-methyl-s-triazolo[1,5-a]pyrimidin-7-yl]thio]methyl]-8-oxo-5-thia-1-azabicyclo[4.2.0]oct-2-ene-2-carboxylic acid used as the starting material can be prepared as follows:

3-Amino-5-methyl-1H-s-triazole (112 mg) and 320 mg of dimethyl 2-oxo-succinate are dissolved in 5 ml of glacial acetic acid. After boiling under reflux for 22 hours the solvent is distilled off in a vacuum. The residue is suspended in warm methanol. After cooling the product is filtered off and washed several times with methanol. After drying in a high vacuum there are obtained 73 mg of methyl 7-hydroxy-2-methyl-s-triazolo[1,5-a]pyrimidine-5-carboxylate as a beige powder, m.p.>220° C.

$^1$H NMR (DMSOd$_6$): signals at, inter alia, $\delta$2.44 (s, 3H), 3.88 (s, 3H), 6.54 (s, 1H).

Methyl 7-hydroxy-2-methyl-s-triazolo[1,5-a]pyrimidine-5-carboxylate (1.0 g) (4.8 mmol) is suspended in 30 ml of phosphorus oxychloride. 0.38 ml (4.8 mmol) of pyridine is added thereto and the mixture is stirred at 90° C. for 5 hours. Subsequently, the mixture is concentrated and ice/water and saturated aqueous sodium chloride solution are added to the residue. The product is extracted with dichloromethane. After drying and evaporation of the extract there remains 0.81 g of methyl 7-chloro-2-methyl-s-triazolo[1,5-a]pyrimidine-5-carboxylate as beige crystals of melting point 170°–174° C.

$^1$H NMR (DMSOd$_6$): signals at, inter alia, $\delta$2.61 (s, 3H), 3.97 (s, 3H), 8.08 (s, 1H).

Methyl 7-chloro-2-methyl-s-triazolo[1,5-a]pyrimidine-5-carboxylate (0.80 g) (3.53 mmol) are suspended in 35 ml of methanol and treated with 0.78 g (10.6 mmol) of sodium hydrogen sulphide hydrate. After stirring at 60° C. for 5 hours the mixture is concentrated and the residue is dissolved in 20 ml of water. The solution is acidified to pH 3 with 3N aqueous hydrochloric acid. The separated product is filtered off under suction and washed with water and methanol. After recrystallization from methanol/dichloromethane there is obtained 0.66 g of methyl 7-mercapto-2-methyl-s-triazolo[1,5-a]pyrimidine-5-carboxylate as yellow crystals of melting point 237° C. (dec.).

$^1$H NMR (DMSOd$_6$): signals at, inter alia, $\delta$2.54 (s, 3H), 3.88 (s, 3H), 7.51 (s, 1H).

Methyl 7-mercapto-2-methyl-s-triazolo[1,5-a]pyrimidine-5-carboxylate (500 mg) (2.23 mmol) are suspended in 100 ml of absolute methanol. 2.95 mg (8.9 mmol) of hydroxylamine are added within 4 days while stirring. The reaction mixture is acidified (pH 6) with 3N aqueous hydrochloric acid. The product is filtered off under suction and washed in succession with water, methanol and diethyl ether. There are obtained 540 mg of N-hydroxy-7-mercapto-2-methyl-s-triazolo[1,5-a]pyrimidine-5-carboxamide as yellow crystals of melting point 178°–179° C.

$^1$H NMR (DMSOd$_6$): signals at, inter alia, $\delta$2.38 (s, 3H), 7.21 (s, 1H).

N-Hydroxy-7-mercapto-2-methyl-s-triazolo[1,5-a]pyrimidine-5-carboxamide (250 mg) (1.1 mmol) and 275 mg (1.0 mmol) of 7-amino-cephalosporanic acid are suspended in 15 ml of sulpholane/dichloromethane (1:1 v/v) and treated at 0° C. with 3.5 ml of boron trifluoride diethyl etherate. The mixture is stirred at 0°–5° C. for 2 hours and at room temperature for 3 hours. Subsequently, 60 ml of dichloromethane are added. Insoluble material is filtered off under suction, dissolved in water and treated with saturated sodium bicarbonate solution until pH value 3 has been reached. The precipitated product is filtered off under suction and washed in succession with water and diethyl ether. There are obtained 295 mg of (6R,7R)-7-amino-3-[[[5-(hydroxycarbamoyl)-2-methyl-s-triazolo[1,5-a]pyrimidin-7-yl]thio]methyl]-8-oxo-5-thia-1-azabicyclo[4.2.0]oct-2-ene-2-carboxylic acid as a beige powder.

$^1$H NMR (DMSOd$_6$): signals at, inter alia, $\delta$2.54 (s, 3H), 3.56 (d, J=18 Hz, 1H), 3.78 (d, J=18 Hz, 1H), 4.45 (d, J=12.5 Hz, 1H), 4.51 (d, J=12.5 Hz, 1H), 4.82 (d, J=5 Hz, 1H), 4.98 (d, J=5 Hz, 1H), 7.72 (s, 1H), 9.34 (s, 1H), 11.88 (s, 1H).

(6R,7R)-7-Amino-3-[[[5-(hydroxycarbamoyl)-2-methyl-s-triazolo[1,5-a]pyrimidin-7-yl]thio]methyl]-8-oxo-5-thia-1-azabicyclo[4.2.0]oct-2-ene-2-carboxylic acid (160 mg) (0.36 mmol) are suspended in 2 ml of absolute dimethylacetamide. 146 mg (0.72 mmol) of O,N-bis-trimethylsilyl-acetamide are added thereto at 0° C. and the mixture is stirred for 2 hours. The solution is subsequently treated with 116 mg (0.36 mmol) of 2-amino-4-thiazolethioglyoxylic acid S-(2-benzothiazolyl) ester and stirred at 0° C. for 2 hours and at room temperature for 16 hours. Some ethanol is added thereto and, after 20 minutes, the mixture is concentrated in a high vacuum at room temperature. The residue is treated with water. The precipitated product is filtered off and washed in succession, with water, ethanol, ethyl acetate and diethyl ether. There are obtained 170 mg of (6R,7R)-7-(2-amino-4-thiazoleglyoxylamido)-3-[[[5-(hydroxycarbamoyl)-2-methyl-s-triazolo[1,5-a]pyrimidin-7-yl]thio]methyl]-8-oxo-5-thia-1-azabicyclo[4.2.0]oct-2-ene-2-carboxylic acid as a beige powder.

$^1$H NMR (DMSOd$_6$): signals at, inter alia, δ2.54 (s, 3H), 3.62 (d, J=18 Hz, 1H), 3.81 (d, J=18 Hz, 1H), 4.47 (d, J=12.5 Hz, 1H), 4.60 (d, J=12.5 Hz, 1H), 5.19 (d, J=5 Hz, 1H), 5.79 (dd, J=5 Hz and J=8 Hz, 1H), 7.41 (s, 2H), 7.74 (s, 1H), 7.82 (s, 1H), 9.34 (s, 1H), 9.80 (d, J=8 Hz, 1H), 11.89 (s, 1H).

EXAMPLE 31

Manufacture of (6R,7R)-7-[(Z)-2-(2-amino-4-thiazolyl)-2-[[(1,4-dihydro-5-hydroxy-4-oxo-2-pyrimidinyl)methoxy]imino]acetamido]-3-[[[5-(hydroxycarbamoyl)-2-methyl-s-triazolo[1,5-a]pyrimidin-7-yl]thio]methyl]-8-oxo-5-thia-1-azabicyclo[4.2.0]oct-2-ene-2-carboxylic acid (6R,7R)-7-(2-Amino-4-thiazoleglyoxylamido)-3-[[[5-(hydroxycarbamoyl)-2-methyl-s-triazolo[1,5-a]pyrimidin-7-yl]thio]methyl]-8-oxo-5-thia-1-azabicyclo[4.2.0]oct-2-ene-2-carboxylic acid (65 mg) (0.11 mmol), 22.5 mg (0.143 mol) of 2-(aminooxy)methyl-5-hydroxy-4(1H)-pyrimidinone and 27 mg (0.143 mmol) of p-toluenesulphonic acid hydrate are dissolved in 2 ml of absolute dimethylacetamide. After stirring at room temperature for 24 hours the solvent is removed in a high vacuum and the residue is treated with water. The precipitated product is filtered off and washed in succession with water and diethyl ether. After drying in a high vacuum there are obtained 55 mg of (6R,7R)-7-[(Z)-2-(2-amino-4-thiazolyl)-2-[[(1,4-dihydro-5-hydroxy-4-oxo-2-pyrimidinyl)methoxy]imino]acetamido]-3-[[[5-(hydroxycarbamoyl)-2-methyl-s-triazolo[1,5-a]pyrimidin-7-yl]thio]methyl]-8-oxo-5-thia-1-azabicyclo[4.2.0]oct-2-ene-2-carboxylic acid as a beige powder.

$^1$H NMR (DMSOd$_6$): signals at, inter alia, δ2.54 (s, 3H), 3.55 (d, J=18 Hz, 1H), 3.84 (d, J=18 Hz, 1H), 4.46 (d, J=12.5 Hz, 1H), 4.56 (d, J=12.5 Hz, 1H), 4.91 (s, 2H), 5.20 (d, J=5 Hz, 1H), 5.85 (dd, J=5 H and J=8 Hz, 1H), 6.85 (s, 1H), 7.38 (s, 1H), 7.73 (s, 1H), 9.90 (d, J=8 Hz, 1H), 11.88 (s, 1H).

EXAMPLE 32

Manufacture of (6R,7R)-7-[(Z)-2-(2-amino-4-thiazolyl)-2-[(1-hydroxycarbamoyl)-1-methylethoxy]imino]acetamido]-3-[[5-(3,4-dihydroxyphenyl)-1H-tetrazol-1-yl]methyl]-8-oxo-5-thia-1-azabicyclo[4.2.0]oct-2-ene-2-carboxylic acid sodium salt (1:1)

(6R,7R)-7-(2-Amino-4-thiazoleglyoxylamido)-3-[[5-(3,4-dihydroxyphenyl)-1H-tetrazol-1-yl]methyl]-8-oxo-5-thia-1-azabicyclo[4.2.0]oct-2-ene-2-carboxylic acid (160 mg) and 80 mg of 2-(aminooxy)-N-hydroxy-2-methylpropionamide hydrochloride are stirred in 2 ml of dimethylacetamide for 24 hours at room temperature. The dimethylacetamide is evaporated in a high vacuum. The residue is treated with 3 ml of water. The resulting precipitate is filtered off, washed with a small amount of cold water and resuspended in about 3 ml of water. The pH value is adjusted to 7 with 1N aqueous sodium hydroxide solution. The solution is chromatographed on Opti-up C$_{12}$® with water and 5% acetonitrile. The uniform product fractions are concentrated and lyophilized. There are obtained 91 mg of (6R,7R)-7-[(Z)-2-(2-amino-4-thiazolyl)-2-[(1-hydroxycarbamoyl)-1-methylethoxy]imino]acetamido]-3-[[5-(3,4-dihydroxyphenyl)-1H-tetrazol-1-yl]methyl]-8-oxo-5-thia-1-azabicyclo[4.2.0]oct-2-ene-2-carboxylic acid sodium salt (1:1) as an almost white powder.

$^1$H-NMR (DMSO-d$_6$, 250 MHz): signals at δ (ppm) 1.43 (s, 3H), 1.46 (s, 3H), 3.29 (d, J=17 Hz, 1H) 3.48 (d, J=17 Hz, 1H), 5.05 (d, J=5 Hz, 1H), 5.16 (d, J=14 Hz, 1H), 5.74 (d,d, J$_1$=5 Hz, J$_2$=8 Hz, 1H), 5.79 (d, J=14 Hz, 1H), 6.82 (s, 1H), 6.88 (d, J=8 Hz, 1H), 7.15 (m, 2H), 7.35 (s, 2H), 8.90 (s, 1H), 9.40 (s, broad, 1H), 9.64 (d, J=8 Hz, 1H), 10.14 (s, 1H), 10.70 (s, broad, 1H). IR: (KBr) 1771 cm$^{-1}$ The (6R,7R)-7-(2-amino-4-thiazoleglyoxylamido)-3-[[5-(3,4-dihydroxyphenyl)-1H-tetrazol-1-yl]methyl]-8-oxo-5-thia-1-azabicyclo[4.2.0]oct-2-ene-2-carboxylic acid used as the starting material can be prepared as follows:

5-Bromo-2,2-diphenyl-1,3-benzodioxol (70 g) in 440 ml of tetrahydrofuran are treated at −78° C. with 125 ml of a 1.6M solution of butyllithium in n-hexane. After 10 minutes 40 ml of dimethylformamide are added thereto and the mixture is left to warm to −10° C. Thereafter, 70 ml of 20% aqueous phosphoric acid and 500 ml of ethyl acetate are added, the organic phase is separated and evaporated. The residue is recrystallized from 130 ml of ethanol. 49.5 g of 2,2-diphenyl-1,3-benzodioxol-5-carbaldehyde are obtained.

2,2-Diphenyl-1,3-benzodioxol-5-carbaldehyde (48.66 g) and 22.40 g of hydroxylamine hydrochloride are stirred at room temperature in 130 ml of dimethylformamide for 1 day. The dimethylformamide is removed in a high vacuum. The residue is partitioned between water and ethyl acetate. The organic phase is dried with water and saturated sodium chloride solution, dried with magnesium sulphate and concentrated. The solid product is recrystallized from 230 ml of ethanol. There are obtained 40.39 g of 2,2-diphenyl-1,3-benzodioxol-5-carboxaldehyde (E and/or Z)-oxime as white crystals of melting point 157°-159° C.

2,2-Diphenyl-1,3-benzodioxol-5-carboxaldehyde (E and/or Z)-oxime (6.00 g) are heated at reflux in 5 ml of acetic anhydride for 1 hour. The reaction mixture is concentrated and subsequently distilled at 160° C. in a high vacuum. The solid product is recrystallized from ethanol. There are obtained 4.98 g of 2,2-diphenyl-1,3-benzodioxol-5-carbonitrile as white crystals of melting point 106°-107° C.

2,2-Diphenyl-1,3-benzodioxol-5-carbonitrile (4.79 g) are heated at 160° C. for 5 hours with 1.71 g of ammonium chloride and 2.08 g of sodium azide. The reaction mixture is cooled to room temperature and partitioned at pH 3 between water and ethyl acetate. The organic phase is shaken with water and the pH value is adjusted to 10 with 1N aqueous sodium hydroxide solution. The aqueous phase (pH 10) is separated, shaken with ethyl acetate and the pH value is adjusted to 4. A white precipitate forms. This is filtered off, dried and recrystallized from 240 ml of acetonitrile. There are obtained 3.84 g of 5-(2,2-diphenyl-1,3-benzodioxol-5-yl)-1H-tetrazole as white crystals of melting point 212°–215° C./dec.

5-(2,2-Diphenyl-1,3-benzodioxol-5-yl)-1H-tetrazole (2.57 g) and 4.10 g of 7-aminocephalosporanic acid are dissolved in 25 ml of sulpholane, treated with 7.50 ml of boron trifluoride diethyl etherate and stirred at room temperature overnight. The reaction mixture is partitioned between water and ethyl acetate, the pH value is adjusted to 7.0 and the aqueous phase is chromatographed on Opti-up $C_{12}$ ® with water and 10% acetonitrile. 2.45 g of beige product as an isomer mixture are obtained after precipitation at pH 2.5. This is brought into solution in 14 ml of water:acetonitrile 1:1 using 0.63 ml of triethylamine and stirred with 2.19 g of 2-amino-4-thiazolethioglyoxylic acid S-(2-benzothiazolyl) ester for 3 hours. The reaction mixture is centrifuged and the clear yellow supernatant is partitioned between water and ethyl acetate (pH about 7.5). The pH value of the aqueous phase is adjusted to 2.5, whereby a fine yellow precipitate results. This is filtered off, dissolved while still moist in 20 ml of trifluoroacetic acid and stirred at 0° C. for about 1 hour. The trifluoroacetic acid is evaporated in a water-jet vacuum and the residue is partitioned at pH 7.5 between water and ethyl acetate. The aqueous phase is chromatographed on Opti-up $C_{12}$ ® with water, 5% aqueous acetonitrile and 10% aqueous acetonitrile. There are obtained as the polar component (first fraction) after precipitation at pH 2 305 mg of (6R,7R)-7-(2-amino-4-thiazoleglyoxylamido)-3-[[5-(3,4-dihydroxyphenyl)-1H-tetrazol-1-yl]methyl]-8-oxo-5-thia-1-azabicyclo[4.2.0]oct-2-ene-2-carboxylic acid as a yellow solid.

$^1$H-NMR (DMSO-$d_6$): signals at δ (ppm): 3.44 (m, 2H), 5.14 (d, J=5 Hz, 1H), 5.47 (d, J=15 Hz, 1H), 5.56 (d, J=15 Hz, 1H), 5.80 (d,d, J=5 Hz, J=8 Hz, 1H), 6.90 (d, J=7 Hz, 1H), 7.02 (d,d, J=7 Hz, J=3 Hz, 1H), 7.15 (d, J=3 Hz, 1H), 7.39 (s, 2H), 7.80 (s, 1H), 9.50 (s, broad, 1H), 9.69 (s, 1H), 9.82 (d, J=8 Hz, 1H), 14.0 (s, broad, 1H).

There are obtained as the less polar component (second fraction), after precipitation at pH 2, 213 mg of (6R,7R)-7-(2-amino-4-thiazoleglyoxylamido)-3-[[5-(3,4-dihydroxyphenyl)-2H-tetrazol-2-yl]methyl]-8-oxo-5-thia-1-azabicyclo[4.2.0]oct-2-ene-2-carboxylic acid as a yellow solid.

$^1$H-NMR (DMSO-$d_6$): signals at δ (ppm): 3.54 (m, 2H), 5.20 (d, J=5 Hz, 1H), 5.57 (d, J=15 Hz, 1H), 5.82 (m, 3H), 6.87 (d, J=8 Hz, 1H), 7.36 (d,d, J=8 Hz, J=3 Hz, 1H), 7.39 (s, 2H), 7.45 (d, J=3 Hz, 1H), 7.81 (s, 1H), 9.35 (s, 1H), 9.44 (s, 1H), 9.82 (d, J=8 Hz, 1H), 14.0 (s, broad, 1H).

EXAMPLE 33

Manufacture of (6R,7R)-7-[(Z)-2-(2-amino-4-thiazolyl)-2-[[(2-fluoro-3,4-dihydroxybenzyl)oxy]imino]acetamido]-3-[[5-(3,4-dihydroxyphenyl)-1H-tetrazol-1-yl]methyl]-8-oxo-5-thia-1-azabicyclo[4.2.0]oct-2-ene-2-carboxylic acid sodium salt (1:1)

(6R,7R)-7-(2-Amino-4-thiazoleglyoxylamido)-3-[[5-(3,4-dihydroxyphenyl)-1H-tetrazol-1-yl]methyl]-8-oxo-5-thia-1-azabicyclo[4.2.0]oct-2-ene-2-carboxylic acid (50 mg) and 67 mg of O-[(4-fluoro-2,2-diphenyl-1,3-benzodioxol-5-yl)methyl]hydroxylamine hydrochloride are dissolved in 2 ml of dimethylacetamide and stirred at room temperature for 24 hours. The solvent is evaporated in a high vacuum. The residue is treated with 2 ml of water. The precipitate formed is filtered off, dissolved in 1 ml of trifluoroacetic acid and stirred at 0° C. for 1 hour. The trifluoroacetic acid is evaporated on a rotary evaporator. The residue is partitioned between water and ethyl acetate at pH 7. The aqueous phase is chromatographed on Opti-up $C_{12}$ ® with water and 5% acetonitrile. The uniform product fractions are concentrated and lyophilized. There are obtained 18 mg of (6R,7R)-7-[(Z)-2-(2-amino-4-thiazolyl)-2-[[(2-fluoro-3,4-dihydroxybenzyl)oxy]imino]acetamido]-3-[[5-(3,4-dihydroxyphenyl)-1H-tetrazol-1-yl]methyl]-8-oxo-5-thia-1-azabicyclo[4.2.0]oct-2-ene-2-carboxylic acid sodium salt (1:1) as a white lyophilizate.

$^1$H-NMR (DMSO-$d_6$, 250 MHz): signals at δ (ppm) 3.22 (d, J=17 Hz, 1H), 3.42 (d, J=17 Hz, 1H), 4.96 (d, J=5 Hz, 1H), 5.04 (s, 2H), 5.12 (d, J=15 Hz, 1H), 5.64 (d,d, J=5 Hz, J=8 Hz, 1H), 5.79 (d, J=15 Hz, 1H), 6.55 (m, 1H), 6.74 (m, 2H), 6.87 (d, J=7 Hz, 1H), 7.12 (m, 1H), 7.17 (m, 1H), 7.25 (s, 2H), 9.61 (d, J=8 Hz, 1H). IR: (KBr) 1768 cm$^{-1}$

EXAMPLE 34

Manufacture of (6R,7R)-7-[(Z)-2-(2-amino-4-thiazolyl)-2-[[(3,4-dihydroxybenzyl)oxy]imino]acetamido]-3-[[5,(3,4-dihydroxyphenyl)-1H-tetrazol-1-yl]methyl]-8-oxo-5-thia-1-azabicyclo[4.2.0]oct-2-ene-2-carboxylic acid This compound is manufactured in analogy to Example 33 from (6R,7R)-7-(2-amino-4-thiazoleglyoxylamido)-3-[[5-(3,4-dihydroxyphenyl)-1H-tetrazol-1-yl]methyl]-8-oxo-5-thia-1-azabicyclo[4.2.0]oct-2-ene-2-carboxylic acid and O-[3,4-[-(diphenylmethylene)dioxy]benzyl]hydroxylamine.

$^1$H-NMR (DMSO-$d_6$, 250 MHz): signals at δ (ppm) 3.40 (m, 2H), 4.92 (s, 2H), 5.10 (d, J=5 Hz, 1H), 5.33 (d, J=14 Hz, 1H), 5.52 (d, J=14 Hz, 1H), 5.80 (d,d, J=5 Hz, J=8 Hz, 1H), 6.7 (m, 4H), 6.9 (m, 1H), 7.0 (m, 1H), 7.15 (m, 1H), 7.23 (s, 2H), 8.86 (s, 1H), 8.89 (s, 1H), 9.50 (s, 1H), 9.68 (d, J=8 Hz, 1H), 9.71 (s, 1H).

EXAMPLE 35

Manufacture of (6R,7R)-7-[(Z)-2-(2-amino-4-thiazolyl)-2-[[(1,6-dihydro-5-hydroxy-6-oxo-2-pyrimidinyl)methoxy]imino]acetamido]-3-[[5-(3,4-dihydroxyphenyl)-1H-tetrazol-1-yl]methyl]-8-oxo-5-thia-1-azabicyclo[4.2.0]oct-2-ene-2-carboxylic acid sodium salt (1:1)

This compound is manufactured in analogy to Example 32 from (6R,7R)-7-(2-amino-4-thiazoleglyoxylamido)-3-[[5-(3,4-dihydroxyphenyl)-1H-tetrazol-1-yl]methyl]-8-oxo-5-thia-1-azabicyclo[4.2.0]oct-2-ene-2-carboxylic acid, 2-(aminooxy)methyl-5-hydroxy-4(1H)-pyrimidinone and methanesulphonic acid.

$^1$H-NMR (DMSO-$d_6$, 250 MHz): signals at δ (ppm) 3.26 (s, J=17 Hz, 1H), 3.42 (d, J=17 Hz, 1H), 4.94 (s, 2H), 5.02 (d, J=5 Hz, 1H), 5.14 (d, J=15 Hz, 1H), 5.70 (d,d, J=5 Hz, J=8 Hz, 1H), 5.78 (d, J=15 Hz, 1H), 6.87 (m, 2H), 7.14 (m, 2H), 7.29 (s, 2H), 7.40 (s, 1H), 9.93 (d, J=8 Hz, 1H). IR: (KBr) 1774 cm$^-$.

EXAMPLE 36

When (6R,7R)-7-(2-amino-4-thiazoleglyoxylamido)-3-[[5-(3,4-dihydroxyphenyl)-2H-tetrazol-2-yl]methyl]-8-oxo-5-thia-1-azabicyclo[4.2.0]oct-2-ene-2-carboxylic acid is used in Examples 32–35 in place of (6R,7R)-7-(2-amino-4-thiazoleglyoxylamido)-3-[[5-(3,4-dihydroxyphenyl)-1H-tetrazol-1-yl]methyl]-8-oxo-5-thia-1-azabicyclo[4.2.0]oct-2-ene-2-carboxylic acid, then there are obtained under otherwise similar conditions:

(6R,7R)-7-[(Z)-2-(2-Amino-4-thiazolyl)-2-[(1-(hydroxycarbamoyl)-1-methylethoxy]imino]acetamido]-3-[[5-(3,4-dihydroxyphenyl)-2H-tetrazol-2-yl]methyl]-8-oxo-5-thia-1-azabicyclo[4.2.0]oct-2-ene-2-carboxylic acid sodium salt (1:1):

$^1$H-NMR (DMSO-d$_6$, 250 MHz): signals at δ (ppm) 1.40 (s, 3H), 1.42 (s, 3H), 3.28 (m, 2H), 5.04 (d, J=5 Hz, 1H), 5.47 (d, J=14 Hz, 1H), 5.18 (d,d, J=5 Hz, J=8 Hz, 1H), 6.18 (d, J=14 Hz, 1H), 6.80 (s, 1H), 6.87 (d, J=7 Hz, 1H), 7.35 (m, 3H), 7.48 (m, 1H), 8.4 (s, 1H), 9.45 (s, broad, 1H), 9.5 (s, broad, 1H), 9.60 (d, J=8 Hz, 1H), 10.12 (s, broad, 1H). IR: (KBr) 1769 cm$^{-1}$;

(6R,7R)-7-[(Z)-2-(2-amino-4-thiazolyl)-2-[[(3,4-dihydroxybenzyl)oxy]imino]acetamido]-3-[[5-(3,4-dihydroxyphenyl)-2H-tetrazol-2-yl]methyl]-8-oxo-5-thia-1-azabicyclo[4.2.0]oct-2-ene-2-carboxylic acid:

$^1$H-NMR (DMSO-d$_6$, 250 MHz): signals at δ (ppm) 3.48 (m, 2H), 4.93 (s, 2H), 5.16 (d, J=5 Hz, 1H), 5.64 (d, J=14 Hz, 1H), 5.80 (d,d, J=5 Hz, J=8 Hz, 1H), 5.82 (d, J=14 Hz, 1H), 6.7 (m, H), 6.88 (d, J=7 Hz) 7.24 (s, 2H), 7.38 (m, 1H), 7.48 (m, 1H), 8.86 (s, 1H), 8.91 (s, 1H), 9.20 (d, J=8 Hz, 1H), 14.0 (s, broad, 1H);

(6R,7R)-7-[(Z)-2-(2-amino-4-thiazolyl)-2-[[(2-fluoro-3,4-dihydroxybenzyl)oxy]imino]acetamido]-3-[[5-(3,4-dihydroxyphenyl)-2H-tetrazol-2-yl]methyl]-8-oxo-5-thia-1-azabicyclo[4.2.0]oct-2-ene-2-carboxylic acid sodium salt (1:1):

$^1$H-NMR (DMSO-d$_6$, 250 MHz): signals at δ (ppm) 3.24 (m, 2H), 4.97 (d, J=5 Hz, 1H), 5.02 (s, 2H), 5.46 (d, J=14 Hz, 1H), 5.57 (d,d, J=5 Hz, J=8 Hz, 1H), 6.16 (d, J=14 Hz, 1H), 6.54 (m, 1H), 6.70 (m, 2H), 6.86 (d, J=7 Hz, 1H), 7.24 (s, 2H), 7.36 (m, 1H), 7.48 (m, 1H), 9.56 (d, J=8 Hz, 1H). IR: (KBr) 1767 cm$^{-1}$;

(6R,7R)-7-[(Z)-2-(2-amino-4-thiazolyl)-2-[[(3,4-dihydro-5-hydroxy-4-oxo-2-pyrimidinyl)methoxy]imino]acetamido]-3-[[5-(3,4-dihydroxyphenyl)-2H-tetrazol-2-yl]methyl]-8-oxo-5-thia-1-azabicyclo[4.2.0]oct-2-ene-2-carboxylic acid sodium salt (1:1):

$^1$H-NMR (DMSO-d$_6$, 250 MHz): signals at δ (ppm) 3.23 (m, 2H), 4.93 (s, 2H), 5.02 (d, J=5 Hz, 1H), 5.43 (d, J=14 Hz, 1H), 5.62 (d,d, J=5 Hz, J=8 Hz, 1H), 6.17 (d, J=14 Hz, 1H), 6.35 (s, 1H), 6.36 (d, J=7 Hz, 1H), 7.27 (s, 1H), 7.35 (d,d, J=7 Hz, J=2,5 Hz, 1H), 7.38 (s, 1H), 7.48 (d, J=2,5 Hz, 1H), 9.90 (d, J=8 Hz, 1H). IR: (KBr) 1768 cm$^{-1}$.

EXAMPLE 37

Manufacture of (6R,7R)-7-[(Z)-2-(2-amino-4-thiazolyl)-2-[[[(S)-α-carboxy-3,4-dihydroxybenzyl]oxy]imino]acetamido]-3-[[[2-[[(3,4-dihydroxyphenyl)sulphonyl]methyl]-5-methyl-s-triazolo[1,5-a]pyrimidin-7-yl]thio]methyl]-8-oxo-5-thia-1-azabicyclo[4.2.0]oct-2-ene-2-carboxylic acid sodium salt (6R,7R)-7-(2-Amino-4-thiazoleglyoxylamido)-3-[[[2-[[(3,4-dihydroxyphenyl)sulphonyl]methyl]-5-methyl-s-triazolo[1,5-a]pyrimidin-7-yl]thio]methyl]-8-oxo-5-thia-1-azabicyclo[4.2.0]oct-2-ene-2-carboxylic acid (250 mg) and 230 mg of tert-butyl (S)-α-(aminooxy)-2,2-diphenyl-1,3-benzodioxol-5-acetate are dissolved in 30 ml of dimethylacetamide and left to stand at room temperature for 24 hours. The dimethylacetamide is evaporated in a high vacuum. The residue is digested with water. The precipitate is filtered off, dissolved while still moist in 10 ml of trifluoroacetic acid and stirred at room temperature 2 hours. The trifluoroacetic acid is evaporated in a high vacuum. The residue is partitioned at pH 7 between water and ethyl acetate. The aqueous phase is chromatographed on Opti-up C$_{12}$® with water, 5% and 10% acetonitrile. The uniform fraction are concentrated and lyophilized. There are obtained 160 mg of (6R,7R)-7-[(Z)-2-(2-amino-4-thiazolyl)-2-[[[(S)-α-carboxy-3,4-dihydroxybenzyl]oxy]imino]acetamido]-3-[[[2-[[(3,4-dihydroxyphenyl)sulphonyl]methyl]-5-methyl-s-triazolo[1,5-a]pyrimidin-7-yl]thio]methyl]-8-oxo-5-thia-1-azabicyclo[4.2.0]oct-2-ene-2-carboxylic acid sodium salt as a white powder.

$^1$H-NMR (DMSO-d$_6$, 250 MHz): signals at δ (ppm) 2.56 (s, 3H), 3.20 (d, J=17 Hz, 1H), 3.48 (d, J=17 Hz, 1H), 4.43 (m, 2H), 4.68 (s, 2H), 5.01 (d, J=5 Hz, 1H), 5.09 (s, 1H), 5.68 (d,d, J=5 Hz, J=8 Hz, 1H), 6.6–6.9 (m, 7H), 7.2 (s, broad, 2H), 7.64 (s, 1H), 11.61 (d, J=8 Hz, 1H). IR: (KBr) 1766 cm$^{-1}$.

The tert-butyl (S)-α-(aminooxy)-2,2-diphenyl-1,3-benzodioxol-5-acetate used as the starting material can be prepared as follows:

5-Bromo-2,2-diphenyl-1,3-benzodioxol (70.6 g) are dissolved in 300 ml of tetrahydrofuran, treated with 125 ml of n-butyllithium in n-hexane at −78° C. and subsequently stirred at this temperature for 10 minutes. This solution is added in one portion to a solution of 50.0 g of di-tert.-butyl oxalate in 300 ml of tetrahydrofuran and the mixture is stirred at −78° C. for a further 10 minutes. Thereupon, 1 liter of semi-concentrated aqueous ammonium chloride solution is added and the mixture is transferred into a separating funnel for the phase separation. The organic phase is washed with saturated aqueous sodium chloride solution. The aqueous phases are extracted with ethyl acetate. The combined organic phases are dried over magnesium sulphate and concentrated. The oily residue is treated with 70 ml of t-butyl methyl ether and diluted with 300 ml of n-hexane. Spontaneous crystallization occurs. The crystals are filtered off and recrystallized from ethanol. After drying there are obtained 31.0 g of tert-butyl [3,4-[(diphenylmethylene)dioxy]phenyl]glyoxylate as white crystals of melting point 120.5°–122° C.

Tert-butyl [3,4-[(diphenylmethylene)dioxy]phenyl]glyoxylate (15 g) are dissolved in 250 ml of methanol:methylene chloride 2.5:1 and hydrogenated under 60 atmospheres hydrogen pressure at room temperature for 144 hours with the addition of 0.5 mol percent of ruthenium chloride [(R)-Biphemp] complex. The reaction mixture is filtered, concentrated and the residue is recrystallized from ethanol. There are obtained 10.7 g of tert.butyl (R)-α-hydroxy-2,2-diphenyl-1,3-benzodioxol-5-acetate of melting point 153°–154.5° C.; $[α]_D^{20} = -37.4°$. The optical purity was determined by means of $^1$H NMR using chiral shift reagents. The substance was enantiomerically pure according to these criteria.

Tert.butyl (R)-α-hydroxy-2,2-diphenyl-1,3-benzodioxol-5-acetate (2.2 g), 1.80 g of N-hydroxyphthalimide and 2.2 g of triphenylphosphine are dissolved in 25 ml of methylene chloride and cooled to 0° C. Thereupon, 1.70 ml of diisopropyl azodicarboxylate dissolved in 10 ml of methylene chloride are added dropwise and the mixture is subsequently stirred at room temperature for 1 hour. The reaction mixture is chromatographed on silica gel with methylene chloride. The least polar product (eluted first) is collected. After concentration there is obtained 0.9 g of a white solid of melting point 132°–133° C. This solid is dissolved in 10 ml of ethanol, treated with 0.20 ml of 3-dimethylamino-1-propylamine and stirred at room temperature for 1 hour. A white precipitate forms. This is filtered off and dried. There are obtained 480 mg of tert-butyl (S)-α-(aminooxy)-2,2-diphenyl-1,3-benzodioxol-5-acetate as white crystals.

$^1$H-NMR (CDCl$_3$, 250 MHz): signals at δ (ppm) 1.44 (s, 9H), 4.90 (s, 1H), 5.72 (s, broad, 2H), 6.8–7.0 (m, 3H), 7.35 (m, 6H), 7.55 (m, 4H). ee≧95% according to $^1$H NMR with the aid of shift reagents.

EXAMPLE 38

Manufacture of (6R,7R)-7-[(Z)-2-(2-amino-4-thiazolyl)-2-[[1-(hydroxycarbamoyl)-1-methylethoxy]imino]acetamido]-3-[[[2-(3,4-dihydroxyphenyl)-5-methyl-s-triazolo[1,5-a]pyrimidin-7-yl]thio]methyl]-8-oxo-5-thia-1-azabicyclo[4.2.0]oct-2-ene-2-carboxylic acid (6R,7R)-7-(2-Amino-4-thiazoleglyoxylamido)-3-[[[2-(3,4-dihydroxyphenyl)-5-methyl-s-triazolo[1,5-a]pyrimidin-7-yl]thio]methyl]-8-oxo-5-thia-1-azabicyclo[4.2.0]oct-2-ene-2-carboxylic acid (1.3 g) and 0.44 g of 2-(aminooxy)-N-hydroxy-2-methylpropionamide hydrochloride are dissolved in 10 ml of dimethylacetamide. After standing overnight the mixture is evaporated in a vacuum. The residue is digested with 20 ml of water and the precipitate formed is filtered off under suction and dried. There are obtained 1.15 g of 6R,7R)-7-[(Z)-2-(2-amino-4-thiazolyl)-2-[[1-(hydroxycarbamoyl)-1-methylethoxy]imino]acetamido]-3-[[[2-(3,4-dihydroxyphenyl)-5-methyl-s-triazolo[1,5-a]pyrimidin-7-yl]thio]methyl]-8-oxo-5-thia-1-azabicyclo[4.2.0]oct-2-ene-2-carboxylic acid $^1$H-NMR (DMSO-d$_6$, 250 MHz): signals at δ1.41 (s, 3H), 1.43 (s, 3H), 2.58 (s, 3H), 3.63 (d, J=18 Hz, 1H), 3.86 (d, J=18 Hz, 1H), 4.38 (d, J=13 Hz, 1H), 4.53 (d, J=13 Hz, 1H), 5.25 (d, J=5 Hz, 1H), 5.95 (dd, J=5 and 8 Hz, 1H), 6.81 (s, 1H), 6.87 (d, J=9 Hz, 1H), 7.23 (s, 1H), 7.52 (dd, J=9 and 1 Hz, 1H), 7.62 (d, J=1 Hz, 1H), 9.70 (d, J=8 Hz, 1H), 10.09 (s, 1H).

The (6R,7R)-7-(2-amino-4-thiazoleglyoxylamido)-3--[[[2-(3,4-dihydroxyphenyl)-5-methyl-s-triazolo[1,5-a]pyrimidin-7-yl]thio]methyl]-8-oxo-5-thia-1-azabicyclo[4.2.0]oct-2-ene-2-carboxylic acid used as the starting material can be prepared as follows:

3,4-Dihydroxybenzoic hydrazide (132 g) and 66 g of cyanamide are boiled under reflux for 16 hours in 1230 ml of 0.64N ethanolic hydrochloric acid and 465 ml of dimethylacetamide. The 1-(3,4-dihydroxybenzamido)-guanidine hydrochloride crystallizes out after cooling. 5 l of diethyl ether are added in order to complete the precipitation. The suction filtered crude product is then heated on a steam bath in 1.16 l of 1N aqueous sodium hydroxide solution for 1 hour. After filtration of the hot solution the pH is adjusted to 6 with 90 ml of 25% aqueous hydrochloric acid, whereby the 4-(5-amino-1H-1,2,4-triazol-3-yl)pyrocatechol formed precipitates. There are obtained 87 g of crystalline product of m.p. 292°–295° C. (dec.).

Eighty-seven grams of the above product are stirred at 80° C. for 17 hours with 106 ml of ethyl acetoacetate in 870 ml of glacial acetic acid. After cooling the resulting precipitate is filtered off, taken up in 1200 ml of water and the resulting 2-(3,4-dihydroxyphenyl)-5-methyl-s-triazolo[1,5-a]pyrimidin-7(4H)-one is precipitated by adjusting the pH value to 6. After drying in a vacuum there are obtained 90.6 g of colourless crystallizate, m.p. above 310° C. For the further reaction, the product is acetylated in 900 ml of pyridine with 95 ml of acetic anhydride. The product is isolated by evaporation of the solvent and recrystallization from 2 l of glacial acetic acid. There are obtained 103.5 g of 2-(3,4-diacetoxyphenyl)-5-methyl-s-triazolo[1,5-a[pyrimidin-7(4H)-one of m.p. 286°–289° C.

Sixty-nine grams of the aforementioned product are placed in 350 ml of phosphorus oxychloride. 25 ml of dimethylaniline are added to the mixture and it is then stirred at 80° C. for 5 hours. After cooling in an ice bath the mixture is suction filtered over a glass suction filter, the precipitate is rinsed with a small amount of ethyl acetate and dried in a vacuum. The crude intermediate is then introduced in the course of one hour into a solution of 765 g of sodium hydrogen sulphide in 850 ml of water. The mixture is stirred overnight, the pH value is lowered to 7 by the addition of about 60 ml of 3N aqueous hydrochloric acid, the paste-like product is filtered off under suction and washed with a small amount of water. It is suspended in 400 ml of acetone and again filtered off under suction, there being obtained 32.8 g of colourless 4-(7-mercapto-5-methyl-s-triazolo[1,5-a]pyrimidin-2-yl)pyrocatechol. $C_{12}H_{16}N_4O_2S.H_2O$ (calculated: C=49.31%, H=4.14%, N=19.17%, S=10.97%; found: C=48.99%, H=4.01%, N=18.84%, S=11.03%).

4-(7-Mercapto-5-methyl-s-triazolo[1,5-a]pyrimidin-2-yl)pyrocatechol (1.8 g) and 1.63 g of 7-amino-cephalosporanic acid are suspended in 30 ml of a 1:1 mixture of dichloromethane and sulpholane. 2.63 g of boron trifluoride etherate are added thereto at 3° C. and the solution is left at the same temperature for 1½ hours. Thereafter, it is diluted dropwise with 60 ml of dichloromethane, the resulting precipitate is filtered off under suction, rinsed with diethyl ether and dissolved immediately in 40 ml of water. Sufficient 20% aqueous sodium hydroxide solution is added while cooling with ice until pH 3.1 has been reached, whereby the product precipitates. This is filtered off under suction, washed with a small amount of water and finally with 20 ml of acetone and dried in a vacuum at 0.1 mmHg. There are obtained 2.17 g of (6R,7R)-7-amino-3-[[[2-(3,4-dihydroxyphenyl)-5-methyl-s-triazolo[1,5-a]pyrimidin-7-yl]thio]methyl]-8-oxo-5-thia-1-azabicyclo[4.2.0]oct-2-ene-2-carboxylic acid.

$^1$H-NMR (DMSO-d$_6$, 250 MHz): signals at δ: 2.57 (s, 3H), 3.59 (d, J=18 Hz, 1H), 3.76 (d, J=18 Hz, 1H), 4.36 (d, J=12.5 Hz, 1H), 4.42 (d, J=12.5 Hz, 1H), 4.83 (d, J=6 Hz, 1H), 5.40 (d, J=6 Hz, 1H), 6.87 (d, J=9 Hz, 1H), 7.22 (s, 1H), 7.51 (m, 1H), 7.63 (d, J=1 Hz, 1H), 9.4 (broad, 2H).

(6R,7R)-7-Amino-3-[[[2-(3,4-dihydroxyphenyl)-5-methyl-s-triazolo[1,5-a]pyrimidin-7-yl]thio]methyl]-8-oxo-5-thia-1-azabicyclo[4.2.0]oct-2-ene-2-carboxylic acid (4.86 g) and 4.01 g of 2-amino-4-thiazolethioglyoxylic acid S-(2-benzothiazolyl) ester in 60 ml of dimethylacetamide are left to react at room temperature for 3 hours. Thereafter, the solvent is evaporated at 25° C. and 0.1 bar and the residue is digested with 125 ml of acetone. The resulting precipitate is filtered off under suction. After repeated treatment with acetone there are obtained, after drying in a vacuum, 4.8 g of (6R,7R)-7-(2-amino-4-thiazoleglyoxylamido)-3--[[[2-(3,4-dihydroxyphenyl)-5-methyl-s-triazolo[1,5-a]pyrimidin-7-yl]thio]methyl]-8-oxo-5-thia-1-azabicyclo[4.2.0]oct-2-ene-2-carboxylic acid.

$^1$H-NMR (DMSO-d$_6$, 250 MHz): signals at δ2.58 (s, 3H), 3.65 (d, J=18 Hz, 1H), 3.82 (d, J=18 Hz, 1H), 4.39 (d, J=13 Hz, 1H), 4.50 (d, J=13 Hz, 1H), 5.24 (d, J=6 Hz, 1H), 5.81 (dd, J=6 and 9 Hz, 1H), 6.86 (d, J=8 Hz, 1H), 7.24 (s, 1H), 7.42 (s, broad, 2H), 7.51 (m, 1H), 7.62

(d, J about 1 Hz, 1H), 7.83 (s, 1H), 9.31 (s, broad, 1H), 9.47 (s, broad, 1H), 9.82 (d, J=9 Hz, 1H).

EXAMPLE 39

Manufacture of (6R,7R)-[(Z)-2-(2-amino-4-thiazolyl)-2-[[(3,4-dihydroxybenzyl)oxy]imino]acetamido]-3-[[[2-(3,4-dihydroxyphenyl)-5-methyl-s-triazolo[1,5-a]pyrimidin-7-yl]thio]methyl]-8-oxo-5-thia-1-azabicyclo[4.2.0]oct-2-ene-2-carboxylic acid S-(2-Benzothiazolyl)-2-amino-4-thiazoleglyoxylate (Z)-O-[3,4-[(diphenylmethylene)dioxy]benzyl]oxime (1.87 g) and 1.46 g of (6R,7R)-7-amino-3-[[[2-(3,4-dihydroxyphenyl)-5-methyl-s-triazolo[1,5-a]pyrimidin-7-yl]thio]methyl]-8-oxo-5-thia-1-azabicyclo[4.2.0]oct-2-ene-2-carboxylate are dissolved in 20 ml of dimethylacetamide. After standing for 48 hours 50 ml of water are added thereto and the precipitated crude product is filtered off. This is resuspended in 50 ml of water and partially brought into solution at pH 7.8 by the addition of sodium bicarbonate. After filtration the reaction product is then precipitated by the addition of 1N aqueous hydrochloric acid, filtered off and dried. The thus-purified product is then introduced into 25 ml of trifluoroacetic acid and 0.1 ml of water. After 1 hour the mixture is evaporated, 35 ml of diethyl ether are added and the precipitate is filtered off under suction. It is again dissolved in 20 ml of dimethylacetamide and 1.4 ml of a 2M solution of sodium 2-ethylcaproate in ethyl acetate are added thereto and the sodium salt of (6R,7R)-[(Z)-2-(2-amino-4-thiazolyl)-2-[[(3,4-dihydroxybenzyl)oxy]imino]acetamido]-3-[[[2-(3,4-dihydroxyphenyl)-5-methyl-s-triazolo[1,5-a]pyrimidin-7-yl]thio]methyl]-8-oxo-5-thia-1-azabicyclo[4.2.0]oct-2-ene-2-carboxylic acid is precipitated as a fine crystalline product by the dropwise addition of 100 ml of ethyl acetate. 1.75 g of beige powder are obtained.

$^1$H-NMR (DMSO-d$_6$): signals at δ2.54 (s, 3H), 3.46 (d, J=18 Hz, 1H), 3.62 (d, J=18 Hz, 1H), 4.40 (d, J=13 Hz, 1H), 4.61 (d, J=13 Hz, 1H), 4.92 (s, 1H), 5.08 (d, J=5 Hz, 1H), 5.66 (dd, J=5 and 8 Hz, 1H), 6.7 (s, 1H), 6.6–6.76 (m, 3H), 6.85 (d, J=8.5 Hz, 1H), 7.5 (m, 2H), 7.63 (m, 1H), 9.58 (d, J=8 Hz, 1H).

EXAMPLE 40

Manufacture of (6R,7R)-7-[(Z)-2-(2-amino-4-thiazolyl)-2-(Z)-[[1-hydroxycarbamoyl)-1-methylethoxy]imino]acetamido]-3-[[[2-(3-chloro-4,5-dihydroxyphenyl)-5,6-dimethyl-s-triazolo[1,5-a]pyrimidin-7-yl]thio]methyl]-8-oxo-5-thia-1-azabicyclo[4.2.0]oct-2-ene-2-carboxylic acid sodium salt (1:1)

In the same manner to that in Example 38, starting from (6R,7R)-7-(2-amino-4-thiazoleglyoxylamido)-3-[[[2-(3-chloro-4,5-dihydroxyphenyl)-5,6-dimethyl-s-triazolo[1,5-a]pyrimidin-7-yl]thio]methyl]-8-oxo-5-thia-1-azabicyclo[4.2.0]oct-2-ene-2-carboxylic acid there is manufactured the compound (6R,7R)-7-[(Z)-2-(2-amino-4-thiazolyl)-2-(Z)-[[1-hydroxycarbamoyl)-1-methylethoxy]imino]acetamido]-3-[[[2-(3-chloro-4,5-dihydroxyphenyl)-5,6-dimethyl-s-triazolo[1,5-a]pyrimidin-7-yl]thio]methyl]-8-oxo-5-thia-1-azabicyclo[4.2.0]oct-2-ene-2-carboxylic acid sodium salt (1:1)

$^1$H-NMR (DMSO-d$_6$, 250 MHz): signals at δ1.41 (s, 3H), 1.44 (s, 3H), 2.45 (s, 3H), 2.59 (s, 3H), 3.63 (d, J=18 Hz, 1H), 3.79 (d, J=18 Hz, 1H), 4.31 (d, J=13 Hz, 1H), 4.43 (d, J=13 Hz, 1H), 5.11 (d, J=6 Hz, 1H), 5.80 (dd, J=6 and 9 Hz, 1H), 6.79 (s, 1H), 7.34 (s, broad, 2H), 7.6–7.65 (m, 2H).

The (6R,7R)-7-(2-amino-4-thiazoleglyoxylamido)-3-[[[2-(3-chloro-4,5-dihydroxyphenyl)-5,6-dimethyl-s-triazolo[1,5-a]pyrimidin-7-yl]thio]methyl]-8-oxo-5-thia-1-azabicyclo[4.2.0]oct-2-ene-2-carboxylic acid required for this can be prepared analogously to (6R,7R)-7-(2-amino-4-thiazoleglyoxylamido)-3-[[[2-(3,4-dihydroxyphenyl)-5-methyl-s-triazolo[1,5-a]pyrimidin-7-yl]thio]methyl]-8-oxo-5-thia-1-azabicyclo[4.2.0]oct-2-ene-2-carboxylic acid. Starting from 3-chloro-4,5-dihydroxybenzoic hydrazide, this is converted into 3-chloro-5-(5-amino-1H-1,2,4-triazol-3-yl)pyrocatechol and this by means of methyl 2-methylacetoacetate is converted into 2-(3-chloro-4,5-dihydroxyphenyl)-5-methyl-s-triazolo[1,5-a]pyrimidin-7(4H)-one. There is initially obtained (6R,7R)-7-amino-3-[[[2-(3-chloro-4,5-dihydroxyphenyl)-5,6-dimethyl-s-triazolo[1,5-a]pyrimidin-7-yl]thio]methyl]-8-oxo-5-thia-1-azabicyclo[4.2.0]oct-2-ene-2-carboxylic acid:

[$^1$H-NMR (DMSO-d$_6$, 250 MHz): signals at δ2.43 (s, 1H), 2.57 (s, 1H), 3.60 (d, J=18 Hz, 1H), 3.75 (d, J=18 Hz, 1H), 4.25 (d, J=12.5 Hz, 1H), 4.32 (d, J=12.5 Hz, 1H), 4.70 (d, J=6 Hz, 1H), 4.81 (d, J=6 Hz, 1H), 7.59 (d, J=1 Hz, 1H), 7.62 (d, J=1 Hz, 1H)]

and from this there is obtained (6R,7R)-7-(2-amino-4-thiazoleglyoxylamido)-3-[[[2-(3-chloro-4,5-dihydroxyphenyl)-5,6-dimethyl-s-triazolo[1,5-a]pyrimidin-7-yl]thio]methyl]-8-oxo-5-thia-1-azabicyclo[4.2.0]oct-2-ene-2-carboxylic acid:

$^1$H-NMR (DMSO-d$_6$, 250 MHz): signals at δ2.40 (s, 3H), 2.53 (s, 3H), 3.38 (d, J=18 Hz, 1H), 3.58 (d, J=18 Hz, 1H), 4.61 (d, J=12.5 Hz, 1H), 4.51 (d, J=12.5 Hz, 1H), 5.00 (d, J=6 Hz, 1H), 5.60 (m, 1H), 7.43 (s, broad, 2H), 7.51 (d, J=1 Hz, 1H), 7.63 (d, J=1 Hz, 1H), 7.80 (s, 1H), 9.73 (d, broad, 1H).

EXAMPLE 41

Manufacture of (6R,7R)-7-[(Z)-2-(2-amino-4-thiazolyl)-2-[[(3,4-dihydroxybenzyl)oxy]imino]acetamido]-3-[[[5-(3,4-dihydroxyphenyl)pyrazolo[1,5-a]pyrimidin-7-yl]thio]methyl]-8-oxo-5-thia-1-azabicyclo[4.2.0]oct-2-ene-2-carboxylic acid sodium salt (1:1)

(6R,7R)-7-(2-Amino-4-thiazoleglyoxylamido)-3-[[[5-(3,4-dihydroxyphenyl)pyrazolo[1,5-a]pyrimidin-7-yl]thio]methyl]-8-oxo-5-thia-1-azabicyclo[4.2.0]oct-2-en-2-carboxylic acid (1.252 g) and 1.065 g of O-[3,4-[(diphenylmethylene)dioxy]benzyl]hydroxylamine are dissolved in 20 ml of dimethylacetamide: The mixture is left at room temperature for 24 hours and in a refrigerator for 3 days, evaporated in a vacuum at 40° C. and the reaction product is precipitated by stirring with 100 ml of water. The product is washed with water and dried. The crude product is then dissolved in 25 ml of trifluoroacetic acid at 0° C. After the addition of 25 drop of water the mixture is left to stand for 1 hour without further cooling and evaporated in a vacuum. The residue is stirred with 100 ml of diethyl ether, whereby the product separates in solid form. It is filtered off, dissolved in water at pH 7 with the addition of sodium bicarbonate and chromatographed over RP12-Kieselgel with water/acetonitrile. The product fraction is concentrated and lyophilized. There are obtained 530 mg of (6R,7R)-7-[(Z)-2-(2-amino-4-thiazolyl)-2-[[(3,4-dihydrooxybenzyl)oxy]imino]acetamido]-3-[[[5-(3,4-dihydroxyphenyl)pyrazolo[1,5-a]pyrimidin-7-yl]thio]methyl]-8-oxo-5-thia-1-azabicyclo[4.2.0]oct-2-ene-2-carboxylic acid sodium salt (1:1) as a beige powder.

$^1$H-NMR (DMSO-d$_6$, 250 MHz): signals at δ3.46 (d, J=18 Hz, 1H), 3.61 (d, J=18 Hz, 1H), 4.59 (d, J=13

Hz, 1H), 4.88 (d, J=13 Hz, 1H), 4.90 (s, 2H), 5.04 (d, J=5 Hz, 1H), 5.59 (dd, J=5 and 8 Hz, 1H), 6.59–6.72 (m, 5H), 6.87 (d, J=9 Hz, 1H), 7.21 (s, broad, 2H), 7.64–7.68 (m, 2H), 7.82 (m, 1H), 8.14 (d, J=2 Hz, 1H), 8.95 (broad, 2H), 9.59 (m, 3H).

EXAMPLE 42

Manufacture of (6R,7R)-7-[(Z)-2-(2-amino-4-thiazolyl)-2-[[1-[3-(3,4-dihydroxybenzoyl)carbazoyl]-1-methylethoxy]imino]acetamido]-3-[[[2-[(3,4-dihydroxybenzenesulphonamido)methyl]-5-methyl-s-triazolo[1,5-a]pyrimidin-7-yl]thio]methyl]-8-oxo-5-thia-1-azabicyclo[4.2.0]oct-2-ene-2-carboxylic acid sodium salt (1:1)

(6R,7R)-7-(2-Amino-4-thiazoleglyoxylamido)-3-[[[2-[(3,4-dihydroxybenzenesulphonamido)methyl]-5-methyl-s-triazolo[1,5-a]pyrimidin-7-yl]thio]methyl]-8-oxo-5-thia-1-azabicyclo[4.2.0]-oct-2-ene-2-carboxylic acid (0.10 g) and 0.10 g of 1-[2-(aminooxy)-2-methylpropionyl]-2-(3,4-dihydroxybenzoyl)hydrazine hydrochloride (known from EPOS 286,145) are stirred in 1 ml of dimethylacetamide for 16 hours at room temperature. The dimethylacetamide is evaporated in a high vacuum and the residue is digested with water. The precipitate is filtered off, resuspended in water, brought into solution at pH 7.0 by the addition of 1N sodium hydroxide solution and lyophilized. There are obtained 1.11 g of (6R,7R)-7-[(Z)-2-(2-amino-4-thiazolyl)-2-[[1-[3-(3,4-dihydroxybenzoyl)carbazoyl]-1-methylethoxy]imino]acetamido]-3-[[[2-[(3,4dihydroxybenzenesulphonamido)methyl]-5-methyl-s-triazolo[1,5-a]pyrimidin-7-yl]thio]methyl]-8-oxo-5-thia-1-azabicyclo[4.2.0]oct-2-ene-2-carboxylic acid sodium salt (1:1) as a pale beige powder.

$^1$H-NMR (DMSO-d$_6$, 250 MHz): signals at δ (ppm) 1.47 (s, 3H), 1.52 (s, 3H), 2.53 (s, 3H), 3.39 (d, J=18 Hz, 1H), 3.67 (d, J=18 Hz, 1H), 4.13 (d, J=12.5 Hz, 1H), 4.15 (s, diffused, 2H), 4.72 (d, J=12.5 Hz, 1H), 5.12 (d, J=5 Hz, 1H), 5.71 (d,d, J=5 Hz, J=8 Hz, 1H), 6.7 (m, 2H), 6.86 (s, 1H), 6.9 (m, 2H), 7.3 (m, 4H), 7,38 (s, 1H), 8.0 (s, strongly diffused, 1H), 9.26 (s, broad, 1H), 9.60 (d, J=8 Hz, 1H) IR: (KBr) 1766 cm$^{-1}$ MS: 985.1 (M+H$^\oplus$)

EXAMPLE 43

Manufacture of (6R,7R)-7-[(Z)-2-(2-amino-4-thiazolyl)-2-[[1-[3-(3,4-dihydroxybenzoyl)carbazoyl]-1-methylethoxy]iminoacetamido]-3-[[[2-[[(3,4-dihydroxybenzoyl)oxy]methyl]-5-methyl-s-triazolo[1,5-a]pyrimidin-7-yl]thio]methyl]-8-oxo-5-thia-1-azabicyclo[4.2.0]oct-2-ene-2-carboxylic acid sodium salt (1:1)

(6R,7R)-7-(2-Amino-4-thiazoleglyoxylamido)-3-[[[2-[[(3,4-dihydroxybenzoyl)oxy]methyl]-5-methyl-s-triazolo[1,5-a]pyrimidin-7-yl]thio]methyl]-8-oxo-5-thia-1-azabicyclo[4.2.0]oct-2-ene-2-carboxylic acid (0.50 g) and 0.25 g of 1-[2-(aminooxy)-2-methylpropionyl]-2-(3,4-dihydroxybenzoyl)-hydrazine hydrochloride are stirred in 5 ml of dimethylacetamide for 16 hours at room temperature. The dimethylacetamide is evaporated in a high vacuum, the residue is digested in water and the resulting precipitate is filtered off. The solid is resuspended in water, brought into solution at pH 7.0 with 1N aqueous sodium hydroxide solution and chromatographed on RP12-kieselgel with water/acetone (RP12-kieselgel="reversed phase" silica gel, e.g. Optiup C$_{12}$ ® from the company ANTEC, Bennwil, Switzerland; a silica gel with a partical size of 0.040–0.063 mm, treated with dodecyltrichlorosilane). The uniform fractions are concentrated and lypholyzed. There is obtained 0.40 g of (6R,7R)-7-[(Z)-2-(2-amino-4-thiazolyl)-2-[[1-3-(3,4-dihydroxybenzoyl)carbazoyl]-1-methylethoxy]iminoacetamido]-3-[[[2-[[(3,4-dihydroxybenzoyl)oxy]methyl]-5-methyl-s-triazolo[1,5-a]pyrimidin-7-yl]thio]methyl]-8-oxo-5-thia-1-azabicyclo[4.2.0]oct-2-ene-2-carboxylic acid sodium salt (1:1) as a pale beige powder.

$^1$H-NMR (DMSO-d$_6$, 250 MHz): signals at δ (ppm) 2.55 (s, 3H), 3.41 (d, J=18 Hz, 1H), 3.64 (d, J=18 Hz, 1H), 4.31 (d, J=12.5 Hz, 1H), 4.68 (d, J=12.5 Hz, 1H), 5.09 (d, J=5 Hz, 1H), 5.44 (s, 2H), 5.71 (dd, J=5 Hz, J=8 Hz, 1H), 6.8 (m, 3H), 7.30 (m, 6H), 7.65 (s, 1H), 9.26 (s, 1H), 9.54 (d, J=8 Hz, 1H) IR (KBr) 1768 cm$^{-1}$ MS: 972 (M+Na$^\oplus$), 950 (M+H$^\oplus$)

EXAMPLE 44

Manufacture of (6R,7R)-7-[(Z)-2-(2-amino-4-thiazolyl)-2-[[1-[3-(3,4-dihydroxyphenyl)sulphonyl]-1-methylethoxy]imino]acetamido]-3-[[[2-[[(3,4-dihydroxyphenyl)sulphonyl]methyl]-5-methyl-s-triazolo[1,5-a]pyrimidin-7-yl]thio]methyl]-8-oxo-5-thia-azabicyclo[4.2.0]oct-2-ene-2-carboxylic acid sodium salt (1:1)

(6R,7R)-7-(2-Amino-4-thiazoleglyoxylamido)-3-[[[2-[[(3,4-dihydroxyphenyl)sulphonyl]methyl]-5-methyl-s-triazolo[1,5-a]pyrimidin-7-yl]thio]methyl]-8-oxo-5-thia-1-azabicyclo[4.2.0]-oct-2-ene-carboxylic acid (0.50 g) and 0.35 g of 1-[2-(aminooxy)-2-methylpropionyl]-2-(3,4-dihydroxybenzoyl)hydrazine hydrochloride are dissolved in 5 ml of dimethylacetamide and stirred at room temperature for 16 hours. The dimethylacetamide is evaporated in a high vacuum and the residue is digested with water. The precipitate formed is filtered off, washed with water, resuspended in water, brought into solution at pH 7.0 (adjusted with 1N aqueous sodium hydroxide solution) and chromatographed on RP12-kieselgel. After lyophilization of the product fractions there is obtained 0.490 g of (6R,7R)-7-[(Z)-2-(2-amino-4-thiazolyl)-2-[[1-[3-(3,4-dihydroxybenzoyl)carbazoyl]-1-methylethoxy]imino]acetamido]-3-[[[-2-[[(3,4-dihydroxyphenyl)sulphonyl]methyl]-5-methyl-s-triazolo[1,5-a]pyrimidin-7-yl]thio]methyl]-8-oxo-5-thia-azabicyclo[4.2.0]oct-2-ene-2-carboxylic acid as a pale beige powder.

$^1$H-NMR (DMSO-d$_6$, 250 MHz): signal at δ (ppm) 1.46 (s, 3H), 1.52 (s, 3H), 2.55 (s, 3H), 3.38 (d, J=18 Hz, 1H), 3.62 (d, J=18 Hz, 1H), 4.32 (d, J=12,5 Hz, 1H), 4.54 (d, J=12.5 Hz, 1H), 4.71 (s, 2H), 5.09 (d, J=5 Hz, 1H), 5.70 (d, broad, J=5 Hz, 1H), 6.71 (m, 2H), 6.65 (s, 1H), 6.93 (m, 2H), 7.20–7.30 (m, 4H), 7.60 (s, 1H) IR: (KBr) 1765 cm$^{-1}$ MS: 992 (M+H$^\oplus$)

EXAMPLE 45

Manufacture of (6R,7R)-7-[(Z)-2-(2-amino-4-thiazolyl)-2-[[1-[3-(3,4-dihydroxybenzoyl)carbazoyl]-1-methylethoxy]imino]acetamido]-3-[[[5-(3,4-dihydroxyphenyl)-1,3,4-oxadiazol-2-yl]thio]methyl]-8-oxo-5-thia-1-azabicyclo[4.2.0]oct-2-ene-2-carboxylic acid (6R,7R)-7-(2-Amino-4-thiazoleglyoxylamido)-3-[[[5-(3,4-dihydroxyphenyl)-1,3,4-oxadiazol-2-yl]thio]methyl]-8-oxo-5-thia-1-azabicyclo[4.2.0]oct-2-ene-2-carboxylic acid (80 mg) (0.1 mmol) and 42 mg (0.13 mmol) of 1-[2-(aminooxy)-2-methylpropionyl]-2-(3,4-dihydroxybenzoyl)hydrazine hydrochloride are dissolved in 2 ml of absolute dimethylacetamide. After stirring for 20 hours the mixture is filtered and the mother liquor is concentrated at room temperature in a high vacuum. The residue is crystallized using ethanol/diethyl ether. The product is filtered off and washed with water. After drying in a high vacuum at room temperature there are obtained 65 mg of (6R,7R)-7-[(Z)-2-(2-amino-4-thiazolyl)-2-[[1-[3-(3,4-dihydroxybenzoyl)carbazoyl]-1-methylethoxy]imino]acetamido]-3-[[[5-(3,4-dihydroxyphenyl)-1,3,4-oxadiazol-2-yl]thio]methyl]-8-oxo-5-thia-1-azabicyclo[4.2.0]oct-2-ene-2-carboxylic acid as a yellow powder.

$^1$H NMR (DMSO-d$_6$): signals at, inter alia, δ1.46 (s, 3H), 1.52 (s, 3H), 3.65 (d, J=18 Hz, 1H), 3.84 (d, J=18 Hz, 1H), 4.26 (d, J=12,5 Hz, 1H), 4.43 (d, J=12,5 Hz, 1H), 5.20 (d, J=5 Hz, 1H), 5.88 (dd, J=5 Hz and J=8 Hz, 1H), 6.75 (d, J=8 Hz, 1H), 6.90 (d, J=8 Hz, 1H), 6.91 (s, 1H), 7.1–7.4 (4H), 9.23 (s, 1H), 9.64 (d, J=8 Hz, 1H), 10.00 (s, 1H).

The (6R,7R)-7-(2-amino-4-thiazoleglyoxylamido)-3-[[[5-(3,4-dihydroxyphenyl)-1,3,4-oxadiazol-2-yl]thio]methyl]-8-oxo-5-thia-1-azabicyclo[4.2.0]oct-2-ene-2-carboxylic acid used as the starting material can be prepared as follows:

7-Aminocephalosporanic acid (10.38 g) (38.4 mmol) and 9.6 g (42.24 mmol) 5-(3,4-dihydroxyphenyl)-1,3,4-oxadiazole-2(3H)-thione-dimethylformamide complex (known from EPOS 241,901) are suspended in 210 ml of water and treated portionwise while stirring with 3.84 g (42.24 mmol) of sodium hydrogen carbonate. After stirring at 40° C. for 3 days the brown suspension obtained is suction filtered and washed in succession with water, ethanol and diethyl ether. After drying in a high vacuum at room temperature there are obtained 11.7 g of white material. This is dissolved in ethanol and treated with p-toluenesulphonic acid. Subsequently, the solution is concentrated and the salt is crystallized from ethanol/diethyl ether. There is obtained white, crystalline (6R,7R)-7-amino-3-[[[5-(3,4-dihydroxyphenyl)-1,3,4-oxadiazol-2-yl]thio]methyl]-8-oxo-5-thia-1-azabicyclo[4.2.0]oct-2-ene-2-carboxylic acid p-toluenesulphonic acid.

$^1$H NMR (DMSO-d$_6$): 2.29 (s, 3H), 3.78 (d, J=18 Hz, 1H), 3.87 (d, J=18 Hz, 1H), 4.32 (d, J=12,5 Hz, 1H), 4.46 (d, J=12,5 Hz, 1H), 5.2 (2H), 6.89 (d, J=8 Hz, 1H), 7.11 (d, J=8 Hz, 2H), 7.27 (dd, J=8 Hz and J=2 Hz, 1H), 7.34 (d, J=2 Hz, 1H), 7.47 (d, J=8 Hz, 2H).

(6R,7R)-7-Amino-3-[[[5-(3,4-dihydroxyphenyl)-1,3,4-oxadiazol-2-yl]thio]methyl]-8-oxo-5-thia-1-azabicyclo[4.2.0]oct-2-ene-2-carboxylic acid p-toluenesulphonic acid (470 mg) (0.7 mmol) and 500 mg (1.5 mmol) of 2-amino-4-thiazolethioglyoxylic acid S-(2-benzothiazolyl) ester are dissolved in 20 ml of absolute dimethylacetamide. After stirring at room temperature for 24 hours the mixture is concentrated in a high vacuum at room temperature. The residue is taken up in about 20 ml of ethanol and filtered. The mother liquor is treated with diethyl ether. The precipitated product is filtered off and washed with diethyl ether/ethanol (98:2 v/v). After drying in a high vacuum there are obtained 400 mg of (6R,7R)-7-(2-amino-4-thiazoleglyoxylamido)-3-[[[5-(3,4-dihydroxyphenyl)-1,3,4-oxadiazol-2-yl]thio]methyl]-8-oxo-5-thia-1-azabicyclo[4.2.0]oct-2-ene-2-carboxylic acid as a yellow powder.

$^1$H NMR (DMSO-d$_6$): signals at, inter alia, δ2.29 (s, 3.9H), 3.69 (d, J=18 Hz, 1H), 3.81 (d, J=18 Hz, 1H), 4.29 (d, J=12,5 Hz, 1H), 4.45 (d, J=12,5 Hz), 5.18 (d, J=5 Hz, 1H), 5.76 (dd, J=5 Hz and J=8 Hz, 1H), 6.89 (d, J=8 Hz, 1H), 7.12 (d, J=7.5 Hz, 2.6H), 7.27 (dd, J=8 Hz and J=2 Hz, 1H), 7.34 (d, J=2 Hz, 1H), 7.48 (d, J=7.5 Hz, 2.6H), 7.96 (s, 1H), 9.88 (d, J=8 Hz, 1H).

EXAMPLE 46

Manufacture of (6R,7R)-7-[(Z)-2-(2-amino-4-thiazolyl)-2-[[1-[3-(3,4-dihydroxybenzoyl)carbazoyl]-1-methylethoxy]imino]acetamido]-3-[[[5-(3,4-dihydroxyphenyl)-2-phenyl-4-pyrimidinyl]thio]methyl]-8-oxo-5-thia-1-azabicyclo[4.2.0]oct-2-ene-2-carboxylic acid (6R,7R)-7-(2-Amino-4-thiazoleglyoxylamido)-3-[[(5-(3,4-dihydroxyphenyl)-2-phenyl-4-pyrimidinyl]thio]methyl]-8-oxo-5-thia-1-azabicyclo[4.2.0]oct-2-ene-2-carboxylic acid (33 mg) (0.05 mmol) and 22 mg (0.065 mmol) of 1-[(2-aminooxy)-2-methylpropionyl]-2-(3,4-dihydroxybenzoyl)hydrazine hydrochloride are dissolved in 0.6 ml of absolute dimethylacetamide. After stirring at room temperature for 18 hours the solvent is distilled off in a high vacuum. The residue is treated with 4 ml of water and 0.3 ml of ethanol. The precipitated product is filtered off and washed with water and diethyl ether. After drying in a high vacuum at room temperature there are obtained 40 mg of (6R,7R)-7-[(Z)-2-(2-amino-4-thiazolyl)-2-[[1-[3-(3,4-dihydroxybenzoyl)carbazoyl]-1-methylethoxy]imino]acetamido]-3-[[[5-(3,4-dihydroxyphenyl)-2-phenyl-4-pyrimidinyl]thio]methyl]-8-oxo-5-thia-1-azabicyclo[4.2.0]oct-2-ene-2-carboxylic acid as a beige powder.

$^1$H NMR (DMSO-d$_6$): signals at, inter alia, δ1.46 (s, 3H), 1.48 (s, 3H), 3.60 (d, J=18 Hz, 1H), 3.85 (d, J=18 Hz, 1H), 4.19 (d, J=12.5 Hz, 1H), 4.78 (d, J=12.5 Hz, 1H), 5.21 (d, J=5 Hz, 1H), 5.86 (dd, J=5 Hz and J=8 Hz, 1H), 6.72–6.94 (5H), 7.20–7.34 (4H), 7.58 (3H), 8.44 (s, 1H), 8.46 (2H), 9.19 (s, 2H), 9.23 (s, 1H), 9.30 (s, 1H), 9.56 (s, 1H), 9.63 (d, J=8 Hz, 1H), 10.00 (s, 1H).

EXAMPLE 47

Manufacture of (6R,7R)-7-[(Z)-2-(2-amino-4-thiazolyl)-2-[[1-[3-(3,4-dihydroxybenzoyl)carbazoyl]-1-methylethoxy]imino]acetamido]-3-[[(3,4-dihydroxyphenyl)sulphonyl]methyl]-8-oxo-5-thia-1-azabicyclo[4.2.0]oct-2-ene-2-carboxylic acid (6R,7R)-7-(2-Amino-4-thiazoleglyoxylamido)-3-[[(3,4-dihydroxyphenyl)sulphonyl]methyl]-8-oxo-5-thia-1-azabicyclo[4.2.0]oct-2-ene-2-carboxylic acid (160 mg) (0.30 mmol) are dissolved in 2.0 ml of dimethylacetamide, treated with 130 mg (0.39 mmol) of 1-[2-(aminooxy)-2-methylpropionyl]-2-(3,4-dihydroxybenzoyl)hydrazine hydrochloride and stirred at room temperature for 20 hours. The dimethylacetamide is evaporated under a high vacuum and the product is precipitated by the addition of water. The purification is effected by chromatography on silica gel with water/acetonitrile as the eluent. After lyophilization there are obtained 200 mg of (6R,7R)-7-[(Z)-2-(2-amino-4-thiazolyl)-2-[[1-[3-(3,4-dihydroxybenzoyl)carbazoyl]-1-methylethoxy]imino]acetamido]-3-[[(3,4-dihydroxyphenyl)sulphonyl]methyl]-8-oxo-5-thia-1-azabicyclo[4.2.0]oct-2-ene-2-carboxylic acid as a white solid.

$^1$H-NMR (D$_2$O, 250 MHz): signals at δ (ppm): 1.65 (s, 6H), 3.46 (m, 2H), 4.02 (d, J=12.5 Hz, 1H), 4.84 (s, 2H), 5.11 (d, J=12.5 Hz, 1H), 5.21 (d, J=5 Hz, 1H), 5.80 (d, J=5 Hz, 1H), 7.00 (m, 2H), 7.10 (s, 1H), 7.30 (m, 4H). MS: 814 (M+H⊕) IR: 1767 cm$^{-1}$

EXAMPLE 48

Manufacture of (6R,7R)-7-[(Z)-2-(2-amino-4-thiazolyl)-2-[[1-[3-(3,4-dihydroxybenzoyl)carbazoyl]-1-methylethoxy]imino]acetamido]-3-[[[2-(hydroxycarbamoyl)-5-methyl-s-triazolo[1,5-a]pyrimidin-7-yl]thio]methyl]-8- oxo-5-thia-1-azabicyclo[4.2.0]oct-2-ene-2-carboxylic acid (6R,7R)-7-(2-Amino-4-thiazoleglyoxylamido)-3-[[[2-(hydroxycarbamoyl)-5-methyl-s-triazolo[1,5-a]pyrimidin-7-yl]thio]methyl]-8-oxo-5-thia-1-azabicyclo[4.2.0]oct-2-ene-2-carboxylic acid (60 mg) (0.101 mmol) and 40 mg (0.1318 mmol) of 1-[2-(aminooxy)-2-methylpropionyl]-2-(3,4-dihydroxybenzoyl)hydrazine hydrochloride are dissolved in 3 ml of absolute dimethylacetamide. After stirring at room temperature for 24 hours the solvent is removed at room temperature in a high vacuum. The residual oil is treated with water and the precipitated product is filtered off. The whole is washed in succession with water, ethanol and diethyl ether and dried at room temperature in a high vacuum. There are obtained 62 mg of (6R,7R)-7-[(Z)-2-(2-amino-4-thiazolyl)-2-[[1-[3-(3,4-dihydroxybenzoyl)carbazoyl]-1-methylethoxy]imino]acetamido]-3-[[[2-(hydroxycarbamoyl)-5-methyl-s-triazolo[1,5-a]pyrimidin-7-yl]thio]methyl]-8-oxo-5-thia-1-azabicyclo[4.2.0]oct-2-ene-2-carboxylic acid as a beige powder.

$^1$H NMR (DMSO-$d_6$): signals at, inter alia, $\delta$1.47 (s, 3H), 1.50 (s, 3H), 2.60 (s, 3H), 3.64 (d, J=18 Hz, 1H), 3.84 (d, J=18 Hz, 1H), 4.36 (d, J=12.5 Hz, 1H), 4.48 (d, J=12.5 Hz, 1H), 5.23 (d, J=5 Hz, 1H), 5.90 (dd, J=5 Hz and J=8 Hz, 1H), 6.74 (d, J=7.5 Hz, 1H), 6.86 (s, 1H), 7.21 (dd, J=7,5 Hz and J=2 Hz, 1H), 7.29 (d, J=2 Hz, 1H), 7.35 (s, 1H), 9.17 (s, 1H), 9.20 (s, 1H), 9.34 (s, 1H), 9.54 (s, 1H), 9.66 (d, J=8 Hz, 1H), 10.00 (s, 1H), 11.66 (s, 1H).

The (6R,7R)-7-(2-amino-4-thiazoleglyoxylamido)-3-[[[2-(hydroxycarbamoyl)-5-methyl-s-triazolo[1,5-a]pyrimidin-7-yl]thio]methyl]-8-oxo-5-thia-1-azabicyclo[4.2.0]oct-2-ene-2-carboxylic acid used as the starting material can be prepared as follows:

(6R,7R)-7-Amino-3-[[[2-(hydroxycarbamoyl)-5-methyl-s-triazolo[1,5-a]pyrimidin-7-yl]thio]methyl]-8-oxo-5-thia-1-azabicyclo[4.2.0]oct-2-ene-2-carboxylic acid (43.7 mg) (0.1 mmol) are suspended in a mixture consisting of 2 ml of water and 1 ml of acetonitrile. 2 ml of 0.1N aqueous potassium hydroxide solution are added dropwise thereto at room temperature while stirring. Subsequently, 84 mg (0.26 mmol) of 2-amino-4-thiazolethioglyoxylic acid S-(2-benzothiazolyl) ester are added to the solution. The suspension is stirred at room temperature for 3 hours and filtered. The filter material is washed with water, the filtrate and wash solution are combined and washed several times with ethyl acetate. The aqueous solution is adjusted to pH 5 with dilute aqueous hydrochloric acid. The precipitated product is filtered off under suction and washed with water and diethyl ether. After drying in a high vacuum there are obtained 30 mg of (6R,7R)-7-(2-amino-4-thiazoleglyoxylamido)-3-[[[2-(hydroxycarbamoyl)-5-methyl-s-triazolo[1,5-a]pyrimidin-7-yl]thio]methyl]-8-oxo-5-thia-1-azabicyclo[4.2.0]oct-2-ene-2-carboxylic acid as a yellow powder.

$^1$H NMR (DMSO-$d_6$): signals at $\delta$2.61 (s, 3H), 3.63 (d, J=18 Hz, 1H), 3.80 (d, J=18 Hz, 1H), 4.40 (d, J=12.5 Hz, 1H), 4.48 (d, J=12.5 Hz, 1H), 5.21 (d, J=5 Hz, 1H), 5.77 (dd, J=5 Hz and J=8 Hz, 1H), 7.40 (s, 3H), 7.82 (s, 1H), 9.35 (s, 1H), 9.81 (d, J=8 Hz, 1H), 11.68 (s, 1H).

EXAMPLE 49

Manufacture of (6R,7R)-7-[(Z)-2-(2-amino-4-thiazolyl)-2-[(1-[3-(2,5-dichloro-3,4-dihydroxybenzoyl)-carbazoyl]-1-methylethoxy]imino]acetamido]-3-[[(2-(hydroxycarbamoyl)-5-methyl-s-triazolo[1,5-a]pyrimidin-7-yl]thio]methyl]-8-oxo-5-thia-1-azabicyclo[4.2.0]oct-2-ene-2-carboxylic acid (6R,7R)-7-(2-Amino-4-thiazoleglyoxylamido)-3-[[[2-(hydroxycarbamoyl)-5-methyl-s-triazolo[1,5-a]pyrimidin-7-yl]thio]methyl]-8-oxo-5-thia-1-azabicyclo[4.2.0]oct-2-ene-2-carboxylic acid (150 mg) (0.25 mmol) and 175 mg (0.32 mmol) of 1-[2-(aminooxy)-2-methylpropionyl]-2-[(4,7-dichloro-2,2-diphenyl-1,3-benzodioxol-5-yl)carbonyl]hydrazine hydrochloride are dissolved in 4 ml of absolute dimethylacetamide. After stirring at room temperature for 20 hours the solvent is distilled off in a high vacuum. The residue is washed several times with diethyl ether and subsequently crystallized using water. The product is filtered off under suction, washed with water and diethyl ether and dried at room temperature in a high vacuum. There are obtained 260 mg of (6R,7R)-7-[(Z)-2-(2-amino-4-thiazolyl)-2-[[1-[3-[(4,7-dichloro-2,2-diphenyl-1,3-benzodioxol-5-yl)carbazoyl]-1-methylethoxy]imino]acetamido]-3-[[[2-(hydroxycarbamoyl)-5-methyl-s-triazolo[1,5-a]pyrimidin-7-yl)thio]methyl]-8-oxo-5-thia-1-azabicyclo[4.2.0]oct-2-ene-2-carboxylic acid as a beige powder.

$^1$H NMR (DMSO-$d_6$): signals at, inter alia, $\delta$1.46 (s, 3H), 1.48 (s, 3H), 2.60 (s, 3H), 3.64 (d, J=18 Hz, 1H), 3.86 (d, J=18 Hz, 1H), 4.38 (d, J=12.5 Hz, 1H), 4.50 (d, J=12.5 Hz, 1H), 5.25 (d, J=5 Hz, 1H), 5.91 (dd, J=5 Hz and J=8 Hz, 1H), 6.86 (s, 1H), 7.18 (s, 1H), 7.38 (s, 1H), 7.4–7.6 (10H), 9.46 (s, 1H), 9.66 (d, J=8 Hz, 1H), 10.26 (s, 1H), 11.70 (s, 1H).

(6R,7R)-7-[(Z)-2-(2-Amino-4-thiazolyl)-2-[[1-[3-[(4,7-dichloro-2,2-diphenyl-1,3-benzodioxol-5-yl)carbazoyl]-1-methylethoxy]imino]acetamido]-3-[[[2-(hydroxycarbamoyl)-5-methyl-s-triazolo[1,5-a]pyrimidin-7-yl)thio]methyl]-8-oxo-5-thia-1-azabicyclo[4.2.0]oct-2-ene-2-carboxylic acid (125 mg) (0.116 mmol) are dissolved in 2 ml of trifluoroacetic acid. After 5 hours the solvent is distilled off at room temperature in a vacuum. The residue is crystallized using diethyl ether. The product is filtered off under suction and washed in succession with diethyl ether, water and diethyl ether. After drying in a high vacuum at room temperature there are obtained 90 mg of (6R,7R)-7-[(Z)-2-(2-amino-4-thiazolyl)-2-[(1-[3-(2,5-dichloro-3,4-d ihydroxybenzoyl)carbazoyl]-1-methylethoxy]imino]acetamido]-3-[[(2-(hydroxycarbamoyl)-5-methyl-s-triazolo[1,5-a]pyrimidin-7-yl]thio]methyl]-8-oxo-5-thia-1-azabicyclo[4.2.0]oct-2-ene-2-carboxylic acid as a beige powder.

$^1$H NMR (DMSO-$d_6$): signals at, inter alia, $\delta$1.47 (s, 3H), 1.48 (s, 3H), 2.61 (s, 3H), 3.64 (d, J=18 Hz, 1H), 3.86 (d, J=18 Hz, 1H), 4.36 (d, J=12.5 Hz, 1H), 4.49 (d, J=12.5 Hz, 1H), 5.25 (d, J=5 Hz, 1H), 5.92 (dd, J=5 Hz and J=8 Hz, 1H), 6.86 (s, 1H), 7.00 (s, 1H), 7.32 (s, 3H), 7.38 (s, 1H), 9.34 (s, 1H), 9.40 (s, 1H), 9.67 (d, J=8 Hz, 1H), 9.96 (s, 1H), 10.11 (s, 1H), 10.17 (s, 1H), 11.68 (s, 1H).

The 1-[2-(aminooxy)-2-methylpropionyl]-2-[(4,7-dichloro-2,2-diphenyl-1,3-benzodioxol-5-yl)carbonyl]hydrazine hydrochloride used as the starting material can be prepared as follows:

Methyl 4,7-dichloro-2,2-diphenyl-1,3-benzodioxol-5-carboxylate (0.50 g) (1.24 mmol) and 0.62 g (12 mmol) of hydrazine hydrate are stirred together at 80° C. for 20 hours. The reaction mixture is concentrated in a high vacuum and the residue is crystallized from ethanol/water. After recrystallization from ethanol/water there are obtained 310 mg of 4,7-dichloro-2,2-diphenyl-1,3- benzodioxol-5-carboxyhydrazide as white crystals of m.p. 131° C.

4,7-Dichloro-2,2-diphenyl-1,3-benzodioxol-5-carboxyhydrazide (3.00 g) (7.42 mmol), 2.92 g (7.42 mmol) of N-[[2-methyl-2-(phthalimidooxy)propionyl]-oxy]phthalimide and 0.62 g (7.42 mmol) of sodium hydrogen carbonate are suspended in 100 ml of absolute tetrahydrofuran. After stirring at room temperature for 24 hours the solvent is distilled off in a vacuum and the residue is chromatographed on 100 g of silica gel (0.063–0.2 mm). The product is eluted with dichloromethane/ethanol (98:2 v/v). After evaporation of the eluate there remain 3.1 g of 1-[(4,7-dichloro-2,2-diphenyl-1,3-benzodioxol-5-yl)carbonyl]-2-[2-phthalimidooxy)-2-methylpropionyl]hydrazine as a colourless oil.

$^1$H NMR (DMSO-d$_6$): signals at, inter alia, δ1.55 (s, 6H), 7.20 (s, 1H), 7.5 (10H), 7.92 (s, 1H), 10.10 (s, 1H), 10.38 (s, 1H).

1-[(4,7-Dichloro-2,2-diphenyl-1,3-benzodioxol-5-yl)carbonyl]-2-[2-phthalimidooxy)-2-methylpropionyl]-hydrazine (3.0 g) (4.7 mmol) are dissolved in 120 ml of absolute tetrahydrofuran and treated with 0.219 g (4.7 mmol) of methylhydrazine at 0° C. while stirring. After one hour the mixture is warmed to room temperature and after a further 4 hours it is concentrated. The residue is chromatographed on 100 g of silica gel (0.063–0.2 mm). The product is eluted with dichloromethane/ethanol (95:5 v/v) and the eluate is concentrated. The residual oil is dissolved in ethanolic hydrochloric acid and crystallized by the addition of diethyl ether. There are obtained 1.6 g of 1-[2-(aminooxy)-2-methylpropionyl]-2-[(4,7-dichloro-2,2-diphenyl-1,3-benzodioxol-5-yl)carbonyl]hydrazine hydrochloride as white crystals, m.p. 96°–99° C.

$^1$H NMR (DMSO-d$_6$): signals at, inter alia, δ1.52 (s, 6H), 7.17 (s, 1H), 7.5 (12H), 10.26 (1H), 10.40 (s, 1H).

EXAMPLE 50

Manufacture of (6R,7R)-7-[(Z)-2-(2-amino-4-thiazolyl)-2-[[1-[3-(5-bromo-2-chloro-3,4-dihydrooxybenzoyl)carbazoyl]-1-methylethoxy]imino]acetamido]-3-[[[2-(hydroxycarbamoyl)-5-methyl-s-triazolo[1,5-a]pyrimidin-7-yl]thio]methyl]-8-oxo-5-thia-1-azabicyclo[4.2.0]oct-2-ene-2-carboxylic acid (6R,7R)-7-(2-Amino-4-thiazoleglyoxylamido)-3-[[[2-(hydroxycarbamoyl)-5-methyl-s-triazolo[1,5-a]pyrimidin-7-yl]thio]methyl]-8-oxo-5-thia-1-azabicyclo[4.2.0]oct-2-ene-2-carboxylic acid (59 mg) (0.10 mmol) and 76 mg (0.13 mmol) of 1-[[2-(aminooxy)-2-methylpropionyl]-2-[(7-bromo-4-chloro-2,2-diphenyl-1,3-benzodioxol-5-yl)carbonyl]hydrazine hydrochloride (1:1) are dissolved in 2 ml of absolute dimethylacetamide. After stirring at room temperature for 20 hours the solvent is distilled off in a high vacuum. The residue is washed several times with diethyl ether and subsequently crystallized using water. The product is filtered off under suction, washed with water and diethyl ether and dried at room temperature in a high vacuum. There are obtained 110 mg of (6R,7R)-7-[(Z)-2-(2-amino-4-thiazolyl)-2-[[1-[3-(7-bromo-4-chloro-2,2-diphenyl-1,3-benzodioxol-5-yl)carbazoyl]-1-methylethoxy]imino]acetamido]-3-[[[2-(hydroxycarbamoyl)-5-methyl-s-triazolo[1,5-a]pyrimidin-7-yl]thio]methyl]-8-oxo-5-thia-1-azabicyclo[4.2.0]oct-2-ene-2-carboxylic acid as a beige powder.

$^1$H NMR (DMSO-d$_6$): signals at, inter alia, δ1.46 (s, 3H), 1.50 (s, 3H), 2.60 (s, 3H), 3.64 (d, J=18 Hz, 1H), 3.86 (d, J=18 Hz, 1H), 4.38 (d, J=12.5 Hz, 1H), 4.50 (d, J=12.5 Hz, 1H), 5.25 (d, J=5 Hz, 1H), 5.92 (dd, J=5 Hz and J=8 Hz, 1H), 6.85 (s, 1H), 7.27 (s, 1H), 7.31 (2H), 7.48 (s, 1H), 7.52 (10), 9.36 (1H), 9.48 (s, 1H), 9.65 (d, J=8 Hz, 1H), 10.26 (1H), 11.69 (s, 1H).

(6R,7R)-7-[(Z)-2-(2-Amino-4-thiazolyl)-2-[[1-[3-(7-bromo-4-chloro-2,2-diphenyl-1,3-benzodioxol-5-yl)carbazoyl]-1-methylethoxy]imino]acetamido]-3-[[[2-(hydroxycarbamoyl)-5-methyl-s-triazolo[1,5-a]pyrimidin-7-yl]thio]methyl]-8-oxo-5-thia-1-azabicyclo[4.2.0]oct-2-ene-2-carboxylic acid (105 mg) (0.093 mmol) are dissolved in 2 ml of trifluoroacetic acid. After 5 hours the trifluoroacetic acid is distilled off in a vacuum. The residue is crystallized by the addition of diethyl ether. There are obtained 90 mg of (6R,7R)-7-[(Z)-2-(2-amino-4-thiazolyl)-2-[[1-[3-(5-bromo-2-chloro-3,4-dihydroxybenzoyl)carbazoyl]-1-methylethoxy]imino]acetamido]-3-[[[2-(hydroxycarbamoyl)-5-methyl-s-triazolo[1,5-a]pyrimidin-7-yl]thio]methyl]-8-oxo-5-thia-1-azabicyclo[4.2.0]oct-2-ene-2-carboxylic acid as a beige powder.

$^1$H NMR (DMSO-d$_6$): signals at, inter alia, δ1.48 (s, 3H), 1.50 (s, 3H), 2.60 (s, 3H), 3.64 (d, J=18 Hz, 1H), 3.85 (d, J=18 Hz, 1H), 4.38 (d, J=12.5 Hz, 1H), 4.50 (d, J=12.5 Hz, 1H), 5.26 (d, J=5 Hz), 5.92 (dd, J=5 Hz and J=8 Hz, 1H), 6.86 (s, 1H), 7.15 (s, 1H), 7.32 (2H), 7.36 (s, 1H), 9.35 (1H), 9.42 (s, 1H), 9.66 (d, J=8 Hz, 1H), 9.97 (1H), 10.11 (s, 2H), 11.69 (s, 1H).

The 1-[2-(aminooxy)-2-methylpropionyl]-2-[(7-bromo-4-chloro-2,2-diphenyl-1,3-benzodioxol-5-yl)carbonyl]hydrazine hydrochloride used as the starting material can be prepared as follows:

A mixture of 9.6 g (40 mmol) of methyl 3-bromo-4,5-dihydroxybenzoate, 8.4 g (62 mmol) of sulphuryl chloride and 400 ml of glacial acetic acid is stirred at 55° C. for 60 hours and subsequently concentrated at 40° C. in a vacuum. The residue is dissolved in 200 ml of methanol and saturated with hydrogen chloride. After standing at room temperature for 5 hours the solvent is distilled off in a vacuum. The residual material is treated with about 100 ml of dichloromethane/ethyl acetate/-petroleum ether (1:1:1 v/v) and filtered. The filtrate is concentrated and the residue is crystallized and recrystallized from diethyl ether/petroleum ether. There are obtained 3.4 g of methyl 5-bromo-2-chloro-3,4-dihydroxybenzoate as white crystals of melting point 103° C.

A mixture of 1.0 g (3.5 mmol) of methyl 5-bromo-2-chloro-3,4-dihydroxybenzoate and 7.5 ml of dichlorodiphenylmethane is held at 150° C. under argon for 2½ minutes. After rapid cooling the product is crystallized from n-pentane. There are obtained 1.3 g of methyl 7-bromo-4-chloro-2,2-diphenyl-1,3-benzodioxol-5-carboxylate as white crystals of melting point 137°–138° C.

A mixture of 620 mg (1.39 mmol) of 7-bromo-4-chloro-2,2-diphenyl-1,3-benzodioxol-5-carboxylate and 700 mg (13.9 mmol) of hydrazine hydrate is held at 80° C. for 20 hours. The reaction mixture is concentrated in a high vacuum and the residue is treated with ethanol/water. The insoluble product is filtered off under suction and washed with ethanol/diethyl ether. There are obtained 580 mg of 7-bromo-4-chloro-2,2-diphenyl-1,3-benzodioxol-5-carboxyhydrazide as white crystals of melting point 124° C.

A mixture of 500 mg (1.122 mmol) of 7-bromo-4-chloro-2,2-diphenyl-1,3-benzodioxol-5-carboxyhydrazide, 442 mg (1.122 mmol) of N-[[2-methyl-2-(phthalimidooxy)propionyl]oxy]phthalimide and 94 mg (1.122 mmol) of sodium hydrogen carbonate in 30 ml of tetrahydrofuran is stirred at room temperature for 20 hours. The solvent is distilled off in a vacuum and the residue is chromatographed on 30 g of silica gel (0.06–0.2 mm). The product is eluted with dichloromethane/ethanol (98:2 v/v). After concentration of the eluate there are obtained 510 mg of 1-[(7-bromo-4-chloro-2,2-diphenyl-1,3-benzodioxol-5-yl)carbonyl]-2-[2-methyl-2-(phthalimidooxy)propionyl]hydrazine as a colourless oil.

$^1$H NMR (DMSO-d$_6$): signals at δ1.55 (s, 6H), 7.29 (s, 1H), 7.5 (10H), 7.92 (s, 4H), 10.10 (s, 1H), 10.37 (s, 1H).

1-[(7-Bromo-4-chloro-2,2-diphenyl-1,3-benzodioxol-5-yl)carbonyl]-2-[2-methyl-2-(phthalimidooxy)propionyl]hydrazine 500 mg (0.77 mmol) are dissolved in 10 ml of tetrahydrofuran and treated at 0° C. with 35 mg (0.77 mmol) of methylhydrazine. After stirring at 0° C. for 2 hours and stirring at room temperature for 3 hours the mixture is concentrated in a vacuum. The residue is chromatographed on 20 g of silica gel (0.06–02 mm). The product is eluted with dichloromethane/ethanol (95:5 v/v). The eluate is concentrated and the residue is treated with ethanolic hydrochloric acid. After crystallization from ethanol/diethyl ether there are obtained 220 mg of 1-[2-(aminooxy)-2-methylpropionyl]-2-[(7-bromo-4-chloro-2,2-diphenyl-1,3-benzodioxol-5-yl)carbonyl]hydrazine hydrochloride (1:1) as white crystals of melting point 216°–218° C.

EXAMPLE 51

Manufacture of (6R,7R)-7-[(Z)-2-(2-amino-4-thiazolyl)-2-[[1-[3-(3,4-dihydroxybenzoyl)carbazoyl]-1-methylethoxy]imino]acetamido]-3-[[[2-(N-hydroxy-N-methylcarbamoyl)-5-methyl-s-triazolo[1,5-a]pyrimidin-7-yl]thio]methyl]-8-oxo-5-thia-1-azabicyclo[4.2.0]oct-2-ene-2-carboxylic acid (6R,7R)-7-(2-Amino-4-thiazoleglyoxylamido)-3-[[[2-(N-hydroxy-N-methylcarbamoyl)-5-methyl-s-triazolo[1,5-a]pyrimidin-7-yl]thio]methyl]-8-oxo-5-thia-1-azabicyclo[4.2.0]oct-2-ene-2-carboxylic acid (40 mg) (0.066 mmol) and 29 mg (0.086 mmol) of 1-[2-(aminooxy)-2-methylpropionyl]-2-(3,4-dihydroxybenzoyl)hydrazine hydrochloride are dissolved in 1 ml of absolute dimethylacetamide. After stirring for 20 hours the solution is concentrated at room temperature in a high vacuum. The residue is crystallized from ethanol. There are obtained 16 mg of (6R,7R)-7-[(Z)-2-(2-amino-4-thiazolyl)-2-[[1-[3-(3,4-dihydroxybenzoyl)carbazoyl]-1-methylethoxy]imino]acetamido]-3-[[[2-(N-hydroxy-N-methylcarbamoyl)-5-methyl-s-triazolo[1,5-a]pyrimidin-7-yl]thio]methyl]-8-oxo-5-thia-1-azabicyclo[4.2.0]oct-2-ene-2-carboxylic acid as a brown powder.

$^1$H NMR (DMSO-d$_6$): signals at, inter alia, δ1.44 (s, 3H), 1.46 (s, 3H), 2.61 (s, 3H), 3.30 (s, 3H), 5.25 (d, J=5 Hz, 1H), 5.91 (dd, J=5 Hz and J=8 Hz, 1H), 6.76 (d, J=7.5 Hz, 1H), 6.88 (s, 1H), 7.25 (dd, J=7,5 Hz and J=2 Hz, 1H), 7.30 (d, J=2 Hz, 1H), 9.24 (s, 1H), 9.68 (d, J=8 Hz, 1H), 9.98 (s, 1H), 10.44 (broad, 1H).

The (6R,7R)-7-(2-amino-4-thiazoleglyoxylamido)-3-[[[2-(N-hydroxy-N-methylcarbamoyl)-5-methyl-s-triazolo[1,5-a]pyrimidin-7-yl]thio]methyl]-8-oxo-5-thia-1-azabicyclo[4.2.0]oct-2-ene-2-carboxylic acid used as the starting material can be prepared as follows:

Methyl 7-mercapto-5-methyl-s-triazolo[1,5-a]pyrimidine-2-carboxylate (3.36 g) (15 mmol) are dissolved in 30 ml of 2N aqueous sodium hydroxide solution. After stirring at room temperature for 18 hours the product is precipitated by the addition of 1N aqueous hydrochloric acid. The precipitate is filtered off under suction and washed with water and acetone. After crystallization from dimethylacetamide/diethyl ether there are obtained 3.0 g of 7-mercapto-5-methyl-s-triazolo[1,5-a]pyrimidine-2-carboxylic acid dimethylacetamide of melting point 180° C. (dec.).

7-Mercapto-5-methyl-s-triazolo[1,5-a]pyrimidine-2-carboxylic acid dimethylacetamide (0.99 g) (3.33 mmol) is suspended in 15 ml of absolute dimethylacetamide and treated while stirring with 530 mg (3.96 mmol) of 1-chloro-N,N,2-trimethyl-1-propenamine. After 4 hours the solution is cooled to −10° C. and treated while stirring with 550 mg (6.6 mmol) of N-methylhydroxylamine hydrochloride and 860 mg (6.6 mmol) of ethyldiisopropylamine. The reaction mixture is stirred at room temperature for 18 hours and subsequently concentrated in a high vacuum. The residue is crystallized using water and recrystallized from dimethylformamide/diethyl ether. There is obtained 0.50 g of N-hydroxy-7-mercapto-N,5-dimethyl-s-triazolo[1,5-a]pyrimidine-2-carboxamide as yellow crystals of melting point 215° C. (dec.).

$^1$H NMR (DMSO-d$_6$): signals at, inter alia, δ2.35 (s, 3H), 3.29 (s, 3H), 6.91 (s, 1H), 10.46 (broad, 1H).

N-Hydroxy-7-mercapto-N,5-dimethyl-s-triazolo[1,5-a]pyrimidine-2-carboxamide (53 mg) (0.22 mmol) and 54 mg (0.2 mmol) of 7-aminocephalosporanic acid are suspended in 1 ml of dichloromethane/sulpholane (1:1 v/v). 0.5 ml of boron trifluoride diethyl etherate is added thereto at 10° C. while stirring and the mixture is stirred at room temperature for a further 20 hours. Subsequently, about 10 ml of dichloromethane are added thereto, the insoluble material is filtered off under suction, dissolved in water and the product is precipitated by the addition of sodium hydrogen carbonate (pH→4). The precipitate is filtered off under suction and washed with water and ethanol. There are obtained 66 mg of (6R,7R)-7-amino-3-[[[2-(N-hydroxy-N-methylcarbamoyl)-5-methyl-s-triazolo[1,5-a]pyrimidin-7-yl]thio]methyl]-8-oxo-5-thia-1-azabicyclo[4,2,0]oct-2-ene-2-carboxylic acid as a white powder.

$^1$H NMR (DMSO-d$_6$): signals at, inter alia, δ2.60 (s, 3H), 3.29 (s, 3H), 3.55 (d, J=18 Hz, 1H), 3.76 (d, J=18 Hz, 1H), 4.34 (d, J=12.5 Hz, 1H), 4.43 (d, J=12.5 Hz, 1H), 4.82 (d, J=5 Hz, 1H), 5.02 (d, J=5 Hz, 1H), 7.36 (s, 1H).

(6R,7R)-7-Amino-3-[[[2-(N-hydroxy-N-methylcarbamoyl)-5-methyl-s-triazolo[1,5-a]pyrimidin-7-yl]thio]methyl]-8-oxo-5-thia-1-azabicyclo[4,2,0]oct-2-ene-2-carboxylic acid (45 mg) (0.1 mmol) are suspended in 1 ml of absolute dimethylacetamide. 0.052 ml (0.2 mmol) of O,N-bis-trimethylsilyl-acetamide is added dropwise thereto at 0° C. while stirring, the mixture is stirred at 0° C. for 1 hour and at room temperature for 2 hours. Subsequently, the solution is treated with 40 mg (0.125 mmol) of 2-amino-4-thiazolethioglyoxylic acid S-(2-benzothiazolyl) ester. After stirring at room temperature for 18 hours the solvent is removed at room temperature in a high vacuum. The product is crystallized by the addition of ethanol. The product is filtered off under suction and washed in succession with ethanol and diethyl ether. There are obtained 50 mg of (6R,7R)-7-(2-amino-4-thiazoleglyoxylamido)-3-[[[2-(N-hydroxy-N-methylcarbamoyl)-5-methyl-s-triazolo[1,5-a]pyrimidin-7-yl]thio]methyl]-8-oxo-5-thia-1-azabicyclo[4.2.0]oct-2-ene-2-carboxylic acid as a brown powder.

$^1$H NMR (DMSO-d$_6$): signals at, inter alia, δ2.61 (s, 3H), 3.29 (s, 3H), 3.63 (d, J=18 Hz, 1H), 3.82 (d, J=18

Hz, 1H), 4.41 (d, J=12.5 Hz, 1H), 4.49 (d, J=12.5 Hz, 1H), 5.21 (d, J=5 Hz, 1H), 5.78 (dd, J=5 Hz and J=8 Hz, 1H), 7.4 (3H), 7.82 (s, 1H), 9.80 (d, J=8 Hz, 1H), 10.44 (broad, 1H).

EXAMPLE 52

Manufacture of (6R,7R)-7-[(Z)-2-(2-amino-4-thiazolyl)-2-[[1-[3-(3,4-dihydroxybenzoyl)carbazoyl]-1-methylethoxy]imino]acetamido]-3-[[[2-(hydroxycarbamoyl)-5-(hydroxymethyl)-s-triazolo[1,5-a]pyrimidin-7-yl]thio]methyl]-8-oxo-5-thia-1-azabicyclo[4.2.0]oct-2-ene-2-carboxylic acid (6R,7R)-7-(2-Amino-4-thiazoleglyoxylamido)-3-[-[[2-(hydroxycarbamoyl)-5-(hydroxymethyl)-s-triazolo[1,5-a]pyrimidin-7-yl]thio]methyl]-8-oxo-5-thia-1-azabicyclo[4.2.0]oct-2-ene-2-carboxylic acid (45 mg) (0.074 mmol) and 31 mg (0.096 mmol) of 1-[2-(aminooxy)-2-methylpropionyl]-2-(3,4-dihydroxybenzoyl)hydrazine hydrochloride are dissolved in 3 ml of absolute dimethylacetamide. After stirring at room temperature for 24 hours the reddish solution is concentrated in a high vacuum. The residue is suspended in 6 ml of water and the product is filtered off under suction. After washing with water and diethyl ether and subsequently drying in a high vacuum there are obtained 50 mg of (6R,7R)-7-[(Z)-2-(2-amino-4-thiazolyl)-2-[[1-[3-(3,4-dihydroxybenzoyl)carbazoyl]-1-methylethoxy]imino]acetamido]-3-[[[2-(hydroxycarbamoyl)-5-(hydroxymethyl)-s-triazolo[1,5-a]pyrimidin-7-yl]thio]methyl]-8-oxo-5-thia-1-azabicyclo[4.2.0]oct-2-ene-2-carboxylic acid as a beige powder.

$^1$H NMR (DMSO-d$_6$): signals at, inter alia, δ1.46 (s, 3H), 1.50 (s, 3H), 3.65 (d, J=18 Hz, 1H), 3.87 (d, J=18 Hz, 1H), 4.42 (d, J=12.5 Hz, 1H), 4.52 (d, J=12.5 Hz, 1H), 4.66 (s, 2H), 5.24 (d, J=5 Hz, 1H), 5.91 (dd, J=5 Hz and J=8 Hz, 1H), 6.74 (d, J=7.5 Hz, 1H), 6.87 (s, 1H), 7.26 (dd, J=7.5 Hz and J=2 Hz, 1H), 7.32 (d, J=2 Hz, 1H), 7.48 (s, 1H), 9.20 (s, 1H), 9.22 (s, 1H), 9.39 (s, 1H), 9.53 (s, 1H), 9.67 (d, J=8 Hz, 1H), 10.01 (s, 1H), 11.69 (s, 1H).

The (6R,7R)-7-(2-amino-4-thiazoleglyoxylamido)-3--[[[2-(hydroxycarbamoyl)-5-(hydroxymethyl)-s-triazolo[1,5-a]pyrimidin-7-yl]thio]methyl]-8-oxo-5-thia-1-azabicyclo[4.2.0]oct-2-ene-2-carboxylic acid used as the starting material can be prepared as follows:

A mixture of 71 mg (0.5 mmol) of methyl 5-amino-4H-s-triazole-3-carboxylate and 188 mg of ethyl 4-acetoxy-3-oxo-butyrate is held at about 160° C. for 40 minutes. After cooling the product is crystallized and recrystallized from methanol. There are obtained 110 mg of methyl 5-(acetoxymethyl)-4,7-dihydro-7-oxo-s-triazolo[1,5-a]pyrimidine-2-carboxylate as beige crystals of melting point 223° C. (dec.).

A suspension of 100 mg (0.38 mmol) of methyl 5-(acetoxymethyl)-4,7-dihydro-7-oxo-s-triazolo[1,5-a]pyrimidine-2-carboxylate in 7 ml of phosphorus oxychloride is held under reflux for 6 hours and subsequently concentrated in a vacuum. The residue is dissolved in dichloromethane. The solution is washed with ice/water, dried over sodium sulphate and concentrated. After crystallization from methanol/diethyl ether there are obtained 70 mg of methyl 5-(acetoxymethyl)-7-chloro-s-triazolo[1,5-a]pyrimidine-2-carboxylate as brown crystals of melting point 120° C.

Methyl 5-(acetoxymethyl)-7-chloro-s-triazolo[1,5-a]pyrimidine-2-carboxylate (380 mg) (1.33 mmol) are dissolved in 20 ml of methanol. After the addition of 296 mg (4 mmol) of sodium hydrogen sulphide monohydrate the mixture is stirred at 60° C. for 5 hours. The reaction mixture is concentrated and brought to pH 3 with dilute aqueous hydrochloric acid. The product is filtered off under suction, washed with water/methanol and crystallized from methanol. There are obtained 290 mg of methyl 5-(hydroxymethyl)-7-mercapto-s-triazolo[1,5-a]pyrimidine-2-carboxylate as a brown powder.

$^1$H NMR (DMSO-d$_6$): signals at, inter alia, δ3.89 (s, 3H), 4.36 (s, 2H), 5.35 (broad, 1H), 7.00 (s, 1H).

Methyl 5-(hydroxymethyl)-7-mercapto-s-triazolo[1,5-a]pyrimidine-2-carboxylate (100 mg) (0.416 mmol) are dissolved in about 5 ml of methanol. 275 mg (8.3 mmol) of hydroxylamine are added thereto at room temperature while stirring within 48 hours. The reaction mixture is made acid (pH 5.5) with 3N aqueous hydrochloric acid. The product is filtered off under suction and crystallized from methanol. There are obtained 60 mg of 7-mercapto-N-hydroxy-5-(hydroxymethyl)-s-triazolo[1,5-a]pyrimidine-2-carboxamide as beige crystals of melting point 238°-239° C. (dec.).

$^1$H NMR (DMSO-d$_6$): signals at, inter alia, 4.36 (s, 2H), 5.34 (broad, 1H), 6.98 (s, 1H).

7-Mercapto-N-hydroxy-5-(hydroxymethyl)-s-triazolo[1,5-a]pyrimidine-2-carboxamide (300 mg) (1.24 mmol) and 305 mg (1.12 mmol) of 7-aminocephalosporanic acid are suspended in 50 ml of sulpholane/dichloromethane (1:1 v/v). 5 ml of boron trifluoride diethyl etherate are added thereto at 0° C. The reaction mixture is stirred at 0° C. for 2½ hours and at room temperature for 24 hours. After the addition of 30 ml of dichloromethane the mixture is stirred for 15 minutes and subsequently filtered. The suction filter material is dissolved in water and adjusted to pH 5 with saturated aqueous sodium hydrogen carbonate solution. The precipitated product is filtered off under suction and washed in succession with water, dichloromethane and diethyl ether. There are obtained 340 mg of (6R,7R)--7-amino-3-[[[2-(hydroxycarbamoyl)-5-(hydroxymethyl)-s-triazolo[1,5-a]pyrimidin-7-yl]thio]methyl]-8-oxo-5-thia-1-azabicyclo[4.2.0]oct-2-ene-2-carboxylic acid as a beige powder.

$^1$H NMR (DMSO-d$_6$): signals at, inter alia, δ3.58 (d, J=18 Hz, 1H), 3.79 (d, J=18 Hz, 1H), 4.40 (d, J=12.5 Hz, 1H), 4.46 (d, J=12.5 Hz, 1H), 4.65 (s, 2H), 4.84 (d, J=5 Hz, 1H), 5.03 (d, J=5 Hz, 1H), 7.49 (s, 1H), 9.36 (s, 1H), 11.69 (s, 1H).

(6R,7R)-7-Amino-3-[[[2-(hydroxycarbamoyl)-5-(hydroxymethyl)-s-triazolo[1,5-a]pyrimidin-7-yl]thio]methyl]-8-oxo-5-thia-1-azabicyclo[4.2.0]oct-2-ene-2-carboxylic acid (45 mg) (0.1 mmol) are suspended in 4 ml of absolute dimethylacetamide. 61 mg (0.3 mmol) of O,N-bis-trimethylsilyl-acetamide are added thereto at 0° C., the mixture is warmed to room temperature and stirred for a further 50 minutes. 39 mg (0.12 mmol) of 2-amino-4-thiazolethioglyoxylic acid S-(2-benzothiazolyl) ester are added to the solution at 0° C. and the mixture is subsequently stirred at room temperature for 24 hours. After the addition of 2 ml of ethanol and stirring for 15 minutes the solvent is removed at room temperature in a high vacuum. The product is crystallized by the addition of ethanol. After drying at room temperature in a high vacuum there are obtained 50 mg of (6R,7R)-7-(2-amino-4-thiazoleglyoxylamido)-3-[[[2-(hydroxycarbamoyl)-5-(hydroxymethyl)-s-triazolo[1,5-a]pyrimidin-7-yl]thio]methyl]-8-oxo-5-thia-1-azabicyclo[4.2.0]oct-2-ene-2-carboxylic acid as a beige powder.

¹H NMR (DMSO-d₆): signals at, inter alia, δ3.63 (d, J=18 Hz, 1H), 3.84 (d, J=18 Hz, 1H), 4.44 (d, J=12.5 Hz, 1H), 4.52 (d, J=12.5 Hz, 1H), 4.66 (s, 2H), 5.21 (d, J=5 Hz, 1H), 5.78 dd (J=5 Hz and J=8 Hz), 7.41 (s, 2H), 7.50 (s, 1H), 7.83 (s, 1H), 9.37 (s, 1H), 9.81 (d, J=8 Hz, 1H), 11.69 (s, 1H).

EXAMPLE 53

Manufacture of (6R,7R)-7-[(Z)-2-(2-amino-4-thiazolyl)-2-[[1-[3-(3,4-dihydroxybenzoyl)carbazoyl]-1-methyl-ethoxy]imino]acetamido]-3-[[[5-(hydroxycarbamoyl)-2-methyl-s-triazolo[1,5-a]pyrimidin-7-yl]thio]methyl]-8-oxo-5-thia-1-azabicyclo[4.2.0]oct-2-ene-2-carboxylic acid (6R,7R)-7-(2-Amino-4-thiazoleglyoxylamido)-3-[[[5-(hydroxycarbamoyl)-2-methyl-s-triazolo[1,5-a]pyrimidin-7-yl]thio]methyl]-8-oxo-5-thia-1-azabicyclo[4.2.-0]oct-2-ene-2-carboxylic acid and 36.9 mg (0.121 mmol) of 1-[2-(aminooxy)-2-methylpropionyl]-2-(3,4-dihydroxybenzoyl)hydrazine hydrochloride (55 mg) (0.093 mmol) are dissolved in 7 ml of absolute dimethylacetamide. After stirring at room temperature for 20 hours a further 18.4 mg (0.060 mmol) of 1-[2-(aminooxy)-2-methylpropionyl]-2-(3,4-dihydroxybenzoyl)hydrazine hydrochloride are added. After a further 24 hours the solvent is removed at room temperature in a high vacuum and the residue is treated with water. The precipitated product is filtered off, washed well with water and dried at room temperature in a high vacuum. There are obtained 37 mg of (6R,7R)-7-[(Z)-2-(2-amino-4-thiazolyl)-2-[[1-[3-(3,4-dihydroxybenzoyl)carbazoyl]-1-methylethoxy]imino]acetamido]-3-[[[5-(hydroxycarbamoyl)-2-methyl-s-triazolo[1,5-a]pyrimidin-7-yl]thio]methyl]-8-oxo-5-thia-1-azabicyclo[4.2.0]oct-2-ene-2-carboxylic acid as a beige powder.

¹H NMR (DMSO-d₆): signals at, inter alia, δ1.47 (s, 3H), 1.50 (s, 3H), 3.64 (d, J=18 Hz, 1H), 3.85 (d, J=18 Hz, 1H), 4.47 (d, J=12.5 Hz, 1H), 4.57 (d, J=12.5 Hz, 1H), 5.24 (d, J=5 Hz, 1H), 5.92 (dd, J=5 Hz and J=8 Hz, 1H), 6.76 (d, J=7.5 Hz, 1H), 6.86 (s, 1H), 7.25 (dd, J=7.5 Hz and J=2 Hz, 1H), 7.30 (d, J=2 Hz, 1H), 7.71 (s, 1H), 9.18 (s, 1H), 9.23 (s, 1H), 9.34 (s, 1H), 9.54 (s, 1H), 9.66 (d, J=8 Hz, 1H), 10.01 (s, 1H), 11.88 (s, 1H).

The (6R,7R)-7-(2-amino-4-thiazoleglyoxylamido)-3-[[[5-(hydroxycarbamoyl)-2-methyl-s-triazolo[1,5-a]pyrimidin-7-yl]thio]methyl]-8-oxo-5-thia-1-azabicyclo[4.2.0]oct-2-ene-2-carboxylic acid used as the starting compound can be prepared as follows:

3-Amino-5-methyl-1H-s-triazole (112 mg) and 320 mg of dimethyl 2-oxo-succinate are dissolved in 5 ml of glacial acetic acid. After boiling under reflux for 22 hours the solvent is distilled off in a vacuum. The residue is suspended in warm methanol. After cooling the product is filtered off and washed several times with methanol. After drying in a high vacuum there are obtained 73 mg of methyl 7-hydroxy-2-methyl-s-triazolo[1,5-a]pyrimidine-5-carboxylate as a beige powder, m.p.>220° C.

¹H NMR (DMSO-d₆): signals at, inter alia, δ2.44 (s, 3H), 3.88 (s, 3H), 6.54 (s, 1H).

Methyl 7-hydroxy-2-methyl-s-triazolo[1,5-a]pyrimidine-5-carboxylate (1.0 g) (4.8 mmol) is suspended in 30 ml of phosphorus oxychloride. 0.38 ml (4.8 mmol) of pyridine is added thereto and the mixture is stirred at 90° C. for 5 hours. Subsequently, the mixture is concentrated and ice/water and saturated aqueous sodium chloride solution are added to the residue. The product is extracted with dichloromethane. After drying and evaporation of the extract there remains 0.81 g of methyl 7-chloro-2-methyl-s-triazolo[1,5-a]pyrimidine-5-carboxylate as beige crystals with melting point 170°–174° C.

¹H NMR (DMSO-d₆): signals at, inter alia, δ2.61 (s, 3H), 3.97 (s, 3H), 8.08 (s, 1H).

Methyl 7-chloro-2-methyl-s-triazolo[1,5-a]pyrimidine-5-carboxylate (0.80 g) (3.53 mmol) are suspended in 35 ml of methanol and treated with 0.78 g (10.6 mmol) of sodium hydrogen sulphide hydrate. After stirring at 60° C. for 5 hours the mixture is concentrated and the residue is dissolved in 20 ml of water. The solution is acidified to pH 3 with 3N aqueous hydrochloric acid. The precipitated product is filtered off under suction and washed with water and methanol. After recrystallization from methanol/dichloromethane there is obtained 0.66 g of methyl 7-mercapto-2-methyl-s-triazolo[1,5-a]pyrimidine-5-carboxylate as yellow crystals of melting point 237° C. (dec.).

¹H NMR (DMSO-d₆): signals at, inter alia, δ2.54 (s, 3H), 3.88 (s, 3H), 7.51 (s, 1H).

Methyl 7-mercapto-2-methyl-s-triazolo[1,5-a]pyrimidine-5-carboxylate (500 mg) (2.23 mmol) are suspended in 10 ml of absolute methanol. 2.95 mg (8.9 mmol) of hydroxylamine are added within 4 days while stirring. The reaction mixture is acidified (pH 6) with 3N aqueous hydrochloric acid. The product is filtered off under suction and washed in sequence with water, methanol and diethyl ether. There are obtained 540 mg of N-hydroxy-7-mercapto-2-methyl-s-triazolo[1,5-a]pyrimidine-5-carboxamide as yellow crystals of melting point 178°–179° C.

¹H NMR (DMSO-d₆): signals at, inter alia, δ2.38 (s, 3H), 7.21 (s, 1H).

N-Hydroxy-7-mercapto-2-methyl-s-triazolo[1,5-a]pyrimidine-5-carboxamide (250 mg) (1.1 mmol) and 275 mg (1.0 mmol) of 7-amino-cephalosporanic acid are suspended in 15 ml of sulpholane/dichloromethane (1:1 v/v) and treated at 0° C. with 3.5 ml of boron trifluoride diethyl etherate. The mixture is stirred at 0°–5° C. for 2 hours and at room temperature for 3 hours. Subsequently, 60 ml of dichloromethane are added thereto. Insoluble material is filtered off under suction, dissolved in water and treated with saturated sodium bicarbonate solution until the pH value 3 has been reached. The precipitated product is filtered off under suction and washed in succession with water and diethyl ether. There are obtained 295 mg of (6R,7R)-7-amino-3-[[[5-(hydroxycarbamoyl)-2-methyl-s-triazolo[1,5-a]pyrimidin-7-yl]thio]methyl]-8-oxo-5-thia-1-azabicyclo[4.2.-0]oct-2-ene-2-carboxylic acid as a beige powder.

¹H NMR (DMSO-d₆): signals at, inter alia, δ2.54 (s, 3H), 3.56 (d, J=18 Hz, 1H), 3.78 (d, J=18 Hz, 1H), 4.45 (d, J=12.5 Hz, 1H), 4.51 (d, J=12.5 Hz, 1H), 4.82 (d, J=5 Hz, 1H), 4.98 (d, J=5 Hz, 1H), 7.72 (s, 1H), 9.34 (s, 1H), 11.88 (s, 1H).

(6R,7R)-7-Amino-3-[[[5-(hydroxycarbamoyl)-2-methyl-s-triazolo[1,5-a]pyrimidin-7-yl]thio]methyl]-8-oxo-5-thia-1-azabicyclo[4.2.0]oct-2-ene-2-carboxylic acid (160 mg) (0.036 mmol) are suspended in 2 ml of absolute dimethylacetamide. 146 mg (0.72 mmol) of O,N-bis-trimethylsilyl-acetamide are added thereto at 0° C. and the mixture is stirred for 2 hours. The solution is subsequently treated with 116 mg (0.36 mmol) of 2-amino-4-thiazolethioglyoxylic acid S-(2-benzothiazolyl) ester and stirred at 0° C. for 2 hours and at room temperature for 16 hours. A small amount of ethanol is added thereto and, after 20 minutes, the mixture is concentrated at room temperature in a high vacuum. The residue is treated with water. The precipitated product is filtered off and washed in succession with water, ethanol, ethyl acetate and diethyl ether. There are obtained 170 mg of (6R,7R)-7-(2-amino-4-thiazoleglyoxylamido)-3-[[[5-(hydroxycarbamoyl)-2-methyl-s-triazolo[1,5-a]pyrimidin-7-yl]thio]methyl]-8-oxo-5-thia-1-azabicyclo[4.2.0]oct-2-ene-2-carboxylic acid as a beige powder.

$^1$H NMR (DMSO-d$_6$): signals at, inter alia, δ2.54 (s, 3H), 3.62 (d, J=18 Hz, 1H), 3.81 (d, J=18 Hz, 1H), 4.47 (d, J=12.5 Hz, 1H), 4.60 (d, J=12.5 Hz, 1H), 5.19 (d, J=5 Hz, 1H), 5.79 (dd, J=5 Hz and J=8 Hz, 1H), 7.41 (s, 2H), 7.74 (s, 1H), 7.82 (s, 1H), 9.34 (s, 1H), 9.80 (d, J=8 Hz, 1H), 11.89 (s, 1H).

EXAMPLE 54

Manufacture of (6R,7R)-7-[(Z)-2-(2-amino-4-thiazolyl)-2-[[1-[3-(3,4-dihydroxybenzoyl)carbazoyl]-1-methylethoxy]imino]acetamido]-3-[[[5-(hydroxycarbamoyl)-2-(hydroxymethyl)-s-triazolo[1,5-a]pyrimidin-7-yl]thio]methyl]-8-oxo-5-thia-1-azabicyclo[4.2.0]oct-2-ene-2-carboxylic acid (6R,7R)-7-(2-Amino-4-thiazoleglyoxylamido)-3-[[[5-(hydroxycarbamoyl)-2-(hydroxymethyl)-s-triazolo[1,5-a]pyrimidin-7-yl]thio]methyl]-8-oxo-5-thia-1-azabicyclo[4.2.0]oct-2-ene-2-carboxylic acid (50 mg) (0.082 mmol) and 34 mg (0.11 mmol) of 1-[2-(aminooxy)-2-methylpropionyl]-2-(3,4-dihydroxybenzoyl)hydrazine hydrochloride are dissolved in 4 ml of absolute dimethylacetamide. After stirring at room temperature for 24 hours the solvent is removed at room temperature. The residue is treated with water. The precipitated product is filtered off under suction and washed in succession with water and diethyl ether. There are obtained 50 mg of (6R,7R)-7-[(Z)-2-(2-amino-4-thiazolyl)-2-[[1-[3-(3,4-d ihydroxybenzoyl)carbazoyl]-1-methylethoxy]imino]acetamido]-3-[[[5-(hydroxycarbamoyl)-2-(hydroxymethyl)-s-triazolo[1,5-a]pyrimidin-7-yl]thio]methyl]-8-oxo-5-thia-1-azabicyclo[4.2.0]oct-2-ene-2-carboxylic acid as a beige powder.

$^1$H NMR (DMSO-d$_6$): signals at, inter alia, δ1.47 (s, 3H), 1.48 (s, 3H), 3.64 (d, J=18 Hz, 1H), 3.88 (d, J=18 Hz, 1H), 4.48 (d, J=12.5 Hz, 1H), 4.58 (d, J=12.5 Hz, 1H), 4.68 (s, 2H), 5.23 (d, J=5 Hz, 1H), 5.92 (dd, J=5 Hz and J=8 Hz), 6.75 (d, J=7.5 Hz), 6.84 (s, 1H), 7.25 (dd, J=7.5 Hz and J=2 Hz, 1H), 7.29 (d, J=2 Hz, 1H), 7.3 (s, 3H), 9.18 (s, 1H), 9.22 (s, 1H) 9.36 (broad, 1H), 9.54 (s, 1H), 9.67 (d, J=8 Hz, 1H), 9.98 (s, 1H), 11.90 (s, 1H).

The (6R,7R)-7-(2-amino-4-thiazoleglyoxylamido)-3-[[[5-(hydroxycarbamoyl)-2-(hydroxymethyl)-s-triazolo[1,5-a]pyrimidin-7-yl]thio]methyl]-8-oxo-5-thia-1-azabicyclo[4.2.0]oct-2-ene-2-carboxylic acid used as the starting material can be prepared as follows:

Methyl 4,7-dihydro-2-(hydroxymethyl)-7-oxo-s-triazolo[1,5-a]pyrimidine-5-carboxylate (2.5 g) (11.1 mmol) are suspended in 20 ml of dichloromethane. After the addition of 1.76 g (22.3 mmol) of pyridine and 2.27 g (22.2 mmol) of acetic anhydride the mixture is stirred at 55° C. for 8 hours. The mixture is concentrated in a vacuum and the product is precipitated with diethyl ether. After recrystallization from methanol there are obtained 1.2 g of methyl 2-(acetoxymethyl)-4,7-dihydro-7-oxo-s-triazolo[1,5-a]pyrimidine-5-carboxylate as white crystals of melting point 260° C.

Methyl 2-(acetoxymethyl)-4,7-dihydro-7-oxo-s-triazolo[1,5-a]pyrimidine-5-carboxylate (500 mg) (1.87 mmol) are suspended in 20 l of phosphorus oxychloride. The suspension is held under reflux for 5 hours. The mixture is concentrated in a water-jet vacuum, the residue is treated with dichloromethane and ice/water and extracted several times with dichloromethane. After drying and evaporation of the extract the product is crystallized from methanol. There are obtained 400 mg of methyl 2-(acetoxymethyl)-7-chloro-s-triazolo[1,5-a]pyrimidine-5-carboxylate.

$^1$H NMR (CDCl$_3$): signals at δ2.21 (s, 3H), 4.09 (s, 3H), 5.47 (s, 2H), 7.99 (s, 1H).

Methyl 2-(acetoxymethyl)-7-chloro-s-triazolo[1,5-a]pyrimidine-5-carboxylate (370 mg) (1.3 mmol) are dissolved in 10 ml of methanol. After the addition of 289 mg (3.9 mmol) of sodium hydrogen sulphide hydrate the mixture is stirred at 60° C. for 4 hours. The yellow solution is concentrated in a vacuum. The residue is dissolved in water and the product is precipitated at pH 3 with 3N aqueous hydrochloric acid. The precipitate is filtered off under suction and crystallized from methanol. There are obtained 360 mg of methyl 2-(acetoxymethyl)-7-mercapto-s-triazolo[1,5-a]pyrimidine-5-carboxylate.

$^1$H NMR (DMSO-d$_6$): signals at, inter alia, δ2.13 (s, 3H), 3.89 (s, 3H), 5.28 (s, 2H), 7.42 (s, 1H).

Methyl 2-(acetoxymethyl)-7-mercapto-s-triazolo[1,5-a]pyrimidine-5-carboxylate (80 mg) (0.28 mmol) are dissolved in 3 ml of absolute methanol. 188 mg (5.7 mmol) of hydroxylamine are added within 4 days while stirring. The product is precipitated (pH 6) with 3N aqueous hydrochloric acid, filtered off under suction and washed with methanol. After crystallization from methanol there are obtained 50 mg of N-hydroxy-2-(hydroxymethyl)-7-mercapto-s-triazolo[1,5-a]pyrimidine-5-carboxamide as a yellow powder.

$^1$H NMR (DMSO-d$_6$): signals at, inter alia, δ4.54 (s, 2H), 7.24 (s, 1H).

N-Hydroxy-2-(hydroxymethyl)-7-mercapto-s-triazolo[1,5-a]pyrimidine-5-carboxamide (190 mg) (0.79 mmol) and 193 mg (0.71 mmol) of 7-amino-cephalosporanic acid are suspended in 20 ml of sulpholane/dichloromethane (1:1 v/v). 4.2 ml of boron trifluoride diethyl etherate are added thereto at 0° C. The mixture is stirred at 0° C. for 2 hours and at room temperature for 20 hours. 80 ml of dichloromethane are added. The precipitated material is separated and dissolved in water. The mixture is adjusted to pH 4 by the addition of saturated aqueous sodium hydrogen carbonate solution. The precipitated product is filtered off under suction and washed in sequence with water, ethanol and diethyl ether. There are obtained 130 mg of (6R,7R)-7-amino-3-[[[5-(hydroxycarbamoyl)-2-(hydroxymethyl)-s-triazolo[1,5-a]pyrimidin-7-yl]thio]methyl]-8-oxo-5-thia-1-azabicyclo[4.2.0]oct-2-ene-2-carboxylic acid as a beige powder.

$^1$H NMR (DMSO-d$_6$): signals at, inter alia, δ3.56 (d, J=18 Hz, 1H), 3.80 (d, J=18 Hz, 1H), 4.44 (d, J=12.5 Hz, 1H), 4.54 (d, J=12.5 Hz, 1H), 4.69 (s, 2H), 4.82 (d, J=5 Hz, 1H), 5.01 (d, J=5 Hz, 1H), 5.63 (broad, 1H), 7.76 (s, 1H), 9.37 (s, 1H), 11.90 (s, 1H).

(6R,7R)-7-Amino-3-[[[5-(hydroxycarbamoyl)-2-(hydroxymethyl)-s-triazolo[1,5-a]pyrimidin-7-yl]thio]methyl]-8-oxo-5-thia-1-azabicyclo[4.2.0]oct-2-ene-2-carboxylic acid (45 mg) (0.1 mmol) are suspended in 4 ml of absolute dimethylacetamide. 61 mg (0.3 mmol) of O,N-bis-trimethylsilylacetamide are added thereto at 0° C. and the mixture is stirred at room temperature for 70 minutes. Subsequently, the solution is cooled to 0° C.

and treated with 39 mg (0.12 mmol) of 2-amino-4-thiazolethioglyoxylic acid S-(2-benzothiazolyl) ester. After stirring at room temperature for 24 hours 0.2 ml of ethanol is added thereto and the mixture is concentrated at room temperature in a high vacuum. The residue is crystallized using ethanol. After suction filtration and washing with ethanol there are obtained 53 mg of (6R,7R)-7-(2-amino-4-thiazoleglyoxylamido)-3-[[[5-(hydroxycarbamoyl)-2-(hydroxymethyl)-s-triazolo[1,5-a]pyrimidin-7-yl]thio]methyl]-8-oxo-5-thia-1-azabicyclo[4.2.0]oct-2-ene-2-carboxylic acid as a beige powder.

$^1$H NMR (DMSO-d$_6$): signals at, inter alia, δ3.64 (d, J=18 Hz, 1H), 3.82 (d, J=18 Hz, 1H), 4.70 (s, 2H), 5.20 (d, J=5 Hz, 1H), 5.78 (dd, J=5 Hz and J=8 Hz), 7.4 (3H), 7.82 (s, 1H), 9.36 (broad, 1H), 9.80 (d, J=8 Hz, 1H), 11.89 (s, 1H).

EXAMPLE 55

Manufacture of (6R,7R)-7-[(Z)-2-(2-amino-4-thiazolyl)-2-[[1-[3-(3,4-dihydroxybenzoyl)carbazoyl]-1-methylethoxy]imino]acetamido]-3-[[[5-[2-(hydroxycarbamoyl)ethyl]-2-methyl-s-triazolo[1,5-a]pyrimidin-7-yl]thio]methyl]-8-oxo-5-thia-1-azabicyclo[4.2.0]oct-2-ene-2-carboxylic acid (6R,7R)-7-(2-Amino-4-thiazoleglyoxylamido)-3-[[[5-[2-(hydroxycarbamoyl)ethyl]-2-methyl-s-triazolo[1,5-a]pyrimidin-7-yl]thio]methyl]-8-oxo-5-thia-1-azabicyclo[4.2.0]oct-2-ene-2-carboxylic acid (41 mg) (0.66 mmol) and 29 mg of 1-[2-(aminooxy)-2-methylpropionyl]-2-(3,4-dihydroxybenzoyl)hydrazine hydrochloride are dissolved in 1 ml of absolute dimethylacetamide. After stirring at room temperature for 20 hours the solvent is removed at room temperature in a high vacuum. The residue is crystallized from ethanol/diethyl ether. The product is filtered off, washed with diethyl ether, water and again with diethyl ether. After drying in a high vacuum at room temperature there are obtained 45 mg of (6R,7R)-7-[(Z)-2-(2-amino-4-thiazolyl)-2-[[1-[3-(3,4-dihydroxybenzoyl)carbazoyl]-1-methylethoxy]imino]acetamido]-3-[[[5-[2-(hydroxycarbamoyl)ethyl]-2-methyl-s-triazolo[1,5-a]pyrimidin-7-yl]thio]methyl]-8-oxo-5-thia-1-azabicyclo[4.2.0]oct-2-ene-2-carboxylic acid as a beige powder.

$^1$H NMR (DMSO-d$_6$): signals at, inter alia, δ1.47 (6H), 3.06 (t, J=8 Hz, 2H), 3.62 (d, J=18 Hz, 1H), 3.84 (d, J=18 Hz, 1H), 4.33 (d, J=12.5 Hz, 1H), 4.47 (d, J=12.5 Hz, 1H), 5.26 (d, J=5 Hz, 1H), 5.90 (dd, J=5 Hz and J=8 Hz, 1H), 6.76 (dd, 1H), 6.86 (s, 1H), 7.16–7.38 (5H), 8.74 (s (broad), 1H), 9.18 (s, 1H), 9.21 (s, 1H), 9.54 (s, 1H), 9.67 (d, J=8 Hz, 1H), 10.02 (s, 1H), 10.5 (s, 1H).

The (6R,7R)-7-(2-amino-4-thiazoleglyoxylamido)-3-[[[5-[2-(hydroxycarbamoyl)ethyl]-2-methyl-s-triazolo[1,5-a]pyrimidin-7-yl]thio]methyl]-8-oxo-5-thia-1-azabicyclo[4.2.0]oct-2-ene-2-carboxylic acid used as the starting material can be prepared as follows:

3-Amino-5-methyl-1H-s-triazole (19.8 g) (about 0.12 mol) (about 70%) and 30 g (0.16 mol) of dimethyl 3-oxoadipate are melted together while gassing with argon for 1 hour in a bath heated at 160° C. In so doing, the volatile products are removed in a water-jet vacuum. After cooling the solid residue is dissolved in dichloromethane/methanol (1:1 v/v). The turbid yellowish solution is filtered and concentrated. The crystals which thereby result are filtered off under suction and washed with ethanol, subsequently with diethyl ether. There are obtained 20 g of methyl 4,7-dihydro-2-methyl-7-oxo-s-triazolo[1,5-a]pyrimidine-5-propionate as a white crystals of melting point 222°–225° C.

A mixture of 5.0 g (21 mmol) of methyl 4,7-dihydro-2-methyl-7-oxo-s-triazolo[1,5-a]pyrimidine-5-propionate, 250 ml of phosphorus oxychloride and 2.5 ml of pyridine is stirred at 100° C. for about 2 hours and subsequently concentrated at 50° C. in a water-jet vacuum. The residue is taken up in 600 ml of dichloromethane and 200 ml of saturated, aqueous sodium chloride solution. After vigorous intermixing the aqueous phase is separated and washed with dichloromethane. The organic solutions are combined, dried over sodium sulphate and concentrated. There remain 5.4 g of methyl 7-chloro-2-methyl-s-triazolo[1,5-a]pyrimidine-5-propionate which becomes solid upon standing.

$^1$H NMR (DMSO-d$_6$): signals at, inter alia, δ2.86 (t, J=8 Hz, 2H), 3.17 (t, J=8 Hz, 2H), 3.59 (s, 3H), 7.64 (s, 1H).

Sodium hydrogen sulphide hydrate (7.0 g) (94 mmol) are added to a mixture of 5.4 g (about 21 mmol) of methyl 7-chloro-2-methyl-s-triazolo[1,5-a]pyrimidine-5-propionate in 200 ml of methanol. The mixture is stirred at 60° C. for 2 hours. Subsequently, the methanol is removed in a vacuum and the residue is treated with 150 ml of cold water. The mixture is adjusted to pH 3, the product is filtered off under suction and washed in succession with water, ethanol and diethyl ether. There are thus obtained 5 g of methyl 2-methyl-7-mercapto-s-triazolo[1,5-a]pyrimidine-5-propionate as yellow crystals of melting point 222° C. (dec.).

$^1$H NMR (DMSO-d$_6$): signals at, inter alia, 2.46 (s, 3H), 2.7–2.9 (4H), 3.60 (s, 3H), 6.93 (s, 1H).

Methyl 2-methyl-7-mercapto-s-triazolo[1,5-a]pyrimidine-5-propionate (100 mg) are dissolved in 10 ml of methanol and treated portionwise with hydroxylamine. After standing at room temperature for 5 days the solvent is removed and the product is crystallized from ethanol. There are obtained 60 mg of N-hydroxy-5-mercapto-2-methyl-s-triazolo[1,5-a]pyrimidine-5-propionamide.

$^1$H NMR (DMSO-d$_6$): signals at, inter alia, δ2.31 (s, 3H), 2.38 (t, J=8 Hz, 2H), 2.69 (t, J=8 Hz, 2H), 6.55 (s, 1H), 8.72 (s, 1H), 10.43 (s, 1H).

Boron trifluoride diethyl etherate (2 ml) are added dropwise at 0° C. to a suspension of 305 mg (1.12 mmol) of 7-aminocephalosporanic acid and 318 mg (1.25 mmol of N-hydroxy-5-mercapto-2-methyl-s-triazolo[1,5-a]pyrimidine-5-propionamide in 4 ml of dichloromethane/sulpholane (1:1 v/v). Subsequently, the mixture is stirred at room temperature for 16 hours. The solution is treated with 50 ml of dichloromethane. A beige substance crystallizes out. It is filtered off, washed with diethyl ether and dissolved in 5 ml of water. The solution is adjusted to about pH 4 with aqueous sodium hydrogen carbonate solution. The product is crystallized by the addition of about 100 ml of ethanol. The crystals are filtered off, washed with ethanol and dried at room temperature in a high vacuum. There are obtained 311 mg of (6R,7R)-7-amino-3-[[[5-[2-(hydroxycarbamoyl)ethyl]-2-methyl-s-triazolo[1,5-a]pyrimidin-7-yl]thio]methyl]-8-oxo-5-thia-1-azabicyclo[4.2.0]oct-2-ene-2-carboxylic acid as a beige powder.

$^1$H NMR (DMSO-d$_6$): signals at, inter alia, δ3.06 (t, J=8 Hz, 2H), 3.53 (d, J=18 Hz, 1H), 3.77 (d, J=18 Hz, 1H), 4.32 (d, J=12.5 Hz, 1H), 4.45 (d, J=12.5 Hz, 1H), 4.81 (d, J=5 Hz, 1H), 5.02 (d, J=5 Hz, 1H), 7.26 (s, 1H), 8.74 (broad signal, 1H), 10.50 (s, 1H).

(6R,7R)-7-Amino-3-[[[5-[2-(hydroxycarbamoyl)ethyl]-2-methyl-s-triazolo[1,5-a]pyrimidin-7-yl]thio]methyl]-8-oxo-5-thia-1-azabicyclo[4.2.0]oct-2-ene-2-carboxylic acid (93 mg) (0.2 mmol) are suspended in 1 ml of absolute dimethylacetamide. After the addition of 0.11 ml (0.4 mmol) of N,O-bis-(trimethylsilyl)-acetamide at 0° C. and stirring at 0° C. for 1 hour and at room temperature for 2 hours 64 mg (0.2 mmol) of 2-amino-4-thiazolethioglyoxylic acid S-(2benzothiazolyl) ester are added at 0° C. to the yellow solution obtained. The reaction mixture is stirred at 0° C. for 30 minutes and at room temperature for 18 hours. The solvent is removed in a high vacuum. The residue is taken up in about 5 ml of ethanol and crystallized. The crystals are dried at room temperature in a high vacuum. There are obtained 100 mg of (6R,7R)-7-(2-amino-4-thiazoleglyoxylamido)-3-[[[5-[2-(hydroxycarbamoyl)ethyl]-2-methyl-s-triazolo[1,5-a]pyrimidin-7-yl]thio]methyl]-8-oxo-5-thia-1-azabicyclo[4.2.0]oct-2-ene-2-carboxylic acid as a beige powder.

$^1$H NMR (DMSO-$d_6$): signals at, inter alia, $\delta$3.07 (t, J=8 Hz, 2H), 3.60 (d, J=18 Hz, 1H), 3.79 (d, J=18 Hz, 1H), 4.36 (d, J=12.5 Hz, 1H), 4.52 (d, J=12.5 Hz, 1H), 5.19 (d, J=5 Hz, 1H), 5.75 (dd, J=5 Hz and J=8 Hz, 1H), 7.28 (s, 1H), 7.40 (s, 2H), 7.82 (s, 1H), 8.75 (s (broad), 1H), 9.80 (d, J=8 Hz, 1H), 10.52 (s, 1H).

EXAMPLE 56

Manufacture of (6R,7R)-7-[(Z)-2-(2-amino-4-thiazolyl)-2-[[1-[3-(3,4-dihydroxybenzoyl)carbazoyl]-1--methylethoxy]imino]acetamido]-3-[[5-(3,4-dihydroxyphenyl)-1H-tetrazol-1-yl]methyl]-8-oxo-5-thia-1-azabicyclo[4.2.0]oct-2-ene-2-carboxylic acid (6R,7R)-7-(2-Amino-4-thiazoleglyoxylamido)-3-[[5-(3,4-dihydroxyphenyl)-1H-tetrazol-1-yl]methyl]-8-oxo-5-thia-1-azabicyclo[4.2.0]oct-2-ene-2-carboxylic acid (150 mg) and 150 mg of 1-[2-(aminooxy)-2-methylpropionyl]-2-(3,4-dihydroxybenzoyl)hydrazine hydrochloride in 3 ml of dimethylacetamide are stirred at room temperature for 24 hours. The dimethylacetamide is evaporated in a high vacuum. The residue is treated with 10 ml of water. The resulting precipitate is filtered off, washed with a small amount of cold water and resuspended in about 5 ml of water. The pH value is adjusted to 7 with 1N aqueous sodium hydroxide solution, whereupon all passes into solution. The solution is chromatographed on Opti-up $C_{12}$® using water and 5% acetonitrile. The uniform product fractions are concentrated and lyophilized. There are obtained 110 mg of (6R,7R)-7-[(Z)-2-(2-amino-4-thiazolyl)-2-[[1-[3-(3,4-dihydroxybenzoyl)carbazoyl]-1-methylethoxy]imino]acetamido]-3-[[5-(3,4-dihydrooxyphenyl)-1H-tetrazol-1-yl]methyl]-8-oxo-5-thia-1-azabicyclo[4.2.0]oct-2-ene-2-carboxylic acid as a white lyophilizate.

$^1$H NMR (DMSO-$d_6$) 250 MHz: $\delta$ (ppm) 1.47 (s, 3H), 1.50 (s, 3H), 3.48 (m, 2H), 5.18 (d, J=5 Hz, 1H), 5.36 (d, J=14 Hz, 1H), 5.54 (d, J=14 Hz, 1H), 5.92 (d,d, J=5 Hz, J=8 Hz, 1H), 6.7–7.4 (m, 9H) 9.20 (s, 1H), 9.25 (s, 1H), 9.52 (s, 1H), 9.57 (s, 1H), 9.70 (d, J=8 Hz, 1H), 9.73 (s, 1H), 10.04 (s, 1H), 14 (s, broad, 1H).

EXAMPLE 57

Manufacture of (6R,7R)-7-[(Z)-2-(2-amino-4-thiazolyl)-2-[[1-[3-(3,4-dihydroxybenzoyl)carbazoyl]-1-methylethoxy]imino]acetamido]-3-[[5-(3,4-dihydroxyphenyl)-2H-tetrazol-2-yl]methyl]-8-oxo-5-thia-1-azabicyclo[4.2.0]oct-2-ene-2-carboxylic acid When (6R,7R)-7-(2-amino-4-thiazoleglyoxylamido)-3-[[5-(3,4-dihydroxyphenyl)-2H-tetrazol-2-yl]methyl]-8-oxo-5-thia-1-azabicyclo[4.2.0]oct-2-ene-2-carboxylic acid is used in Example 56 in place of (6R,7R)-7-(2-amino-4-thiazoleglyoxylamido)-3-[[5-(3,4-dihydroxyphenyl)-1H-tetrazol-1-yl]methyl]-8-oxo-5-thia-1-azabicyclo[4.2.0]oct-2-ene-2-carboxylic acid, then there is obtained under otherwise similar conditions:

(6R,7R)-7-[(Z)-2-(2-amino-4-thiazolyl)-2-[[1-[3-(3,4-dihydroxybenzoyl)carbazoyl]-1-methylethoxy]imino]acetamido]-3-[[5-(3,4-dihydroxyphenyl)-2H-tetrazol-2-yl]methyl]-8-oxo-5-thia-1-azabicyclo[4.2.0]oct-2-ene-2-carboxylic acid:

$^1$H-NMR (DMSO-$d_6$, 250 MHz): signals at $\delta$ (ppm) 1.47 (s, 3H), 1.51 (s, 3H), 3.58 (m, 2H), 5.25 (d, J=5 Hz, 1H), 5.65 (d, J=14 Hz, H), 5.86 (d, J=14 Hz, 1H), 5.94 (d,d, J=5 Hz, J=8 Hz, 1H), 6.75–7.5 (m, 9H), 9.21 (s, 1H), 9.24 (s, 1H), 9.39 (s, 1H), 9.47 (s, 1H), 9.59 (s, 1H), 9.70 (d, J=8 Hz, 1H), 10.04 (s, 1H), 14 (s, broad, 1H).

EXAMPLE 58

Manufacture of (6R,7R)-7-[(Z)-2-(2-amino-4-thiazolyl)-2-[[1-[3-(3,4-dihydroxybenzoyl)carbazoyl]-1-methylethoxy]imino]acetamido]-3-[[[2-(3,4-dihydroxyphenyl)-5-methyl-s-triazolo[1,5-a]pyrimidin-7-yl]thio]methyl]-8-oxo-5-thia-1-azabicyclo[4.2.0]oct-2-ene-2-carboxylic acid (6R,7R)-7-(2-Amino-4-thiazoleglyoxylamido)-3-[[[2-(3,4-dihydroxyphenyl)-5-methyl-s-triazolo[1,5-a]pyrimidin-7-yl]thio]methyl]-8-oxo-5-thia-1-azabicyclo[4.2.0]oct-2-ene-2-carboxylic acid (1.3 g) and 0.79 g of 1-[2-(aminooxy)-2-methylpropionyl]-2-(3,4-dihydroxybenzoyl)hydrazine hydrochloride are dissolved in 10 ml of dimethylacetamide. After standing overnight the mixture is evaporated in a vacuum. The residue is digested with 25 ml of water and the precipitate formed is filtered off under suction and dried. There are obtained 1.7 g of (6R,7R)-7-[(Z)-2-(2-amino-4-thiazolyl)-2-[[1-[3-(3,4-dihydroxybenzoyl)carbazoyl]-1-methylethoxy]imino]acetamido]-3-[[[2-(3,4-dihydroxyphenyl)-5-methyl-s-triazolo[1,5-a]pyrimidin-7-yl]thio]methyl]-8-oxo-5-thia-1-azabicyclo[4.2.0]oct-2-ene-2-carboxylic acid as a colourless powder.

$^1$H-NMR (DMSO-$d_6$, 250 MHz): signals at $\delta$ (ppm) 1.49 (s, 3H), 1.52 (s, 3H), 2.57 (s, 3H), 3.64 (d, J=18 Hz, 1H), 3.89 (d, J=18 Hz, 1H), 4.35 (d, J=13 Hz, 1H), 4.54 (d, J=13 Hz,), 5.26 (d, J=5 Hz, 1H), 5.91 (dd, J=5 and 8 Hz, 1H), 6.90 (s, 1H), 6,7–7.65 (m, ca. 9H), 9.23 (s, 1H), 9.70 (d, J=8 Hz, 1H), 10.05 (s, 1H).

EXAMPLE 59

Manufacture of (6R,7R)-7-[(Z)-2-(2-amino-4-thiazolyl)-2-[[1-[3-(3,4-dihydroxybenzoyl)carbazoyl]-1-methylethoxy]imino]acetamido]-3-[[[2-(3-chloro-4,5-dihydroxyphenyl)-5,6-dimethyl-s-triazolo[1,5-a]pyrimidin-7-yl]thio]methyl]-8-oxo-5-thia-1-azabicyclo[4.2.0]oct-2-ene-2-carboxylic acid sodium salt (1:1)

In an analogous manner to that in Example 58, starting from (6R,7R)-7-(2-amino-4-thiazoleglyoxylamido)-3-[[[2-(3-chloro-4,5-dihydroxyphenyl)-5,6-dimethyl-s-triazolo[1,5-a]pyrimidin-7-yl]thio]methyl]-8-oxo-5-thia-1-azabicyclo[4.2.0]oct-2-ene-2-carboxylic acid there is manufactured the compound (6R,7R)-7-[(Z)-2-(2-amino-4-thiazolyl)-2-[[1-[3-(3,4-dihydroxybenzoyl)carbazoyl]-1-methylethoxy]imino]acetamido]-3-[[[2-(3-chloro-4,5-dihydroxyphenyl)-5,6-dimethyl-s-triazolo[1,5-a]pyrimidin-7-yl]thio]methyl]-8- oxo-5-thia-1-azabicyclo[4.2.0]oct-2-ene-2-carboxylic acid sodium salt (1:1).

¹H-NMR (DMSO-d₆, 250 MHz): signals at δ (ppm) 2.42 (s, 3H), 2.59 (s, 3H), 3.47 (d, J=18 Hz, 1H), 3.64 (d, J=18 Hz, 1H), 4.37 (d, J=13 Hz, 1H), 4.50 (d, J=13 Hz, 1H), 5.07 (d, J=6 Hz, 1H), 5.71 (dd, J=6 and 9 Hz, 1H), 6.75 (d, J=9 Hz, 1H), 6.85 (s, 1H), 7.22 (m, 1H), 7.33 (broad, 2H), 7.53 (d, J=1 Hz, 1H), 7.65 (d, J=1 Hz, 1H), 9.27 (s, broad, 1H), 9.55 (d, J=9 Hz, 1H), 9.9 (broad, 1H).

EXAMPLE 60

Manufacture of (6R,7R)-7-[(Z)-2-(2-amino-4-thiazolyl)-2-[[1-[3-(3,4-dihydroxybenzoyl)carbazoyl]-1-methylethoxy]imino]acetamido]-3-[[[5-(3,4-dihydroxyphenyl)pyrazolo[1,5-a]pyrimidin-7-yl]thio]methyl]-8-oxo-5-thia-1-azabicyclo[4.2.0]oct-2-ene-2-carboxylic acid (6R,7R)-7-(2-Amino-4-thiazoleglyoxylamido)-3-[[[5-(3,4dihydroxyphenyl)pyrazolo[1,5-a]pyrimidin-7-yl]thio]methyl]-8-oxo-5-thia-1-azabicyclo[4.2.0]oct-2-en-2-carboxylic acid (625 mg) and 500 mg of 1-[2-(aminooxy)-2-methylpropionyl]-2-(3,4-dihydroxybenzoyl)hydrazine hydrochloride are dissolved in 10 ml of dimethylacetamide and left at room temperature for 24 hours. Thereafter, the solvent is evaporated at 30° C. in a vacuum. The residue is triturated with 30 ml of water, whereby it becomes solid. It is filtered off under suction, washed with water and dried at 0.1 mmHg/40° C. and there are obtained 800 mg of beige (6R,7R)-7-[(Z)-2-(2-amino-4-thiazolyl)-2-[[1-[3-(3,4-dihydroxybenzoyl)carbazoyl]-1-methylethoxy]imino]-acetamido]-3-[[[5-(3,4-dihydroxyphenyl)pyrazolo[1,5-a]pyrimidin-7-yl]thio]methyl]-8-oxo-5-thia-1-azabicyclo[4.2.0]oct-2-ene-2-carboxylic acid.

Elementary analysis: Found: 48.99% C, 3.75% H, 15.92% N, 10.80% S; Calculated: 49.31% C, 3.68% H, 15.97% N, 10.97% S.

¹H-NMR (DMSO-d₆, 250 MHz): signals at δ (ppm) 1.47 (s, 3H), 1.50 (s, 3H), 3.69 (s, J=18 Hz, 1H), 3.89 (d, J=18 Hz, 1H), 4.52 (m, 2H), 5.37 (d, J=5 Hz, 1H), 5.90 (dd, J=5 and 8.5 Hz, 1H), 6.67 (d, J=2 Hz, 1H), 6.76 (d, J=8,5 Hz, 1H), 6.77 (m, 2H), 7.2–7,4 (m, 6H), 7.55 (m, 1H), 8.18 (d, J=2 Hz, 1H), 9.2 (m, 3H), 9.55 (m, 2H), 9.67 (d, J=8.5 Hz, 1H), 10.02 (s, 1H).

EXAMPLE 61

Manufacture of (6R,7R)-7-[(Z)-2-(2-amino-4-thiazolyl)-2-[[1-[3-(3,4-dihydroxybenzoyl)carbazoyl]-1-methylethoxy]imino]acetamido]-3-[[[2-[[(3,4-dihydroxybenzoyl)amino]methyl]-5-methyl-s-triazolo[1,5-a]pyrimidin-7-yl]thio]methyl]-8-oxo-5-thiaazabicyclo[4.2.0]oct-2-ene-2-carboxylic acid sodium salt (1:1)

This compound is manufactured as a pale yellowish lyophilizate in analogy to Example 42 from (6R,7R)-7-(2-amino-4-thiazoleglyoxylamido)-3-[[[2-[(3,4-dihydroxybenzoyl)amino]methyl]-5-methyl-s-triazolo[1,5-a]pyrimidin-7-yl]thio]methyl]-8-oxo-5-thia-1-azabicyclo[4.2.0]oct-2-ene-2-carboxylic acid and 1-[2-(aminooxy)-2-methylpropionyl]-2-(3,4-dihydroxybenzoyl)-hydrazine hydrochloride.

¹H-NMR, DMSOd₆, δ (ppm) inter alia 1.46 (s, 3H), 1.51 (s, 3H), 2.50 (s, 3H), 3.38 (d, J=17.5 Hz, 1H), 3.62 (d, J=17.5 Hz, 1H), 4.29 (d, J=12.5 Hz, 1H), 4.60 (d, J=5 Hz, 1H), 4.71 (d, J=12.5 Hz, 1H), 5.15 (d, J=5 Hz, 1H), 5.70 (d, d, J₁=5 Hz, J₂=8 Hz, 1H), 6.75 (m, 3H), 7.25 (m, 6H), 7.54 (s, 1H), 8.81 (t, J=5 Hz, 1H), 9.25 (s, 1H), 9.55 (d, J=8 Hz, 1H), 9.90 (s, 1H)

The (6R,7R)-7-(2-amino-4-thiazoleglyoxylamido)-3-[[[2-[(3,4-dihydroxybenzoyl)amino]methyl]-5-methyl-s-triazolo[1,5-a]pyrimidin-7-yl]thio]methyl]-8-oxo-5-thia-1-azabicyclo-[4.2.0]oct-2-ene-2-carboxylic acid used as the starting material can be prepared as follows:

2-(Hydroxymethyl)-5-methyl-s-triazolo[1,5-a]pyrimidin-7(4H)-one (U.S. Pat. No. 2,835,581) (1.8 g) is suspended in 5 ml of dimethylformamide, treated with 0.45 ml of phosphorus tribromide at 0° C. and stirred at this temperature for ½ hour. The dimethylformamide is evaporated in a high vacuum and the residue is digested with ice-cold water. The resulting precipitate is filtered off under suction and dried in a high vacuum (40° C.). There are obtained 1.97 g of 2-bromomethyl-5-methyl[1.2.4]triazolo[1,5-a]pyrimidin-7-ol as white crystals of melting point 217°–222° C.

2-Bromomethyl-5-methyl[1.2.4]triazolo[1,5-a]pyrimidin-7-ol (3.6 g) are dissolved in 50 ml of dimethylformamide, treated with 0.99 g of sodium azide and stirred at room temperature for 2.5 hours. The dimethylformamide is evaporated in a high vacuum at 40° C. and the residue is treated with 35 ml of water. The thus-obtained suspension is stirred in an ice bath for 45 minutes. A white precipitate is filtered off under suction, washed with a small amount of water and dried in a high vacuum. There are obtained 2.0 g of 2-azidomethyl-5-methyl[1.2.4]-triazolo[1,5-a]pyrimidin-7-ol as white crystals of melting point 193°–194° C.

2-Azidomethyl-5-methyl[1.2.4]-triazolo[1,5-a]pyrimidin-7-ol (3.1 g) are suspended in 20 ml of freshly distilled phosphorus oxychloride and 1.1 ml of pyridine and stirred at 50° C. for 4.5 hours. The phosphorus oxychloride is evaporated in a vacuum and the residue is taken up in 40 ml of ethyl acetate and 40 ml of water. The resulting suspension is stirred in an ice bath for 45 minutes. The product is filtered off under suction and dried in a vacuum at 40° C. There are obtained 2.1 g of 2-azidomethyl-7-chloro-5-methyl[1.2.4]triazolo[1,5-a]pyrimidine as white crystals of melting point 130°–132° C.

2-Azidomethyl-7-chloro-5-methyl[1.2.4]triazolo-[1,5-a]pyrimidine (2.98 g) are suspended in 70 ml of ethanol, treated with 1.1 g of thiourea and heated at reflux for 45 minutes. The reaction mixture is stirred in an ice bath for 30 minutes. The resulting precipitate is filtered off under suction and dried in a vacuum at 40° C. There are obtained 2.76 g of 2-azidomethyl-5methyl[1.2.4]-triazolo[1,5-a]pyrimidine-7-thiol as yellow crystals of melting point 214°–215° C.

A solution of 6.25 ml of n-butyllithium (1.6M in n-hexane) in 50 ml of tetrahydrofuran is treated at −78° C. with 3.5 g of 5-bromo-2,2-diphenyl-1,3-benzodioxol and stirred for 10 minutes. The resulting solution is treated with about 10 g of solid carbon dioxide and subsequently warmed to room temperature. The precipitate formed is filtered off and dried. There are obtained 2.66 g of 2,2-diphenyl-1,3-benzodioxol-5-carboxylic acid lithium salt (1:1) as a white powder. This is dissolved in 20 ml of dimethylformamide and stirred at room temperature for 1 hour with 3.03 g of O-benzotriazol-1-yl-N,N,N′,N′-tetra-methyluronium hexafluorophosphate (HBTU). The solvent is evaporated in a high vacuum, the residue is taken up in 15 ml of water and 15 ml of ethyl acetate and stirred in an ice bath for 45 minutes. The solid formed is filtered off under suction and dissolved in 40 ml of boiling ethyl acetate. A small amount of insoluble material is filtered off and the mother liquor is treated with n-hexane. The mixture is now concentrated until a suspension, which can still be filtered well, is obtained. The product is filtered off under suction and dried in a vacuum at 40° C. There are obtained 2.55 g of 1H-benzotriazol-1-yl 2,2-diphenyl-1,3-benzodioxol-5-carboxylate as white crystals of melting point 158°–160° C.

A dried solution of 2.0 g of sodium hydrogen sulphide monohydrate (drying agent molecular sieve 4 Å) in 100 ml of dimethylformamide is treated with 2.2 g of 2-azidomethyl-5-methyl[1.2.4]triazolo[1,5-a]pyrimidine-7-thiol and stirred until the evolution of gas has finished (about 15 minutes). Thereupon, 4.35 g of 1H-benzotriazol-1-yl 2,2-diphenyl-1,3-benzodioxol-5-carboxylate are added and the reaction mixture is stirred at room temperature for 20 hours and at 45° C. for 24 hours. The solvent is evaporated in a high vacuum, the residue is taken up in 200 ml of ethyl acetate and 200 ml of water and stirred in an ice bath for 30 minutes. The resulting precipitate is filtered off under suction, washed with water and ethyl acetate and dried in a vacuum at 40° C. The yellow product is dissolved in 100 ml of methanol, a small amount of insoluble material is removed by filtration and the filtrate is concentrated to dryness. The residue in 100 ml of acetonitrile is heated at reflux on a steam bath for 1 hour. After cooling in an ice bath the product is filtered off under suction and dried. There are obtained 4.25 g of N-[(7-mercapto-5-methyl-s-triazolo[1,5-a]pyrimidin-2-yl)methyl]-2,2-diphenyl-1,3-benzodioxol-5-carboxamide as a yellow solid of melting point 267°–271° C. (dec.).

N-[(7-Mercapto-5-methyl-s-triazolo[1,5-a]-pyrimidin-2-yl)methyl]-2,2-diphenyl-1,3-benzodioxol-5-carboxamide (22.7 g) are stirred for 1 hour in 210 ml of trifluoroacetic acid and 5 ml of water. A small amount of insoluble material is filtered off and the mother liquor is evaporated to dryness. The yellow residue is treated with 900 ml of ethyl acetate, stirred in an ultrasound bath for 1 hour and subsequently cooled in an ice bath. The yellow solid is filtered off and dried in a vacuum at 40° C. There are obtained 14.4 g of 3,4-dihydroxy-N-(7-mercapto-5-methyl[1.2.4]triazolo[1,5-a]pyrimidin-2-ylmethyl)-benzamide as a yellow powder.

$^1$H-NMR, DMSOd$_6$, δ (ppm) inter alia 2.32 (s, 1H), 4.57 (d, J=6H, 2H), 6.75 (m, 2H), 7.25 (m, 2H), 8.80 (t, J=6H, 1H), 9.15 (s, 1H), 9.51 (s, 1H), 14.00 (s, broad, 1H)

3,4-Dihydroxy-N-(7-mercapto-5-methyl[1.2.4]-triazolo[1,5-a]-pyrimidin-2-ylmethyl)-benzamide is converted by reaction with 7-aminocephalosporanic acid in analogy to Example 1 into (6R,7R)-7-amino-3-[[[2-[[(3,-4-dihydroxybenzoyl)amino]methyl]-5-methyl-s-triazolo[1,5-a]pyrimidin-7-yl]thio]methyl]-8-oxo-5-thia-1-azabicyclo[4.2.0]oct-2-ene-2-carboxylic acid.

$^1$H-NMR, DMSOd$_6$, δ (ppm) inter alia 2.56 (s, 3H), 3.52 (d, J=17.5 Hz, 1H), 3.74 (d, J=17.5 Hz, 1H), 4.30 (d, J=12.5 Hz, 1H), 4.43 (d, J=12.5 Hz, 1H), 4.61 (d, J=6 Hz, 2H), 4.80 (d, J=5 Hz, 1H), 5.01 (d, J=5 Hz, 1H), 6.75 (d, J=8.5 Hz, 1H), 7.27 (m, 3H), 8.79 (t, J=6 Hz, 1H), 9.15 (s, broad, 1H), 9.48 (s, broad, 1H)

(6R,7R)-7-Amino-3-[[[2-[[(3,4-dihydroxybenzoyl)amino]methyl]-5-methyl-s-triazolo[1,5-a]pyrimidin-7-yl]thio]methyl]-8-oxo-5-thia-1-azabicyclo[4.2.0]oct-2-ene-2-carboxylic acid is converted by reaction with 2-amino-4-thiazolethioglyoxylic acid S-(2-benzothiazolyl) ester in analogy to Example 1 into (6R,7R)-7-(2-amino-4-thiazoleglyoxylamido)-3-[[[2-[[(3,4-dihydroxybenzoyl)amino]methyl]-5-methyl-s-triazolo[1,5-a]pyrimidin-7-yl]thio]methyl]-8-oxo-5-thia-1-azabicyclo[4.2.0]oct-2-ene-2-carboxylic acid.

$^1$H-NMR, DMSOd$_6$, δ (ppm) inter alia 2.56 (s, 3H), 3.59 (d, J=17.5 Hz, 1H), 3.78 (d, J=17.5 Hz, 1H), 4.34 (d, J=12.5 Hz, 1H), 4.48 (d, J=12.5 Hz, 1H), 4.60 (d, J=6 Hz, 2H), 5.20 (d, J=5 Hz, 1H), 5.78 (d, d, J$_1$=5 Hz, J$_2$=8 Hz, 1H), 6.77 (d, J=8 Hz, 1H), 7.35 (m, 5H), 7.82 (s, 1H), 8.81 (t, J=6 Hz, 1H), 9.17 (s, 1H), 9.50 (s, 1H), 9.81 (d, J=8 Hz, 1H)

Example A

Manufacture of dry ampoules for intramuscular administration:

A lyophilizate of 1 g of the sodium salt of 7-[(Z)-2-(2--amino-4-thiazolyl)-2-[[(2-fluoro-3,4-dihydroxybenzyl)oxy]imino]acetamido]-3-[[[2-[(3,4-dihydroxybenzenesulphonamido)methyl]-5-methyl-s-triazolo[1,5-a]pyrimidin-7-yl]thio]methyl]-8-oxo-5-thia-1-azabicyclo[4.2.0]oct-2-ene-2-carboxylic acid is manufactured in the usual manner and filled into an ampoule. Prior to administration the lyophilizate is treated with 2.5 ml of a 2% aqueous lidocaine hydrochloride solution.

The same procedure can be used on the end products of Examples 5, 6, 10, 11, 14, 15, 43, 44, 47 and 61.

What is claimed is:

1. A cephalosporin derivative of the formula:

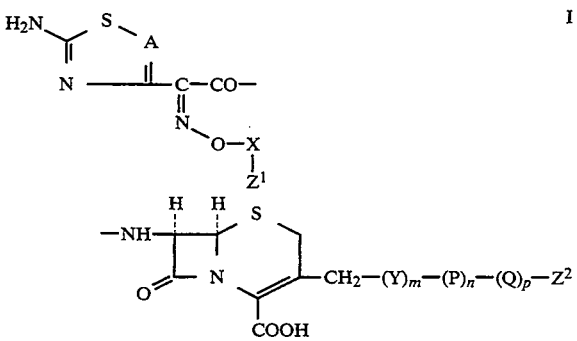

wherein $Z^1$ and $Z^2$ each independently is a 6-membered aromatic ring which is substituted by two vicinal —OR$^1$ groups wherein R$^1$ represents hydrogen or lower alkanoyl, each of $Z^1$ and $Z^2$ independently can contain 1 or 2 oxygen or nitrogen atoms and can be substituted by halogen, carboxy or carboxy-lower alkyl; A is a nitrogen atom or —CH=; X is lower alkylene, phenylene or lower alkylene-phenylene, which is optionally substituted by carboxy and optionally linked via one of the groups —S—, —SO—, —SO$_2$—, —CO—, —OCO—, —NHCO—, —NHSO$_2$— or —CONHNHCO—; Y is selected from the group consisting of —O—, —OCO—, —OCH$_2$—, —S—, —SCO—, —SO— and —SO$_2$; P is an 8- to 10-membered N-biheterocycle, which is optionally substituted by lower alkyl, carboxy, lower alkoxycarbonyl, carbamoyl, hydroxymethyl or lower alkanoyloxymethyl; Q is lower alkylene, phenylene or lower alkylene-phenylene, which is optionally linked via one of the groups —CO—, —OCO—, —SO$_2$—, —NHCO— or —NHSO$_2$—, or Q is selected from the group consisting of —S—, —SO—, —SO$_2$—, —CO—, —OCO—, —NHCO—, —NHSO$_2$— and —CONHNHCO—; and m, n and p each is the number 0 or 1;

and the readily hydrolyzable esters and pharmaceutically compatible salts of these compounds and hydrates of compounds of formula I and of their esters and salts.

2. The cephalosporin derivative according to claim 1, wherein X is lower alkylene, phenylene or lower alkylene-phenylene, which is optionally substituted by carboxy and optionally linked via a group selected from the group consisting of —S—, —SO—, —SO$_2$—, —CO—, —OCO—, —NHCO— and —NHSO$_2$—.

3. The cephalosporin derivative according to claim 1, wherein X is the group -(lower alkylene)-CONHNHCO—.

4. The cephalosporin derivative according to claim 1, wherein P is the 2-(5-methyl-s-triazolo[1,5-a]pyrimidin-7-yl)-ene group of the formula:

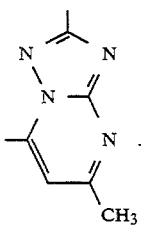

5. The cephalosporin derivative according to claim 1, wherein (Q)$_p$—Z$^2$ is (3,4-dihydroxybenzenesulphonamido)methyl.

6. The cephalosporin derivative according to claim 1, wherein (Q)$_p$—Z$^2$ is [(3,4-dihydroxybenzoyl)oxy]methyl.

7. The cephalosporin derivative according to claim 1, wherein (Q)$_p$—Z$^2$ is [(3,4-dihydroxyphenyl)sulphonyl]methyl.

8. The cephalosporin derivative according to claim 1, wherein (Q)$_p$—Z$^2$ is [(3,4-dihydroxybenzoyl)amino]methyl.

9. The cephalosporin derivative according to claim 1, wherein (Y)$_m$—(P)$_n$—(Q)$_p$—Z$^2$ is (3 4-dihydroxyphenyl)sulphonyl.

10. The cephalosporin derivative according to claim 1, wherein X—Z$^1$ is 3,4-dihydroxybenzyl.

11. The cephalosporin derivative according to claim 1, wherein X—Z$^1$ is 2-fluoro-3,4-dihydroxybenzyl.

12. The cephalosporin derivative according to claim 1, wherein X—Z$^1$ is 1-[3-(3,4-dihydroxybenzoyl)carbazoyl]-1-methylethyl.

13. (6R,7R)-7-[(Z)-2-(2-Amino-4-thiazolyl)-2-[[3,4--dihydroxybenzyl)oxy]imino]acetamido]-3-[[[2-[(3,4-dihydroxybenzenesulphonamido)methyl]-5-methyl-s-triazolo[1,5-a]pyrimidin-7-yl]thio]methyl]-8-oxo-5-thia-1-azabicyclo[4.2.0]oct-2-ene-2-carboxylic acid and the pharmaceutically compatible salts and hydrates thereof, and the hydrates of the salts.

14. 7-[(Z)-2-(2-Amino-4-thiazolyl)-2-[[(2-fluoro-3,4-dihydroxybenzyl)oxy]imino]acetamido]-3-[[[2-[-(3,4-dihydroxybenzenesulphonamido)methyl]-5-methyl-s-triazolo[1,5-a]pyrimidin-7-yl]thio]methyl]-8-oxo-5-thia-1-azabicyclo[4.2.0]oct-2-ene-2-carboxylic acid and the pharmaceutically compatible salts and hydrates thereof, and the hydrates of the salts.

15. (6R,7R)-7-[(Z)-2-(2-Amino-4-thiazolyl)-2-[[3,4-dihydroxybenzyl)oxy]imino]acetamido]-3-[[[2-[[(3,4-dihydroxybenzoyl)oxy]methyl]-5-methyl-s-triazolo[1,5-a]pyrimidin-7-yl]thio]methyl]-8-oxo-5-thia-1-azabicyclo[4.2.0]oct-2-ene-2-carboxylic acid and the pharmaceutically compatible salts and hydrates thereof, and the hydrates of the salts.

16. (6R,7R)-7-[(Z)-2-(2-Amino-4-thiazolyl)-2-[[[(3,4-dihydroxy-2-fluorobenzyl)oxy]imino]acetamido]-3-[[[2-[[(3,4-dihydroxybenzoyl)oxy]methyl]-5-methyl-s-triazolo[1,5-a]pyrimidin-7-yl]thio]methyl]-8-oxo-5-thia-1-azabicyclo[4.2.0]oct-2-ene-2-carboxylic acid and the pharmaceutically compatible salts and hydrates thereof, and the hydrates of the salts.

17. (6R,7R)-7-[(Z)-2-(2-Amino-4-thiazolyl)-2-[[(3,4-di hydroxybenzyl)oxy]imino]acetamido]-3-[[[2-[[(3,4-dihydroxyphenyl)sulphonylmethyl]-5-methyl-s-triazolo[1,5-a]pyrimidin-7-yl]thio]methyl]-8-oxo-5-thia-1-azabicyclo[4.2.0]oct-2-ene-2-carboxylic acid and the pharmaceutically compatible salts and hydrates thereof, and the hydrates of the salts.

18. (6R,7R)-7-[(Z)-2-(2-Amino-4-thiazolyl)-2-[[(2-fluoro-3,4-dihydroxybenzyl)oxy]imino]acetamido]-3-[[[2-[[(3,4-dihydroxyphenyl)sulphonyl]methyl]-5-methyl-s-triazolo[1,5-a]pyrimidin-7-yl]thio]methyl]-8-oxo-5-thia-1-azabicyclo[4.2.0]oct-2-ene-2-carboxylic acid and the pharmaceutically compatible salts and hydrates thereof, and the hydrates of the salts.

19. (6R,7R)-7-[(Z)-2-(2-Amino-4-thiazolyl)-2-[[1-[3-(3,4-dihydroxybenzoyl)carbazoyl]-1-methylethoxy]imino]acetamido]-3-[[[2-[(3,4-dihydroxybenzenesulphonamido)methyl]-5-methyl-s-triazolo[1,5-a]pyrimidin-7-yl]thio]methyl]-8-oxo-5-thia-1-azabicyclo[4.2.0]oct-2-ene-2-carboxylic acid and the pharmaceutically compatible salts and hydrates thereof, and the hydrates of the salts.

20. (6R,7R)-7-[(Z)-2-(2-Amino-4-thiazolyl)-2-[[1-[-3-(3,4-dihydroxybenzoyl)carbazoyl]-1-methylethoxy]imino]acetamido]-3-[[[2-[(3,4-dihydroxybenzoyl)oxy]-methyl]-5-methyl-s-triazolo[1,5-a]pyrimidin-7-yl]thio]-methyl]-8-oxo-5-thia-1-azabicyclo[4.2.0]oct-2-ene-2-carboxylic acid and the pharmaceutically compatible salts and hydrates thereof, and the hydrates of the salts.

21. (6R,7R)-7-[(Z)-2-(2-Amino-4-thiazolyl)-2-[[1-[3-(3,4-dihydroxybenzoyl)carbazoyl]-1-methylethoxy]imino]acetamido]-3-[[[2-[(3,4-dihydroxyphenyl)sulphonyl]methyl]-5-methyl-s-triazolo[1,5-a]pyrimidin-7-yl]thio]methyl]-8-oxo-5-thia-1-azabicyclo[4.2.0]oct-2-ene-2-carboxylic acid and the pharmaceutically compatible salts and hydrates thereof, and the hydrates of the salts.

22. (6R,7R)-7-[(Z)-2-(2-Amino-4-thiazolyl)-2-[[1-[3-(3,4-dihydroxybenzoyl)carbazoyl]-1-methylethoxy]imino]acetamido]-3-[[[2-[[(3,4-dihydroxybenzoyl)amino]methyl]-5-methyl-s-triazolo[1,5-a]pyrimidin-7-yl]thio]methyl]-8-oxo-5-thia-1-azabicyclo[4.2.0]oct-2-ene-2-2-carboxylic acid and the pharmaceutically compatible salts and hydrates thereof, and the hydrates of the salts.

23. A compound of the formula:

Ia

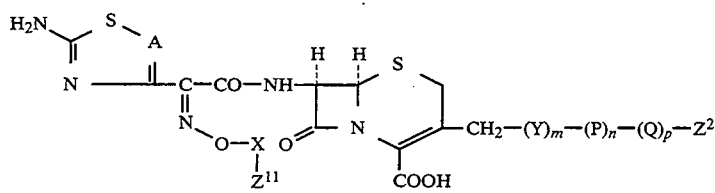

wherein A is a nitrogen atom or —CH=, X is lower alkylene, phenylene or lower alkylene-phenylene, which is optionally substituted by carboxy and optionally linked via one of the groups —S—, —SO—, —SO$_2$—, —CO—, —OCO—, —NHCO—, —NHSO$_2$— and —CONHNHCO—; Y is one of the groups —O—, —OCO—, —OCH$_2$—, —S—, —SCO—, —SO— and —SO$_2$—; P is an 8- or 10-membered N-biheterocycle, which is optionally substituted by lower alkyl, carboxy, lower alkoxycarbonyl, carbamoyl, hydroxymethyl or lower alkanoyloxymethyl; Q is lower alkylene, phenylene or lower alkylene-phenylene, and is optionally linked via one of the groups —CO—, —OCO—, —SO$_2$—, —NHCO— and —NHSO$_2$—, or Q is one of the groups —S—, —SO—, —SO$_2$—, —CO—, —OCO—, —NHCO—, —NHSO$_2$— or —CONHNHCO; Z$^2$ is a 6-membered aromatic ring which is substituted by two vicinal —OR$^1$ groups; m, n and p each is the number 0 or 1; and Z$^{11}$ is a 2,2-diphenyl-1,3-benzodioxol-5-yl group which is optionally halogenated in the benzodioxol residue, and the salts of these compounds.

24. A medicament containing a therapeutically effective amount of a compound or the formula:

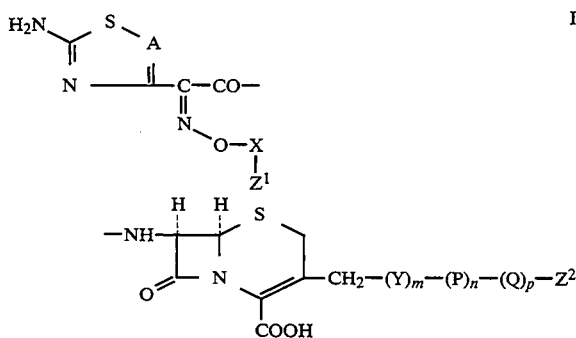

I wherein Z$^1$ and Z$^2$ each independently is a 6-membered aromatic ring which is substituted by two vicinal —OR$^1$ groups wherein R$^1$ represents hydrogen or lower alkanoyl, each of Z$^1$ and Z$^2$ independently can contain 1 or 2 oxygen or nitrogen atoms and can be substituted by halogen, carboxy or carboxy-lower alkyl; A is a nitrogen atom or —CH=; X is lower alkylene, phenylene or lower alkylene-phenylene, which is optionally substituted by carboxy and optionally linked via one of the groups —S—, —SO—, —SO$_2$—, —CO—, —OCO—, —NHCO—, —NHSO$_2$— or —CONHNHCO—; Y is selected from the group consisting of —O—, —OCO—, —OCH$_2$—, —S—, —SCO—, —SO— and —SO$_2$; P is an 8- to 10- membered N-biheterocycle, which is optionally substituted by lower alkyl, carboxy, lower alkoxycarbonyl, carbamoyl, hydroxymethyl or lower alkanoyloxymethyl; Q is lower alkylene, phenylene or lower alkylene-phenylene, which is optionally linked via one of the groups —CO—, —OCO—, —SO$_2$—, —NHCO— or —NHSO$_2$—, or Q is selected from the group consisting of —S—, —SO—, —SO$_2$—, —CO—, —OCO—, —NHCO—, —NHSO$_2$— and —CONHNHCO—; and m, n and p each is the number 0 or 1;

and the readily hydrolyzable esters and pharmaceutically compatible salts of these compounds and hydrates of compounds of formula I and of their esters and salts.

25. A cephalosporin derivative of the formula:

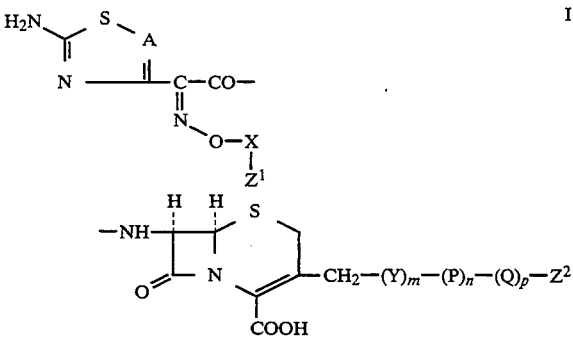

I wherein the group —(Q)$_p$—Z$^2$ is a group —(Q$^1$-)$_p$—CONR$^3$OH, Q$^1$ is lower alkylene, phenylene or lower alkylene-phenylene, and R$^3$ is hydrogen, lower alkyl or phenyl; Z$^1$ is a 6-membered aromatic ring which is substituted by two vicinal —OR$^1$ groups wherein R$^1$ represents hydrogen or lower alkanoyl, Z$^1$ can contain 1 or 2 oxygen or nitrogen atoms and can be substituted by halogen, carboxy or carboxy-lower alkyl, and X is lower alkylene, phenylene or lower alkylene-phenylene, which is optionally substituted by carboxy and optionally linked via one of the groups —S—, —SO—, —SO$_2$—, —CO—, —OCO—, —NHCO—, —NHSO$_2$— or —CONHNHCO—, or the group —X—Z$^1$ is a group —X$^1$—CONR$^2$OH, X$^1$ is lower alkylene, phenylene or lower alkylene-phenylene, and R$^2$ is hydrogen, lower alkyl or phenyl; A is a nitrogen atom or —CH=; Y is selected from the group consisting of —O—, —OCO—, —OCH$_2$—, —S—, —SCO—, —SO— and —SO$_2$; P is an 8-to 10-membered N-biheterocycle, which is optionally substituted by lower alkyl, carboxy, lower alkoxycarbonyl, carbamoyl, hydroxymethyl or lower alkanoyloxymethyl; and m, n and p each is the number 0 or 1;

and the readily hydrolyzable esters and pharmaceutically compatible salts of these compounds and hydrates of compounds of formula I and of their esters and salts.

26. The cephalosporin derivative according to claim 25, wherein P is the 2-(5-methyl-s-triazolo[1,5-a]pyrimidin-7-yl)-ene group of the formula:

27. A medicament containing a therapeutically effective amount of a compound of the formula:

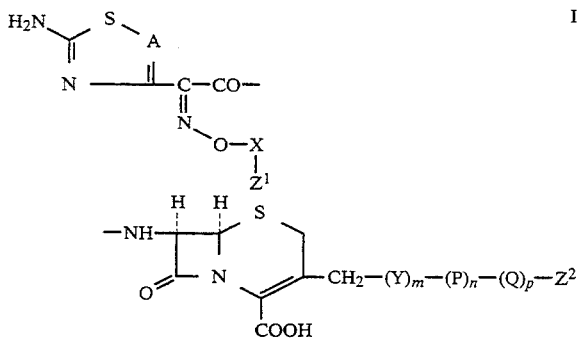

wherein the group —(Q)$_p$—Z$^2$ is a group —(Q$^1$)—CONR$^3$OH, Q$^1$ is lower alkylene, phenylene or lower alkylene-phenylene, and R$^3$ is hydrogen, lower alkyl or phenyl; Z$^1$ is a 6-membered aromatic ring which is substituted by two vicinal —OR$^1$ groups wherein R$^1$ represents hydrogen or lower alkanoyl, Z$^1$ can contain 1 or 2 oxygen or nitrogen atoms and can be substituted by halogen, carboxy or carboxy-lower alkyl, and X is lower alkylene, phenylene or lower alkylene-phenylene, which is optionally substituted by carboxy and optionally linked via one of the groups —S—, —SO—, —SO$_2$—, —CO—, —OCO—, —NHCO—, —NHSO$_2$— or —CONHNHCO—, or the group —X—Z$^1$ is a group —X$^1$—CONR$^2$OH, X$^1$ is lower alkylene, phenylene or lower alkylene-phenylene, and R$^2$ is hydrogen, lower alkyl or phenyl; A is a nitrogen atom or —CH=; Y is selected from the group consisting of —O—, —OCO—, —OCH$_2$—, —S—, —SCO—, —SO— and —SO$_2$; P is an 8-to 10-membered N-biheterocycle, which is optionally substituted by lower alkyl, carboxy, lower alkoxycarbonyl, carbamoyl, hydroxymethyl or lower alkanoyloxymethyl; and m, n and p each is the number 0 or 1; and the readily hydrolyzable esters and pharmaceutically compatible salts of these compounds and hydrates of compounds of formula I and of their esters and salts.

28. A cephalosporin derivative of the formula:

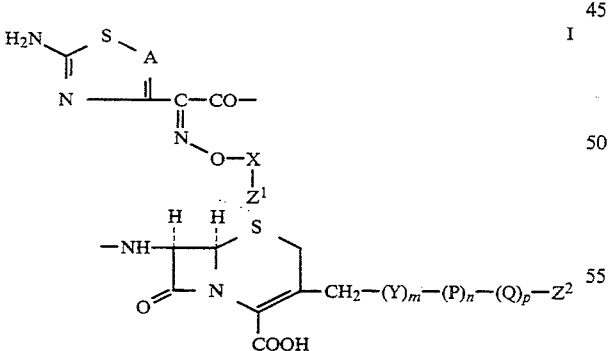

wherein the group —X—Z$^1$ is a group —X$^1$—CONR$^2$OH, X$^1$ is lower alkylene, phenylene or lower alkylene-phenylene, and R$^2$ is hydrogen, lower alkyl or phenyl; Z$^2$ is a 6-membered aromatic ring which is substituted by two vicinal —OR$^1$ groups wherein R$^1$ represents hydrogen or lower alkanoyl, Z$^2$ can contain 1 or 2 oxygen or nitrogen atoms and can be substituted by halogen, carboxy or carboxy-lower alkyl, Q is lower alkylene, phenylene or lower alkylene-phenylene, which is optionally linked via one of the groups —CO—, —OCO—, —SO$_2$—, —NHCO— and —NHSO$_2$—, or Q is selected from the group consisting of —S—, —SO—, —SO$_2$—, —CO—, —OCO—, —NHCO—, —NHSO$_2$— and —CONHNHCO—, or the group —(Q)$_p$—Z$^2$ is a group —(Q$^1$)$_p$—CONR$^3$OH, Q$^1$ is lower alkylene, phenylene or lower alkylene-phenylene, and R$^3$ is hydrogen, lower alkyl or phenyl; A is a nitrogen atom or —CH=; Y is selected from the group consisting of —O—, —OCO—, —OCH$_2$—, —S—, —SCO—, —SO— and —SO$_2$; P is an 8- to 10-membered N-biheterocycle, which is optionally substituted by lower alkyl, carboxy, lower alkoxycarbonyl, carbamoyl, hydroxymethyl or lower alkanoyloxymethyl; and m, n and p each is the number 0 or 1; and the readily hydrolyzable esters and pharmaceutically compatible salts of these compounds and hydrates of compounds of formula I and of their esters and salts.

29. The cephalosporin derivative according to claim 28, wherein P is the 2-(5-methyl-s-triazolo[1,5-a]pyrimidin-7-yl)-ene group of the formula:

30. A medicament containing a therapeutically effective amount of a compound of the formula:

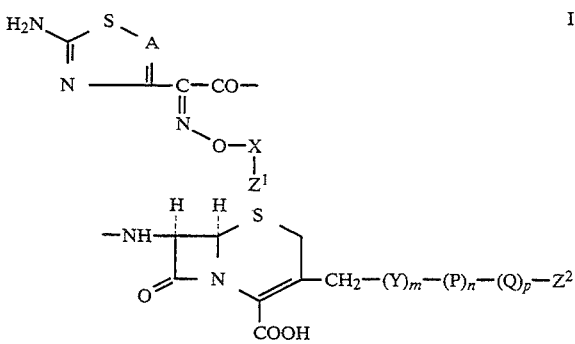

wherein the group —X—Z$^1$ is a group —X$^1$—CONR$^2$OH, X$^1$ is lower alkylene, phenylene or lower alkylene-phenylene, and R$^2$ is hydrogen, lower alkyl or phenyl; Z$^2$ is a 6-membered aromatic ring which is substituted by two vicinal —OR$^1$ groups wherein R$^1$ represents hydrogen or lower alkanoyl, Z$^2$ can contain 1 or 2 oxygen or nitrogen atoms and can be substituted by halogen, carboxy or carboxy-lower alkyl, Q is lower alkylene, phenylene or lower alkylene-phenylene, which is optionally linked via one of the groups —CO—, —OCO—, —SO$_2$—, —NHCO— and —NHSO$_2$—, or Q is selected from the group consisting of —S—, —SO—, —SO$_2$—, —CO—, —OCO—, —NHCO—, —NHSO$_2$— and —CONHNHCO—, or the group —(Q)$_p$—Z$^2$ is a group —(Q$^1$)$_p$—CONR$^3$OH, Q$^1$ is lower alkylene, phenylene or lower alkylene-phenylene, and R$^3$ is hydrogen, lower alkyl or phenyl; A is a nitrogen atom or —CH=; Y is selected from the group consisting of —O—, —OCO—, —OCH$_2$—, —S—, —SCO—, —SO— and —SO$_2$; P is an 8-to 10-membered N-biheterocycle, which is optionally substituted by lower alkyl, carboxy, lower alkoxycarbonyl, carbamoyl, hydroxymethyl or lower alkanoyloxymethyl; and m, n and p each is the number 0 or 1; and the readily hydrolyzable esters and pharmaceutically compatible salts of these compounds and hydrates of compounds of formula I and of their esters and salts.

* * * * *

UNITED STATES PATENT AND TRADEMARK OFFICE
CERTIFICATE OF CORRECTION

PATENT NO. : 5,438,052
DATED : August 1, 1995
INVENTOR(S) : Peter Angehrn, et al.

It is certified that error appears in the above-indentified patent and that said Letters Patent is hereby corrected as shown below:

In claim 26, column 92, line 68, please insert the following formula:

--

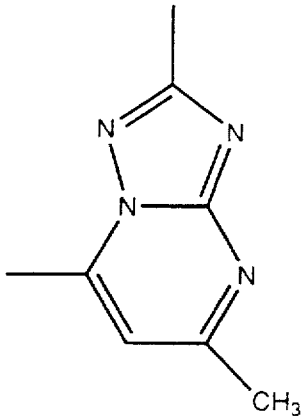

--.

In claim 27, column 93, lines 18-19, delete "$(Q^1)$-" and insert -- $(Q^1)_p$- --.

UNITED STATES PATENT AND TRADEMARK OFFICE
CERTIFICATE OF CORRECTION

PATENT NO. : 5,438,052
DATED : August 1, 1995
INVENTOR(S) : Peter Angehrn, et al.

It is certified that error appears in the above-indentified patent and that said Letters Patent is hereby corrected as shown below:

In claim 29, column 94, line 23, please insert the following formula:

--

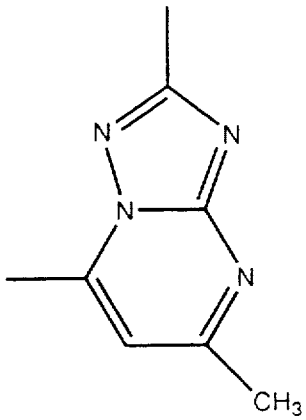

--.

Signed and Sealed this

Tenth Day of October, 1995

*Attest:*

BRUCE LEHMAN

*Attesting Officer*   Commissioner of Patents and Trademarks